(12) United States Patent
Zhong et al.

(10) Patent No.: US 8,552,181 B2
(45) Date of Patent: *Oct. 8, 2013

(54) SUBSTITUTED HYDROXYETHYL AMINE COMPOUNDS AS BETA-SECRETASE MODULATORS AND METHODS OF USE

(75) Inventors: Wenge Zhong, Thousand Oaks, CA (US); Stephen Hitchcock, Jupiter, FL (US); Vinod F. Patel, Acton, MA (US); Michael Croghan, Thousand Oaks, CA (US); Thomas Dineen, Somerville, MA (US); Scott Harried, Woodland Hills, CA (US); Daniel Horne, Simi Valley, CA (US); Ted Judd, Simi Valley, CA (US); Matthew Walker, Ventura, CA (US); Charles Kreiman, Watertown, MA (US); Patricia Lopez, West Hills, CA (US); Holger Monenschein, Jupiter, FL (US); Thomas Nguyen, Thousand Oaks, CA (US); Matthew Weiss, Boston, MA (US); Qiufen Xue, Newbury Park, CA (US); Bryant Yang, Simi Valley, CA (US); Russell Graceffa, Hampton, NH (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/410,201

(22) Filed: Mar. 1, 2012

(65) Prior Publication Data

US 2012/0220583 A1 Aug. 30, 2012

Related U.S. Application Data

(62) Division of application No. 12/154,513, filed on May 23, 2008, now Pat. No. 8,163,909.

(60) Provisional application No. 60/931,702, filed on May 25, 2007, provisional application No. 61/127,022, filed on May 8, 2008.

(51) Int. Cl.
C07D 471/10 (2006.01)
C07D 491/107 (2006.01)
C07D 495/10 (2006.01)

(52) U.S. Cl.
USPC .................... 544/70; 546/16; 546/18

(58) Field of Classification Search
None
See application file for complete search history.

(56) References Cited

U.S. PATENT DOCUMENTS

| | | |
|---|---|---|
| 5,441,870 A | 8/1995 | Seubert et al. |
| 5,712,130 A | 1/1998 | Hajko et al. |
| 5,942,400 A | 8/1999 | Anderson et al. |
| 6,864,290 B2 | 3/2005 | Schostarez et al. |
| 6,982,264 B2 | 1/2006 | John et al. |
| 6,992,103 B2 | 1/2006 | Faller et al. |
| 7,067,542 B2 | 6/2006 | Schostarez et al. |
| 7,074,799 B2 | 7/2006 | Bakthavatchalam et al. |
| 7,109,217 B2 | 9/2006 | Coburn et al. |
| 7,115,652 B2 | 10/2006 | Yang |
| 7,115,747 B2 | 10/2006 | Reeder et al. |
| 7,132,568 B2 | 11/2006 | Yang et al. |
| 7,176,242 B2 | 2/2007 | John et al. |
| 7,223,774 B2 | 5/2007 | Aquino et al. |

(Continued)

FOREIGN PATENT DOCUMENTS

| | | |
|---|---|---|
| WO | 00/17369 A2 | 3/2000 |
| WO | 01/70671 A2 | 9/2001 |

(Continued)

OTHER PUBLICATIONS

Berge, et al., "Pharmaceutical Salts", J. of Pharmaceutical Sciences, 66(1), 1-19 (1977).

(Continued)

*Primary Examiner* — Janet Andres
*Assistant Examiner* — Timothy R. Rozof
(74) *Attorney, Agent, or Firm* — G. Prabhakar Reddy

(57) ABSTRACT

The present invention comprises a new class of compounds useful for the modulation of Beta-secretase activity and for the treatment of diseases, including Alzheimer's disease (AD) and related CNS conditions, mediated thereby. In one embodiment, the compounds have a general Formula I

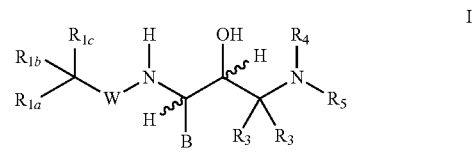

or Formula II

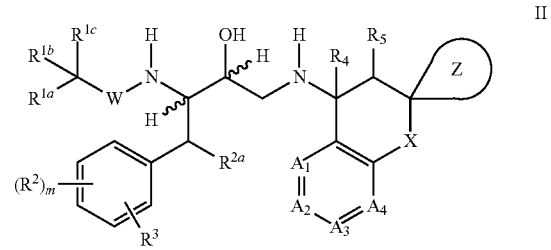

wherein $R^{1a-1c}$, B, $R^{3-5}$ and W of Formula I, and $R^{1a-1c}$, $R^{2-5}$, $A^{1-4}$, W, X, Z, m and n of Formula II are defined herein. The invention further provides compounds of Formula III and IV and sub-Formulas II-A-II-D and III-A-III-D. The compounds may be used in pharmaceutical compositions for treating, prophylactically or therapeutically, disorders related to the activity of beta-secretase protein, including without limitation, AD, cognitive deficits and impairment, schizophrenia and other similar central nervous system conditions.

12 Claims, No Drawings

(56) References Cited

U.S. PATENT DOCUMENTS

| | | |
|---|---|---|
| 7,244,755 B2 | 7/2007 | Fisher et al. |
| 7,253,198 B2 | 8/2007 | Demont et al. |
| 7,291,620 B2 | 11/2007 | Coburn et al. |
| 7,312,360 B2 | 12/2007 | TenBrink et al. |
| 7,348,448 B2 | 3/2008 | Nantermet et al. |
| 7,351,738 B2 | 4/2008 | Pulley et al. |
| 7,371,853 B2 | 5/2008 | Coburn et al. |
| 2003/0109559 A1 | 6/2003 | Gailunas et al. |
| 2003/0166580 A1 | 9/2003 | Warpehoski et al. |
| 2004/0180939 A1 | 9/2004 | John et al. |
| 2005/0027007 A1 | 2/2005 | Hom |
| 2005/0038019 A1 | 2/2005 | Beck |
| 2005/0054690 A1 | 3/2005 | Aquino et al. |
| 2005/0267199 A1 | 12/2005 | Hom et al. |
| 2006/0211740 A1 | 9/2006 | Demont et al. |
| 2006/0229302 A1 | 10/2006 | Demont et al. |
| 2006/0241133 A1 | 10/2006 | Shearman et al. |

FOREIGN PATENT DOCUMENTS

| | | |
|---|---|---|
| WO | 02/02505 A2 | 1/2002 |
| WO | 03/002518 A1 | 1/2003 |
| WO | 2004/099376 A2 | 11/2004 |
| WO | 2005/095326 A2 | 10/2005 |

OTHER PUBLICATIONS

Citron, M., "β-Secretase Inhibition for the Treatment of Alzheimer's Disease—Promise and Challenge", Trends in Pharmacological Sciences, 25(2), 92-97 (2004).

Corey, et al., "The Application of a Mechanistic Model Leads to the Extension of the Sharpless Asymmetric Dihydroxylation to Allylic 4-Methoxybenzoates and Conformationally Related Aine and Homoallylic Alcohol Derivatives", J. of Am. Chem. Soc., 117, 10805-10816 (1995).

Joachim, et al., "The Seminal Role of β-Amyloid in the Pathogenesis of Alzheimer Disease", Alzheimer Disease and Associated Disorders, 6(1), 7-34 (1992).

Luo, et al., "Mice deficient in BACE1, the Alzheimer's β-secretase, have normal phenotype and abolished β-amyloid generation", Nature Neuroscience, 4(3), 231-232 (2001).

Reynaud, et al., "New Synthesis of the Thiazole Ring", Bulletin de la Societe chimique de France, 1735-1738 (1962).

Sabbagh, et al.,"β-Amyloid and Treatment Opportunities for Alzheimer's Disease", Alzheimer's Disease Review, 3, 1-19 (1998).

Selkoe, D.M., "The Molecular Pathology of Alzheimer's Disease", Neuron, 6, 487-498 (1991).

Seubert, et al., "Isolation and Quantification of Soluble Alzheimer's β-Peptide from Biological Fluids", Nature, 359, 325-327 (1992).

Sinha, et al., "Purification and Cloning of Amyloid Precursor Protein β-Secretase from Human Brain", Nature, 402, 537-540 (1999).

Strangeland, et al., "Use of Thiazoles in the Halogen Dance Reaction: Application to the Total Synthesis of WS75624 B", J. Org. Chem., 69, 2381-2385 (2004).

SUBSTITUTED HYDROXYETHYL AMINE COMPOUNDS AS BETA-SECRETASE MODULATORS AND METHODS OF USE

This application is a Divisional Patent Application filed under 35 U.S.C. §121 and claims the benefit under 35 U.S.C. §120 to U.S. patent application Ser. No. 12/154,513, filed May 23, 2008, now U.S. Pat. No. 8,163,909, which in turn claims the benefit of U.S. Provisional Application No. 60/931,702 filed 25 May 2007 and U.S. Provisional Application No. 61/127,022, filed 8 May 2008, all three specifications of which are hereby incorporated herein by reference in their entireties.

FIELD OF THE INVENTION

The invention relates generally to pharmaceutically active compounds, pharmaceutical compositions and methods of use thereof, to treat Beta-Secretase mediated diseases and conditions, including, without limitation, Alzheimer's disease, plaque formation on the brain and related disorders.

BACKGROUND OF THE INVENTION

Alzheimer's disease (AD) affects greater than 12 million aging people worldwide. AD accounts for the majority of dementia clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to effectively treat AD upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). The second change in AD is the formation of intraneuronal tangles, consisting of an aggregate form of the protein tau. Amyloid plaques are thought to be specific for AD, while intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron,* 6:487 (1991). Release of A-beta from neuronal cells grown in culture and the presence of A-beta in cerebrospinal fluid (CSF) of both normal individuals and AD patients has been demonstrated. Seubert et al., *Nature,* 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide ranging in about 39-42 amino acid residues. A-beta 42 (42 amino acids long) is thought to be the major component of these plaque deposits. Citron, *Trends in Pharmacological Sciences,* 25(2):92-97 (2004).

Several aspartyl proteases are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A decription of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature,* 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. BACE1 knockout mice have failed to produce A-beta. When crossed with transgenic mice that over express APP, the progeny show reduced amounts of A-beta in brain extracts as compares with control animals (Luo et al., *Nature Neuroscience,* 4:231-232 (2001)). This evidence further supports the concept that inhibition of beta secretase activity and a corresponding reduction of A-beta in the brain should provide a therapeutic method for treating AD and other beta amyloid or plaque related disorders.

Several approaches have been taken to potentially treat AD and plaque-related disorders. One approach has been to attempt to reduce the formation of plaque on the brain, by inhibiting or reducing the activity of BACE. For example, each of the following PCT publications: WO 03/045913, WO 04/043916, WO 03/002122, WO 03/006021, WO 03/002518, WO 04/024081, WO 03/040096, WO 04/050619, WO 04/080376, WO 04/099376, WO 05/004802, WO 04/080459, WO 04/062625, WO 04/042910, WO 05/004803, WO 05/005374, WO 03/106405, WO 03/062209, WO 03/030886, WO 02/002505, WO 01/070671, WO 03/057721, WO 03/006013, WO 03/037325, WO 04/094384, WO 04/094413, WO 03/006423, WO 03/050073, WO 03/029169 and WO 04/000821, describe inhibitors of BACE, useful for treating AD and other beta-secretase mediated disorders.

BRIEF DESCRIPTION OF THE INVENTION

The present invention provides a new class of compounds useful for the modulation of beta secretase activity. To that end, the compounds of the invention are useful for the regulation or reduction of the formation of A-beta peptide and, consequently, the regulation and/or reduction of beta amyloid plaque formation on the brain. Accordingly, the compounds are useful for the treatment of Alzheimer's disease and other beta secretase and/or plaque mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, solvates, pharmaceutically acceptable salts, derivatives or prodrugs thereof, are generally defined by Formula I

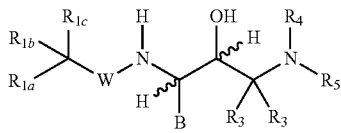

wherein $R^{1a}$, $R^{1b}$, $R^{1c}$, W, B, $R^3$, $R^4$ and $R^5$, are described below specific for Formula I, and of Formula II,

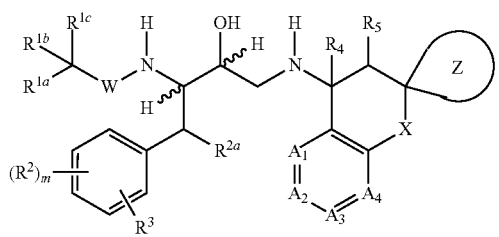

wherein $R^{1a}$, $R^{1b}$, $R^{1c}$, W, $R^2$, $R^{2a}$, $R^3$, $R^4$, $R^5$, X, Z and m are described below specific for Formula II. The invention also provides procedures for making compounds of Formula I, II, III and sub-Formulas, as well as intermediates useful in such procedures.

The invention further provides pharmaceutical compositions, which comprise one or more compounds of the invention, methods for the treatment of beta secretase mediated diseases, such as AD, using the compounds and compositions of the invention. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are generally defined by

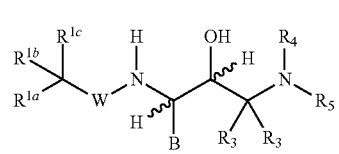

wherein $R^{1a}$ is H, halo, $C_{1-10}$alkyl, $C_{2-8}$-alkenyl or $C_{2-8}$-alkynyl, wherein 1, 2 or 3 carbon atoms of said $C_1$-$C_{10}$alkyl, $C_2$-$C_8$-alkenyl or $C_2$-$C_8$-alkynyl is optionally replaced with a heteroatom selected from O, S, S(O), S(O)$_2$ and N, and optionally substituted independently with one or more substituents of $R^7$;

$R^{1b}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or NH$_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

alternatively, $R^{1a}$ and $R^{1b}$ taken together with the carbon atom to which they are attached form a partially or fully saturated 3, 4-, 5- or 6-membered ring of carbon atoms optionally including 1-2 heteroatoms selected from O, N, or S, the ring optionally substituted independently with 1-3 substituents of $R^7$;

$R^{1c}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or NH$_2$;

W is —C(=O)—, —OC(=O)—, —NHC(=O)—, —S(=O)$_b$— or —NHS(=O)$_b$—, wherein b is 1 or 2;

B is $R^2$—(CR$^{2a}$R$^{2a}$)$_h$—, wherein $R^2$ is a partially or fully saturated or unsaturated 3-8 membered monocyclic or 6-12 membered bicyclic, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of oxo, $R^7$, NR$^7$R$^7$, OR$^7$, SR$^7$, C(O)R$^7$, OC(O)R$^7$, COOR$^7$, C(O)NR$^7$R$^7$, NR$^7$C(O)R$^7$, NR$^7$C(O)NR$^7$R$^7$, NR$^7$(COOR$^7$), OC(O)NR$^7$R$^7$, S(O)$_2$NR$^7$R$^7$, NR$^7$S(O)$_2$NR$^7$R$^7$ or NR$^7$S(O)$_2$R$^7$;

each $R^{2a}$, independently, is H, OH, NO$_2$, CN, NH$_2$, $C_1$-$C_{10}$ alkyl, $C_1$-$C_{10}$ alkoxyl or haloalkyl; and h is 0, 1, 2 or 3;

each $R^3$, independently, is H, haloalkyl, CN, $C_{1-6}$-alkyl, $C_{2-8}$-alkenyl, $C_{2-8}$-alkynyl, $C_{3-8}$-cycloalkyl or $C_{4-8}$-cycloalkenyl, each of the $C_{1-6}$-alkyl, $C_{2-8}$-alkenyl, $C_{2-8}$-alkynyl, $C_{3-8}$-cycloalkyl and $C_{4-8}$-cycloalkenyl optionally comprising 1-2 heteroatoms selected from N, O and S and optionally substituted with 1-5 substituents of $R^7$;

$R^4$ is H, haloalkyl, CN, $C_{1-6}$-alkyl, $C_{1-6}$-alkenyl, $C_{1-6}$-alkynyl or $C_{1-6}$-cycloalkyl, wherein each of the $C_{1-6}$-alkyl, $C_{1-6}$- alkenyl, $C_{1-6}$-alkynyl and $C_{1-6}$-cycloalkyl is optionally substituted with 1-5 substitutions of $R^7$;

$R^5$ is

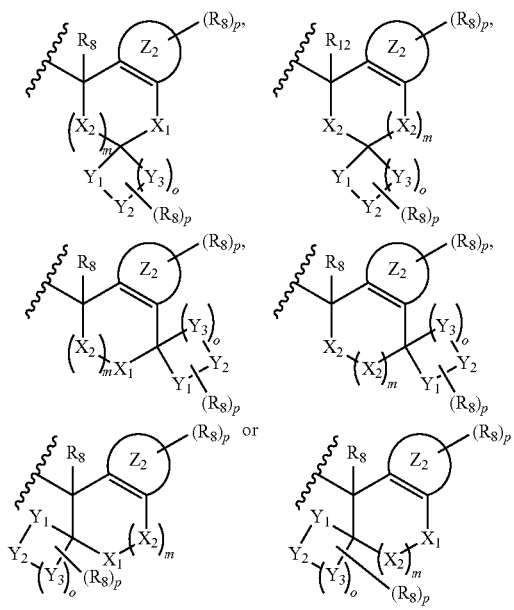

wherein $X^1$ is $CR^8R^8$, $C(=O)$, O, S, $S(O)_2$ or $NR^8$;
each $X^2$, independently, is $CR^8R^8$;
each of $Y^1$, $Y^2$ and $Y^3$, independently, is $CR^8R^8$, O, S or $NR^8$;
$Z^2$ taken together with the carbon atoms to which it is attached is a partially or fully unsaturated 5-6 membered monocyclic ring, said ring formed of carbon atoms optionally including 1-3 heteroatoms selected from O, N and S;
m is 0, 1 or 2;
o is 0, 1, 2, 3, 4 or 5; and
p is 0, 1, 2, 3, 4 or 5 provided that (a) no more than two of $Y^1$, $Y^2$ and $Y^3$ is O, S or $NR^8$ and (b) when o is 0, then each of $Y^1$ and $Y^2$ is $CR^8R^8$;
each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;
each $R^8$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$; and $R^9$ is halo, haloalkyl, CN, OH, $NO_2$, $NH_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, $C_{1-10}$-alkylamino-, $C_{1-10}$-dialkylamino-, $C_{1-10}$-thioalkoxyl or a partially or fully saturated or unsaturated 3-6 membered monocyclic formed of carbon atoms optionally including 1-3 heteroatoms selected from O, N, or S, optionally substituted independently with 1-5 substituents of halo, haloalkyl, CN, $NO_2$, $NH_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl, provided the compound is not n is 0, 1 or 2, provided the compound is not N-((2S,3R)-4-(S)-6-ethyl-2,2'-spirocyclobutylchroman-4-ylamino)-3-hydroxy-1-(4-phenyl-phenyl)-butan-2-yl)acetamide;

(3S)-N-((1S,2R)-1-(3-cyanophenyl)methyl)-3-((4S)-6-ethyl-3,4-dihydrospiro[chromene-2,1'-cyclobutan]-4-yl)amino)-2-hydroxypropyl)-1-cyclobutyl-5-oxo-3-pyrrolidinecarboxamide;

N-((1S,2R)-1-(3-cyanophenyl)methyl)-3-(((4'S)-6'-ethyl-3',4'-dihydrospiro[cyclobutane-1,2'-pyrano[2,3-b]pyridin]-4'-yl)amino)-2-hydroxypropyl)acetamide;

N-((1S,2R)-1-(3-cyanophenyl)methyl)-3-(((4S)-6-ethyl-3,4-dihydrospiro[chromene-2,1'-cyclobutan]-4-yl)amino)-2-hydroxypropyl)tetrahydro-2-furancarboxamide;

N-((1S,2R)-1-(3-cyanophenyl)methyl)-3-(((4S)-6-ethyl-3,4-dihydrospiro[chromene-2,1'-cyclobutan]-4-yl)amino)-2-hydroxypropyl)propanamide;

N-((1S,2R)-1-(3-cyanophenyl)methyl)-3-(((4S)-6-ethyl-3,4-dihydrospiro[chromene-2,1'-cyclobutan]-4-yl)amino)-2-hydroxypropyl)-2-((cyclopropylmethyl)oxy)acetamide;

N-((1S,2R)-1-(3-cyanophenyl)methyl)-3-(((4'S)-6'-ethyl-3',4'-dihydrospiro[cyclobutane-1,2'-pyrano[2,3-b]pyridin]-4'-yl)amino)-2-hydroxypropyl)-2-(methyloxy)acetamide;

N-((1S,2R)-1-(3-cyanophenyl)methyl)-3-(((2S,4S)-6-ethyl-3,4,4',5'-tetrahydrospiro[chromene-2,3'-furan]-4-yl)amino)-2-hydroxypropyl)-2-(methyloxy)acetamide;

N'-((1S,2R)-1-(3-cyanophenyl)methyl)-3-(((4S)-6-ethyl-3,4-dihydrospiro-2,2-spirocyclobutyl[chromene-2,1'-cyclobutan]-4-yl)amino)-2-hydroxypropyl)-N,N-dimethylbutanediamide;

N-((1S,2R)-1-(3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide;

N-((1S,2R)-1-((3-cyanophenyl)methyl)-2-hydroxy-3-(((4S)-6-(4-morpholinyl)-3,4-dihydrospiro-2,2-spirocyclobutyl[chromene-2,1'-cyclobutan]-4-yl)amino)propyl)-2-(methyloxy)acetamide;

N-((1S,2R)-1-((3-cyano-5-fluorophenyl)methyl)-3-(((4S)-6-ethyl-3,4-dihydrospiro[chromene-2,1'-cyclobutan]-4-yl)amino)-2-hydroxypropyl)acetamide;

N-((1S,2R)-1-((3-cyanophenyl)methyl)-2-hydroxy-3-
(((4S)-6-(4-morpholinyl)-3,4-dihydrospiro-2,2-spirocyclobutyl [chromene-2,1'-cyclobutan]-4-yl)amino)propyl)
acetamide;
2-(((1S,2R)-1-((3-cyanophenyl)methyl)-2-hydroxy-3-
(((4S)-6-(4-morpholinyl)-3,4-dihydrospiro[chromene-2,
1'-cyclobutan]-4-yl)amino)propyl)amino)-2-oxoethyl
dimethylcarbamate;
N-((1S,2R)-3-(((4S)-8-bromo-6-chloro-3,4-dihydrospiro
[chromene-2,1'-cyclobutan]-4-yl)amino)-1-(3-cyanophenyl)methyl)-2-hydroxypropyl)acetamide;
N-((1S,2R)-3-(((4S)-6-chloro-8-(4-morpholinyl)-3,4-dihydrospiro[chromene-2,1'-cyclobutan]-4-yl)amino)-1-(3-cyanophenyl)methyl)-2-hydroxypropyl)acetamide;
N-((1S,2R)-1-(3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;
N-((1S,2R)-1-((3-cyanophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)
acetamide;
N-((1S,2R)-1-(3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;
N-((1S,2R)-1-(3-cyanophenyl)methyl)-2-hydroxy-3-4(5'S)-3'-methyl-5',8'-dihydro-6'H-spiro[cyclobutane-1,7'-quinolin]-5'-yl)amino)propyl)acetamide;
N-((1S,2R)-1-(3-cyanophenyl)methyl)-2-hydroxy-3-(((4'S)-6'-(trifluoromethyl)-3',4'-dihydrospiro[cyclobutane-1,2'-pyrano[2,3-b]pyridin]-4'-yl)amino)propyl)acetamide;
N-1-((1S,2R)-3-(((4S)-6-bromo-3,4-dihydrospiro
[chromene-2,1'-cyclobutan]-4-yl)amino)-1-((3-cyanophenyl)methyl)-2-hydroxypropyl)-N~2~,N~2~-dimethylglycinamide;
Methyl (4S)-4-(((2R,3S)-4-(3-cyanophenyl)-3-((N,N-dimethylglycyl)amino)-2-hydroxybutyl)amino)-3,4-dihydrospiro[chromene-2,1'-cyclobutane]-6-carboxylate;
Methyl (4S)-4-(((2R,3S)-3-(acetylamino)-4-(3-cyanophenyl)-2-hydroxybutyl)amino)-3,4-dihydrospiro[chromene-2,1'-cyclobutane]-6-carboxylate;
Methyl (4S)-4-(((2R,3S)-4-(3-cyanophenyl)-2-hydroxy-3-(((methyloxy)acetyl)amino)butyl)amino)-3,4-dihydrospiro[chromene-2,1'-cyclobutane]-6-carboxylate;
N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;
N-((1S,2R)-1-(1,3-benzodioxol-5-ylmethyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)
acetamide; and
N-((1S,2R)-1-(3-cyanophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide.

In another embodiment, the compounds of Formula I includes compounds wherein B is $R^2$—$(CR^{2a}R^{2a})_h$— wherein $R^2$ is a partially or fully saturated or unsaturated 3-8 membered monocyclic or 6-12 membered bicyclic, said ring system formed of carbon atoms optionally including 1-3 heteroatoms if monocyclic or 1-6 heteroatoms if bicyclic, said heteroatoms selected from O, N, or S and said ring system optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$, each $R^{2a}$, independently, is H, OH, $NO_2$, CN, $NH_2$, $C_1$-$C_{10}$ alkyl, $C_1$-$C_{10}$ alkoxyl or haloalkyl, and h is 1, 2 or 3, in conjunction with any of the above or below embodiments.

In another embodiment, the compounds of Formula I includes compounds wherein B is $R^2$—$(CR^{2a}R^{2a})_h$— wherein $R^2$ is phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, benzodioxolyl, cyclopropyl, cyclobutyl, cyclopentyl, cyclohexyl or cycloheptyl, each of is optionally substituted independently with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$, in conjunction with any of the above or below embodiments.

In another embodiment, the compounds of Formula I includes compounds wherein B is $R^2$—$(CH_2)$— wherein $R^2$ is phenyl, pyridyl, pyrimidyl, pyridazinyl, pyrazinyl, naphthyl, quinolinyl, isoquinolinyl, quinazolinyl, isoquinazolinyl, phthalazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, benzodioxolyl, cyclopropyl, cyclobutyl, cyclopentyl, cyclohexyl or cycloheptyl, each of is optionally substituted independently with a chemical moiety which reduces CYP enzyme acitivity and optionally with one or more substituents of oxo, $R^7$, $NR^7R^7$, $OR^7$, $SR^7$, $C(O)R^7$, $OC(O)R^7$, $COOR^7$, $C(O)NR^7R^7$, $NR^7C(O)R^7$, $NR^7C(O)NR^7R^7$, $NR^7(COOR^7)$, $OC(O)NR^7R^7$, $S(O)_2NR^7R^7$, $NR^7S(O)_2NR^7R^7$ or $NR^7S(O)_2R^7$, in conjunction with any of the above or below embodiments.

In another embodiment, the compounds of Formula I includes compounds wherein one $R^{2a}$ is H and the other $R^{2a}$ is OH, $NO_2$, CN, $NH_2$, $C_1$-$C_{10}$ alkyl, $C_1$-$C_{10}$ alkoxyl or haloalkyl, in conjunction with any of the above or below embodiments.

In another embodiment, the compounds of Formula I includes compounds wherein each $R^{2a}$, independently, is H, in conjunction with any of the above or below embodiments.

In another embodiment, the compounds of Formula I includes compounds wherein h is 1, in conjunction with any of the above or below embodiments.

In another embodiment, the compounds of Formula I includes compounds wherein h is 2, in conjunction with any of the above or below embodiments.

In another embodiment, the compounds of Formula I includes compounds wherein B is $R^2$—O—$(CR^{2a}R^{2a})_h$— and each $R^{2a}$, independently, is H, OH, $NO_2$, CN, $NH_2$, $C_1$-$C_{10}$ alkyl, $C_1$-$C_{10}$ alkoxyl or haloalkyl, in conjunction with any of the above or below embodiments.

In another embodiment, the compounds of Formula I includes compounds wherein B is $R^2$—S—$(CR^{2a}R^{2a})_h$— and each $R^{2a}$, independently, is H, OH, $NO_2$, CN, $NH_2$, $C_1$-$C_{10}$ alkyl, $C_1$-$C_{10}$ alkoxyl or haloalkyl, in conjunction with any of the above or below embodiments.

In another embodiment, the compounds of Formula I includes compounds wherein B is $R^2$—$NR^{2a}$—$(CR^{2a}R^{2a})_h$— and each $R^{2a}$, independently, is H, OH, $NO_2$, CN, $NH_2$, $C_1$-$C_{10}$ alkyl, $C_1$-$C_{10}$ alkoxyl or haloalkyl, in conjunction with any of the above or below embodiments.

In another embodiment, the compounds of Formula I includes compounds wherein B is $R^2$—O—$(CH_2)_h$—, in conjunction with any of the above or below embodiments.

In another embodiment, the compounds of Formula I includes compounds wherein B is $R^2$—S—$(CH_2)_h$—, in conjunction with any of the above or below embodiments.

In another embodiment, the compounds of Formula I includes compounds wherein B is $R^2$—NH—$(CH_2)_h$—, in conjunction with any of the above or below embodiments.

In another embodiment, the compounds of Formula I includes compounds wherein $R^2$ is an optionally substituted ring selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, tetrazolyl, thiazolyl, oxazolyl, isoxazolyl, isothiazolyl, indolyl, isoindolyl, benzofuranyl, benzothienyl, benzodioxolyl and benzimidazolyl, in conjunction with any of the above or below embodiments.

In another embodiment, the compounds of Formula I includes compounds wherein each $R^3$, independently, is H, haloalkyl, CN, $C_{1-6}$-alkyl, $C_{2-8}$-alkenyl, $C_{2-8}$-alkynyl, $C_{3-8}$-cycloalkyl or $C_{4-8}$-cycloalkenyl, each of the $C_{1-6}$-alkyl, $C_{2-8}$-alkenyl, $C_{2-8}$-alkynyl, $C_{3-8}$-cycloalkyl and $C_{4-8}$-cycloalkenyl optionally comprising 1-2 heteroatoms selected from N, O and S and optionally substituted with 1-5 substituents of $R^7$, in conjunction with any of the above or below embodiments.

In another embodiment, the compounds of Formula I includes compounds wherein $R^3$ is H, haloalkyl, CN, $C_{1-10}$-alkyl, $C_{2-10}$-alkenyl or $C_{2-10}$-alkynyl, in conjunction with any of the above or below embodiments.

In another embodiment, the compounds of Formula I includes compounds wherein $R^3$ is H, haloalkyl or $C_{1-10}$-alkyl, in conjunction with any of the above or below embodiments.

In another embodiment, the compounds of Formula I includes compounds wherein each $R^3$, independently, is H, in conjunction with any of the above or below embodiments.

In another embodiment, the compounds of Formula I includes compounds wherein $R^4$ is H, haloalkyl, CN, $C_{1-6}$-alkyl, $C_{1-6}$-alkenyl, $C_{1-6}$-alkynyl or $C_{1-6}$-cycloalkyl, wherein each of the $C_{1-6}$-alkyl, $C_{1-6}$-alkenyl, $C_{1-6}$-alkynyl and $C_{1-6}$-cycloalkyl is optionally substituted with 1-5 substitutions of $R^7$, in conjunction with any of the above or below embodiments.

In another embodiment, the compounds of Formula I includes compounds wherein $R^4$ is H, haloalkyl, CN or $C_{1-6}$-alkyl, in conjunction with any of the above or below embodiments.

In another embodiment, the compounds of Formula I includes compounds wherein $R^4$ is H, in conjunction with any of the above or below embodiments.

In another embodiment, the compounds of Formula I includes compounds wherein $R^5$ is

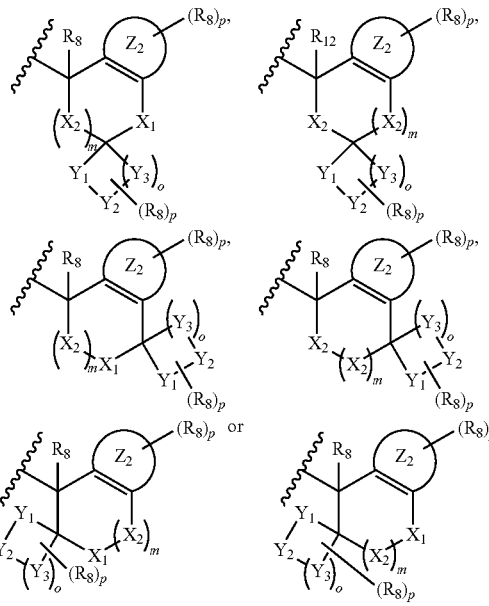

wherein $X^1$ is $CR^8R^8$, C(=O), O, S, $S(O)_2$ or $NR^8$;
each $X^2$, independently, is $CR^8R^8$;
each of $Y^1$, $Y^2$ and $Y^3$, independently, is $CR^8R^8$, O, S or $NR^8$;
$Z^2$ taken together with the carbon atoms to which it is attached is a partially or fully unsaturated 5-6 membered monocyclic ring, said ring formed of carbon atoms optionally including 1-3 heteroatoms selected from O, N and S;
m is 0, 1 or 2;
o is 0, 1, 2, 3, 4 or 5; and
p is 0, 1, 2, 3, 4 or 5
provided that (a) no more than two of $Y^1$, $Y^2$ and $Y^3$ is O, S or $NR^8$ and (b) when o is 0, then each of $Y^1$ and $Y^2$ is $CR^8R^8$, in conjunction with any of the above or below embodiments.

In the immediately preceeding embodiment, the compounds of Formula I includes compounds wherein $X^1$ is $CR^8R^8$, in conjunction with any of the above or below embodiments.

In the preceeding embodiment, the compounds of Formula I includes compounds wherein $X^1$ is C(=O), in conjunction with any of the above or below embodiments.

In the preceeding embodiment, the compounds of Formula I includes compounds wherein $X^1$ is O, in conjunction with any of the above or below embodiments.

In the preceeding embodiment, the compounds of Formula I includes compounds wherein $X^1$ is S, in conjunction with any of the above or below embodiments.

In the preceeding embodiment, the compounds of Formula I includes compounds wherein $X^1$ is $S(O)_2$, in conjunction with any of the above or below embodiments.

In the preceeding embodiment, the compounds of Formula I includes compounds wherein $X^1$ is $NR^8$, in conjunction with any of the above or below embodiments.

In the preceeding embodiment, the compounds of Formula I includes compounds wherein $X^2$ is $CR^8R^8$, in conjunction with any of the above or below embodiments.

In the preceeding embodiment, the compounds of Formula I includes compounds wherein $X^2$ is $CH_2$, in conjunction with any of the above or below embodiments.

In the preceeding embodiment, Formula I includes compounds wherein each of $Y^1$, $Y^2$ and $Y^3$, independently, is $CR^8R^8$, in conjunction with any of the above or below embodiments.

In the preceeding embodiment, the compounds of Formula I includes compounds wherein each of $Y^1$, $Y^2$ and $Y^3$, independently, is $CR^8R^8$, O, S or $NR^8$, in conjunction with any of the above or below embodiments.

In the preceeding embodiment, the compounds of Formula I includes compounds wherein each of $Y^1$, $Y^2$ and $Y^3$, independently, is $CHR^8$, in conjunction with any of the above or below embodiments.

In the preceeding embodiment, the compounds of Formula I includes compounds wherein each of $Y^1$, $Y^2$ and $Y^3$, independently, is $CH_2$, in conjunction with any of the above or below embodiments.

In the preceeding embodiment, the compounds of Formula I includes compounds wherein no more than two of $Y^1$, $Y^2$ and $Y^3$, independently, is 0 and the remaining of $Y^1$, $Y^2$ and $Y^3$, independently, is $CR^8R^8$, in conjunction with any of the above or below embodiments.

In the preceeding embodiment, the compounds of Formula I includes compounds wherein one of $Y^1$, $Y^2$ and $Y^3$, independently, is O and the other two of $Y^1$, $Y^2$ and $Y^3$, independently, is $CR^8R^8$, in conjunction with any of the above or below embodiments.

In the preceeding embodiment, the compounds of Formula I includes compounds wherein $Y^2$ is O and $Y^1$ and $Y^3$, independently, are $CR^8R^8$, in conjunction with any of the above or below embodiments.

In the preceeding embodiment, the compounds of Formula I includes compounds wherein $Y^2$ is S and $Y^1$ and $Y^3$, independently, are $CR^8R^8$, in conjunction with any of the above or below embodiments.

In the preceeding embodiment, the compounds of Formula I includes compounds wherein $Y^2$ is —$NR^8$— and $Y^1$ and $Y^3$, independently, are $CR^8R^8$, in conjunction with any of the above or below embodiments.

In another embodiment, the compounds of Formula I includes compounds wherein $Z^2$ is an optionally substituted phenyl, pyridine, pyrimidine, triazine, pyridazine, pyrazine, pyridone, pyrrole, imidazole, pyrazole, triazole, thiophene, thiazole, thiadiazole, isothiazole, furan, oxazole, oxadiazole or isoxazole ring, in conjunction with any of the above or below embodiments.

In another embodiment, the compounds of Formula I includes compounds wherein $Z^2$ is a 5- or 6-membered aromatic ring which is preferably substituted with a chemical moiety which reduces CYP enzyme activity, in conjunction with any of the above or below embodiments.

In another embodiment, the compounds of Formula I includes compounds wherein $Z^2$ is a phenyl, pyridine, pyrimidine, triazine, pyridazine, pyrazine, pyridone, pyrrole, imidazole, pyrazole, triazole, thiophene, thiazole, thiadiazole, isothiazole, furan, oxazole, oxadiazole or isoxazole ring, each of which is preferably substituted with a chemical moiety which reduces CYP enzyme activity, in conjunction with any of the above or below embodiments.

In another embodiment, the compounds of Formula I includes compounds wherein $R^5$ is

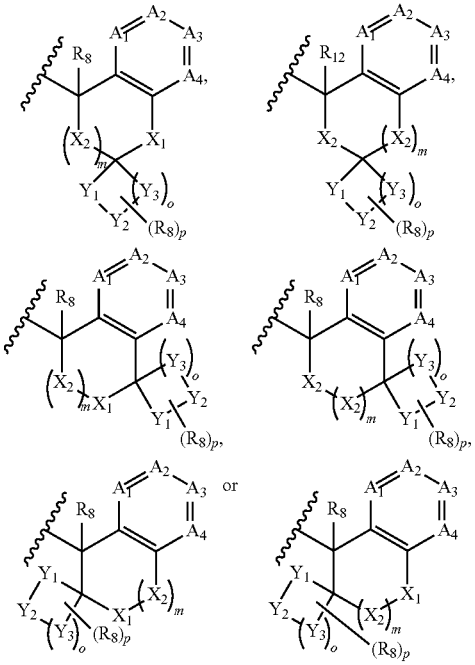

wherein each of $A^1$, $A^2$, $A^3$ and $A^4$, independently, is $CR^8$ or N, provided that no more than two of $A^1$, $A^2$, $A^3$ and $A^4$ is N;
m, o, $R^8$, $X^2$, $Y^1$, $Y^2$ and $Y^3$ are as defined herein;
$X^1$ is $CR^8$, C(=O), O, S, $S(O)_2$ or $NR^8$; and
p is 0, 1, 2 or 3, in conjunction with any of the above or below embodiments.

In the immediately preceeding embodiment, the compounds of Formula I includes compounds wherein each of $A^1$, $A^2$, $A^3$ and $A^4$, independently, is $CR^8$ or N, provided that no more than one of $A^1$, $A^2$, $A^3$ and $A^4$ is N, in conjunction with any of the above or below embodiments.

In another embodiment, the compounds of Formula I includes compounds wherein $R^5$ is

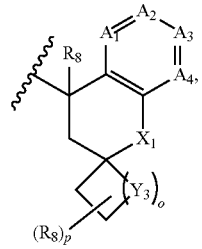

wherein o is 1 or 2;
p is 0, 1, 2 or 3;
each of $A^1$, $A^2$, $A^3$ and $A^4$, independently, is $CR^8$ or N, provided that no more than two of $A^1$, $A^2$, $A^3$ and $A^4$ is N;
$X^1$ is CH, C(=O), O or $NR^{12}$;
$Y^3$ is $CR^{12}$ or O; and
each $R^8$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a ring selected from phenyl, pyridyl, pyrimidinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, isoxazolyl, isothiazolyl, oxazolinyl, isoxazolinyl, pyrrolidinyl, pyrazolinyl, morpholinyl, piperidinyl, piperazinyl, pyranyl, dioxolyl, dioxazinyl, cyclopropyl, cyclobutyl, azetidinyl, cyclopentyl, cyclohexyl and cycloheptyl, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl, in conjunction with any of the above or below embodiments.

In another embodiment, Formula I includes compounds wherein $R^{1a}$ is $C_{1-6}$-alkyl, $C_{2-6}$alkenyl, $C_{2-6}$-alkynyl, $C_{1-6}$alkyl-O—$C_{1-3}$-alkyl-, $C_{1-6}$-alkyl-S—$C_{1-3}$-alkyl-, $C_{1-6}$-alkyl-$S(O)_2$—$C_{1-3}$-alkyl-, $C_{1-6}$-alkyl-NH—$C_{1-3}$-alkyl-, di-($C_{1-3}$-alkyl)-N—$C_{1-3}$-alkyl, $C_{1-3}$ alkyl-, $C_{2-4}$-alkenyl-S—$C_{1-3}$ alkyl-, $C_{2-4}$-alkenyl-NH—$C_{1-3}$-alkyl- or $C_{2-4}$-alkynyl-NH—$C_{1-3}$-alkyl-, wherein the alkyl, alkenyl or alkynyl moiety of each is optionally substituted with 1-3 substituents of $R^7$;

W is —C(=O)—;

B is $R^2$—$(CR^{2a}R^{2a})_h$—, wherein each $R^{2a}$, independently, is H or $C_1$-$C_6$ alkyl;

h is 1 or 2; and $R^2$ is ring selected from phenyl, naphthyl, pyridyl, pyrimidyl, pyridazinyl, pyrazinyl, triazinyl, quinolinyl, isoquinolinyl, quinazolinyl, isoquinazolinyl, phthalazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, benzodioxolyl, cyclopropyl, cyclobutyl, cyclopentyl, cyclohexyl and cycloheptyl, said ring optionally substituted independently with 1-5 substituents of $R^7$;

each $R^3$, independently, is H, haloalkyl, CN, $C_{1-6}$-alkyl, $C_{2-6}$-alkenyl or $C_{2-6}$-alkynyl;

$R^4$ is H, CN or $C_{1-10}$-alkyl;

$R^5$ is

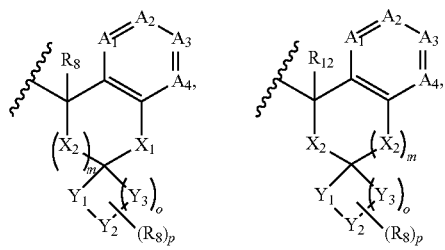

-continued

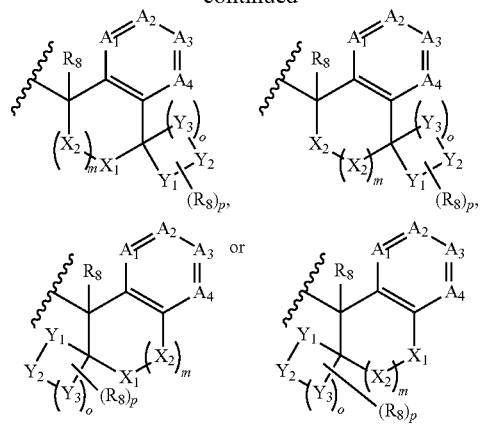

wherein each of $A^1$, $A^2$, $A^3$ and $A^4$, independently, is $CR^8$ or N, provided that no more than one of $A^1$, $A^2$, $A^3$ and $A^4$ is N;

m, o, $R^8$, $X^2$, $Y^1$, $Y^2$ and $Y^3$ are as defined in claim 1;

$X^1$ is $CR^8$, C(=O), O, S, $S(O)_2$ or $NR^8$; and p is 0, 1, 2 or 3;

each $R^7$, independently, is H, Cl, F, Br, I, haloalkyl, CN, OH, $NO_2$, $NH_2$, acetyl, methyl, methoxyl, ethyl, ethoxyl, allyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

each $R^8$, independently, is Cl, F, Br, I, haloalkyl, CN, OH, $NO_2$, $NH_2$, acetyl, methyl, methoxyl, ethyl, ethoxyl, allyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, neopentyl, cyclopentyl, hexyl, cyclohexyl, $C_{1-10}$-alkylamino-, $C_{1-10}$-dialkylamino-, $C_{1-10}$-thioalkoxyl or a ring system selected from phenyl, pyridyl, pyrimidinyl, triazinyl, thiophenyl, furyl, tetrahydrofuranyl, pyrrolyl, pyrazolyl, thieno-pyrazolyl, imidazolyl, triazolyl, tetrazolyl, thiazolyl, thiadiazolyl, oxazolyl, oxadiazolyl, oxadiazolyl, isoxazolyl, isothiazolyl, oxazolinyl, isoxazolinyl, thiazolinyl, pyrrolidinyl, pyrazolinyl, morpholinyl, piperidinyl, piperazinyl, pyranyl, dioxozinyl, 2,3-dihydro-1,4-benzoxazinyl, 1,3-benzodioxolyl and azetidinyl, said ring system optionally substituted independently with 1-3 substituents of $R^9$; and $R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-7}$-cycloalkyl, $C_{4-7}$-cycloalkenyl, $C_{1-10}$-alkylamino-, $C_{1-10}$-dialkylamino-, $C_{1-10}$-alkoxyl, $C_{1-10}$-thioalkoxyl.

Incorporation of a chemical moiety ($R^3$) at specific regions or locations of compounds of Formula I (including without limitation, on variable B and on variable $R^5$ of Formula I), the $R^3$ group of Formulas II, II-A, II-B, II-C, II-D, III-A, III-B, III-C and III-D, and on $R^2$ in Formula IV, have been unexpectedly found to generally modify, and more specifically improve, the compound's characteristics and properties, particularly as they relate to projected in-vivo properties, including pharmacokinetic and pharmacodynamic properties. In essence, such moieties have been surprisingly found to generally improve the ability of a given compound to be useful in treatment and therapy of AD and other BACE mediated diseases linked to plaque formation and deposition in subjects. It has also been found that compounds where $R^2$ group of Formula I, or the benzyl moiety, optionally substituted with m number of $R^2$ groups, having 2 adjacent $R^2$ groups tied together to form a dioxolyl group has generally improved in-vivo properties. Accordingly, in another embodiment, the invention provides compounds of Formula II:

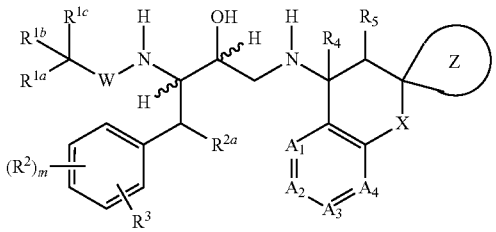

or a pharmaceutically acceptable salt thereof, wherein
each of $A^1$, $A^2$, $A^3$ and $A^4$, independently, is N, CH or $CR^6$, provided that no more than two of $A^1$, $A^2$, $A^3$ and $A^4$ is N;

$R^{1a}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

$R^{1c}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

alternatively, $R^{1a}$ and $R^{1b}$ taken together with the carbon atom to which they are attached form a partially or fully saturated 3-, 4-, 5- or 6-membered ring of carbon atoms optionally including 1-2 heteroatoms selected from O, N, or S, the ring optionally substituted independently with 1-3 substituents of $R^7$;

$R^{1c}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$;

W is —C(=O)—, —C(=S)—, —OC(=O)—NHC(=O)—, —S(=O)$_b$— or —NHS(=O)$_b$—, wherein b is 1 or 2;

each $R^2$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl CN, OH, $NH_2$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

alternatively, two adjacent $R^2$ groups taken together with the carbon atoms to which they are attached form a dioxolyl ring optionally substituted by 1 or 2 halo;

$R^{2a}$ is H or F;

$R^3$ is CN, $C_{2-3}$alkynyl, a partially or fully unsaturated 5- or 6-membered monocyclic ring formed of carbon atoms wherein said ring optionally including 1-3 heteroatoms selected from O, N, or S and optionally substituted with 1-5 substituents of $R^7$, or $R^3$ is F or absent when two adjacent $R^2$ groups taken together with the carbon atoms to which they are attached form a dioxolyl ring;

$R^4$ is H, halo or $C_{1-6}$-alkyl;

$R^5$ is H, halo, haloalkyl, oxo, $C_{1-6}$-alkyl, —O—$C_{1-6}$-alkyl, —S—$C_{1-6}$-alkyl, —NH—$C_{1-6}$alkyl, —N-di-$C_{1-6}$-alkyl, CN, OH or $NH_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

X is $CH_2$, $CHR^6$, $CR^6R^6$, C(=O), O, NH, $NR^6$, or S(O)$_o$ wherein o is 0, 1 or 2;

Z is a 3-6 membered spirocyclic ring formed of carbon atoms optionally including 1-3 heteroatoms selected from O, N and S and optionally substituted independently with 1-5 substituents of $R^7$;

each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OR$^7$, NHR$^7$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

or $R^6$ is a fully saturated or partially or fully unsaturated 5- or 6-membered monocyclic or bicyclic ring formed of carbon atoms, said ring optionally including 1-4 heteroatoms selected from O, N, or S and optionally substituted with one or more substituents of $R^7$ each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl; and m is 0, 1, 2 or 3, provided the compound of Formula II is not
N-((1S,2R)-1-(3-cyanophenyl)methyl)-3-(((4'S)-6'-(2-fluoro-2-methylpropyl)-3',4'-dihydrospiro[cyclobutane-1, 2'-pyrano[2,3-b]pyridin]-4'-yl)amino)-2-hydroxypropyl) acetamide;
N-((1S,2R)-1-(3-cyanophenyl)methyl)-3-(((4'S)-6'-ethyl-3', 4'-dihydrospiro[cyclobutane-1,2'-pyrano[2,3-b]pyridin]-4'-yl)amino)-2-hydroxypropyl)acetamide;
N-((1S,2R)-1-((3-cyanophenyl)methyl)-3-(((4S)-6-ethyl-3, 4-dihydrospiro[chromene-2,1'-cyclobutan]-4-yl)amino)-2-hydroxypropyl)tetrahydro-2-furancarboxamide;
N-((1S,2R)-1-((3-cyanophenyl)methyl)-3-(((4S)-6-ethyl-3, 4-dihydrospiro[chromene-2,1'-cyclobutan]-4-yl)amino)-2-hydroxypropyl)-2-((cyclopropylmethyl)oxy)acetamide;
N-((1S,2R)-1-((3-cyanophenyl)methyl)-3-(((4'S)-6'-ethyl-3',4'-dihydrospiro[cyclobutane-1,2'-pyrano[2,3-b]pyridin]-4'-yl)amino)-2-hydroxypropyl)-2-(methyloxy)acetamide;
N'-((1S,2R)-1-(3-cyanophenyl)methyl)-3-(((4S)-6-ethyl-3, 4-dihydrospiro-2,2-spirocyclobutyl[chromene-2,1'-cyclobutan]-4-yl)amino)-2-hydroxypropyl)-N,N-dimethylbutanediamide;
N-((1S,2R)-1-(3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide;

N-((1S,2R)-1-((3-cyanophenyl)methyl)-2-hydroxy-3-(((4S)-6-(4-morpholinyl)-3,4-dihydrospiro-2,2-spirocyclobutyl[chromene-2,1'-cyclobutan]-4-yl)amino)propyl)-2-(methyloxy)acetamide;

N-((1S,2R)-1-((3-cyanophenyl)methyl)-2-hydroxy-3-(((4S)-6-(4-morpholinyl)-3,4-dihydrospiro-2,2-spirocyclobutyl[chromene-2,1'-cyclobutan]-4-yl)amino)propyl)acetamide;

2-(((1S,2R)-1-((3-cyanophenyl)methyl)-2-hydroxy-3-(((4S)-6-(4-morpholinyl)-3,4-dihydrospiro[chromene-2,1'-cyclobutan]-4-yl)amino)propyl)amino)-2-oxoethyl dimethylcarbamate;

N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

N-((1S,2R)-1-((3-cyanophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide;

N-((1S,2R)-1-(3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

N-((1S,2R)-1-(3-cyanophenyl)methyl)-2-hydroxy-3-(((5'S)-3'-methyl-5',8'-dihydro-6'H-spiro[cyclobutane-1,7'-quinolin]-5'-yl)amino)propyl)acetamide;

N-((1S,2R)-1-(3-cyanophenyl)methyl)-2-hydroxy-3-(((4'S)-6'-(trifluoromethyl)-3',4'-dihydrospiro[cyclobutane-1,2'-pyrano[2,3-b]pyridin]-4'-yl)amino)propyl)acetamide;

N~1~-((1S,2R)-3-(((4S)-6-bromo-3,4-dihydro spiro[chromene-2,1'-cyclobutan]-4-yl)amino)-1-((3-cyanophenyl)methyl)-2-hydroxypropyl)-N~2~,N~2~-dimethylglycinamide;

methyl (4 S)-4-(((2R,3S)-4-(3-cyanophenyl)-3-((N,N-dimethylglycyl)amino)-2-hydroxybutyl)amino)-3,4-dihydrospiro[chromene-2,1'-cyclobutane]-6-carboxylate;

methyl (4S)-4-(((2R,3S)-3-(acetylamino)-4-(3-cyanophenyl)-2-hydroxybutyl)amino)-3,4-dihydrospiro[chromene-2,1'-cyclobutane]-6-carboxylate;

methyl (4S)-4-(((2R,3S)-4-(3-cyanophenyl)-2-hydroxy-3-(((methyloxy)acetyl)amino)butyl)amino)-3,4-dihydrospiro[chromene-2,1'-cyclobutane]-6-carboxylate;

N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide;

N-((1S,2R)-1-(1,3-benzodioxol-5-ylmethyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide; and N-((1S,2R)-1-((3-cyanophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)acetamide.

Thus, the specific compounds listed above are excluded from the scope of the present invention and from the scope of Formulas I and II described herein.

In another embodiment, the compounds of Formulas I and II include compounds wherein $R^{1a}$ is H, halo, $C_{1-10}$-alkyl, $C_{2-8}$-alkenyl or $C_{2-8}$-alkynyl, wherein 1, 2 or 3 carbon atoms of said $C_1$-$C_{10}$alkyl, $C_2$-$C_8$-alkenyl or $C_2$-$C_8$-alkynyl is optionally replaced with a heteroatom selected from O, S, S(O), S(O)$_2$ and N, and optionally substituted independently with one or more substituents of $R^7$, in conjunction with any of the above or below embodiments.

In another embodiment, the compounds of Formulas I and II include compounds wherein $R^{1a}$ is H, halo, $C_{1-10}$-alkyl, $C_{2-8}$-alkenyl or $C_{2-8}$-alkynyl, wherein 1, 2 or 3 carbon atoms of said $C_1$-$C_{10}$alkyl, $C_2$-$C_8$-alkenyl or $C_2$-$C_8$-alkynyl is optionally replaced with a heteroatom selected from O, S, S(O), S(O)$_2$ and N, and optionally substituted independently with 1-3 substituents of halo, haloalkyl, CN, OH, NO$_2$, NH$_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-di-alkylamino-, $C_{1-10}$-alkoxyl and $C_{1-10}$-thioalkoxyl, in conjunction with any of the above or below embodiments.

In another embodiment, the compounds of Formulas I and II include compounds wherein $R^{1a}$ is $C_{1-6}$-alkyl, $C_{2-6}$alkenyl, $C_{2-6}$-alkynyl, —O—$C_{1-6}$-alkyl-, —S—$C_{1-6}$-alkyl-, —NH—$C_{1-6}$-alkyl-, —O—$C_{1-6}$-alkenyl-, —S—$C_{2-6}$-alkenyl-, —NH—$C_{2-6}$-alkenyl-, —O—$C_{1-6}$-alkynyl-, —S—$C_{1-6}$alkynyl-, —NH—$C_{1-6}$-alkynyl-, —$C_{1-4}$alkyl-O—$C_{1-4}$-alkyl-, —$C_{1-4}$-alkyl-S—$C_{1-4}$-alkyl- or —$C_{1-4}$-alkyl-NH—$C_{1-4}$-alkyl-, in conjunction with any of the above or below embodiments.

In another embodiment, the compounds of Formulas I and II include compounds wherein $R^{1a}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or NH$_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$, in conjunction with any of the above or below embodiments.

In another embodiment, the compounds of Formulas I and II include compounds wherein $R^{1a}$ is $C_{1-6}$-alkyl, —O—$C_{1-6}$-alkyl, —S—$C_{1-6}$-alkyl, —NH—$C_{1-6}$-alkyl, wherein the $C_{1-6}$-alkyl and the $C_{1-6}$-alkyl portion of —O—$C_{1-6}$-alkyl, —S—$C_{1-6}$-alkyl and —NH—$C_{1-6}$-alkyl is optionally substituted independently with 1-5 substituents of $R^7$, in conjunction with any of the above or below embodiments.

In another embodiment, the compounds of Formulas I and II include compounds wherein $R^{1b}$ is H, halo, haloalkyl, —O—$C_{1-6}$-alkyl, —S—$C_{1-6}$-alkyl, —NH—$C_{1-6}$-alkyl, —N-di-$C_{1-6}$-alkyl, CN, OH or NH$_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$, in conjunction with any of the above or below embodiments.

In another embodiment, the compounds of Formulas I and II include compounds wherein $R^{1b}$ is H, halo, haloalkyl, —O—$C_{1-6}$-alkyl, —S—$C_{1-6}$-alkyl, —NH—$C_{1-6}$ alkyl, —N-di-$C_{1-6}$ alkyl, CN, OH or NH$_2$, wherein the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$, in conjunction with any of the above or below embodiments.

In another embodiment, the compounds of Formulas I and II include compounds wherein $R^{1b}$ is H, halo, haloalkyl, —O—$C_{1-6}$-alkyl, —S—$C_{1-6}$-alkyl, —NH—$C_{1-6}$ alkyl, N-di-$C_{1-6}$ alkyl, CN, OH or NH$_2$, in conjunction with any of the above or below embodiments.

In another embodiment, the compounds of Formulas I and II include compounds wherein $R^{1b}$ is H, F, Cl, Br, CF$_3$, C$_2$F$_5$, $C_{1-6}$-alkyl, —O—$C_{1-6}$-alkyl, —S—$C_{1-6}$-alkyl, alkyl, wherein the $C_{1-6}$-alkyl and the $C_{1-6}$-alkyl portion of —O—$C_{1-6}$-alkyl, —S—$C_{1-6}$-alkyl and —NH—$C_{1-6}$-alkyl is optionally substituted independently with 1-3 substituents of $R^7$, in conjunction with any of the above or below embodiments.

In another embodiment, the compounds of Formulas I and II include compounds wherein each of $R^{1a}$ and $R^{1b}$, independently, is H, methyl, ethyl, propyl, butyl, methoxyl, ethoxyl, propoxyl, butoxyl, each of which is optionally substituted independently with 1-3 substituents of halo, OH, $NH_2$ and CN, and provided that both of $R^{1a}$ and $R^{1b}$ are not H, in conjunction with any of the above or below embodiments.

In another embodiment, the compounds of Formulas I and II include compounds wherein $R^{1a}$ and $R^{1b}$ taken together with the carbon atom to which they are attached form a partially or fully saturated 3,4-, 5- or 6-membered ring of carbon atoms optionally including 1-2 heteroatoms selected from O, N, or S, the ring optionally substituted independently with 1-3 substituents of $R^7$, in conjunction with any of the above or below embodiments.

In another embodiment, the compounds of Formulas I and II include compounds wherein $R^{1a}$ and $R^{1b}$ taken together with the carbon atom to which they are attached form a partially or fully saturated 4-, 5- or 6-membered ring of carbon atoms optionally including 1-2 heteroatoms selected from O, N, or S, the ring optionally substituted independently with 1-3 substituents of $R^7$, in conjunction with any of the above or below embodiments.

In another embodiment, the compounds of Formulas I and II include compounds wherein $R^{1a}$ and $R^{1b}$ taken together with the carbon atom to which they are attached form a ring selected from tetrahydrofuran-2-yl, tetrahydrofuran-3-yl, morpholin-2-yl, cyclopropyl, cyclobutyl and cyclohexyl, the ring optionally substituted independently with 1-3 substituents of $R^7$, in conjunction with any of the above or below embodiments.

In another embodiment, the compounds of Formulas I and II include compounds wherein $R^{1c}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, in conjunction with any of the above or below embodiments.

In another embodiment, the compounds of Formulas I and II include compounds wherein $R^{1c}$ is H, halo, haloalkyl, $C_{1-6}$-alkyl, CN, OH or $NH_2$, in conjunction with any of the above or below embodiments.

In another embodiment, the compounds of Formulas I and II include compounds wherein $R^{1a}$ is $C_{1-6}$-alkyl, $C_{2-6}$alkenyl, $C_{2-6}$-alkynyl, —O—$C_{1-6}$-alkyl-, —S—$C_{1-6}$-alkyl-, —NH—$C_{1-6}$-alkyl-, —O—$C_{1-6}$-alkenyl-, —S—$C_{2-6}$-alkenyl-, —NH—$C_{2-6}$-alkenyl-, —O—$C_{1-6}$-alkynyl-, —S—$C_{1-6}$alkynyl-, —NH—$C_{1-6}$-alkynyl-, —$C_{1-4}$alkyl-O—$C_{1-4}$-alkyl-, —$C_{1-4}$-alkyl-S—$C_{1-4}$-alkyl- or —$C_{1-4}$-alkyl-NH—$C_{1-4}$-alkyl-;

$R^{1b}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$; and $R^{1c}$ is H, in conjunction with any of the above or below embodiments. In another embodiment, the compounds of Formulas I and II include compounds wherein each of $R^{1a}$ and $R^{1b}$, independently, is H, methyl, ethyl, propyl, butyl, methoxyl, ethoxyl, propoxyl, butoxyl, each of which is optionally substituted independently with 1-3 substituents of halo, OH, $NH_2$ and CN, and provided that both of $R^{1a}$ and $R^{1b}$ are not H, and $R^{1c}$ is H, in conjunction with any of the above or below embodiments.

In another embodiment, the compounds of Formulas I and II include compounds wherein $R^{1a}$ and $R^{1b}$ taken together with the carbon atom to which they are attached form a partially or fully saturated 3,4-, 5- or 6-membered ring of carbon atoms optionally including 1-2 heteroatoms selected from O, N, or S, the ring optionally substituted independently with 1-3 substituents of $R^7$ and $R^{1c}$ is H, in conjunction with any of the above or below embodiments.

In another embodiment, the compounds of Formulas I and II include compounds wherein $R^{1a}$ and $R^{1b}$ taken together with the carbon atom to which they are attached form a partially or fully saturated 4-, 5- or 6-membered ring of carbon atoms optionally including 1-2 heteroatoms selected from O, N, or S, the ring optionally substituted independently with 1-3 substituents of $R^7$ and $R^{1c}$ is H, in conjunction with any of the above or below embodiments.

In another embodiment, the compounds of Formulas I and II include compounds wherein $R^{1a}$ and $R^{1b}$ taken together with the carbon atom to which they are attached form a ring selected from tetrahydrofuran-2-yl, tetrahydrofuran-3-yl, cyclopropyl, cyclobutyl and cyclohexyl, the ring optionally substituted independently with 1-3 substituents of $R^7$ and $R^{1c}$ is H, in conjunction with any of the above or below embodiments.

In another embodiment, the compounds of Formulas I and II include compounds wherein each of $R^{1a}$ and $R^{1b}$, independently, is H, methyl, ethyl, propyl, butyl, methoxyl, ethoxyl, propoxyl, butoxyl, each of which is optionally substituted independently with 1-3 substituents of halo, OH, $NH_2$ and CN, and provided that both of $R^{1a}$ and $R^{1b}$ are not H, and $R^{1c}$ is H, in conjunction with any of the above or below embodiments.

In another embodiment, the compounds of Formulas I and II include compounds wherein W is —C(=O)—, in conjunction with any of the above or below embodiments.

In another embodiment, the compounds of Formulas I and II include compounds wherein W is —OC(=O)—, in conjunction with any of the above or below embodiments.

In another embodiment, the compounds of Formulas I and II include compounds wherein W is —NHC(=O)—, in conjunction with any of the above or below embodiments.

In another embodiment, the compounds of Formulas I and II include compounds wherein W is —S(=O)$_b$— wherein b is 1 or 2, in conjunction with any of the above or below embodiments.

In another embodiment, the compounds of Formulas I and II include compounds wherein W is —NHS(=O)$_b$— wherein b is 1 or 2, in conjunction with any of the above or below embodiments.

In another embodiment, the compounds of Formulas I and II include compounds wherein W is —C(=O)—, —C(=S)—, —OC(=O)—NHC(=O)—, —S(=O)$_b$— or —NHS(=O)$_b$—, wherein b is 1 or 2, in conjunction with any of the above or below embodiments.

In another embodiment, the compounds of Formulas I and II include compounds wherein W is —C(=O)—, —C(=S)— or —S(=O)$_b$—, wherein b is 1 or 2, in conjunction with any of the above or below embodiments.

In another embodiment, the compounds of Formulas II includes compounds wherein each of $A^1$, $A^2$, $A^3$ and $A^4$, independently, is N, CH or $CR^6$, provided that no more than two of $A^1$, $A^2$, $A^3$ and $A^4$ is N, in conjunction with any of the above or below embodiments.

In another embodiment, the compounds of Formulas II includes compounds wherein each of $A^1$ and $A^2$, independently, is CH and one of $A^3$ and $A^4$, independently, is N while the other of $A^3$ and $A^4$, independently, is CH or $CR^6$, in conjunction with any of the above or below embodiments.

In another embodiment, the compounds of Formulas II includes compounds wherein $A^1$ is CH, $A^2$ is $CR^6$ and one of $A^3$ and $A^4$, independently, is N while the other of $A^3$ and $A^4$, independently, is CH or $CR^6$, in conjunction with any of the above or below embodiments.

In another embodiment, the compounds of Formulas II includes compounds wherein $A^1$ is CH, $A^2$ is $CR^6$, $A^3$ is N and $A^4$ is CH or $CR^6$, in conjunction with any of the above or below embodiments.

In another embodiment, the compounds of Formulas II includes compounds wherein $A^1$ is CH, $A^2$ is $CR^6$, $A^3$ is CH or $CR^6$ and $A^4$ is N, in conjunction with any of the above or below embodiments.

In another embodiment, the compounds of Formulas II includes compounds wherein $A^1$ is CH, $A^2$ is $CR^6$ and each of $A^3$ and $A^4$, independently, CH, $CR^6$ or N, provided no more than one of $A^3$ and $A^4$ is N, in conjunction with any of the above or below embodiments.

In another embodiment, the compounds of Formulas II includes compounds wherein $A^1$ is CH, $A^2$ is $CR^6$ and each of $A^3$ and $A^4$, independently, CH or $CR^6$, in conjunction with any of the above or below embodiments.

In another embodiment, the compounds of Formulas II includes compounds wherein $A^1$ is CH, $A^2$ is $CR^6$, $A^3$ is CH and $A^4$ is $CR^6$, in conjunction with any of the above or below embodiments.

In another embodiment, the compounds of Formulas II includes compounds wherein each $R^2$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

alternatively, two adjacent $R^2$ groups taken together with the carbon atoms to which they are attached form a dioxolyl ring optionally substituted by 1 or 2 halo, in conjunction with any of the above or below embodiments.

In another embodiment, the compounds of Formula II includes compounds wherein each $R^2$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$ alkyl, CN, OH, $NH_2$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$, in conjunction with any of the above or below embodiments.

In another embodiment, the compounds of Formula II includes compounds wherein each $R^2$, independently, is F, Cl, Br, $CF_3$, $C_2F_5$, $C_{1-6}$-alkyl, —O—$C_{1-6}$-alkyl, —S—$C_{1-6}$-alkyl, —NH—$C_{1-6}$-alkyl, —N-di-$C_{1-6}$ alkyl, CN, OH, $NH_2$, $C_{2-6}$-alkenyl, $C_{2-6}$-alkynyl or $C_{3-8}$-cycloalkyl, wherein the $C_{1-6}$-alkyl, $C_{2-6}$-alkenyl, $C_{2-6}$-alkynyl, $C_{3-8}$-cycloalkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-3 substituents of $R^7$, in conjunction with any of the above or below embodiments.

In another embodiment, the compounds of Formula II includes compounds wherein two adjacent $R^2$ groups taken together with the carbon atoms to which they are attached form a dioxolyl ring optionally substituted by 1 or 2 halo, in conjunction with any of the above or below embodiments.

In another embodiment, the compounds of Formula II includes compounds wherein $R^{2a}$ is H or F, in conjunction with any of the above or below embodiments.

In another embodiment, the compounds of Formula II includes compounds wherein $R^{2a}$ is H, in conjunction with any of the above or below embodiments.

In another embodiment, the compounds of Formula II includes compounds wherein $R^{2a}$ is F, in conjunction with any of the above or below embodiments.

In another embodiment, the compounds of Formula II includes compounds wherein $R^3$ is CN, $C_{2-3}$alkynyl, a partially or fully unsaturated 5- or 6-membered monocyclic ring formed of carbon atoms wherein said ring optionally including 1-3 heteroatoms selected from O, N, or S and optionally substituted with 1-5 substituents of $R^7$, or $R^3$ is F or absent when two adjacent $R^2$ groups taken together with the carbon atoms to which they are attached form a dioxolyl ring, in conjunction with any of the above or below embodiments.

In another embodiment, the compounds of Formula II includes compounds wherein $R^3$ is CN, $C_{2-3}$alkynyl, a partially or fully unsaturated 5- or 6-membered monocyclic ring formed of carbon atoms wherein said ring optionally including 1-3 heteroatoms selected from O, N, or S and optionally substituted with 1-5 substituents of $R^7$, or $R^3$ is absent when two adjacent $R^2$ groups taken together with the carbon atoms to which they are attached form a dioxolyl ring, in conjunction with any of the above or below embodiments.

In another embodiment, the compounds of Formula II includes compounds wherein $R^3$ is $C_{2-3}$alkynyl or a partially or fully unsaturated 5- or 6-membered monocyclic ring formed of carbon atoms wherein said ring optionally including 1-3 heteroatoms selected from O, N, or S and optionally substituted with 1-5 substituents of $R^7$, or $R^3$ is absent when two adjacent $R^2$ groups taken together with the carbon atoms to which they are attached form a dioxolyl ring, in conjunction with any of the above or below embodiments.

In another embodiment, the compounds of Formula II includes compounds wherein $R^3$ is $C_{2-3}$alkynyl or a fully unsaturated 5- or 6-membered monocyclic ring formed of carbon atoms wherein said ring optionally including 1-3 heteroatoms selected from O, N, or S and optionally substituted with 1-5 substituents of $R^7$, or $R^3$ is absent when two adjacent $R^2$ groups taken together with the carbon atoms to which they are attached form a dioxolyl ring, in conjunction with any of the above or below embodiments.

In another embodiment, the compounds of Formula II includes compounds wherein $R^3$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of $R^7$, in conjunction with any of the above or below embodiments.

In another embodiment, the compounds of Formula II includes compounds wherein $R^3$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of $R^7$, or $R^3$ is absent when two adjacent $R^2$ groups taken together with the carbon atoms to which they are attached form a dioxolyl ring, in conjunction with any of the above or below embodiments.

In another embodiment, the compounds of Formula II includes compounds wherein $R^3$ is a ring selected from 1H-imidazol-1-yl, 1H-imidazol-2-yl, 1H-imidazol-4-yl, 1H-imidazol-5-yl, 1,3-thiazol-5-yl, 1,3-thiazol-4-yl, 1,3-thiazol-2-yl, 4-pyridyl, 3-pyridyl, 2-pyridyl, pyrimidyl, pyridazinyl, pyrazinyl, pyrazolyl, 1,3-oxazol-2-yl, 1,3-oxazol-4-yl, 1,3-oxazol-5-yl, isoxazolyl, isothiazolyl, thiadiazolyl and oxadiazolyl, said ring optionally substituted with 1-5 substituents of $R^7$, or $R^3$ is absent when two adjacent $R^2$ groups taken together with the carbon atoms to which they are attached form a dioxolyl ring, in conjunction with any of the above or below embodiments.

In another embodiment, the compounds of Formula II includes compounds wherein $R^3$ is absent and two adjacent $R^2$ groups taken together with the carbon atoms to which they are attached form a 1,3-dioxolyl ring, in conjunction with any of the above or below embodiments.

In another embodiment, the compounds of Formula II includes compounds wherein $R^4$ is H, halo or $C_{1-6}$-alkyl, in conjunction with any of the above or below embodiments.

In another embodiment, the compounds of Formula II includes compounds wherein $R^4$ is H, halo or $C_{1-4}$-alkyl, in conjunction with any of the above or below embodiments.

In another embodiment, the compounds of Formula II includes compounds wherein $R^4$ is H or $C_{1-6}$-alkyl, in conjunction with any of the above or below embodiments.

In another embodiment, the compounds of Formula II includes compounds wherein $R^4$ is H, F or methyl, in conjunction with any of the above or below embodiments.

In another embodiment, the compounds of Formula II includes compounds wherein $R^4$ is H or methyl, in conjunction with any of the above or below embodiments.

In another embodiment, the compounds of Formula II includes compounds wherein $R^4$ is H, in conjunction with any of the above or below embodiments.

In another embodiment, the compounds of Formula II includes compounds wherein $R^5$ is H, halo, haloalkyl, oxo, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$, in conjunction with any of the above or below embodiments.

In another embodiment, the compounds of Formula II includes compounds wherein $R^5$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, in conjunction with any of the above or below embodiments.

In another embodiment, the compounds of Formula II includes compounds wherein $R^5$ is H, F, Cl, Br, $CF_3$, $C_2F_5$, $CH_2CF_3$, methyl, ethyl, methoxyl, ethoxyl, CN, OH or $NH_2$, in conjunction with any of the above or below embodiments.

In another embodiment, the compounds of Formula II includes compounds wherein each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, $OR^7$, $NHR^7$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

or $R^6$ is a fully saturated or partially or fully unsaturated 5- or 6-membered monocyclic or bicyclic ring formed of carbon atoms, said ring optionally including 1-4 heteroatoms selected from O, N, or S and optionally substituted with one or more substituents of $R^7$, in conjunction with any of the above or below embodiments.

In another embodiment, the compounds of Formula II includes compounds wherein each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, $OR^7$, $NHR^7$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$, in conjunction with any of the above or below embodiments.

In another embodiment, the compounds of Formula II includes compounds wherein $R^6$ is a fully saturated or partially or fully unsaturated 5- or 6-membered monocyclic or bicyclic ring formed of carbon atoms, said ring optionally including 1-4 heteroatoms selected from O, N, or S and optionally substituted with one or more substituents of $R^7$, in conjunction with any of the above or below embodiments.

In another embodiment, the compounds of Formula II includes compounds wherein each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, $OR^7$, $NHR^7$, $C_{2-6}$-alkenyl, $C_{2-6}$-alkynyl, $C_{3-8}$-cycloalkyl, $C_{4-8}$-cycloalkenyl or a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl, ring and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$, in conjunction with any of the above or below embodiments.

In another embodiment, the compounds of Formula II includes compounds wherein each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, $OR^7$, $NHR^7$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$, in conjunction with any of the above or below embodiments.

In another embodiment, the compounds of Formula II includes compounds wherein X is $CH_2$, $CHR^6$, $CR^6R^6$, C(=O), O, NH, $NR^6$, or S(O), wherein o is 0, 1 or 2, in conjunction with any of the above or below embodiments.

In another embodiment, the compounds of Formula II includes compounds wherein X is $CH_2$, in conjunction with any of the above or below embodiments.

In another embodiment, the compounds of Formula II includes compounds wherein X is $CHR^6$, in conjunction with any of the above or below embodiments.

In another embodiment, the compounds of Formula II includes compounds wherein X is $CR^6R^6$, in conjunction with any of the above or below embodiments.

In another embodiment, the compounds of Formula II includes compounds wherein X is C(=O), in conjunction with any of the above or below embodiments.

In another embodiment, the compounds of Formula II includes compounds wherein X is O, in conjunction with any of the above or below embodiments.

In another embodiment, the compounds of Formula II includes compounds wherein X is NH, in conjunction with any of the above or below embodiments.

In another embodiment, the compounds of Formula II includes compounds wherein X is $NR^6$, in conjunction with any of the above or below embodiments.

In another embodiment, the compounds of Formula II includes compounds wherein X is S(O)$_o$ wherein o is 0, 1 or 2, in conjunction with any of the above or below embodiments.

In another embodiment, the compounds of Formula II includes compounds wherein X is CH$_2$, CHR$^6$, O, NH, NR$^6$, or S(O)$_o$ wherein o is 0, 1 or 2, in conjunction with any of the above or below embodiments.

In another embodiment, the compounds of Formula II includes compounds wherein X is CH$_2$, C(=O), O, NH, NR$^6$, or S(O)$_o$ wherein o is 0, 1 or 2, in conjunction with any of the above or below embodiments.

In another embodiment, the compounds of Formula II includes compounds wherein X is C(=O), O, NH, NR$^6$, or S(O)$_o$ wherein o is 0, 1 or 2, in conjunction with any of the above or below embodiments.

In another embodiment, the compounds of Formula II includes compounds wherein X is O, NH, NR$^6$, or S(O)$_o$ wherein o is 0, 1 or 2, in conjunction with any of the above or below embodiments.

In another embodiment, the compounds of Formula II includes compounds wherein X is O, NH or NR$^6$, in conjunction with any of the above or below embodiments.

In another embodiment, the compounds of Formula II includes compounds wherein Z is a 3-6 membered spirocyclic ring formed of carbon atoms optionally including 1-3 heteroatoms selected from O, N and S and optionally substituted independently with 1-5 substituents of R$^7$, in conjunction with any of the above or below embodiments.

In another embodiment, the compounds of Formula II includes compounds wherein Z is a cyclopropyl, cyclobutyl or cyclopentyl ring wherein 0, 1 or 2 carbon atoms of the ring are, independently, replaced with an oxygen atom and the ring optionally substituted independently with 1-5 substituents of R$^7$, in conjunction with any of the above or below embodiments.

In another embodiment, the compounds of Formula II includes compounds wherein Z is a ring of

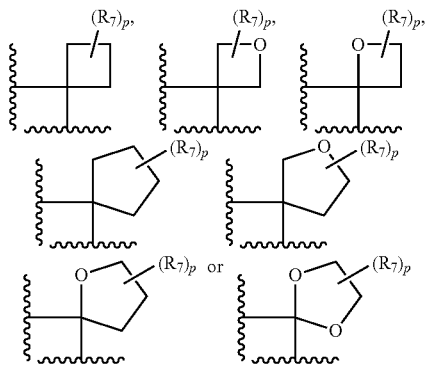

wherein R$^7$ is as defined herein and p is 0, 1, 2, 3 or 4, in conjunction with any of the above or below embodiments.

In another embodiment, the compounds of Formula II includes compounds wherein Z is a 3-6 membered spirocyclic ring formed of carbon atoms optionally including 1-3 heteroatoms selected from O, N and S and optionally substituted independently with 1-5 substituents of R$^7$, in conjunction with any of the above or below embodiments.

In another embodiment, the compounds of Formula II includes compounds and pharmaceutically acceptable salt forms thereof, wherein
A$^1$ is CH;
A$^2$ is CR$^6$;
each of A$^3$ and A$^4$, independently, CH, CR$^6$ or N, provided no more than one of A$^3$ and A$^4$ is N;
R$^{1a}$ is C$_{1-6}$-alkyl, C$_{2-6}$alkenyl, C$_{2-6}$-alkynyl, C$_{1-6}$alkyl-O—C$_{1-3}$-alkyl-, C$_{1-6}$-alkyl-S—C$_{1-3}$-alkyl-, C$_{1-6}$-alkyl-S(O)$_2$—C$_{1-3}$-alkyl-, C$_{1-6}$-alkyl-NH—C$_{1-3}$-alkyl, alkyl, C$_{2-4}$-alkenyl-O—C$_{1-3}$-alkyl-, C$_{2-4}$-alkenyl-S—C$_{1-3}$-alkyl-, C$_{2-4}$-alkenyl-NH—C$_{1-3}$-alkyl- or C$_{2-4}$-alkynyl-NH—C$_{1-3}$-alkyl-, wherein the alkyl, alkenyl or alkynyl moiety of each is optionally substituted with 1-3 substituents of R$^7$;
R$^{1b}$ is H, halo, haloalkyl, C$_{1-6}$-alkyl, —O—C$_{1-6}$-alkyl, —S—C$_{1-6}$-alkyl, —NH—C$_{1-6}$-alkyl, —N-di-C$_{1-6}$-alkyl, CN, OH or NH$_2$;
alternatively, R$^{1a}$ and R$^{1b}$ taken together with the carbon atom to which they are attached form a partially or fully saturated 5- or 6-membered ring of carbon atoms optionally including 1-2 heteroatoms selected from O, N, or S, the ring optionally substituted independently with 1-3 substituents of R$^7$;
R$^{1c}$ is H;
W is —C(=O)—;
each R$^2$, independently, is halo, haloalkyl, C$_{1-4}$-alkyl, —O—C$_{1-4}$-alkyl, —S—C$_{1-4}$-alkyl, —NH—C$_{1-4}$-alkyl, —N-di-C$_{1-4}$-alkyl, CN, OH, NH$_2$, C$_{2-4}$-alkenyl, C$_{2-4}$-alkynyl, C$_{3-8}$-cycloalkyl or C$_{4-8}$-cycloalkenyl, wherein the C$_{1-6}$-alkyl, C$_{2-6}$-alkenyl, C$_{2-6}$-alkynyl, C$_{3-8}$-cycloalkyl, C$_{4-8}$-cycloalkenyl and the C$_{1-6}$-alkyl portion of —O—C$_{1-6}$-alkyl, —S—C$_{1-6}$-alkyl, —NH—C$_{1-6}$-alkyl and —N-di-C$_{1-6}$-alkyl are optionally substituted with 1-5 substituents of R$^7$;
alternatively, two adjacent R$^2$ groups taken together with the carbon atoms to which they are attached form a dioxolyl ring optionally substituted by 1 or 2 halo;
R$^{2a}$ is H;
R$^3$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of R$^7$, or R$^3$ is absent when two adjacent R$^2$ groups taken together with the carbon atoms to which they are attached form a dioxolyl ring;
R$^4$ is H or C$_{1-4}$-alkyl;
R$^5$ is H, halo, haloalkyl, C$_{1-6}$-alkyl, —O—C$_{1-6}$-alkyl, —S—C$_{1-6}$-alkyl, —NH—C$_{1-6}$-alkyl, —N-di-C$_{1-6}$-alkyl, CN, OH or NH$_2$;
X is CH$^2$, CHR$^6$, C(=O) or O;
Z is a cyclopropyl, cyclobutyl or cyclopentyl ring wherein 0, 1 or 2 carbon atoms of the ring are, independently, replaced with an oxygen atom and the ring optionally substituted independently with 1-5 substituents of R$^7$; and
each R$^6$, independently, is halo, haloalkyl, C$_{1-6}$-alkyl, —O—C$_{1-6}$-alkyl, —S—C$_{1-6}$-alkyl, —NH—C$_{1-6}$-alkyl, —N-di-C$_{1-6}$-alkyl, CN, OR$^7$, NHR$^7$, C$_{2-6}$-alkenyl, C$_{2-6}$-alkynyl, C$_{3-8}$-cycloalkyl, C$_{4-8}$-cycloalkenyl or a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, wherein the C$_{1-6}$-alkyl, C$_{2-6}$-alkenyl, C$_{2-6}$-alkynyl, C$_{3-8}$-cycloalkyl, C$_{4-8}$-cycloalkenyl, ring and the C$_{1-6}$-alkyl portion of —O—C$_{1-6}$-alkyl, —S—C$_{1-6}$-alkyl, —NH—$C_{1-6}$-alkyl and —N-di-$C_{1-6}$-alkyl are optionally substituted with 1-5 substituents of $R^7$.

In another embodiment, the invention provides compounds, and pharmaceutically acceptable salt forms thereof, having a general Formula II-A:

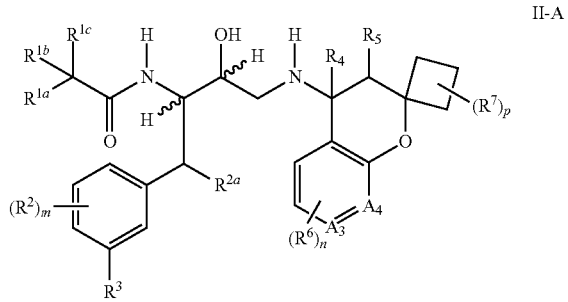

II-A wherein each of $A^3$ and $A^4$, independently, CH, $CR^6$ or N, provided no more than one of $A^3$ and $A^4$ is N;

$R^{1a}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

$R^{1b}$ K is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

alternatively, $R^{1a}$ and $R^{1b}$ taken together with the carbon atom to which they are attached form a partially or fully saturated 4-, 5- or 6-membered ring of carbon atoms optionally including 1-2 heteroatoms selected from O, N, or S, the ring optionally substituted independently with 1-3 substituents of $R^7$;

$R^{1c}$ is H, F, Cl, methyl, ethyl, methoxyl, ethyoxyl, CN, OH or $NH_2$;

each $R^2$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

alternatively, two adjacent $R^2$ groups taken together with the carbon atoms to which they are attached form a dioxolyl ring optionally substituted by 1 or 2 halo;

$R^{2a}$ is H or F;

$R^3$ is CN, $C_{2-3}$alkynyl or a ring selected from imidazolyl, thiazolyl, pyridyl, pyazolyl, furyl, pyrimidyl, pyridazinyl, pyrazinyl, triazinyl, thiophenyl, pyrrolyl, triazolyl, tetrazolyl, oxazolyl, isoxazolyl, isothiazolyl, thiadiazolyl or oxadiazolyl, said ring optionally including 1-3 heteroatoms selected from O, N, or S and optionally substituted with 1-3 substituents of $R^7$;

$R^4$ is H, halo or $C_{1-4}$-alkyl;

$R^5$ is H, halo, haloalkyl, $C_{1-4}$-alkyl, —O—$C_{1-4}$-alkyl, —S—$C_{1-4}$-alkyl, —NH—$C_{1-4}$-alkyl, CN, OH or $NH_2$, wherein the $C_{1-6}$-alkyl and the $C_{1-4}$-alkyl portion of —O—$C_{1-4}$-alkyl, —S—$C_{1-4}$-alkyl and —N—$C_{1-4}$-alkyl are optionally substituted independently with 1-3 substituents of $R^7$;

each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, $OR^7$, $NHR^7$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

m is 0, 1, 2 or 3;

n is 0, 1 or 2; and p is 0, 1 or 2.

In another embodiment, the compounds of Formula II and II-A include compounds wherein m is 0, 1, 2 or 3, in conjunction with any of the above or below embodiments.

In another embodiment, the compounds of Formula II and II-A include compounds wherein m is 0, 1 or 2, in conjunction with any of the above or below embodiments.

In another embodiment, the compounds of Formula II and II-A include compounds wherein m is 0 or 1, in conjunction with any of the above or below embodiments.

In another embodiment, the compounds of Formula II and II-A include compounds wherein m is 1 or 2, in conjunction with any of the above or below embodiments.

In another embodiment, the compounds of Formula II and II-A include compounds wherein m is 1, in conjunction with any of the above or below embodiments.

In another embodiment, the compounds of Formula II and II-A include compounds wherein m is 0, in conjunction with any of the above or below embodiments.

In another embodiment, the compounds of Formula II and II-A include compounds wherein n is 0, 1 or 2, in conjunction with any of the above or below embodiments.

In another embodiment, the compounds of Formula II and II-A include compounds wherein n is 0 or 1, in conjunction with any of the above or below embodiments.

In another embodiment, the compounds of Formula II and II-A include compounds wherein n is 1, in conjunction with any of the above or below embodiments.

In another embodiment, the compounds of Formula II and II-A include compounds wherein n is 0, in conjunction with any of the above or below embodiments.

In another embodiment, the compounds of II-A include compounds wherein $R^{1a}$ is $C_{1-6}$-alkyl, —O—$C_{1-6}$-alkyl, —S—$C_{1-6}$-alkyl, —NH—$C_{1-6}$-alkyl, wherein the $C_{1-6}$-alkyl and the $C_{1-6}$-alkyl portion of —O—$C_{1-6}$-alkyl, —S—$C_{1-6}$-alkyl and —NH—$C_{1-6}$-alkyl is optionally substituted independently with 1-5 substituents of $R^7$;

$R^{1b}$ is H, halo, haloalkyl, $C_{1-6}$-alkyl, —O—$C_{1-6}$-alkyl, —S—$C_{1-6}$-alkyl, —NH—$C_{1-6}$-alkyl, wherein the $C_{1-6}$-alkyl and the $C_{1-6}$-alkyl portion of —O—$C_{1-6}$-alkyl, —S—$C_{1-6}$-alkyl and —NH—$C_{1-6}$-alkyl is optionally substituted independently with 1-5 substituents of $R^7$;

alternatively, $R^{1a}$ and $R^{1b}$ taken together with the carbon atom to which they are attached form a partially or fully saturated 4- or 5-membered ring of carbon atoms optionally including 1 or 2 oxygen atoms and optionally substituted independently with 1-3 substituents of $R^7$; and $R^{1c}$ is H, F, Cl, methyl or ethyl, in conjunction with any of the above or below embodiments.

In another embodiment, the compounds of Formula II-A includes compounds wherein each of the specific embodiments for $A^3$, $A^4$, $R^{1a}$, $R^{1b}$, $R^{1c}$, $R^2$, $R^{2a}$, $R^3$, $R^4$, $R^5$, $R^6$, $R^7$, m, n and p, respectively, of compounds of Formula II above apply for compounds of Formula II-A.

In another embodiment, the invention provides compounds, and pharmaceutically acceptable salt forms thereof, having a general Formula II-B:

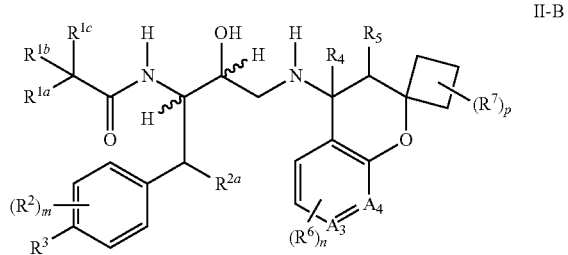

II-B wherein each of the independent embodiments for $A^3$, $A^4$, $R^{1a}$, $R^{1b}$, $R^{1c}$, $R^2$, $R^{2a}$, $R^3$, $R^4$, $R^5$, $R^6$, $R^7$, m, n and p, respectively, of compounds of Formulas II and II-A apply for compounds of Formula II-B.

In another embodiment, the invention provides compounds of Formula II-C:

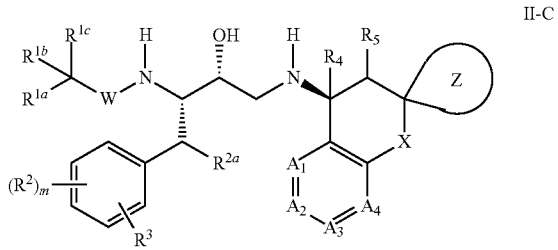

II-C or a pharmaceutically acceptable salt thereof, wherein
each of $A^1$, $A^2$, $A^3$ and $A^4$, independently, is N, CH or $CR^6$, provided that no more than one of $A^1$, $A^2$, $A^3$ and $A^4$ is N;

$R^{1a}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

$R^{1b}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

alternatively, $R^{1a}$ and $R^{1b}$ taken together with the carbon atom to which they are attached form a partially or fully saturated 3-, 4-, 5- or 6-membered ring of carbon atoms optionally including 1-2 heteroatoms selected from O, N, or S, the ring optionally substituted independently with 1-3 substituents of $R^7$;

$R^{1c}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$;

W is —C(=O)—, —C(=S)—, —OC(=O)—NHC(=O)—, —S(=O)$_b$— or —NHS(=O)$_b$—, wherein b is 1 or 2;

each $R^2$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

alternatively, two adjacent $R^2$ groups taken together with the carbon atoms to which they are attached form a dioxolyl ring optionally substituted by 1 or 2 halo;

$R^{2a}$ is H or F;

$R^3$ is CN, $C_{2-3}$alkynyl, a partially or fully unsaturated 5- or 6-membered mono cyclic ring formed of carbon atoms wherein said ring optionally including 1-3 heteroatoms selected from O, N, or S and optionally substituted with 1-5 substituents of $R^7$, or $R^3$ is absent when two adjacent $R^2$ groups taken together with the carbon atoms to which they are attached form a dioxolyl ring;

$R^4$ is H, halo or $C_{1-6}$-alkyl;

$R^5$ is H, halo, haloalkyl, oxo, $C_{1-6}$-alkyl, —O—$C_{1-6}$-alkyl, —S—$C_{1-6}$-alkyl, —NH—$C_{1-6}$alkyl, —N-di-$C_{1-6}$-alkyl, CN, OH or $NH_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

X is $CH_2$, $CHR^6$, $CR^6R^6$, C(=O), O, NH, $NR^6$, or $S(O)_o$ wherein o is 0, 1 or 2;

Z is a 3-6 membered spirocyclic ring formed of carbon atoms optionally including 1-3 heteroatoms selected from O, N and S and optionally substituted independently with 1-5 substituents of $R^7$;

each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, $OR^7$, $NHR^7$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

or $R^6$ is a fully saturated or partially or fully unsaturated 5- or 6-membered monocyclic or bicyclic ring formed of carbon atoms, said ring optionally including 1-4 heteroatoms selected from O, N, or S and optionally substituted with one or more substituents of $R^7$ each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl; and m is 0, 1, 2 or 3.

In another embodiment, the invention provides compounds, and pharmaceutically acceptable salt forms thereof, wherein each of the independent embodiments for Formulas II and II-A apply for compounds of Formula II-C.

In another embodiment, the invention provides compounds, and pharmaceutically acceptable salt forms thereof, having a general Formula II-D:

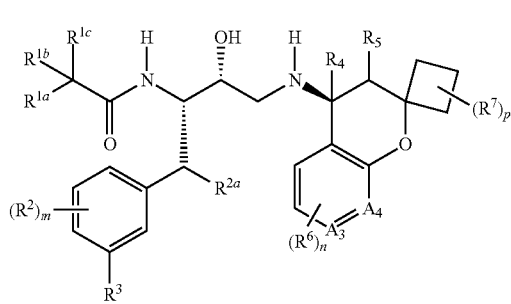

II-D wherein each of $A^3$, $A^4$, $R^{1a}$, $R^{1b}$, $R^{1c}$, $R^2$, $R^{2a}$, $R^3$, $R^4$, $R^5$, $R^6$, $R^7$, m, n and p are defined herein with respect to Formula II, II-A and II-B above.

In another embodiment, the invention provides the compound of Formula II, or a pharmaceutically acceptable salt thereof, selected from (2R)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)tetrahydro-2-furancarboxamide;

(2R)-N-((1S,2R)-1-(1,3-benzodioxol-5-ylmethyl)-3-((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-fluoropropanamide;

N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-oxetanecarboxamide;

(2R)-N-((1S,2R)-1-(1,3-benzodioxol-5-ylmethyl)-3-((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-oxetanecarboxamide;

N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2,2-dimethoxyacetamide;

N-((1S,2R)-1-(1,3-benzodioxol-5-ylmethyl)-3-((4'S)-6'-((1R)-2,2-dimethylcyclopropyl)-3',4'-dihydrospiro[cyclobutane-1,2'-pyrano[2,3-b]pyridin]-4'-yl)amino)-2-hydroxypropyl)-2-methoxyacetamide;

N-((1S,2R)-3-((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1H-imidazol-1-yl)benzyl)propyl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(4-pyridinyl)benzyl)propyl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-2-yl)benzyl)-2-hydroxypropyl)acetamide;

N-((1S,2R)-3-(((4S)-6-(2,2-dimethylpropyl)-3,4-dihydrospiro[chromene-2,1'-cyclobutan]-4-yl)amino)-2-hydroxy-1-(3-(1,3-thiazol-2-yl)benzyl)propyl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(4-pyridinyl)benzyl)propyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-2-yl)benzyl)-2-hydroxypropyl)-2-methoxyacetamide;

(2R)-N-((1S,2R)-1-(1,3-benzodioxol-5-ylmethyl)-3-(((4'S)-8'-chloro-6'-(2-methylpropyl)-3',4'-dihydrospiro[cyclobutane-1,2'-pyrano[2,3-c]pyridin]-4'-yl)amino)-2-hydroxypropyl)-2-methoxypropanamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-5-yl)benzyl)propyl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-4-fluorobenzyl)-2-hydroxypropyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-5-yl)benzyl)-2-hydroxypropyl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1H-imidazol-1-yl)benzyl)-2-hydroxypropyl)acetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-4-yl)benzyl)-2-hydroxypropyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-5-yl)benzyl)-2-hydroxypropyl)-2-methoxyacetamide;

N-((1S,2R)-1-(3-fluoro-5-(1,3-thiazol-2-yl)benzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1H-imidazol-1-yl)benzyl)propyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-4-yl)benzyl)propyl)-2-methoxyacetamide;

N-((1R,2S)-3-(((4S)-6-(2,2-dimethylpropyl)-3,4-dihydrospiro[chromene-2,1'-cyclobutan]-4-yl)amino)-2-hydroxy-1-(3-(1,3-thiazol-2-yl)benzyl)propyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-5-fluorobenzyl)-2-hydroxypropyl)acetamide;

N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-1-(4-fluoro-3-(1,3-thiazol-2-yl)benzyl)-2-hydroxypropyl)-2-methoxyacetamide;

N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-(3-fluoro-5-(1,3-thiazol-2-yl)benzyl)-2-hydroxypropyl)-2-methoxyacetamide;

(2R)-N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-(3-fluoro-5-(1,3-thiazol-2-yl)benzyl)-2-hydroxypropyl)-2-methoxypropanamide;

N-((1S,2R)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide;

N-((1S,2R)-3-(((1s,3S,4'S)-6'-(2,2-dimethylpropyl)-3-hydroxy-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide;

N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide;

N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)propanamide;

(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxypropanamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)-2-methoxyacetamide;

(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxypropanamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1-methyl-1H-imidazol-2-yl)benzyl)-2-hydroxypropyl)-2-methoxyacetamide;

N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2,2-dimethoxyacetamide;

N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-thiazol-2-yl)benzyl)propyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(5-methyl-1,3-thiazol-2-yl)benzyl)propyl)-2-methoxyacetamide;

N-((1S,2R)-3-(6'-(2,2-difluoropropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide;

(2R)-N-((1S,2R)-3-((6'-(2,2-difluoropropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxypropanamide;

(2R)-N-((1S,2R)-1-(4-fluoro-3-(1,3-thiazol-2-yl)benzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxypropanamide;

N-((1S,2R)-1-(3-fluoro-5-(1,3-thiazol-2-yl)benzyl)-2-hydroxy-3-(((4S)-6-(2-methylpropyl)-3,4-dihydrospiro[chromene-2,1'-cyclobutan]-4-yl)amino)propyl)-2-methoxyacetamide;

N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-ethoxyacetamide;

N-((1S,2R)-1-(3-ethynyl-4-fluorobenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-oxazol-2-yl)benzyl)propyl)-2-methoxyacetamide;

(2S)—N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxypropanamide;

(2S)—N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide;

(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide;

N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2,2-dimethoxyacetamide;

N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-1-(3-ethynylbenzyl)-2-hydroxypropyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-oxazol-2-yl)benzyl)propyl)-2,2-dimethoxyacetamide;

N-((1S,2R)-3-(((3S,4'R)-6'-(2,2-dimethylpropyl)-3',4,4',5-tetrahydrospiro[furan-3,2'-pyrano[2,3-b]pyridin]-4'-yl)amino)-2-hydroxy-1-(3-(1,3-thiazol-2-yl)benzyl)propyl)-2-methoxyacetamide;

(2R)-N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxypropanamide;

(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-oxazol-2-yl)benzyl)propyl)-2-methoxypropanamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(2-pyridinyl)benzyl)propyl)-2-methoxyacetamide;

N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxy-1-(3-(1,3-thiazol-2-yl)benzyl)propyl)-2-methoxyacetamide;

(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)-2-methoxypropanamide;

N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-ethoxyacetamide;

N-((1S,2R)-1-(3-ethynyl-5-fluorobenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)-2,2-dimethoxyacetamide;

(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-5-fluorobenzyl)-2-hydroxypropyl)-2-methoxypropanamide;

(2R)-N-((1S,2R)-1-(3-ethynylbenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxypropanamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-5-fluorobenzyl)-2-hydroxypropyl)-2-methoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)-2-ethoxyacetamide;

N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-ethoxyacetamide;

N-((1S,2R)-3-(((4'S)-6'-(2,2-dimethylpropyl)-3',4'-dihydrospiro[cyclobutane-1,2'-pyrano[2,3-c]pyridin]-4'-yl)amino)-1-(3-fluoro-5-(1,3-thiazol-2-yl)benzyl)-2-hydroxypropyl)-2-methoxyacetamide;

N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide;

N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-thiazol-2-yl)benzyl)propyl)-2,2-dimethoxyacetamide;

N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-oxazol-2-yl)benzyl)propyl)-2-methoxyacetamide;

(2R)-N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-thiazol-2-yl)benzyl)propyl)-2-methoxypropanamide; and N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-ethoxyacetamide.

In another embodiment, the invention provides compound of Formula III-A generally defined by

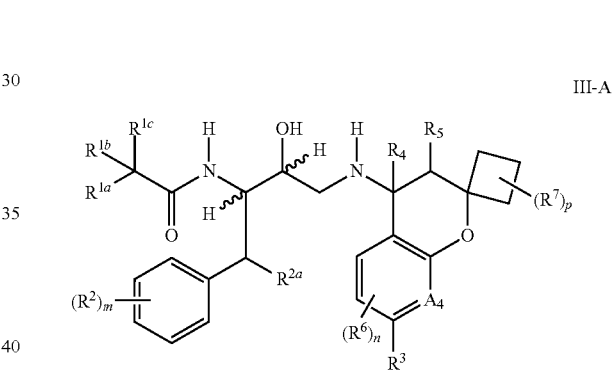

III-A wherein each of $A^4$, $R^{1a}$, $R^{1b}$, $R^{1c}$, $R^2$, $R^{2a}$, $R^3$, $R^4$, $R^5$, $R^6$, $R^7$, m, n and p are defined herein with respect to Formula II and II-A above.

In another embodiment, the invention provides compound of Formula III-B generally defined by

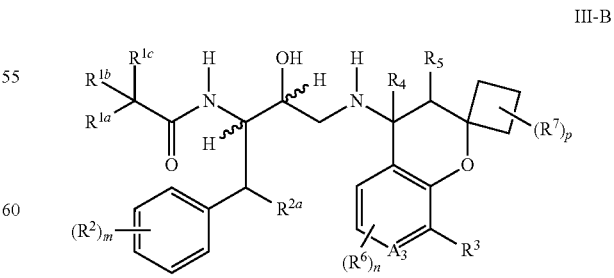

III-B wherein each of $A^3$, $R^{1a}$, $R^{1b}$, $R^{1c}$, $R^2$, $R^{2a}$, $R^3$, $R^4$, $R^5$, $R^6$, $R^7$, m, n and p are defined herein with respect to Formula II and II-A above.

In another embodiment, the invention provides compound of Formula III-C generally defined by

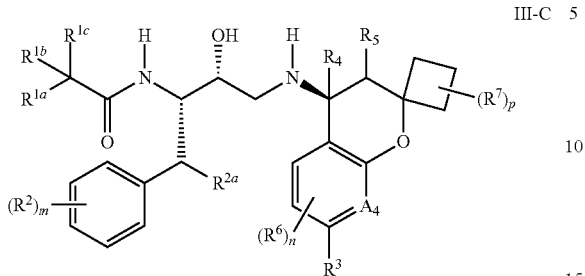

III-C wherein each of $A^4$, $R^{1a}$, $R^{1b}$, $R^{1c}$, $R^2$, $R^{2a}$, $R^3$, $R^4$, $R^5$, $R^6$, $R^7$, m, n and p are defined herein with respect to Formula II and II-A above.

In another embodiment, the invention provides compound of Formula III-D generally defined by

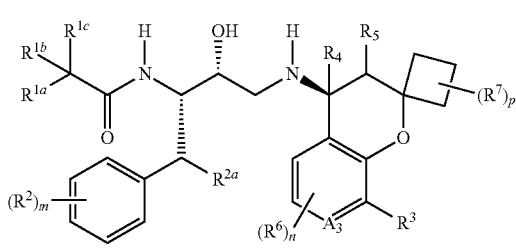

III-D wherein each of $A^3$, $R^{1a}$, $R^{1b}$, $R^{1c}$, $R^2$, $R^{2a}$, $R^3$, $R^4$, $R^5$, $R^6$, $R^7$, m, n and p are defined herein with respect to Formula II and II-A above.

For example, and in another embodiment, the compounds of Formulas III-A and B include compounds wherein $R^3$ is CN, $C_{2-3}$alkynyl, a partially or fully unsaturated 5- or 6-membered monocyclic ring formed of carbon atoms wherein said ring optionally including 1-3 heteroatoms selected from O, N, or S and optionally substituted with 1-5 substituents of $R^7$, in conjunction with any of the above or below embodiments.

In another embodiment, the compounds of Formulas III-A and B include compounds wherein $R^3$ is $C_{2-3}$alkynyl or a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of $R^7$, in conjunction with any of the above or below embodiments.

In another embodiment, the compounds of Formulas III-A and B include compounds wherein $R^3$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of $R^7$, in conjunction with any of the above or below embodiments.

In another embodiment, the present invention includes compounds generally defined by Formula IV:

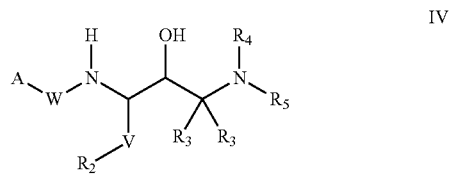

IV and stereoisomers, tautomers, solvates, pharmaceutically acceptable salts, derivatives and prodrugs thereof, wherein A is $C_{1-6}$-alkyl, $C_{2-6}$-alkenyl or $C_{2-6}$alkynyl, wherein 1, 2 or 3 carbon atoms of said $C_{1-6}$-alkyl, $C_{2-6}$-alkenyl and $C_{2-6}$alkynyl is optionally replaced with a heteroatom selected from O, S, S(O), S(O)$_2$ and NH, and optionally substituted independently with 1-3 substituents of $R^7$;

W is —C(=O)—, —OC(=O)—, —NHC(=O)—, —S(=O)$_b$— or —NHS(=O)$_b$—, wherein b is 1 or 2;

V is —(CR$^{2a}$R$^{2a}$)$_h$—, —O—(CR$^{2a}$R$^{2a}$)$_h$—, —S—(CR$^{2a}$R$^{2a}$)$_h$— or —NR$^{2a}$—(CR$^{2a}$R$^{2a}$)$_h$—, wherein each R$^{2a}$, independently, is H, $C_{1-4}$alkyl or haloalkyl, and h is 1 or 2;

$R^2$ is a ring selected from phenyl, pyridyl, pyrimidyl, pyridazinyl, pyrazinyl, triazinyl, tetrahydroquinolinyl, tetrahydroisoquinolinyl, tetrahydroquinazolinyl, tetrahydroisoquinazolinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, indolinyl, indazolyl, indazolinyl, benzofuranyl, benzothiophenyl, benzimidazolyl, benzoxazolyl, benzisoxazolyl, benzothiazolyl, benzoisothiazolyl, benzotriazolyl, tetrahydrofuranyl, pyrrolidinyl, oxazolinyl, isoxazolinyl, thiazolinyl, pyrazolinyl, morpholinyl, benzomorpholinyl, piperidinyl, piperazinyl, pyranyl, benzopyranyl, dioxazinyl and benzodioxolyl, said ring optionally substituted independently with 1-5 substituents of $R^7$;

each $R^3$, independently, is H, haloalkyl, CN or $C_{1-6}$-alkyl;

$R^4$ is H, haloalkyl, CN or $C_{1-6}$-alkyl;

$R^5$ is

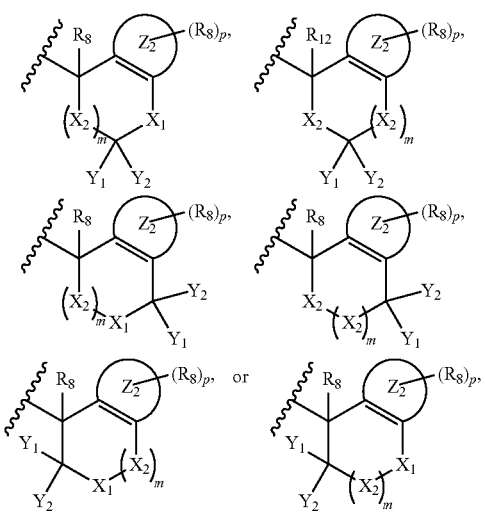

wherein $X^1$ is CR$^8$R$^8$, C(=O), O, S, S(O)$_2$ or NR$^8$;

each $X^2$, independently, is CR$^8$R$^8$;

each of $Y^1$ and $Y^2$, independently, is $C_{1-6}$-alkyl, —O—$C_{1-6}$-alkyl, —S—$C_{1-6}$-alkyl, —NH—$C_{1-6}$-alkyl or $C_{3-8}$-cycloalkyl;

alternatively $Y^1$ and $Y^2$ taken together with the carbon atom to which they are attached form a partially or fully saturated 3,4-, 5- or 6-membered spirocyclic ring, said ring formed of carbon atoms optionally including 1-3 heteroatoms selected from O, N and S and optionally substituted with 1-5 substiuents of $R^8$, provided that said ring includes no more than two heteroatoms selected from O, S and N;

$Z^2$ taken together with the carbon atoms to which it is attached is a partially or fully unsaturated 5-6 membered monocyclic ring, said ring formed of carbon atoms optionally including 1-3 heteroatoms selected from O, N and S;

m is 0, 1 or 2; and p is 0, 1, 2, 3, 4 or 5 each $R^7$, independently, is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

each $R^8$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of $R^9$; and $R^9$ is halo, haloalkyl, CN, OH, $NO_2$, $NH_2$, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl, phenyl, $C_{1-10}$-alkylamino-, $C_{1-10}$-dialkylamino-, $C_{1-10}$-thioalkoxyl or a partially or fully saturated or unsaturated 3-6 membered monocyclic formed of carbon atoms optionally including 1-3 heteroatoms selected from O, N, or S, and optionally substituted independently with 1-5 substituents of halo, haloalkyl, CN, $NO_2$, $NH_2$, OH, oxo, acetyl, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, benzyl or phenyl.

In another embodiment, the compounds of Formula IV includes compounds wherein A is $C_{1-6}$-alkyl, $C_{2-6}$alkenyl, $C_{2-6}$-alkynyl, $C_{1-6}$alkyl-O—$C_{1-3}$-alkyl-, $C_{1-6}$-alkyl-S—$C_{1-3}$-alkyl-, $C_{1-6}$-alkyl-S(O)$_2$—$C_{1-3}$-alkyl-, $C_{1-6}$-alkyl-NH—$C_{1-3}$-alkyl, di-($C_{1-6}$-alkyl)-N—$C_{1-3}$-alkyl, $C_{2-6}$-alkenyl-O—$C_{1-3}$-alkyl-, $C_{2-6}$-alkenyl-S—$C_{1-3}$-alkyl-, $C_{2-6}$-alkenyl-S(O)$_2$—$C_{1-3}$-alkyl-, $C_{2-6}$-alkenyl-NH—$C_{1-3}$-alkyl- or $C_{2-6}$-alkynyl-NH—$C_{1-3}$-alkyl-, wherein the alkyl, alkenyl or alkynyl moiety of each is optionally substituted with 1-3 substituents of $R^7$;

W is —C(=O)—;

V is —(CR$^{2a}$R$^{2a}$)$_h$— wherein each $R^{2a}$, independently, is H, $C_1$-$C_{10}$ alkyl or haloalkyl, and h is 1;

$R^2$ is ring selected from phenyl, pyridyl, pyrimidyl, pyridazinyl, pyrazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, indolyl, isoindolyl, benzofuranyl, benzothiophenyl, benzimidazolyl, benzoxazolyl, benzisoxazolyl, benzothiazolyl, benzoisothiazolyl, benzotriazolyl, pyrrolidinyl, oxazolinyl, isoxazolinyl, thiazolinyl, pyrazolinyl, benzomorpholinyl, benzopyranyl and benzodioxolyl, the ring optionally substituted with 1-3 substituents of $R^7$;

$R^3$ is H, haloalkyl, CN, $C_{1-10}$-alkyl, $C_{2-10}$-alkenyl or $C_{2-10}$-alkynyl;

$R^4$ is H, CN or $C_{1-10}$-alkyl;

$R^5$ is

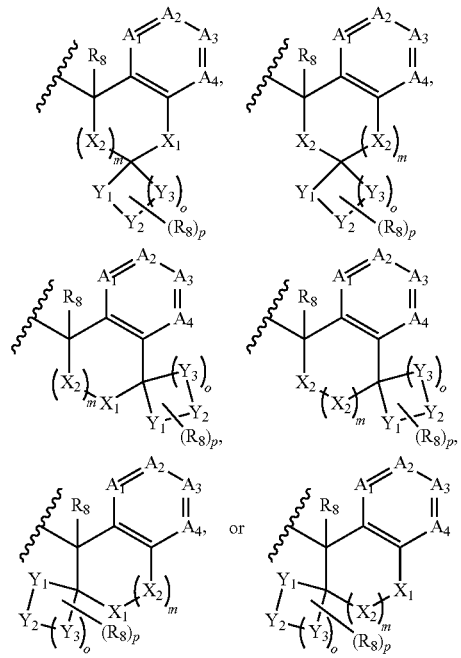

wherein each of $A^1$, $A^2$, $A^3$ and $A^4$, independently, is $CR^8$ or N, provided that no more than one of $A^1$, $A^2$, $A^3$ and $A^4$ is N;

m, $X^2$, $Y^1$ and $Y^2$ are as defined herein;

$X^1$ is $CR^8R^8$, O, S or S(O)$_2$; and each $Y^3$, independently, is $CHR^8$, O, S or $NR^8$;

o is 0, 1, 2 or 3; and p is 0, 1, 2 or 3;

each $R^7$, independently, is halo, haloalkyl, haloalkoxyl, CN, OH, $NO_2$, $NH_2$, acetyl, $C_{1-6}$-alkyl, $C_{2-8}$-alkenyl, $C_{2-8}$-alkynyl, $C_{3-8}$-cycloalkyl, $C_{1-6}$-alkylamino-, $C_{1-6}$-dialkylamino-, $C_{1-6}$-alkoxyl or $C_{1-6}$-thioalkoxyl; and each $R^8$, independently, is H, halo, haloalkyl, haloalkoxyl, CN, OH, $NO_2$, $NH_2$, acetyl, $C_{1-6}$-alkyl, $C_{2-8}$-alkenyl, $C_{2-8}$- alkynyl, $C_{3-8}$-cycloalkyl, $C_{1-6}$-alkylamino-, $C_{1-6}$-dialkylamino-, $C_{1-6}$-alkoxyl or $C_{1-6}$-thioalkoxyl.

In yet another embodiment, the compounds of Formula IV includes compounds wherein $R^5$ is

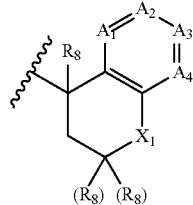

wherein each of $A^1$, $A^2$, $A^3$ and $A^4$, independently, is $CR^8$ or N, provided that no more than one of $A^1$, $A^2$, $A^3$ and $A^4$ is N;

$X^1$ is $CR^8R^8$, $C(=O)$, O or $NR^8$; and each $R^8$, independently, is H, halo, haloalkyl, haloalkoxyl, CN, OH, $NO_2$, $NH_2$, acetyl, $C_{1-6}$-alkyl, $C_{2-8}$-alkenyl, $C_{2-8}$-alkynyl, $C_{3-8}$-cycloalkyl, $C_{1-6}$-alkylamino-, $C_{1-6}$-dialkylamino-, $C_{1-6}$-alkoxyl or $C_{1-6}$-thioalkoxyl, in conjunction with any of the above or below embodiments.

In another embodiment, the compounds of Formula IV include compounds wherein $X^1$ is 0, in conjunction with any of the above or below embodiments.

In another embodiment, the compounds of Formula IV includes compounds wherein $X^1$ is S, in conjunction with any of the above or below embodiments.

In another embodiment, the compounds of Formula IV include compounds wherein $X^1$ is $SO_2$, in conjunction with any of the above or below embodiments.

In another embodiment, the compounds of Formula IV includes compounds wherein $X^1$ is $C(O)$, in conjunction with any of the above or below embodiments.

In another embodiment, the compounds of Formula IV include compounds wherein $X^1$ is $CHR^8$, in conjunction with any of the above or below embodiments.

In another embodiment, the compounds of Formula IV includes compounds wherein $X^1$ is $NR^8$, in conjunction with any of the above or below embodiments.

In another embodiment, the compounds of Formula IV includes compounds wherein each $R^7$, independently, is methyl, ethyl, propyl, isopropyl, butyl, isobutyl or sec-butyl as, in conjunction with any of the above or below embodiments.

In another embodiment, the compounds of Formula IV include each independent embodiment, as described herein for variables $R^{1a}$, $R^{1b}$, $R^{1c}$, B, V, W, $R^2$, $R^3$, $R^4$, $R^5$, $R^7$, $R^8$, $R^9$, $X^1$, $X^2$, $Y^1$, $Y^2$, $Y^3$ and $Z^2$ for compounds of Formula I, independently, in conjunction with any of the above or below embodiments for compounds of Formula IV.

In another embodiment, the invention provides each of the Examplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

DEFINITIONS

The following definitions should assist in understanding the invention described herein.

The term "comprising" is meant to be open ended, i.e., all encompassing and non-limiting. It may be used herein synonymously with "having." Comprising is intended to include each and every indicated component while not excluding any other components or elements.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O-ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where $R^7$ may be defined as a $C_{\alpha-\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha-\beta}$alkoxyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy, fluoropropoxy and cyclopropylmethoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—$CH_2$—O— or —O—$CH_2$—$CH_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-12'-benzo[d]isothiazol-6-yl, dihydropyranyl, dihydrofuryl and dihydrothiazolyl, and the like.

The phrase "a saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S" as used herein is intended to encompass all monocyclic and bicyclic rings as small as three atoms to as large as 12 atoms in size, including both carbocyclic rings and heterocyclic, aromatic and non-aromatic rings. The non-aromatic rings may be partially or fully saturated in nature.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "aminocarbonyl" denotes an amide group of the formula —C(=O)NH$_2$.

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, (CH$_3$S—).

The term "Formula I" includes any sub formulas, such as Formulas I-A, II, II-A, III-A, III-B or IV.

The term "pharmaceutically-acceptable" when used with reference to a compound of Formulas I-IV is intended to refer to a form of the compound that is safe for administration. For example, a salt form, a solvate, a hydrate, a prodrug or derivative form of a compound of Formulas I-IV, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-IV are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-IV may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-IV include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-IV.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate an enzyme.

The term "pharmaceutically-acceptable derivative" as used herein, denotes a derivative which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I-IV. A "pharmaceutically-acceptable prodrug" as used herein, denotes a prodrug which is pharmaceutically acceptable. Pharmaceutically acceptable modifications to the compounds of Formula I-IV are readily appreciated by those of ordinary skill in the art.

The compound(s) of Formulas I-IV may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-IV. The compounds of Formulas I-IV can be synthesized according to the procedures described in the following Schemes 1, 2, 3a, 3b, 3c, 4, 5a, 5b and 5c, wherein the substituents are as defined for Formulas I-IV above, except where further noted. The synthetic methods described below are merely exemplary, and the compounds of the invention may also be synthesized by alternate routes utilizing alternative synthetic strategies, as appreciated by persons of ordinary skill in the art. The following list of abbreviations used throughout the specification represent the following and should assist in understanding the invention:

| | |
|---|---|
| ACN, MeCN | acetonitrile |
| Aq., aq. | aqueous |
| Ar | argon (gas) |
| BOP | benzotriazol-1-yl-oxy Hexafluorophosphate |
| BuLi | Butyllithium |
| $Cs_2CO_3$ | cesium carbonate |
| $CHCl_3$ | chloroform |
| $CH_2Cl_2$, DCM | dichloromethane, methylene chloride |
| Cu(1)I | copper(1) iodide |
| DCC | dicyclohexylcarbodiimide |
| DIC | 1,3-diisopropylcarbodiimide |
| DIEA, DIPEA | diisopropylethylamine |
| DME | dimethoxyethane |
| DMF | dimethylformamide |
| DMAP | 4-dimethylaminopyridine |
| DMS | dimethylsulfide |
| DMSO | dimethylsulfoxide |
| EDC, EDCI | 1-(3-dimethylaminopropyl)-3-ethylcarbodiimide |
| $Et_2O$ | diethyl ether |
| EtOAc | ethyl acetate |
| FBS | fetal bovine serum |
| G, gm | gram |
| h, hr | hour |
| $H_2$ | hydrogen |
| $H_2O$ | water |
| HATU | O-(7-azabenzotriazol-1-yl)-N,N,N',N'-tetramethyluroniumhexafluorophosphate |
| HBr | hydrobromic acid |
| HCl | hydrochloric acid |
| HOBt | 1-hydroxybenzotriazole hydrate |
| HOAc | acetic acid |
| HPLC | high pressure liquid chromatography |
| IPA, IpOH | isopropyl alcohol |
| $K_2CO_3$ | potassium carbonate |
| KI | potassium iodide |
| LG | leaving group |
| LDA | Lithium diisopropylamide |
| LiOH | lithium hydroxide |
| $MgSO_4$ | magnesium sulfate |
| MS | mass spectrum |
| MeOH | methanol |
| $N_2$ | nitrogen |
| $NaCNBH_3$ | sodium cyanoborohydride |
| $Na_2CO_3$ | sodium carbonate |
| $NaHCO_3$ | sodium bicarbonate |
| NaH | sodium hydride |
| NaI | sodium iodide |
| $NaBH_4$ | sodium borohydride |
| NaOH | sodium hydroxide |
| $Na_2SO_4$ | sodium sulfate |
| $NH_4Cl$ | ammonium chloride |
| $NH_4OH$ | ammonium hydroxide |
| $P(t-bu)_3$ | tri(tert-butyl)phosphine |
| PBS | phospate buffered saline |
| Pd/C | palladium on carbon |
| $Pd(PPh_3)_4$ | palladium(0)triphenylphosphine tetrakis |
| $Pd(dppf)Cl_2$ | palladium(1,1-bisdiphenylphosphinoferrocene) II chloride |
| $Pd(PhCN)_2Cl_2$ | palladium di-cyanophenyl dichloride |
| $Pd(OAc)_2$ | palladium acetate |
| $Pd_2(dba)_3$ | tris(dibenzylideneacetone) dipalladium |
| PyBop | benzotriazol-1-yl-oxy-tripyrrolidino-phosphonium hexafluorophosphate |
| RT, rt | room temperature |
| RBF, rbf | round bottom flask |
| TLC, tlc | thin layer chromatography |
| TBAF | Tetrabutylammonium flouride |
| TBTU | O-benzotriazol-1-yl-N,N,N,N'-tetramethyluronium tetrafluoroborate |

| | |
|---|---|
| TEA, Et₃N | triethylamine |
| TFA | trifluoroacetic acid |
| THF | tetrahydrofuran |
| UV | ultraviolet light |

While the synthetic strategy for preparing the compounds of Formulas I-IV may vary, as appreciated by persons skilled in the art, one strategy for devising a method of making compounds of these formulas is by retro-synthetic disconnection. For example,

I

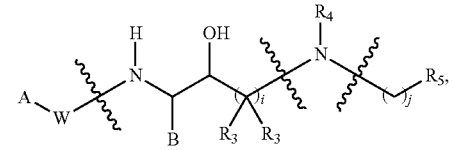

II

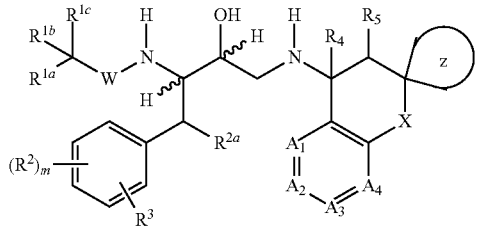

II-A

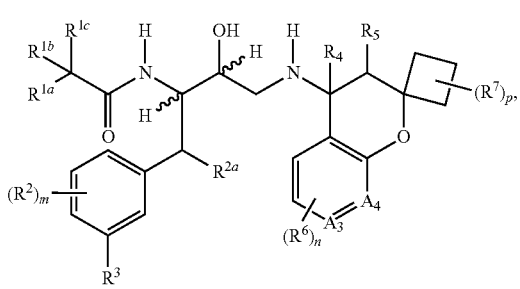

III-A

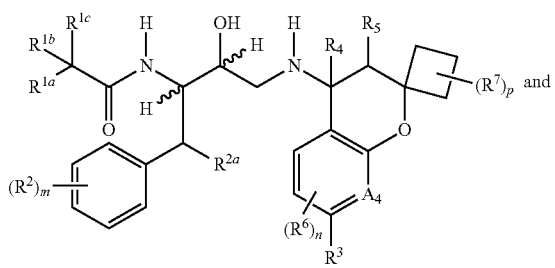

IV

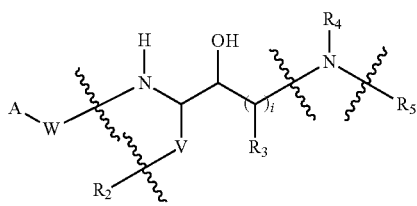

as shown in Formulas I-IV above, each squiggly line represents a possible point of bond-construction, whose order is generally dependent upon the particular compound being synthesized. Such bond construction methods are generally described in synthetic Schemes 1-5c below.

Scheme 1

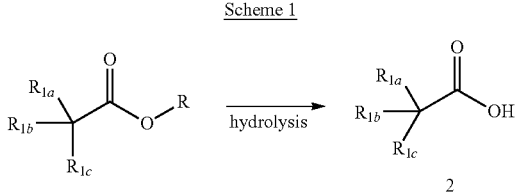

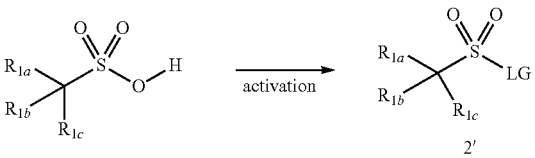

Scheme 1 describes a few methods for preparing $C(R^{1a})(R^{1b})(R^{1c})$—W acids, useful for preparing compounds of Formulas I-IV (see scheme 2) wherein W is —C(O)— or —S(O)2— and each of $R^{1a}$, $R^{1b}$ and $R^{1c}$, independently, is $C_{1-10}$-alkyl, $C_{2-10}$-alkenyl, $C_{2-10}$-alkynyl, R1-$C_{1-10}$-alkyl-, R1-$C_{2-10}$-alkenyl- or $R^1$—$C_{2-10}$-alkynyl-("L" in scheme 1 corresponds to the $C_{1-10}$-alkyl, $C_{2-10}$-alkenyl or $C_{2-10}$-alkynyl of A defined in A-W above or of $C(R^{1a})(R^{1b})(R^{1c})$ defined herein). Desired $C(R^{1a})(R^{1b})(R^{1c})$—W groups and A-W groups may be commercially available and purchased, or may be made by known, conventional methods. As shown, esters 1 can be hydrolyzed to their corresponding acids 2 using known bases, such as NaOH or LiOH. Acids 2 can then be coupled to an amine (not shown) to prepare compounds of Formula I-IV. Similarly, sulfonic acids 1' can be converted to an activated sulfonate 2' by reaction with oxalyl chloride, for example, to prepare the corresponding sulfonyl chloride 2'. The sulfonyl chloride 2' can be reacted with an amine to prepare compounds of Formula I-IV.

Scheme 2

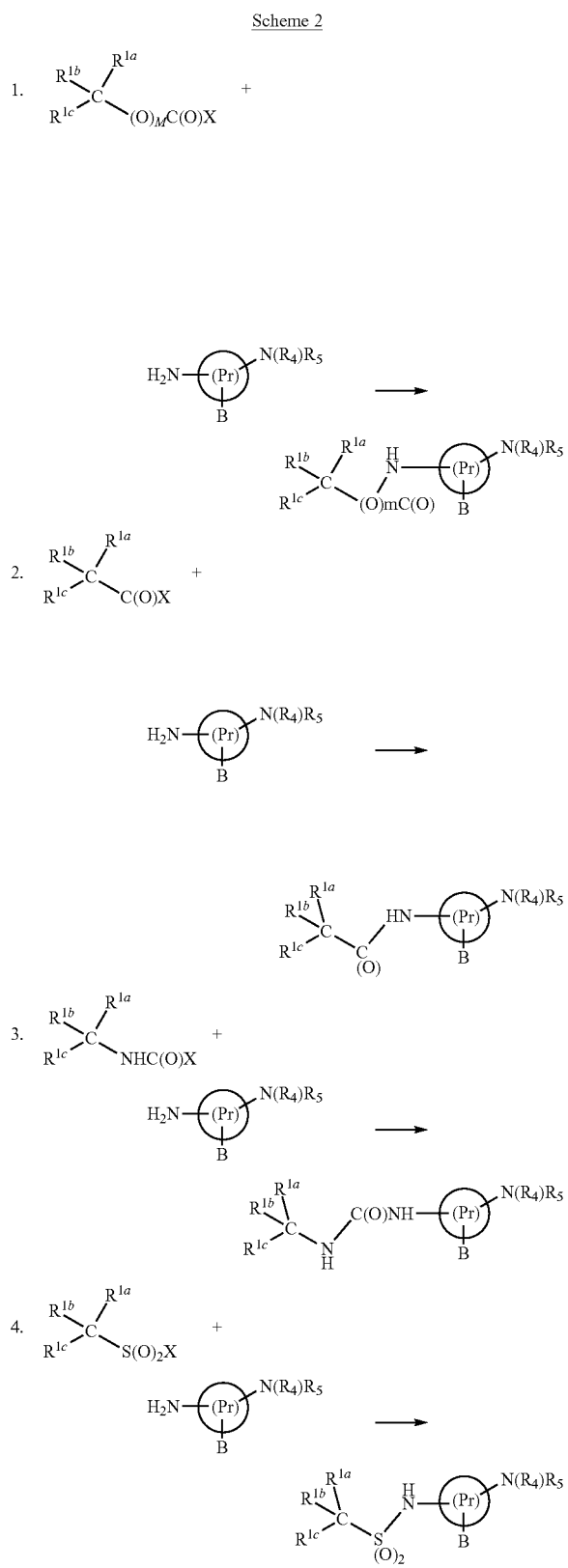

Desired $C(R^{1a})(R^{1b})(R^{1c})$—W groups of Formulas I, II, II-A, III-A and III-B and A-W groups of Formula IV, which may be substituted with various substitutions including one or more $R^7$ groups, can be coupled to the core hydroxyl-propyl backbone structure, generally designated in Scheme 2 as "Pr" group, by various coupling methods as described in Scheme 2. In each of the 4 sub-schemes, X refers generally to a "LG" or a "leaving group" such as a halide (bromine, chlorine, iodine or fluorine), alkylsulfonate and other known groups (also see definitions herein) which generally forms an electrophilic species ($E^+$) and m is an integer from 0-1. The $NH_2$ group (primary amine) is a nucleophilic species ($Nu^-$), as is secondary amines, hydroxides, alkoxides, an anionic carbon species and the like, which should be sufficiently strong to the attack the $E^+$ species and displace the leaving group X thereby effecting a coupling of A-W to the Pr backbone. Examples of suitable electrophilic carbonyl species include, without limitation, acid halides, mixed anhydrides, aldehydes, carbamoyl-chlorides, sulfonyl chlorides, acids activated by coupling with activating reagents such as TBTU, HBTU, HATU, HOBT, BOP, PyBOP and carbodiimides (DCC, EDC and the like), and other electrophilic species including halides, isocyanates, daizonium ions and the like.

The coupled adduct of $C(R^{1a})(R^{1b})(R^{1c})$—W and Pr or A-W and Pr, shown as products in sub-schemes 1-4, can be brought about using various conventional methods. For example, an amide or a sulfonamide linkage, as shown in sub-schemes 2 and 4, can be made utilizing an amine on the Pr intermediate and an activated electrophilic species, on the A-W group such as the acid chloride or sulfonyl chloride as shown. The reaction proceeds generally in the presence of a suitable solvent and/or base. Suitable solvents include, without limitation, generally non-nucleophilic, anhydrous solvents such as toluene, $CH_2Cl_2$, THF, DMF, N,N-dimethylacetamide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Similarly, carbamates as illustrated in sub-scheme 1 and ureas as illustrated in sub-scheme 3 may be made as shown, wherein X has the same definition as above, using the same coupling methods described above for sub-schemes 2 and 4. While the above methods are so described, they are not exhaustive, and other methods for linking $C(R^{1a})(R^{1b})(R^{1c})$—W groups and A-W groups and desired Pr groups together may be utilized as appreciated by those skilled in the art.

The coupling methods described in sub-schemes 1-4 of scheme 2 are also applicable for coupling desired $C(R^{1a})(R^{1b})(R^{1c})$—W and A-W intermediates to desired Pr intermediates not containing desired $R^5$ groups, although sub-schemes 1-4 as illustrated do contain $R^5$ groups.

Scheme 3a
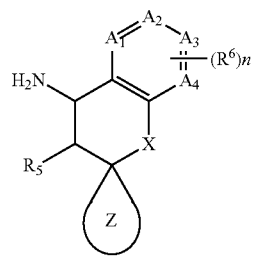
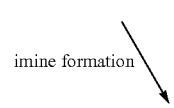
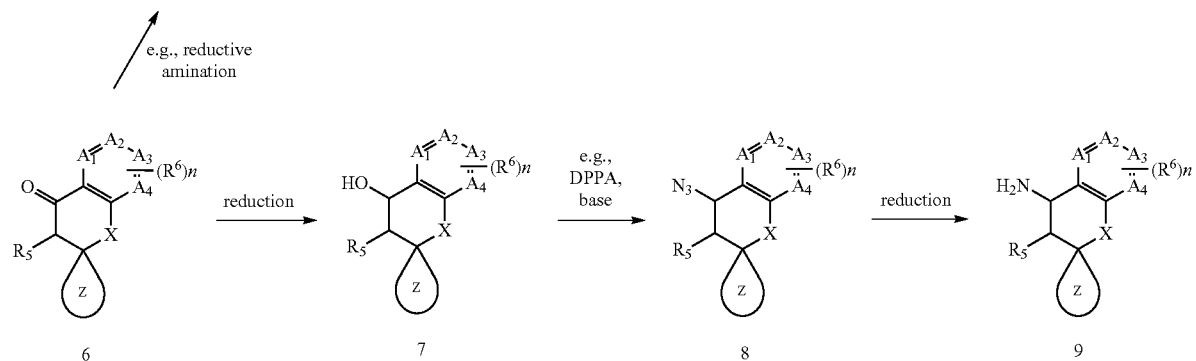
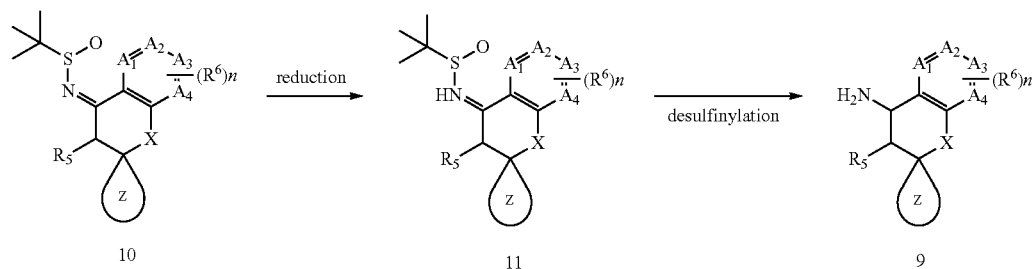

Amine intermediate 9 (one embodiment of an $R^5$ ring of the compounds of Formula I) can be prepared according to the method generally described in Scheme 3a. As shown, spiro-substituted-(ring Z) or gem-dialky-substituted (not shown) oxo-$R^5$ ring intermediates 6 (shown where $R^5$ of Formula I is a spiro fused chroman or aza-chroman ring, as in Formulas II, II-A, III-A and III-B) can be converted directly to the amino-intermediate 9 using known reductive amination methods, such as in the presence of sodium cyanoborohydride and ammonium acetate. Alternatively, the carbonyl may be reduced to the corresponding alcohol using conventional reducing reagents or catalytic hydrogenation conditions, andthen converted to form the corresponding azido-intermediate 8 using known reagents, such as DPPA, in the presence of a suitable base as shown. Intermediate 8 may be reduced with a suitable reducing agent or by known methods, including triphenylphosphine, trimethylphosphine or lithium aluminum hydride (LAH), to produce the desired amino adduct 9.

Yet another method of forming the amine adduct 9, can be via an imine formation to form compound 10. The imine double bond of compound 10 may then be successively reduced and deprotected to yield the primary amine product 9. Such steps may be conducted using known, conventional methods, as appreciated by those skilled in the art.

Scheme 3b

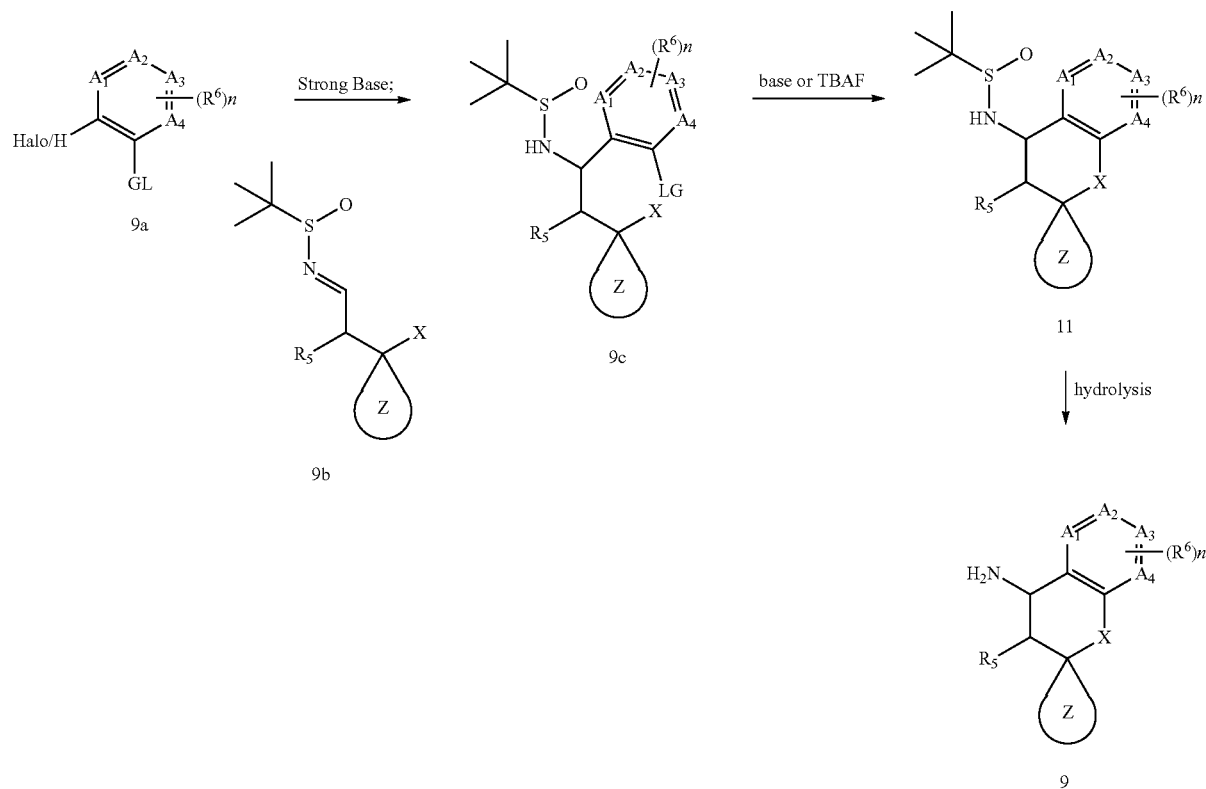

Alternatively, amine intermediates 9 may be prepared by the method shown in scheme 3b above. Desirably substituted compounds 9a may first be treated with a strong base, such as LDA or n-butyl lithium, to form an anion that may then be added to a sufinylimine intermediate 9b (nucleophilic group X may be protected or unprotected as appreciated by one of ordinary skill in the art) to form the corresponding coupled adduct 9c. Open intermediate 9c (X may first be deprotected as necessary) may subsequently be treated with a strong base, such as NaH (wherein, e.g., X is a nucleophile such as OH or $NHR^6$) or TBAF (wherein, e.g., X is $OSiR_3$) to form intermediate 11. Intermediate 11 may then be deprotected to provide spiro amine compound 9.

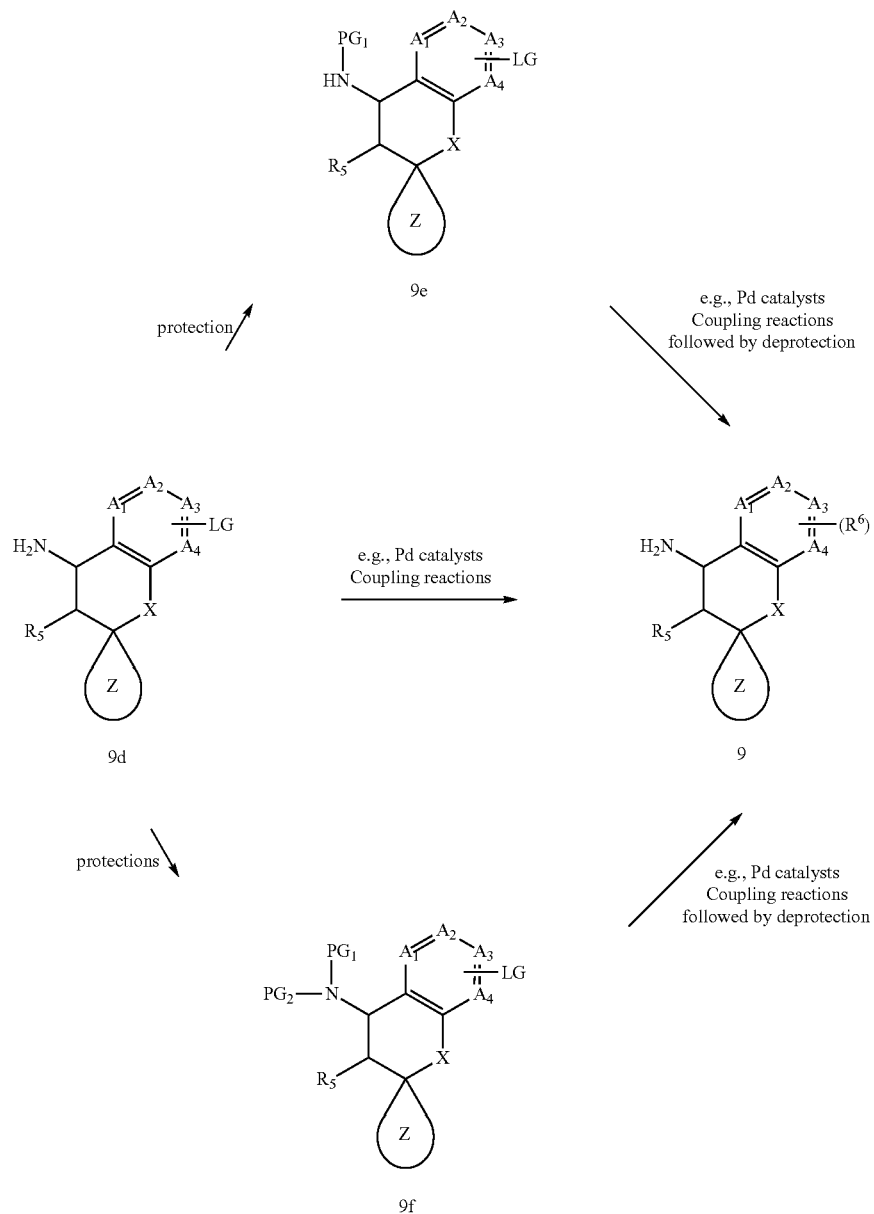

Amine intermediate 9 can also be prepared from other amine 9 precursors such as 9d containing an appropriate leaving group (LG, e.g., Cl, Br, I, OTf, etc) as shown in scheme 3c above. Using this method, compound 9d, with the amino group used as is, mono-protected (compound 9e), or doubly protected (compound 9f having PG1 and PG2 protecting groups as shown), can be coupled with the requisite neucleophilic reagents with a catalyst such as a Pd-catalyst selected from appropriate sources. The said neucleophilic reagents can be selected from, but not limited to, commercial or pre-formed boronic reagents, stannane reagents, Zinc- or Magnesium-derived metallic reagents. After deprotection if necessary, amine intermediate 9 can be obtained.

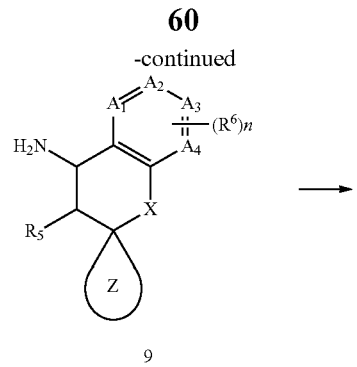

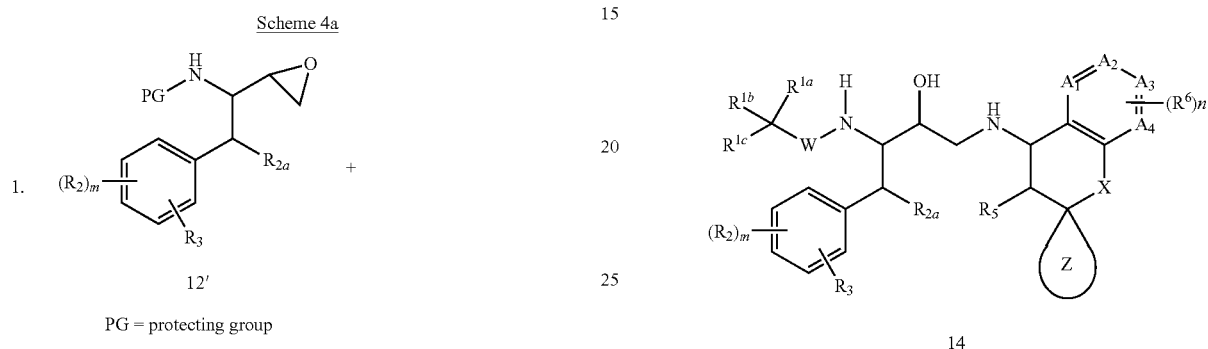

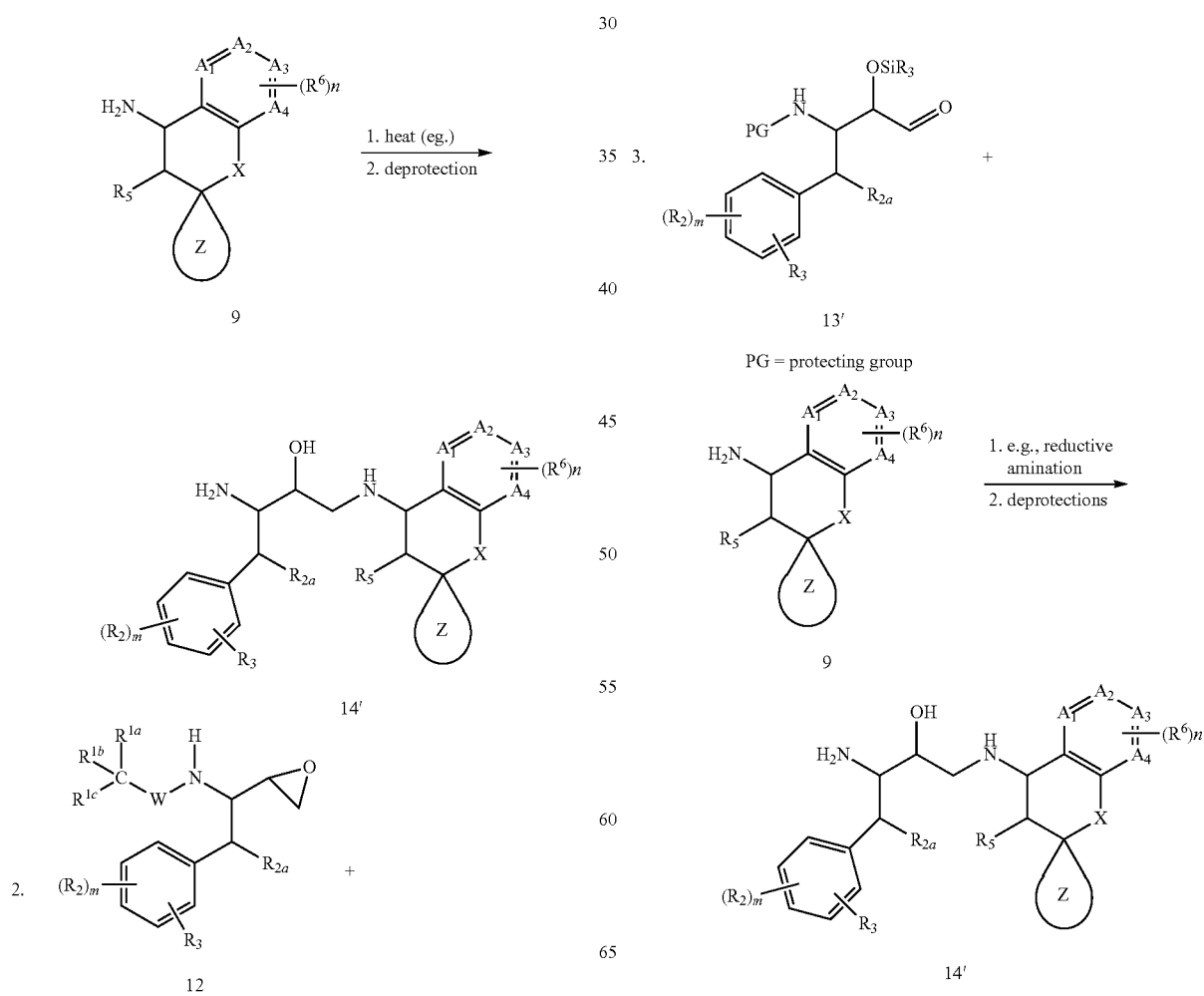

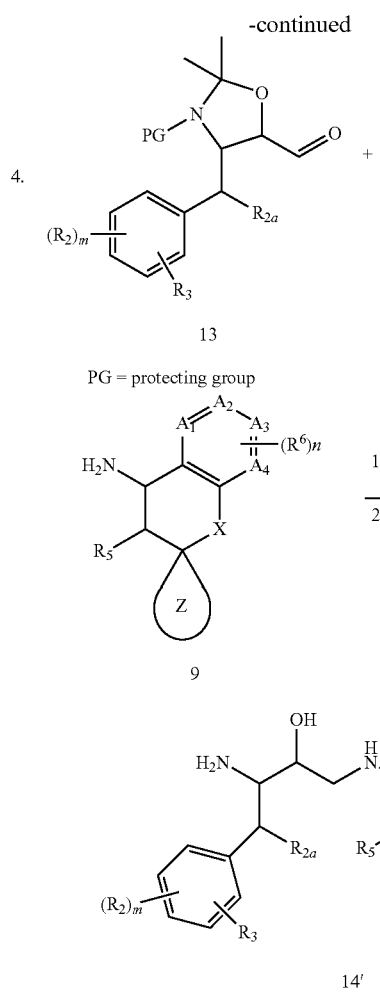

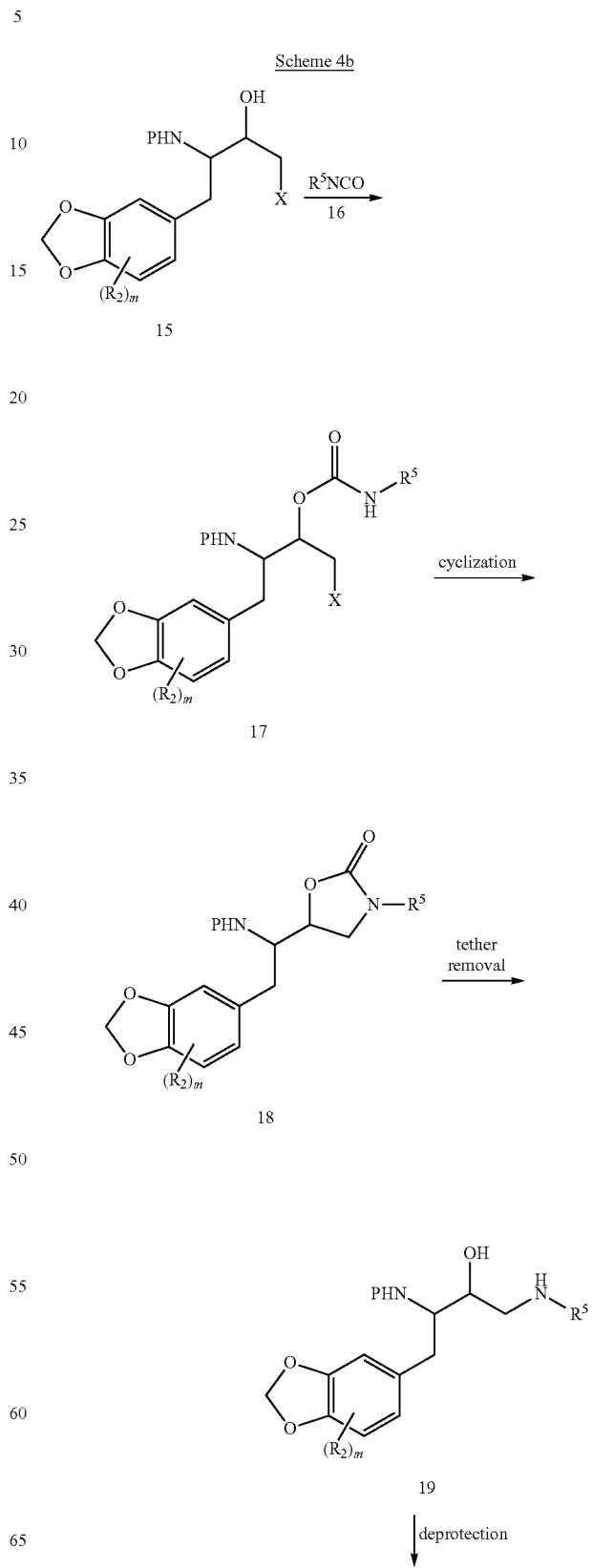

The imine can then be reduced using a known reducing agent, such as a hydride or borohydride, the reduced intermediate may be deprotected to provide an intermediate 14' having an amine useful to prepare compounds 14 of Formulas I-IV.

Scheme 4a describes, generally, multiple different methods for constructing the bond between the amino-propyl backbone starting material (also referred to herein as "Pr") or intermediate 12' (sub-scheme 1) or 12 (sub-scheme 2) and an $R^5$ ring intermediate 9, thereby synthesizing a desired intermediate 14' or a final compound 14 of Formulas I-IV (as shown, $R^2$ of Formula I is a substituted phenyl ring. As appreciated, the scope of the invention is not so limited, and $R^2$ can also be other rings, such as pyridine, as defined and/or exemplified herein). One method to make this bond is to react an epoxide intermediate 12 or 12' (Note: the epoxide 12 or 12' may be purchased commercially or made via known, published methods such as from the olefin precursor), with an amino-$R^5$ intermediate 9, as shown. The reaction may proceed in the presence of a polar solvent, such as an alcohol or dioxanes, and may require additional reagents, as appreciated by those skilled in the art. Additionally, the reaction may require heat for a period of time. Note that while the scheme described the addition of heat, this is by way of example only, and not every reaction would necessarily require heat, as appreciated by those of ordinary skill in the art. The protecting group may be removed using an acid, such as HCl, such that the bonded adduct 14' is recovered as an HCl salt.

Alternatively, desired intermediates 14' may be synthesized starting with an amine-protected aldehyde intermediate 13' (sub-scheme 3) or 13 (sub-scheme 4) and condensing the aldehyde with a primary or secondary amine 9 to form an imine (not shown, generally formed in-situ and not isolated).

-continued

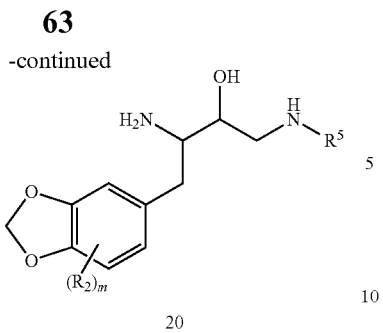

20

X = halogen (e.g. Cl) or other leaving group
P = protecting group

Scheme 4b describes, generally, a method for preparing analogs of intermediate 20, which locks in a desired benzodioxyl $R^2$ group with a desired $R^5$ group, as defined in Formulas I-IV. The strategy, as shown, generally involves use of an internal tether to provide the desired intermediate 20. Intermediate 15, where X is a leaving group such as a halogen (chloride for example) and P is a protecting group, can be reacted with the isocyanate of a desired $R^5$-amine 16, such as chromans, aza-chromans, and the like described in the definitions of $R^5$ herein, to afford the halo-carbamate 17. The amine of carbamate 17 can be used to internally displace leaving group X to form a tethered cyclic intermediate 18. The tethered ring of 18 can be opened to afford desired amine protected intermediate 19. The protecting group may be removed using an acid such as HCl (or base or other suitable conditions depending upon the protecting group used) such that the amine adduct 20 is recovered as an HCl salt.

Scheme 4c

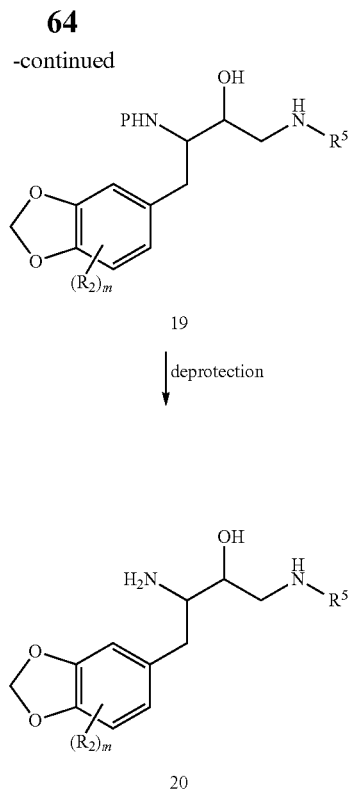

-continued

19

↓ deprotection

20

Y = linker (e.g. C = O)
X = halogen (e.g. Cl) or other leaving group
LG = Leaving group (e.g. OAr or imidazole)

Scheme 4c describes, generally, another method for preparing analogs of intermediate 20, which locks in a desired benzodioxyl $R^2$ group with a desired $R^5$ group, as defined in Formulas I-IV. As shown, the desired tethered intermediate 18b may be formed in another way. For example, and as shown in scheme 4c, an activated carbonated form of intermediate 16b (without the NH—$R^5$) could react with the desired amine to form the open, untethered intermediate 17b. For instance, a desired chlorohydrin 15 (scheme 4b) can be acylated with 4-nitrophenylchloroformate to generate an active carbonate (not shown). This active carbonate should readily react with a desired chromyl amine or azachromyl amine fragment (NH$_2$—$R^5$) to form the chlorourethane 17b (where X is Cl and Y is C(O)). Cyclization of this intermediate without isolation affords the oxazolidinone 18b which then can be deprotected to form the intermediate oxazolidinone bis hydrochloride salt 19. The amine of salt 19 can be further deprotected and isolated as the tris-HCl salt useful for preparing compounds of Formulas I-IV.

Another example may utilize a different activating agent, such as 1,1'-carbonyldiimidazole, in place of 4-nitrophenylchloroformate to form an activated chlorohydrin or halohydrin type intermediate, which functions similar to intermediate 17.

Scheme 5a

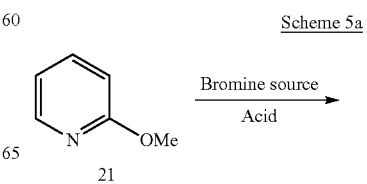

21

-continued

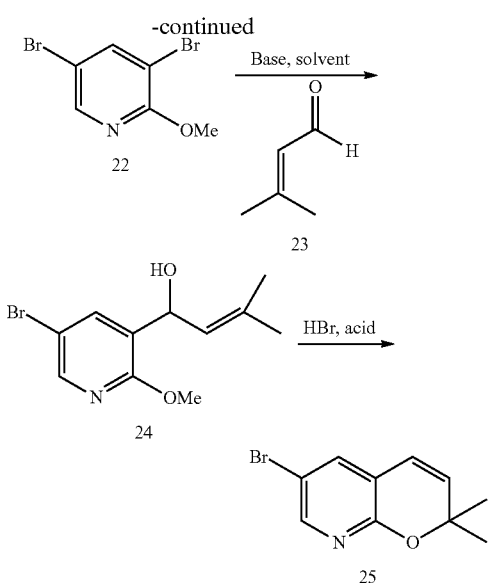

Scheme 5a describes, generally, one method for constructing gem-dialkyl or spiro Z ring compounds (not shown) 9 in schemes 3a and 3b above, by first preparing the corresponding bromo-intermediate 25 as schematically illustrated above. As shown, a methoxy pyridine compound 21 can be reacted with a bromine source, such as bromine in HOAc, in the presence of an acid to form the corresponding dibrominated intermediate 22. Compound 22 can be treated with a suitably strong base, such as a lithium base (e.g. BuLi) in the presence of a suitable non-protic, anhydrous colvent, such as ether, to form the lithiated species, which may then be treated with a suitable aldehyde, such as the allylic aldehyde shown above, to afford the corresponding alcohol adduct 24. Intermediate 24 may then be treated with a suitable acid, such as HBr, to protonate and condense the compound effecting ring closure to afford the cyclized adduct 25.

Scheme 5b describes, generally, another method for constructing gem-dialkyl (not shown) or spirocyclobutane Z ring compounds (shown) 9 in schemes 3a and 3b above, by first preparing the corresponding bromo-keto-intermediate 31 as schematically illustrated above. As shown, a methoxy picolinic acid 26 can be reacted with an aqueous bromine source, such bromine, in the presence of a suitable solvent, such as DCM/water, to form the corresponding brominated intermediate 27. The acid group of compound 27 can be converted to the corresponding Weinreb amide under known conditions, such as using EDC-HCl in the presence of HOBt, a base such as TEA, and a suitable solvent such as DCM. Weinreb 28 may be treated with a desired Grignard reagent, such as vinylmagnesium bromide as shown above, in the presence of a suitable solvent, such as THF, to form the allylic ketone species 29. Alternatively, the Weinreb amide species may be bypassed by treating compounds 28 directly with the Grignard reagents, such the one shown above, to afford compounds 29. Compound 29 can undergo a Grubb's metathesis, such as by utilizing exo-methylene cyclobutane as shown above, to form intermediate 30, which may then be cyclized to ring closure using a suitable acidic environment, such as in EtOH/HCl, to provide the desired compounds 31. An additional method to prepare mono-substituted aza-chroman compounds, but not gem-dialkyl or spiro aza-chroman compounds 31 is described in Sarges et at, *J. Med. Chem.,* 1990, 33, 1859-1865, which disclosure is hereby incorporated herein by reference in its entirety. The keto-intermediate 31 can then be converted to the corresponding primay amino species using the chemistry taught herein.

Scheme 5b

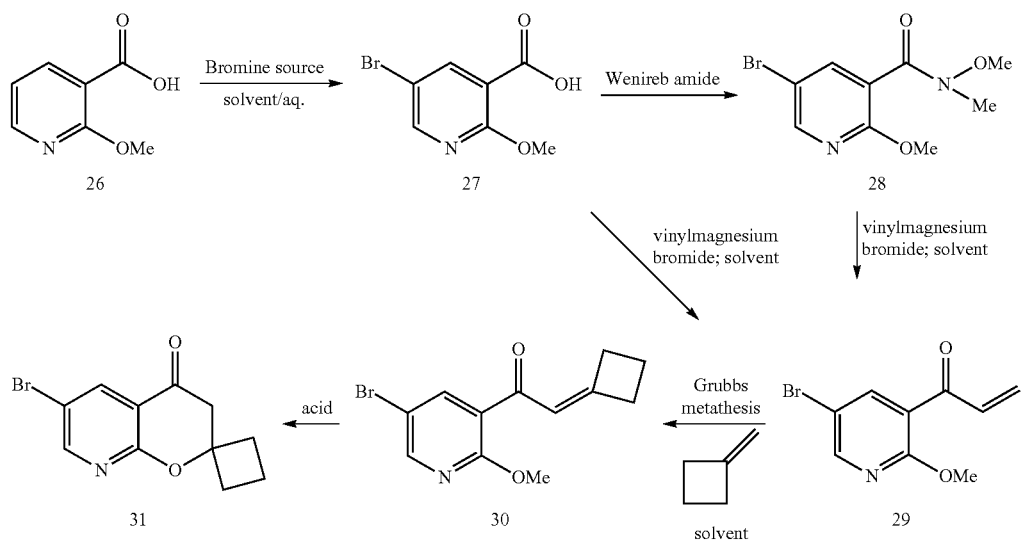

Scheme 5c

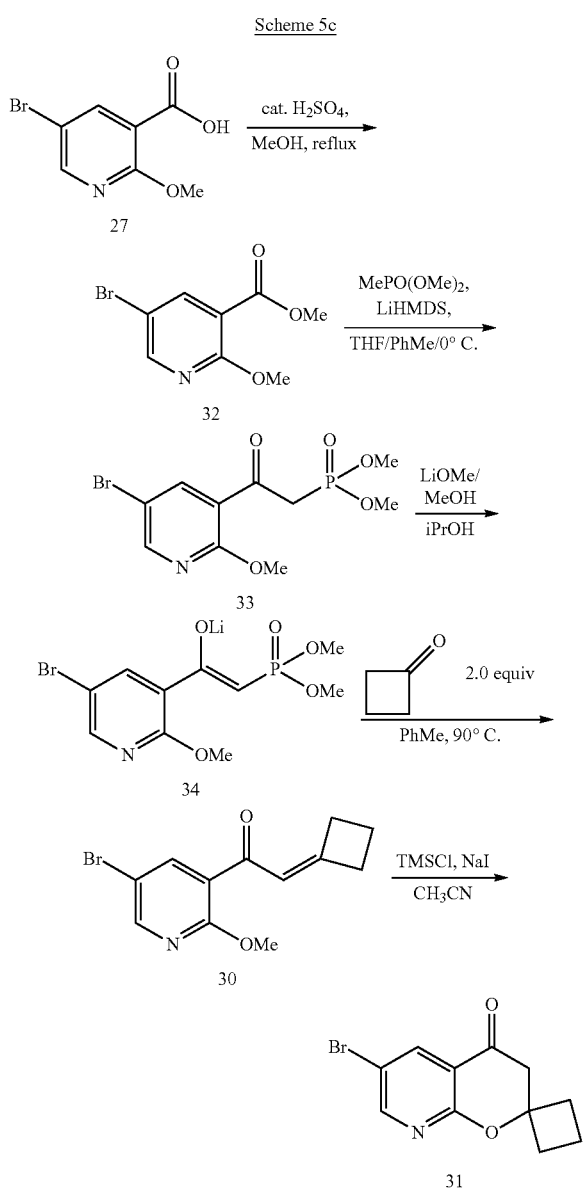

Scheme 5c describes, generally, yet another method for constructing gem-dialkyl (not shown) or spirocyclobutane Z ring intermediates (shown) 30 in scheme 5b above. Compound 30 in turn may be converted to the desired bromo-keto-intermediate 31 as schematically illustrated above. As shown, brominated intermediate 27 from scheme 5b can be treated with an acid, such as sulfuric acid as shown, in a protic solvent, such as MeOH, to form the corresponding methyl ester intermediate 32. The ester group of compound 32 can be converted to the corresponding phosphonate ester under Horner-Emmons type conditions, which are known in the art, such as using a phosphonate species in the presence of a strong base, such as LiHMDS as shown, and a suitable solvent such as THF and toluene. The resulting phosphonate adduct 33 may be deprotonated with a strong base, such as with liOMe in the presence of an alcoholic solvent such as MeOH and/or i-PrOH, and the lithium enolate can then be reacted with cyclobutanone to afford the adduct compound 30 in high yield. Intermediate 30 may then be cyclized to ring closure using suitable conditions, such as those shown above in scheme 5c, to provide the desired compounds 31. Additional description of useful methods which may be used to prepare compounds similar to compound 31 are described in general in Harada et at, JP patent application no. JP08099982A, Yasuda et al, *J. Org. Chem.* 2004, 69, pg 1958, Yazbeck et al, *Org. Process Res. Dev.* 2006, 10, pg 655, and in Keneko et al, *Chem. Pharm. Bull.*, 2004, 52, pg 675, which disclosures are hereby incorporated herein by reference in its entirety. The keto-intermediate 31 can then be converted to the corresponding primay amino species using the chemistry taught herein.

It should be appreciated that schemes 5a, 5b and 5c illustrate exemplary methods for preparing the right-side spiro or gem-dialkyl pieces of compounds of Formulas I-IV. Reaction yields for each step in schemes 5a and 5b range from about 50% to 90+%. Accordingly, these methods may provide a more efficient process for preparing desired intermediates 31. Further, utilizing these methods may afford other spirocyclic rings of differing sizes and heteroatoms, encompassed in the compounds of the present invention.

To enhance the understanding and appreciation of the present invention, the following specific examples (starting reagents, intermediates and compounds of Formulas I-IV) are set forth. The following analytical methods were used to purify and/or characterize the compounds, and intermediates, described in the examples below.

Chromatography:

Unless otherwise indicated, crude product-containing residues were purified by passing the crude material or concentrate through an ISCO brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a solvent gradient of 0% to 40% EtOAc in Hexanes.

Preparative HPLC Method:

Unless otherwise indicated, the compounds described herein were purified via reverse phase HPLC using one of the following instruments: Shimadzu, varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300

MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 8.0 software, available in Chem Office, or (2) by the ISIS database software (Advanced Chemistry Design Labs or ACD software). In some instances, compounds were named with the term "spirocarbocycle" inserted where appropriate. For example, where the chroman is substituted with 2,2-spirocyclobutyl, "2,2-spirocyclobutyl" have been added to the Chem-Draw nomenclature in the appropriate place.

EXAMPLES

The Examples, described herein below, represent various exemplary starting materials, intermediates and compounds of Formulas I-IV, which should assist in a better understanding and appreciation of the scope of the present invention and of the various methods which may be used to synthesize compounds of Formulas I-IV. It should be appreciated that the general methods above and specific examples below are illustrative only, for the purpose of assistance and of understanding the present invention, and should not be construed as limiting the scope of the present invention in any manner.

Example 1

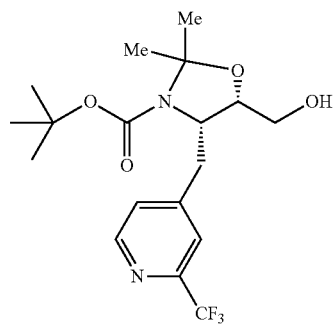 [SMILES: CC(C)(C)OC(=O)N1[C@@H](Cc2ccnc(C(F)(F)F)c2)[C@@H](CO)OC1(C)C]

(4S,5S)-tert-Butyl 5-(hydroxymethyl)-2,2-dimethyl-4-(2-(trifluoromethyl)pyridin-4-yl)methyl)oxazolidine-3-carboxylate Step 1: (S)-Methyl 2-(tert-butoxycarbonyl)-3-(2-(trifluoromethyl)pyridin-4-yl)propanoate The title compound was prepared according to previously reported procedure (see pending U.S. patent application Ser. No. 11/575,187) from (R)-methyl 2-(tert-butoxycarbonyl)-3-iodopropanoate and 4-iodo-2-(trifluoromethyl)pyridine (this starting material was prepared according to a procedure described in *Eur. J. Org. Chem.* 2003, 1559-1568).

Step 2: (4S,5S)-tert-Butyl 5-(hydroxymethyl)-2,2-dimethyl-4-((2-(trifluoromethyl)pyridin-4-yl)methyl) oxazolidine-3-carboxylate The title compound was prepared according to procedure described in U.S. patent application Ser. No. 11/575,187,
from (S)-methyl 2-(tert-butoxycarbonyl)-3-(2-(trifluoromethyl)pyridin-4-yl)propanoate.

Example 2

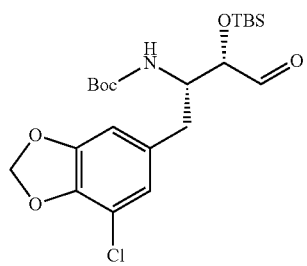 [SMILES: CC(C)(C)OC(=O)N[C@@H](Cc1cc(Cl)c2c(c1)OCO2)[C@@H](C=O)O[Si](C)(C)C(C)(C)C]

tert-Butyl (2S,3S)-3-(tert-butyldimethylsilyloxy)-1-(7-chlorobenzo[d][1,3]dioxol-5-yl)-4-oxobutan-2-ylcarbamate Step 1: (5)-tert-Butyl 3-(7-chlorobenzo[d][1,3]dioxol-5-yl)-1-oxo-1-(thiazol-2-yl)propan-2-ylcarbamate A solution of 2-bromothiazole (3 ml, 37 mmol) in ether (75 mL) was cooled to −78° C. and treated with n-butyllithium 2M in hexanes (18 ml, 37 mmol). After stirring the reaction for 30 minutes, a solution of (S)-methyl 2-(tert-butoxycarbonyl)-3-(7-chlorobenzo[d][1,3]dioxol-5-yl)propanoate (6.610 g, 18 mmol) in ether (75 mL) was added, and the reaction mixture was allowed to stir at −78° C. for 1 hour. The reaction mixture was quenched with saturated NH$_4$Cl solution, washed with water and brine. The organic layers were dried over MgSO$_4$ and concentrated under reduced pressure. Purification of the crude residue by column chromatography gave (5)-tert-butyl 3-(7-chlorobenzo[d][1,3]dioxol-5-yl)-1-oxo-1-(thiazol-2-yl)propan-2-ylcarbamate (4.22 g, 56% yield) as a yellow oil.

Step 2: tert-Butyl (1S,2S)-3-(7-chlorobenzo[d][1,3]dioxol-5-yl)-1-hydroxy-1-(thiazol-2-yl)propan-2-ylcarbamate A cooled solution (0° C.) of (5)-tert-butyl 3-(7-chlorobenzo[d][1,3]dioxol-5-yl)-1-oxo-1-(thiazol-2-yl)propan-2-ylcarbamate (4.220 g, 10 mmol) in EtOH (60 mL) was added dropwise via cannula to a cooled solution (−78° C.) of lithium tri-tert-butoxyaluminum hydride 1M in THF (21 ml, 21 mmol) in EtOH (40 mL). After stirring for 2 hours, the reaction mixture was quenched with 1N HCl and diluted with EtOAc. The organic layer was washed with water, saturated NaHCO$_3$ solution, and brine. The organic layer was dried over MgSO$_4$ and concentrated under reduced pressure. The crude residue was crystallized from hot EtOH/water and the solid was collected yielding tert-butyl (1S,2S)-3-(7-chlorobenzo[d][1,3]dioxol-5-yl)-1-hydroxy-1-(thiazol-2-yl)propan-2-ylcarbamate (3.250 g, 77% yield) as a white solid.

Step 3: tert-Butyl (1S,2S)-1-(tert-butyldimethylsilyloxy)-3-(7-chlorobenzo[d][1,3]dioxol-5-yl)-1-(thiazol-2-yl)propan-2-ylcarbamate A suspension of tert-butyl (1S,2S)-3-(7-chlorobenzo[d][1, 3]dioxol-5-yl)-1-hydroxy-1-(thiazol-2-yl)propan-2-ylcarbamate (3.250 g, 8 mmol) in DCM (24 mL) was treated with 2,6-lutidine (1 ml, 12 mmol) followed by tert-butyldimethylsilyl triflate (2 ml, 9 mmol) and was allowed to stir at RT for 2 hours. An additional equivalent of TBS triflate was added followed by an additional equivalent of base. After 1 hour, DIEA (2 ml, 12 mmol) was added, followed by di-tert-butyl-dicarbonate 1M in THF (8 ml, 8 mmol), and the reaction mixture was allowed to stir at RT overnight. The reaction mixture was quenched with 2N HCl solution, diluted with DCM, and washed with saturated NaHCO$_3$ solution and brine. The organics were dried over MgSO$_4$ and concentrated under reduced pressure. Purification of the crude residue by column chromatography gave tert-butyl (1S,2S)-1-(tert-butyldimethylsilyloxy)-3-(7-chlorobenzo[d][1,3]dioxol-5-yl)-1-(thiazol-2-yl)propan-2-ylcarbamate (1.850 g, 45% yield).

Step 4: tert-Butyl (2S,3S)-3-(tert-butyldimethylsilyloxy)-1-(7-chlorobenzo[d][1,3]dioxol-5-yl)-4-oxobutan-2-ylcarbamate A solution tert-butyl (1S,2S)-1-(tert-butyldimethylsilyloxy)-3-(7-chlorobenzo[d][1,3]dioxol-5-yl)-1-(thiazol-2-yl)propan-2-ylcarbamate (1.85 g, 3.51 mmol) in MeCN (14 mL) was treated with 4A mol. seives and was allowed to stir at RT for 10 minutes. Methyl trifluoromethanesulfonate (0.464 ml, 4.21 mmol) was added, and the reaction mixture was allowed to stir for 30 minutes. The reaction mixture was then concentrated under reduced pressure, and the crude residual material was dissolved in MeOH (14 mL), and cooled to 0° C. The mixture was then treated with sodium borohydride (0.398 g, 10.5 mmol) and allowed to warm to RT and stir for an additional 20 minutes. The reaction mixture was diluted with EtOAc, filtered through celite and concentrated under reduced pressure. The residue was dissolved in ACN (10 mL) and water (4 mL) and was treated with mercury(II) chloride (0.953 g, 3.51 mmol). After stirring for 30 minutes the reaction mixture was diluted with ether and filtered through a short plug of silica. The filtrate was then concentrated under reduced pressure and the crude residue was purified by column chromatography yielding tert-butyl (2S,3S)-3-(tert-butyldimethylsilyloxy)-1-(7-chlorobenzo[d][1,3]dioxol-5-yl)-4-oxobutan-2-ylcarbamate.

Example 3

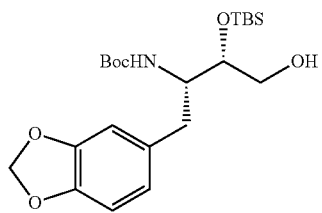 [SMILES: CC(C)(C)OC(=O)N[C@@H](Cc1ccc2c(c1)OCO2)[C@@H](CO)O[Si](C)(C)C(C)(C)C]

tert-Butyl (2S,3S)-1-(benzo[d][1,3]dioxol-5-yl)-3-(tert-butyldimethylsilyloxy)-4-hydroxybutan-2-ylcarbamate Step 1: N-((2S,3S)-1-(benzo[d][1,3]dioxol-4-yl)-3,4-bis(tert-butyldimethylsilyloxy)butan-2-yl)-2-methylpropane-2-sulfinamide To a slurry of magnesium turnings (1.09 g, 44.8 mmol) in 5 mL of THF was added iodine (0.0650 g, 0.256 mmol), followed by a solution of 5-(chloromethyl)benzo[d][1,3]dioxole (6.55 g, 38.4 mmol) in 30 mL of THF. After 1 minute, the exothermic reaction mixture was placed in an ice bath for 1 minute and then stirred at ambient temperature for 1 hour. TMEDA (7.68 ml, 51.2 mmol) was added to the reaction and the mixture was cooled to −78° C. for 5 minutes at which point a solution of (E)-N-((S)-2,3-bis(tert-butyldimethylsilyloxy)propylidene)-2-methylpropane-2-sulfinamide (5400 mg, 12.8 mmol) in 25 mL THF was added via a syring pump over 15 minutes. The reaction was allowed to warm to RT over the course of 2 hours then stirred at RT for an additional hour. The mixture was diluted with ethyl acetate (100 mL) and poured in saturated ammonium chloride (250 mL). The aqueous layer was extracted with ethyl acetate (2×250 mL) and the combined organic layers were washed with water and then brine and dried over Na$_2$SO$_4$. The organic colvents were filtered, concentrated under reduced pressure and the crude material was purified by silica gel to provide N-((2R,3S)-1-(benzo[d][1,3]dioxol-5-yl)-3,4-bis(tert-butyldimethylsilyloxy)butan-2-yl)-2-methylpropane-2-sulfinamide (4.51 g, 63.1% yield) as a colorless oil.

Step 2: tert-Butyl (2S,3S)-1-(benzo[d][1,3]dioxol-4-yl)-3-(tert-butyldimethylsilyloxy)-4-hydroxybutan-2-ylcarbamate To a solution of N-((2S,3S)-1-(benzo[d][1,3]dioxol-5-yl)-3,4-bis(tert-butyldimethylsilyloxy)butan-2-yl)-2-methylpropane-2-sulfinamide (2300 mg, 4 mmol) in 25 mL of ethanol at 0° C. was added 4M HCl in dioxane (6 ml, 25 mmol). After stirring at 0° C. for a total of 7 hours, TEA (4 ml, 29 mmol) was added dropwise followed by addition of 25 mL of DCM and di-tert-butyl dicarbonate (2 g, 9 mmol). The mixture was stirred at rt for 48 hours, then diluted with DCM (50 mL) and poured in saturated ammonium chloride (250 mL). The aqueous layer was extracted with DCM (4×100 mL). The combined organic layers were washed with water and brine and dried over Na$_2$SO$_4$, filtered and concentrated under reduced pressure, to provide an oil that was flashed through a plug of silica gel to provide tert-butyl (2S,3S)-1-(benzo[d][1,3]dioxol-5-yl)-3-(tert-butyldimethylsilyloxy)-4-hydroxybutan-2-ylcarbamate as a colorless oil.

Example 4

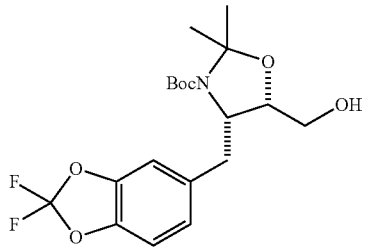

(4S,5S)-tert-Butyl 4-((2,2-difluorobenzo[d][1,3]dioxol-5-ylmethyl)-5-(hydroxymethyl)-2,2-dimethyloxazolidine-3-carboxylate Step 1: (S)-Methyl 2-(tert-butoxycarbonyl)-3-(2,2-difluorobenzo[d][1,3]dioxol-5-yl)propanoate To a 25 mL RBF was added zinc powder (1.03 g, 15.8 mmol) and iodine (0.0161 g, 0.0633 mmol). The mixture was heated with a heat gun for 5 minutes and the resulting mixture was then flushed with nitrogen 3 times and allowed to cool to rt. A solution of (R)-methyl 2-(tert-butoxycarbonyl)-3-iodopropanoate (3.47 g, 10.5 mmol) in 5 mL of DMF was added dropwise to the mixture over 3 minutes and the resulting grey slurry was stirred at 0° C. for 20 minutes before being warmed to rt. After stirring at rt for 30 minutes, 5-bromo-2,2-difluorobenzo[d][1,3]dioxole (2.50 g, 10.5 mmol), $Pd_2(dba)_3$ (0.193 g, 0.211 mmol) and S(Phos) (0.346 g, 0.844 mmol) were added and the reaction mixture was heated to 40° C. for 2 hours. The resulting mixture was cooled to rt and partitioned between ethyl acetate (50 mL) and a solution of ~9:1 saturated ammonium chloride/ammonium hydroxide pH=9 (250 mL). The aqueous layer was extracted with ethyl acetate (3×100 mL) and the combined organic layers were washed with water, brine, and dried over sodium sulfate. Concentration of the filtered solvents and purification of resulting crude material by silica gel chromatography provided (S)-methyl 2-(tert-butoxycarbonyl)-3-(2,2-difluorobenzo[d][1,3]dioxol-5-yl)propanoate (1.89 g, 49.9% yield) as a slightly brown oil.

Step 2: S-2-tert-Butoxycarbonyl)-3-(2,2-difluorobenzo[d][1,3]dioxol-5-yl)propanoic acid To a solution of (S)-methyl 2-(tert-butoxycarbonyl)-3-(2,2-difluorobenzo[d][1,3]dioxol-5-yl)propanoate (1850 mg, 5 mmol) in 50 mL of THF at 0° C. was added LiOH (0.2 M, 26 ml, 5 mmol) over 10 minutes. The reaction was stirred for 2 hours and was then washed with ether (200 mL), acidified to pH 4 with 2 N HCl and extracted with ethyl acetate (4×100 mL). The organics were washed with water and brine and dried over sodium sulfate. Concentration provided (S)-2-(tert-butoxycarbonyl)-3-(2,2-difluorobenzo[d][1,3]dioxol-5-yl)propanoic acid (1.75 g, 98% yield) as a colorless oil.

Step 3: (S)-3-(tert-Butoxycarbonyl)-4-(2,2-difluorobenzo[d][1,3]dioxol-5-yl)-2-oxobutyl acetate To a solution of (S)-2-(tert-butoxycarbonyl)-3-(2,2-difluorobenzo[d][1,3]dioxol-5-yl)propanoic acid (1650 mg, 5 mmol) in 50 mL of THF at 0° C. was added TEA (0.7 ml, 5 mmol) and isobutyl chloroformate (0.6 ml, 5 mmol). The reaction mixture was stirred at 0° C. for 1.5 hours then filtered through a frit containing celite. The solution was cooled to 0° C. and treated with freshly prepared diazomethane (0.5 M in ether, 14 ml, 7 mmol). After stirring for 1 hour at 0° C. the reaction was poured into saturated sodium bicarbonate 250 mL and the aqueous layer was extracted with ethyl acetate (3×100 mL). The combined organic layers were washed with water and then brine and dried over $Na_2SO_4$. Concentration of solvents under reduced pressure provided the diazo ketone as a yellow solid that was carried on without further purification. The derived diazo ketone was taken up in 50 mL of THF and cooled to 0° C. at which point hydrobromic acid, 33 wt. % in acetic acid (0.7 ml, 12 mmol) was added dropwise over 1 minute. After stirring at 0° C. for 1 hour potassium carbonate (1.0 g, 7 mmol) and sodium acetate (4 g, 48 mmol) were added to the mixture. The THF was removed in vacuo and 15 mL of DMF was added to the reaction. The resulting slurry was stirred for 10 minutes at which point the reaction mixture was diluted with ethyl acetate (50 mL) and poured in water 100 mL. The aqueous layer was extracted with ethyl acetate (2×100 mL). The combined organic layers were washed with water and then brine and dried over $Na_2SO_4$. Concentration of the solvents under reduced provided (S)-3-(tert-butoxycarbonyl)-4-(2,2-difluorobenzo[d][1,3]dioxol-5-yl)-2-oxobutyl acetate (1.10 g, 57% yield) as a white solid.

Step 4: (2S,3S)-3-(tert-butoxycarbonyl)-4-(2,2-difluorobenzo[d][1,3]-dioxol-5-yl)-2-hydroxybutyl acetate A solution of (S)-3-(tert-butoxycarbonyl)-4-(2,2-difluorobenzo[d][1,3]dioxol-5-yl)-2-oxobutyl acetate (1100 mg, 2741 µmol) in 45 mL of ethanol cooled to 0° C. was added to lithium aluminum tri-tert-butoxyhydride (1 M in THF, 5481 µA 5481 µmol) in 15 mL of ethanol at −78° C. dropwise via cannula over 5 minutes. After stirring at −78° C. for 2 hours the reaction was quenched with 10 mL of 1 N HCl and the mixture was diluted with ethyl acetate (500 mL). The reaction was poured into 200 mL of water, the layers were separated and the aqueous layer was extracted with ethyl acetate (3×100 mL). The combined organics were washed with water, brine, and dried over sodium sulfate, filtered and concentrated to provide (2S,3S)-3-(tert-butoxycarbonyl)-4-(2,2-difluorobenzo[d][1,3]dioxol-5-yl)-2-hydroxybutyl acetate (1060 mg, 96% yield) as a white solid.

Step 5: (4S,5S)-tert-butyl 4-((2,2-difluorobenzo[d][1,3]dioxol-5-yl)methyl)-5-(hydroxymethyl)-2,2-dimethyloxazolidine-3-carboxylate To a solution of (2S,3S)-3-(tert-butoxycarbonyl)-4-(2,2-difluorobenzo[d][1,3]dioxol-5-yl)-2-hydroxybutyl acetate (1050 mg, 2603 µmol) in 5 mL of DMF was added 2-methoxypropene (872 µl, 9111 µmol) and CSA (181 mg, 781 µmol). The mixture was stirred at rt overnight, and 91 mg of CSA and 0.872 mL of 2-methoxypropene were added. The reaction was stirred for 2 hours, then poured into ice-cold aqueous saturated sodium bicarbonate (150 mL) and extracted with ethyl acetate (3×50 mL). The combined organic layers were washed with water, brine, and dried over sodium sulfate. The derived yellow oil was taken up in 10 mL of methanol cooled to 0° C. and treated with potassium carbonate (1079 mg, 7809 µmol). After warming to rt over the course of 1 hour the reaction was diluted with ethyl acetate (25 mL) and poured in saturated ammonium chloride (50 mL). The aqueous layer was extracted with ethyl acetate (3×50 mL) and the combined organic layers were washed with water and then brine and dried over $Na_2SO_4$. Concentration of the solvents under reduced pressure and purification by silica gel provided (4S,5S)-tert-butyl 4-(2,2-difluorobenzo[d][1,3]dioxol-5-yl)methyl)-5-(hydroxymethyl)-2,2-dimethyloxazolidine-3-carboxylate as a colorless oil.

Example 5

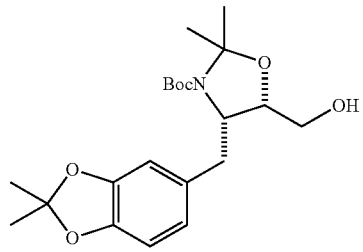

(4S,5S)-tert-Butyl 4-((2,2-dimethylbenzo[d][1,3]dioxol-5-yl]methyl)-5-(hydroxymethyl)-2,2-dimethyloxazolidine-3-carboxylate

Step 1: (Z)-Methyl 2-(tert-butoxycarbonyl)-3-(2-methylbenzo[d][1,3]dioxol-5-yl)acrylate To a solution of methyl 2-(tert-butoxycarbonyl)-2-(dimethoxyphosphoryl)acetate (5255 mg, 17678 µmol) in 25 mL of DCM at 0° C. was added DBU (2665 µl, 17678 µmol) dropwise. To the mixture was then added a solution of 2,2-dimethylbenzo[d][1,3]dioxole-5-carbaldehyde (3000 mg, 16836 µmol) in 10 mL of DCM over 5 minutes so as to maintain internal temperature below 10° C. The reaction was warmed to rt and stiffed overnight before being diluted with DCM (25 mL) and poured in saturated ammonium chloride (100 mL). The aqueous layer was extracted with DCM (1×50 mL). The combined organic layers were washed with 10% aqueous sodium bicarbonate then water then brine and dried over $Na_2SO_4$. Concentration under reduced pressure and purification by silica gel provided (Z)-methyl 2-(tert-butoxycarbonyl)-3-(2,2-dimethylbenzo[d][1,3]dioxol-5-yl)acrylate (5005 mg, 85.1% yield) as a white solid.

Step 2: (S)-Methyl 2-(tert-butoxycarbonyl)-3-(2,2-dimethylbenzo[d][1,3]dioxol-5-yl)propanoate To a slurry of (Z)-methyl 2-(tert-butoxycarbonyl)-3-(2,2-dimethylbenzo[d][1,3]dioxol-5-yl)acrylate (5000 mg, 14311 µmol) in 30 mL of MeOH was added [(1S,1S',2R,2R') Rh(du-anphos)cod]$BF_4$ (101.1 mg, 143.1 µmol) followed by an additional 15 mL of methanol. The mixture was purged with hydrogen 3 times and then sealed at 50 psi of $H_2$. After 3 hours reaction the reaction was concentrated and purified by silica gel chromatography to provide (S)-methyl 2-(tert-butoxycarbonyl)-3-(2,2-dimethylbenzo[d][1,3]dioxol-5-yl)propanoate (5000 mg, 99.43% yield) as a colorless oil.

Step 3: (S)-2-(tert-Butoxycarbonyl)-3-(2,2-dimethyl-benzo[d][1,3]dioxol-5-yl)propanoic acid To a solution of (S)-methyl 2-(tert-butoxycarbonyl)-3-(2,2-dimethylbenzo[d][1,3]dioxol-5-yl)propanoate (5000 mg, 14229 µmol) in 100 mL of THF at 0° C. was added lithium hydroxide (0.2 M, 28458 µl, 14229 µmol) over 10 minutes. After stirring at 0° C. for 1 hour the reaction was poured into a separatory funnel and 100 mL of water was added. The mixture was washed with 150 mL of ether, then acidified to pH 2-3-with 1 N HCl. Ethyl acetate was added, the layers were separated and the aqueous layer was extracted with ethyl acetate (3×100 mL). The combined organics were washed with water and then brine before being dried over sodium sulfate, filtered and concentrated to furnish (S)-2-(tert-butoxycarbonyl)-3-(2,2-dimethylbenzo[d][1,3]dioxol-5-yl) propanoic acid (4005 mg, 83% yield) as a colorless viscous oil.

Step 4: (S)-3-(tert-Butoxycarbonyl)-4-(2,2-dimethyl-benzo[d][1,3]-dioxol-5-yl)-2-oxobutyl acetate To a solution of (S)-2-(tert-butoxycarbonyl)-3-(2,2-dimethylbenzo[d][1,3]dioxol-5-yl)propanoic acid (4000 mg, 11857 mmol) in 100 mL of THF at 0° C. was added TEA (1653 µl, 11857 mmol) and isobutyl chloroformate (1551 µA, 11857 mmol). Reaction was stirred at 0° C. for 2 hours then filtered through a small frit of celite. The filtered solution was cooled to 0° C. and freshly prepared diazomethane (0.5 M in ether, 35570 µl, 17785 µmol) was added. The reaction solution was maintained at 0° C. for 1 hour then poured into saturated sodium bicarbonate 250 mL. The aqueous layer was extracted with ethyl acetate (3×100 mL). The combined organic layers were washed with water and then brine and dried over $Na_2SO_4$. Concentration under reduced pressure provided the diazo ketone as a yellow oil that was carried on without further purification. The diazo ketone was taken up in 100 mL of THF, cooled to 0° C. and treated with HBr (33 wt % in AcOH) (2147 µl, 11857 µmol). After stirring for 30 minutes potassium carbonate (2458 mg, 17785 µmol) and sodium acetate (9726 mg, 118565 µmol) were added and the THF was removed in vacuo. 25 mL of DMF was added and the reaction slurry was stirred at rt for 10 minutes, then diluted with ethyl acetate (50 mL) and poured into water (100 mL). The aqueous layer was extracted with ethyl acetate (2×100 mL) and the combined organic layers were washed with water and then brine and dried over $Na_2SO_4$. Concentration under reduced pressure and purification of the crude by silica gel chromatography (Analogix, 120 g) 0-25% ethyl acetate in hexanes provided (S)-3-(tert-butoxycarbonyl)-4-(2,2-dimethylbenzo[d][1,3]dioxol-5-yl)-2-oxobutyl acetate (3560 mg, 76% yield) as a slightly yellow oil.

Step 5: (2S,3S)-3-(tert-Butoxycarbonyl)-4-(2,2-dimethylbenzo[d][1,3]dioxol-5-yl)-2-hydroxybutyl acetate A solution of (S)-3-(tert-butoxycarbonyl)-4-(2,2-dimethylbenzo[d][1,3]dioxol-5-yl)-2-oxobutyl acetate (3270 mg, 8311 µmol) in 100 mL of ethanol was cooled to −78° C. and added to a solution of lithium aluminum tri-tert-butoxyhydride (16623 µl, 16623 µmol) in 45 mL of ethanol at −78 C dropwise via a cannula over 10 minutes. After stirring at −78° C. for 2 hours the reaction was quenched with 25 mL of 1 N HCl and diluted with ethyl acetate (500 mL). The mixture was poured into 200 mL of water, the layers were separated and the aqueous layer was extracted with ethyl acetate (3×100 mL). The combined organics were washed with water, brine, and dried over sodium sulfate and concentrated to provide (2S,3S)-3-(tert-butoxycarbonyl)-4-(2,2-dimethylbenzo[d][1,3]dioxol-5-yl)-2-hydroxybutyl acetate (3220 mg, 98% yield) as a white solid.

Step 6: (4S,5S)-tert-butyl 4-((2,2-dimethylbenzo[d][1,3]dioxol-5-yl)methyl)-5-(hydroxymethyl)-2,2-dimethyloxazolidine-3-carboxylate To a solution of (2S,3S)-3-(tert-butoxycarbonyl)-4-(2,2-dimethylbenzo[d][1,3]dioxol-5-yl)-2-hydroxybutyl acetate (1350 mg, 3414 mmol) in 5 mL of DMF was added 2-methoxyprop-1-ene (1961 µl, 20483 µmol) and ((1S,4R)-7,7-dimethyl-2-oxobicyclo[2.2.1]heptan-1-yl)methanesulfonic acid (397 mg, 1707 µmol). After stirring for 20 hours the reaction was poured into ice-cold aqueous saturated sodium bicarbonate (150 mL) and extracted with ethyl acetate (3×50 mL). The combined organic layers were washed with water, brine, and dried over sodium sulfate. The orange oil was taken up in 30 mL of methanol, cooled to 0° C. and treated with potassium carbonate (1415 mg, 10242 µmol). The reaction was allowed to warm to rt over the course of 1 hour and stirred for a total of 2 hours. The reaction was diluted with ethyl acetate (25 mL) and poured in saturated ammonium chloride 50 mL. The aqueous layer was extracted with ethyl acetate (3×50 mL). The combined organic layers were washed with water, brine dried over $Na_2SO_4$, filtered, concentrated under reduced pressure and purification of the resulting crude material by silica gel chromatography provided (4S,5S)-tert-butyl 4-((2,2-dimethylbenzo[d][1,3]dioxol-5-yl)methyl)-5-(hydroxymethyl)-2,2-dimethyloxazolidine-3-carboxylate as an orange foam.

Example 6

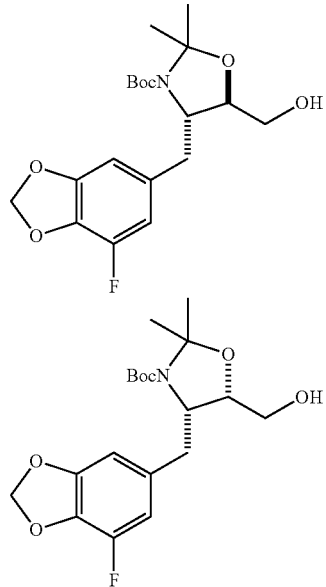

(4S,5R)-tert-Butyl 4-((7-fluorobenzo[d][1,3]dioxol-5-ylmethyl)-5-(hydroxymethyl)-2,2-dimethyloxazolidine-3-carboxylate and (4S,5S)-tert-butyl 4-((7-fluorobenzo[d][1,3]dioxol-5-yl)methyl)-5-(hydroxymethyl)-2,2-dimethyloxazolidine-3-carboxylate Step 1: (Z)-Methyl 2-(tert-butoxycarbonyl)-3-(7-fluorobenzo[d][1,3]dioxol-5-yl)acrylate To a solution of n-tert-butyloxycarbonyl-α-phosphonoglycine trimethyl ester (7.85 g, 26.4 mmol) in 50 mL of DCM at 0° C. was added DBU (6.54 ml, 43.7 mmol) dropwise over 1 minute. A solution of 7-fluorobenzo[d][1,3]dioxole-5-carbaldehyde (7000 mg, 41.6 mmol) in 25 mL of DCM was added dropwise over 10 minutes, and the mixture was warmed to rt and stirred for 2 hours. The reaction was diluted with DCM (25 mL) and poured in saturated ammonium chloride (100 mL). The aqueous layer was extracted with DCM (1×50 mL) and the combined organic layers were washed with 10% aqueous sodium bicarbonate, then with water, brine and dried over $Na_2SO_4$. Concentration under reduced pressure to and purification by silica gel chromatography provided (Z)-methyl 2-(tert-butoxycarbonyl)-3-(7-fluorobenzo[d][1,3]dioxol-5-yl)acrylate (12.9 g, 91.3%) as a white solid.

Step 2: (S)-Methyl 2-(tert-butoxycarbonyl)-3-(7-fluorobenzo[d][1,3]dioxol-5-yl)propanoate To a slurry of (Z)-methyl 2-(tert-butoxycarbonyl)-3-(7-fluorobenzo[d][1,3]dioxol-5-yl)acrylate (8000 mg) in 70 mL of methanol was added [(1S,1S',2R,2R') [Rh(duanphos)cod] $BF_4$ (41.64 mg, 58.94 µmol; Strem). The mixture was purged with hydrogen 5 times and then sealed at 50 psi of $H_2$ and stirred for 8 hours. Concentration and purification of the reaction crude by silica gel chromatography provided (S)-methyl 2-(tert-butoxycarbonyl)-3-(7-fluorobenzo[d][1,3]dioxol-5-yl)propanoate (12.0 g, 99.4%) as a colorless oil.

Step 3: (S)-2-(tert-Butoxycarbonyl)-3-(7-fluorobenzo[d][1,3]dioxol-5-yl)propanoic acid To a solution of (S)-methyl 2-(tert-butoxycarbonyl)-3-(7-fluorobenzo[d][1,3]dioxol-5-yl)propanoate (12000 mg, 35 mmol) in 200 mL of THF at 0° C. was added LiOH (0.2 M) (52735 µl, 52735 µmol) dropwise over 10 minutes. After stirring for 1 hour, more LiOH (0.2 M) (17578 µl, 17578 mmol) was added and the mixture was stirred for another 1 hr. The reaction mixture was washed with ether (2×250 mL), the aqueous layer was acidified with 2N HCl to pH of about 4 and extracted with EtOAc (3×300 mL). The combined organics were washed with water, brine, dried over sodium sulfate, filtered and concentrated to provide (S)-2-(tert-butoxycarbonyl)-3-(7-fluorobenzo[d][1,3]dioxol-5-yl)propanoic acid (11.3 g, 98% yield) as a colorless oil.

Step 4: (S)-3-(tert-Butoxycarbonyl)-4-(7-fluorobenzo[d][1,3]dioxol-5-yl)-2-oxobutyl acetate To a solution of (S)-2-(tert-butoxycarbonyl)-3-(7-fluorobenzo[d][1,3]dioxol-5-yl)propanoic acid (11300 mg, 35 mmol) in 400 mL of THF at 0° C. was added TEA (5 ml, 35 mmol) and isobutyl carbonochloridate (5 ml, 35 mmol). After stirring for 75 minutes the reaction was filtered through celite and then cooled to 0° C. at which point freshly prepared diazomethane (0.5 M in ether) (104 ml, 52 mmol) was added. After stirring for 1 hour the reaction was poured into saturated sodium bicarbonate 500 mL. The aqueous layer was extracted with ethyl acetate (3×300 mL). The combined organic layers were washed with water and then brine and dried over $Na_2SO_4$. Concentration under reduced pressure provided the diazo ketone as a yellow solid that was carried on without further purification. The diazo ketone was taken up in 400 mL of THF and cooled to 0° C. at which point HBr (33% in Acetic acid) (7 ml, 41 mmol) was added over 1 minute. The reaction was maintained at 0° C. for 15 minutes before potassium carbonate (7 g, 52 mmol) and sodium acetate (28 g, 345 mmol) were added. The THF was removed in vacuo and 100 mL of DMF was added. The resulting slurry was allowed to stir for 1 hour at which point the reaction was diluted with ethyl acetate (250 mL) and poured in water (300 mL). The aqueous layer was extracted with ethyl acetate (2×200 mL). The combined organic layers were washed with water and then brine and dried over $Na_2SO_4$. Concentration of the filtered solvents under reduced pressure provided (S)-3-(tert-butoxycarbonyl)-4-(7-fluorobenzo[d][1,3]dioxol-5-yl)-2-oxobutyl acetate (12.5 g, 94% yield) as a yellow oil.

Step 5: (2R,3S)-3-(tert-Butoxycarbonyl)-4-(7-fluorobenzo[d][1,3]dioxol-5-yl)-2-hydroxybutyl acetate and (3S)-3-(tert-butoxycarbonyl)-4-(7-fluorobenzo[d][1,3]dioxol-5-yl)-2-hydroxybutyl acetate To a slurry of lithium tri-tert-butoxyhydroaluminate (65211 µl, 65211 µmol, 1 M in THF) in 100 mL of ethanol at −78° C. was added a slurry of (S)-3-(tert-butoxycarbonyl)-4-(7-fluorobenzo[d][1,3]dioxol-5-yl)-2-oxobutyl acetate (12500 mg, 32606 µmol) in 300 mL of ethanol cooled to −50

C over the course of 20 minutes via cannula. The reaction was maintained at between −78 and −40 C for 8 hours before being allowed to warm to −25 C until LCMS and TLC showed complete consumption of starting material. The reaction was then quenched with 300 mL of 1 N HCl. The mixture was diluted with ethyl acetate (1000 mL) and 200 mL of water, the layers were separated and the aqueous layer was extracted with 3×300 mL of ethyl acetate. The combined organic layers were washed with water, brine, and dried over sodium sulfate, filtered and concentrated to provide a slurry. The slurry was taken up in 500 mL of DCM and washed with brine, then dried over sodium sulfate, and purified by silica gel to provide an inseparable 4:1 mixture of (2R,3S)-3-(tert-butoxycarbonyl)-4-(7-fluorobenzo[d][1,3]dioxol-5-yl)-2-hydroxybutyl acetate and (2S,3S)-3-(tert-butoxycarbonyl)-4-(7-fluorobenzo[d][1,3]dioxol-5-yl)-2-hydroxybutyl acetate (7.25 g, 57%).

Step 6: (4S,5R)-tert-Butyl 4-((7-fluorobenzo[d][1,3]dioxol-5-yl)methyl)-5-(hydroxymethyl)-2,2-dimethyloxazolidine-3-carboxylate and (4S,5S)-tert-butyl 4-((7-fluorobenzo[d][1,3]dioxol-5-yl)methyl)-5-(hydroxymethyl)-2,2-dimethyloxazolidine-3-carboxylate 2-Methoxy-1-propene (7.6 ml, 81 mmol) and (+/−)-10-camphorsulfonic acid (1.6 g, 6.7 mmol) were successively added to a solution containing a 4:1 mixture of (2R,3S)-3-(tert-butoxycarbonyl)-4-(7-fluorobenzo[d][1,3]dioxol-5-yl)-2-hydroxybutyl acetate and (2S,3S)-3-(tert-butoxycarbonyl)-4-(7-fluorobenzo[d][1,3]dioxol-5-yl)-2-hydroxybutyl acetate (5.2 g, 13 mmol) in 50 mL of DMF. The mixture was stirred at rt overnight and another 2 mL of methoxypropene and 200 mg of CSA were added to the reaction. After stirring for another 5 hours, the reaction was diluted with ethyl acetate (100 mL) and poured in saturated sodium bicarbonate (250 mL). The layers were separated and the aqueous layer was extracted with ethyl acetate (3×100 mL). The combined organic layers were washed with water and then brine, dried over $Na_2SO_4$ and filtered. Concentration of the solvents under reduced pressure provided an acetonide that was used immediately in the next step. The acetonide (5700 mg, 13.4 mmol) was dissolved in 150 mL of MeOH and cooled to 0° C. at which point potassium carbonate (5.55 g, 40.2 mmol) was added. After stirring at 0° C. for 2 hours 300 mL of water was added and the organics were removed in vacuo. The aqueous layer was extracted with ethyl acetate (3×200 mL) and the combined organic layers were washed with brine, dried and concentrated. Purification of the crude concentrated material by HPLC provided both title compounds as white solids.

Example 7

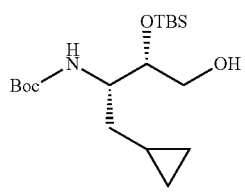 [SMILES: CC(C)(C)OC(=O)N[C@@H](CC1CC1)[C@@H](CO)O[Si](C)(C)C(C)(C)C]

tert-Butyl(2S,3S)-3-(tert-butyldimethylsilyloxy)-1-cyclopropyl-4-hydroxybutan-2-ylcarbamate The title compound was obtained using a method analogous to that described in step 2 of Example 3. MS m/z: 260 (M+1).

Example 8

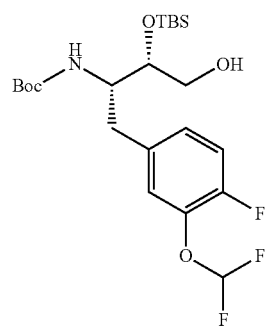 [SMILES: CC(C)(C)OC(=O)N[C@@H](Cc1ccc(F)c(OC(F)F)c1)[C@@H](CO)O[Si](C)(C)C(C)(C)C]

tert-Butyl (2S,3S)-3-(tert-butyldimethylsilyloxy)-1-(3-(difluoromethoxy)-4-fluorophenyl)-4-hydroxybutan-2-ylcarbamate The title compound was obtained using a method analogous to that described in steps 1 & 2 of Example 3. MS m/z: 380 (M+1).

Example 9

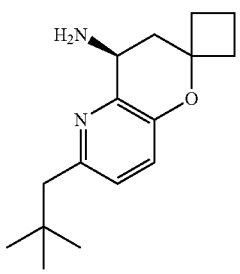 [SMILES: CC(C)(C)Cc1ccc2c(n1)[C@@H](N)CC1(CCC1)O2]

(4S)-2,2-Spirocyclobutan-6-neopentyl-3,4-dihydro-2H-pyrano[3,2-b]pyridin-4-amine Step 1:
5-(methoxymethoxy)-2-neopentylpyridine-N-oxide 5-(Methoxymethoxy)-2-neopentylpyridine (11.0 g, 52.6 mmol) was dissolved in $CH_2Cl_2$ (200 mL) to which mCPBA (18.1 g, 105 mmol) was added, and the mixture was stirred under $N_2$ for about 4 h. The mixture was quenched with 1M NaOH (200 mL) and stirring was continued vigorously for 10 min. The mixture was extracted with $CH_2Cl_2$ (2×200 mL), the combined organic layers were washed with saturated NaCl, dried ($Na_2SO_4$), and evaporated to give 5-(methoxymethoxy)-2-neopentylpyridine-N-oxide (11.8 g, 99.7% yield) as a brown oil which was used without purification in the next step.

Step 2: 3-(methoxymethoxy)-6-neopentylpicolinonitrile 5-(Methoxymethoxy)-2-neopentylpyridine-N-oxide (11.5 g, 51 mmol) was dissolved in $CH_2Cl_2$ (50 mL) to which benzoyl chloride (12 ml, 102 mmol) and (trimethylsilyl)formonitrile (14 ml, 102 mmol) were added. The mixture was stirred under $N_2$ 4 h, quenched with saturated $NaHCO_3$ (150 mL), and extracted with $CH_2Cl_2$ (3×100 mL). The combined organic layers were washed with saturated $NaHCO_3$ (2×50 mL), dried ($MgSO_4$), and evaporated to give the crude product as a brown oil, which was purified by ISCO (330 g $SiO_2$, 0-40% EtOAc/Hexane) to give 3-(methoxymethoxy)-6-neopentylpicolinonitrile (8.8 g, 74% yield) as a clear oil.

Step 3: 1-(3-(methoxymethoxy)-6-neopentylpyridin-2-yl)ethanone 3-(Methoxymethoxy)-6-neopentylpicolinonitrile (8.3 g, 35 mmol) was dissolved in THF (125 mL). The solution was cooled to 0° C. and methylmagnesium chloride (24 ml, 71 mmol) (3.0 M in $Et_2O$) was added. The reaction mixture stirred for 2 h at rt under $N_2$ then quenched with saturated $NH_4Cl$ (50 mL) and extracted with EtOAc (3×50 mL). The organic layer was dried over $MgSO_4$ and evaporated to give the crude product as a yellow oil. Purification of the crude residue by ISCO (40 g $SiO_2$, 0-40% EtOAc/Hexane) gave 1-(3-(methoxymethoxy)-6-neopentylpyridin-2-yl)ethanone (3.8 g, 43% yield) as a clear, light orange oil.

Step 4: 1-(3-hydroxy-6-neopentylpyridin-2-yl)ethanone

A solution of 1-(3-(methoxymethoxy)-6-neopentylpyridin-2-yl)ethanone (3.75 g, 15 mmol) in (2:1:1) 5 M HCl: i-PrOH:THF (100 mL) was stirred 16 h at rt. The mixture was concentrated to remove the THF and i-PrOH. The resulting solution consisting of the product in aqueous HCl was quenched by slow addition to a solution of saturated aqueous $NaHCO_3$ (500 mL) containing excess solid $NaHCO_3$ (28 g). The aqueous layer was extracted with $CH_2Cl_2$ (3×100 mL), the organic layers combined and washed with saturated aqueous NaCl (100 mL), dried ($MgSO_4$), and concentrated to give the crude product as a brown oil. The product was purified by ISCO (0-10% EtOAc/Hexanes) to give 1-(3-hydroxy-6-neopentylpyridin-2-yl)ethanone (1.98 g, 64% yield) as a clear, colorless oil.

Step 5: 2,2-spirocyclobutan-6-neopentyl-2,3-dihydropyrano[3,2-b]pyridin-4-one A mixture of 1-(3-hydroxy-6-neopentylpyridin-2-yl)ethanone (1.90 g, 9167 μmol), pyrrolidine (2296 μl, 27501 μmol), and cyclobutanone (2570 mg, 36667 μmol) in $CH_3CN$ (20 mL) was heated in a 65° C. oil bath for 3 h. The mixture was cooled to rt, then diluted with EtOAc (25 mL), washed with $H_2O$, saturated aqueous $NH_4Cl$, saturated aqueous NaCl, dried ($MgSO_4$), and concentrated. Purification of the resulting crude material by ISCO (40 g $SiO_2$, 10-20% EtOAc/Hexanes) gave 2,2-spirocyclobutan-6-neopentyl-2,3-dihydropyrano[3,2-b]pyridin-4-one (710 mg, 29.9% yield) as a yellow solid.

Step 6: (4R)-2,2-spirocyclobutan-6-neopentyl-3,4-dihydro-2H-pyrano[3,2-b]pyridin-4-ol To a vial containing 2,2-spirocyclobutan-6-neopentyl-2,3-dihydropyrano[3,2-b]pyridin-4-one (710 mg, 2738 μmol) was added sodium formate (1862 mg, 27377 μmol) and tetrabutylammonium bromide (26.5 mg, 82.1 mmol). Toluene (5 mL) and $H_2O$ (2.5 mL) were added and the solution purged 3× with $N_2$, then with an Ar balloon for 15 min. [(1R,2R)-2-Amino-1,2-diphenyl-N-(p-tolylsulfonyl)ethylamido]chloro ($\eta^6$-p-cymene)ruthenium(II) (53.4 mg, 82.1 mmol) was added and the biphasic reaction was stirred at rt under Ar for 24 h. $H_2O$ (10 mL) was added and the reaction was extracted with $CH_2Cl_2$ (3×20 mL). The combined organic layers were dried ($Na_2SO_4$), and concentrated to give a brown oil, which was purified by ISCO (40 g $SiO_2$, 5-40% EtOAc/Hexane) gives (4R)-2,2-spirocyclobutan-6-neopentyl-3,4-dihydro-2H-pyrano[3,2-b]pyridin-4-ol (460 mg, 64.3% yield) as a clear oil.

Step 7: (4S)-4-azido-2,2-spirocyclobutan-6-neopentyl-3,4-dihydro-2H-pyrano[3,2-b]pyridine To a solution of (4R)-2,2-spirocyclobutan-6-neopentyl-3,4-dihydro-2H-pyrano[3,2-b]pyridin-4-ol (460 mg, 1760 mmol) in toluene (4 mL) is added diphenylphosphoryl azide (531 μl, 2464 μmol) then 1,8-diazabicyclo(5.4.0)-7-undecene (368 μl, 2464 μmol). The reaction mixture was stirred under $N_2$ at rt 23 h. The clear, light yellow solution first turned into a brown cloudy/opaque solution after 30 min. To speed up the reaction rate, the mixture was heated to 40° C. and stirred an additional 5 h. Water (20 mL) was added and the reaction mixture was extracted with EtOAc (3×20 mL). The combined organic layers were dried ($Na_2SO_4$), and concentrated to give the crude product as a brown oil, which was purified by ISCO (40 g $SiO_2$, 0-20% EtOAc/Hexane) gives (4S)-4-azido-2,2-spirocyclobutan-6-neopentyl-3,4-dihydro-2H-pyrano[3,2-b] pyridine (250 mg, 49.6% yield) as a white solid.

Step 8: (4S)-2,2-spirocyclobutan-6-neopentyl-3,4-dihydro-2H-pyrano[3,2-b]pyridin-4-amine A solution of (4S)-4-azido-2,2-spirocyclobutan-6-neopentyl-3,4-dihydro-2H-pyrano[3,2-b]pyridine (250 mg, 873 μmol) in methanol (10 mL) was purged with $N_2$ (3×), then palladium (260 mg, 244 μmmol) (10 wt % on carbon) was added. The reaction was purged with $H_2$ (3×), then stiffed at rt under $H_2$ 1.5 h. The suspension was filtered through a pad of Celite®, MeOH wash (4×5 mL), and the solution concentrated to give the crude product (245 mg) as a white oily solid, which was purified by ISCO (12 g $SiO_2$, 0-10% MeOH/ $CH_2Cl_2$) to give the title compound as a white solid.

Example 10

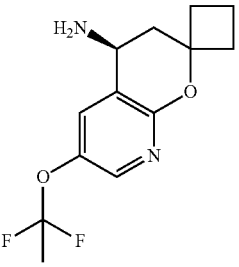 [SMILES: CC(F)(F)Oc1cnc2c(c1)[C@@H](N)CC1(CCC1)O2]

(4S)-6-(1,1-Difluoroethoxy)-2,2-spirocyclobutan-3,4-dihydro-2H-pyrano[2,3-b]pyridin-4-amine

Step 1: (4S)-tert-Butyl-6-acetyl-2,2-spirocyclobutan-3,4-dihydro-2H-pyrano[2,3-b]pyridin-4-yl(allyl) carbamate To a solution of (4S)-tert-butyl 6-bromo-2,2-spirocyclobutan-3,4-dihydro-2H-pyrano[2,3-b]pyridin-4-yl(allyl)carbamate (8.1 g, 20 mmol) in Et$_2$O (100 mL) at −78° C. was added tert-butyllithium (23 ml, 40 mmol) over 3 minutes. The reaction was allowed to stir 10 min. at −78° C., then acetaldehyde (4.5 ml, 79 mmol) was added, the reaction was then warmed to rt over 30 min, and quenched with NH$_4$Cl (200 mL). The reaction was extracted with EtOAc (3×100 mL), the combined organic layers were washed with saturated NaCl (100 mL), dried (Na$_2$SO$_4$), and concentrated to give crude product as a dark yellow/orange oil. The crude was carried on into the next step without purification. To a solution of the crude product from above in CH$_2$Cl$_2$ (50 mL) at 0° C., was added sodium bicarbonate (6.64 g, 79.0 mmol) and Dess-Martin periodinane (10.5 g, 24.7 mmol) simultaneously. The ice bath was removed and the reaction was stirred for 2 h at rt, then quenched with saturated Na$_2$SO$_3$ (300 mL), extracted with CH$_2$Cl$_2$ (3×200 mL), and concentrated. The crude material was purified by ISCO (10-50% EtOAc/Hexane) to give the title compound (4.10 g, 55.7% yield over 2 steps) as a clear, light yellow oil.

Step 2: (4S)-1-(4-amino-2,2-spirocyclobutan-3,4-dihydro-2H-pyrano[2,3-b]pyridin-6-yl)ethanone To a 150 mL rbf with (45)-tert-butyl 6-acetyl-2,2-spirocyclobutan-3,4-dihydro-2H-pyrano[2,3-b]pyridin-4-yl(allyl) carbamate (2.05 g, 5504 µmol) and CH$_2$Cl$_2$ (50 mL) was added 2,2,2-trifluoroacetic acid (5089 µl, 66048 µmol). The reaction was allowed to stir at RT for 5 h, then diluted with CH$_2$Cl$_2$ (50 mL). The mixture was washed with saturated NaHCO$_3$ (2×100 mL) and the organic layer degassed with Argon for 10 minutes. The degassed solution was treated with 1,3-dimethylpyrimidine-2,4,6(1H,3H,5H)-trione (2.21 g, 14154 µmol) and tetrakistriphenylphosphine palladium(0) (254 mg, 220 µmol) and stirred at rt for 24 hours. The reaction mixture was washed with NaOH (1N, 2×50 mL), and HCl (1N, 2×50 mL). The acidic aqueous layer was then basified to pH 14 with NaOH (5N, 25 mL) and extracted with DCM (3×50 mL). The combined organic layers were dried (Na$_2$SO$_4$) and concentrated to give (4S)-1-(4-amino-2,2-spirocyclobutan-3,4-dihydro-2H-pyrano[2,3-b]pyridin-6-yl)ethanone (810 mg, 63.4%) as a light yellow oil.

Step 3: (4S)-6-(1,1-difluoroethoxy)-2,2-spirocyclobutyl-3,4-dihydro-2H-pyrano[2,3-b]pyridin-4-amine To a 20 mL polyethylene vial was added (4S)-1-(4-amino-2,2-spirocyclobutan-3,4-dihydro-2H-pyrano[2,3-b]pyridin-6-yl)ethanone (410 mg, 1765 µmol) and HF/pyridine (1 mL). Xenon difluoride (359 mg, 2118 µmol) was added to the mixture followed by CH$_2$Cl$_2$ (1 mL). The reaction was stirred at rt 24 h, then quenched by slowly adding it to saturated NaHCO$_3$ (100 mL) with solid NaHCO$_3$ (5 g). The mixture was extracted with CH$_2$Cl$_2$ (3×50 mL). The combined organic layers were collected, dried (Na$_2$SO$_4$) and concentrated to give the crude product as a brown oil. The crude was purified by ISCO (2×12 g SiO$_2$ stacker, 0-8% MeOH/CH$_2$Cl$_2$) to give (4S)-6-(1,1-difluoroethoxy)-2,2-spirocyclobutyl-3,4-dihydro-2H-pyrano[2,3-b]pyridin-4-amine as an orange oil.

Example 11

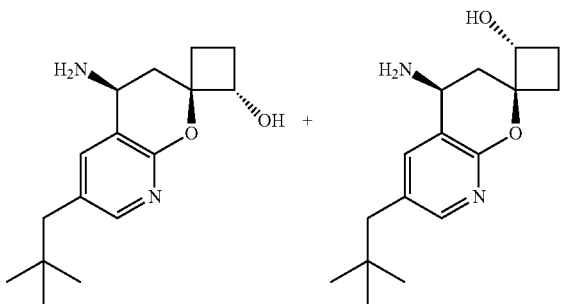 [SMILES: CC(C)(C)Cc1cnc2c(c1)[C@@H](N)C[C@@]1(CC[C@@H]1O)O2 ; CC(C)(C)Cc1cnc2c(c1)[C@@H](N)C[C@]1(CC[C@H]1O)O2]

(1R,2S,4'S)-2-Hydroxy-3',4'dihydrospiro[cyclobutane-1,2'-pyrano[2,3-b]pyridin-4'-amine and (1S,2R,4'S)-2-hydroxy-3',4'dihydrospiro[cyclobutane-1,2'-pyrano[2,3-b]pyridin-4'-amine

Step 1: (cis)-1-Allyl-2-(benzyloxy)cyclobutanol and (trans)-1-allyl-2-(benzyloxy)cyclobutanol To a RBF under argon was added 2-(benzyloxy)cyclobutanone (8.0 g, 45 mmol) and THF (100 mL). The reaction was cooled to 0° C. and allylmagnesium bromide (113 ml, 113 mmol) (1.0 M in Et$_2$O) was added over 20 min. The clear colorless solution turned into a tan solution with a white suspension. The ice bath was removed and the reaction warmed to rt and stirred 7 h. The reaction was quenched by slow addition to saturated aqueous NH$_4$Cl (500 mL). The reaction was diluted with EtOAc (300 mL) and extracted. The aqueous layer was extracted with EtOAc (2×250 mL), the combined organic layers washed with saturated NaCl (250 mL), dried (Na$_2$SO$_4$), and concentrated to give a clear, light yellow oil, which was purified by ISCO (330 g SiO$_2$, 10-40% EtOAc/Hexane) gives the less polar isomer (cis)-1-allyl-2-(benzyloxy)cyclobutanol (4.0 g, 40% yield) followed by the more polar isomer (trans)-1-allyl-2-(benzyloxy)cyclobutanol (2.4 g, 24% yield) as a clear, colorless oils.

Step 2: ((1,2-cis)-1-Allyl-2-(benzyloxy)cyclobutoxy)(tert-butyl)dimethylsilane (Cis)-1-Allyl-2-(benzyloxy)cyclobutanol (4.00 g, 18.3 mmol) was dissolved in CH$_2$Cl$_2$ (100 mL) to which tert-butyldimethylsilyl trifluoromethanesulfonate (5.05 ml, 22.0 mmol) and N-ethyl-N-isopropylpropan-2-amine (3.99 ml, 22.9 mmol) were added. The reaction mixture was stirred at rt for 5 h. The reaction was quenched with 10% NaCO$_3$ (300 mL), and the aqueous layer was extracted with CH$_2$Cl$_2$ (2×100 mL). The combined organic layers were washed with saturated NaCl (50 mL), dried (Na$_2$SO$_4$), and concentrated to give a yellow oil, which was purified by ISCO (40 g SiO$_2$, 100% Hexane to give ((cis)-1-allyl-2-(benzyloxy)cyclobutoxy)(tert-butyl)dimethylsilane (5.38 g, 88.3% yield) as a clear, colorless oil.

Step 3: 2-((1,2-cis)-2-(Benzyloxy)-1-(tert-butyldimethylsilyloxy)cyclobutyl)acetaldehyde ((cis)-1-Allyl-2-(benzyloxy)cyclobutoxy)(tert-butyl)dimethylsilane (5.37 g, 16 mmol) was dissolved in t-butanol (30 mL, 319 mmol) and H$_2$O (30 mL) followed by the addition of 4-methylmorpholine n-oxide (3.4 g, 29 mmol) in one portion. After the reactants dissolved, osmium tetroxide (5.1 mL, 0.40 mmol) was added and the reaction mixture was stirred at RT for 17 h. The reaction mixture was worked up by the addition of 6 g of sodium sulfite and allowed to stir for 1 h. The reaction mixture was extracted with ether and the organic phase was concentrated and used directly in the next step. The crude was dissolved in 1:1 t-BuOH/H$_2$O (60 mL) and sodium periodate (6.2 g, 29 mmol) was added. The mixture was stirred for 3 h. Then H$_2$O (100 mL) was added and the mixture was extracted with Et$_2$O (3×100 mL). The combined organic layers were dried (MgSO$_4$) and concentrated. The crude was purified by ISCO (120 g SiO$_2$, 5-20% EtOAc/Hexane to give 2-((cis)-2-(benzyloxy)-1-(tert-butyldimethylsilyloxy)cyclobutyl)acetaldehyde (4.0 g, 74% yield) as a clear, colorless oil.

Step 4: 2-((1,2-cis)-2-(Benzyloxy)-1-(tert-butyldimethylsilyloxy)cyclobutyl)-1-(2-fluoro-5-neopentylpyridin-3-yl)ethanol To a flame-dried 250 mL rbf with 2,2,6,6-tetramethylpiperidine (3.41 ml, 20.1 mmol) was added THF (40 mL) and the solution is cooled to −78° C. n-Butyllithium (10.8 ml, 1.60 M, 17.2 mmol) was added dropwise and the reaction was warmed to 0° C. and stirred 5 min. The reaction was recooled to −78° C. and 2-fluoro-5-neopentylpyridine (2.40 g, 14.3 mmol) in THF (10 mL) was added and the reaction stirred 45 min at −78° C. Then 2-((cis)-2-(benzyloxy)-1-(tert-butyldimethylsilyloxy)cyclobutyl)acetaldehyde (4.00 g, 12.0 mmol) in THF (10 mL) was added dropwise. The reaction mixture was stirred 15 min at −78° C., then quenched by addition of saturated NH$_4$Cl (50 mL), warmed to rt, diluted with H$_2$O (50 mL) and extracted with Et$_2$O (3×100 mL). The combined organic layers were washed with saturated NaCl (100 mL), dried (Na$_2$SO$_4$), and concentrated to give a crude product, which was purified by ISCO (120 g SiO$_2$, O-20% EtOAc/Hexane) to give the title compound (5.18 g, 86.3%) as a 1:1 mixture of diastereomers, as a clear, light yellow oil.

Step 5: (1,2-cis)-2-(Benzyloxy)-1-(2-(2-fluoro-5-neopentylpyridin-3-yl)-2-hydroxyethyl)cyclobutanol To a flame-dried 100 mL rbf with 2-((1,2-cis)-2-(benzyloxy)-1-(tert-butyldimethylsilyloxy)cyclobutyl)-1-(2-fluoro-5-neopentylpyridin-3-yl)ethanol (5.18 g, 10 mmol) was added THF (10 mL) followed by TBAF (12 ml, 1.0 M in THF, 12 mmol). The reaction was stirred at rt for 30 min, then diluted with H$_2$O (100 mL) and extracted with Et$_2$O (3×50 mL). The combined organic layers were washed with saturated NaCl (100 mL), dried (Na$_2$SO$_4$) and concentrated to give a crude materiall, which was purified by ISCO (120 g SiO$_2$, 0-20% EtOAc/Hexane) to give (1,2-cis)-2-(benzyloxy)-1-(2-(2-fluoro-5-neopentylpyridin-3-yl)-2-hydroxyethyl)cyclobutanol (3.25 g, 81%) as a 1:1 mixture of diastereomers, a clear, light yellow oil.

Step 6: (1,2-cis)-2-Benzyloxy-6'neopentyl-3',4'dihydrospiro[cyclobutane-1,2'-pyrano[2,3-b]pyridin-4'-one To a flame-dried 100 mL rbf with (1,2-cis)-2-(benzyloxy)-1-(2-(2-fluoro-5-neopentylpyridin-3-yl)-2-hydroxyethyl)cyclobutanol (3.06 g, 7.9 mmol) was added THF (500 mL) followed by NaH (1.6 g, 39 mmol, 60% in mineral oil). The reaction was heated in a 60° C. oil bath under N$_2$ for 4 h, then cooled to rt and quenched with saturated NH$_4$Cl (200 mL). The aqueous layer was extracted with EtOAc (3×100 mL), and the combined organic layers dried (MgSO$_4$) and concentrated to give the crude alcohol, which was used in the next step without purification. The crude material was dissolved in CH$_2$Cl$_2$ (100 mL) and Dess-Martin periodinane (3.3 g, 7.9 mmol) and sodium bicarbonate (0.66 g, 7.9 mmol) were added at the same time. The reaction was stirred for 2 h at rt. The reaction was quenched with saturated aqueous Na$_2$SO$_3$ (100 mL), extracted, then extracted with additional CH$_2$Cl$_2$ (2×100 mL). The combined organic layers were washed with saturated NaCl (100 mL), dried (Na$_2$SO$_4$), and concentrated to give the crude product as a yellow oil. Purification of the oil by ISCO (120 g SiO$_2$, 0-80% EtOAc/Hexane) gave the title compound (2.67 g, 93%) as a clear, light yellow oil.

Step 7: (1R,2S,4'R)-2-Benzyloxy-3',4'dihydrospiro[cyclobutane-1,2'-pyrano[2,3-b]pyridin-4'-ol To a stirred solution of (s)-2-methyl-cbs-oxazaborolidine (0.70 ml, 0.70 mmol) in THF (10 mL) at 0° C. was added borane-methyl sulfide complex (1.2 ml, 12 mmol) followed by a solution of (1,2-cis)-2-benzyloxy-6'neopentyl-3',4'dihydrospiro[cyclobutane-1,2'-pyrano[2,3-b]pyridin-4'-one (2.57 g, 7.0 mmol) in THF (20 mL) dropwise via syringe pump over about 2.8 h. The reaction was stirred an additional 30 min, then was quenched by dropwise addition (1 drop/10 sec) of 5 M HCl (25 mL) at 0° C. After 15 mL HCl was added, bubbling had ceased and the addition rate was increased as the ice bath was removed. The reaction was stirred an additional 2 h at rt. The reaction was recooled to 0° C. and neutralized with 5 M NaOH (27 mL). The mixture was then extracted with EtOAc (2×150 mL), washed with saturated aqueous NaCl (200 mL), dried (MgSO$_4$), and concentrated to give a yellow oil. Purification of the oil by ISCO (120 g SiO$_2$, 20% EtOAc/Hexane) gave a mixture of (1R,2S,4'R)-2-benzyloxy-6'-neopentyl-3',4'dihydrospiro[cyclobutane-1,2'-pyrano[2,3-b]pyridin-4'-ol (1.3 g, 50%) and (1S,2R,4'R)-2-benzyloxy-6'-neopentyl-3',4'dihydrospiro[cyclobutane-1,2'-pyrano[2,3-b]pyridin-4'-ol (1.3 g, 50%) as a white foam.

Step 9: (1R,2S,4'S)-2-Benzyloxy-6'-neopentyl-3',4'dihydrospiro[cyclobutane-1,2'-pyrano[2,3-b]pyridin-4'-azide and (1S,2R,4'S)-2-benzyloxy-6'neopentyl-3',4'dihydrospiro[cyclobutane-1,2'-pyrano[2,3-b]pyridin-4'-azide To a solution of (1,2-cis, 4'R)-2-benzyloxy-6'-neopentyl-3',4'dihydrospiro[cyclobutane-1,2'-pyrano[2,3-b]pyridin-4'-ol (2.6 g, 7.1 mmol) (1:1 mixture of 1,2-spirocyclobutyl diastereomers) in toluene (14 mL) was added diphenylphosphoryl azide (2.1 ml, 9.9 mmol) then 1,8-diazabicyclo(5.4.0)-7-undecene (1.5 ml, 9.9 mmol). The reaction was stirred under N$_2$ at rt for 18 h. The clear, light yellow solution turned into a yellow cloudy/opaque solution after 10 min. Water (100 mL) was added and the reaction mixture extracted with EtOAc (3×200 mL). The combined organic layers were washed with saturated NaCl (150 mL), dried (MgSO$_4$), and concentrated to give the crude product as a brown oil.

To a solution of the brown oil from above in 10:1 THF/H$_2$O (40 mL) at 0° C. is added NaOH (2.85 ml, 14.3 mmol). After 5 min, trimethylphosphine (2.52 ml, 28.5 mmol) was added dropwise over 4 min. The ice bath was allowed to melt as the reaction warmed to rt and stirred a total of 18 h. The mixture was recooled to 0° C. and 5 N HCl (50 mL) was added. The resulting mixture was extracted with CH$_2$Cl$_2$ (3×100 mL), the combined organic layers were washed with 2.5 N HCl (2×50 mL). The combined aqueous layers were cooled to 0° C. and basified to pH 14 with 5 N NaOH (200 mL). The aqueous layer was extracted with CH$_2$Cl$_2$ (3×100 mL) the combined organic layers dried (Na$_2$SO$_4$), and concentrated to give 2.9 g crude product as a viscous yellow oil. Purification of the oil by ISCO (120 SiO$_2$, 0-10% MeOH/CH$_2$Cl$_2$ gradient elution) gave a 1:1 mixture of the title compounds (1.870 g, 71.6% yield) as a yellow oil.

Step 10: (1R,2S,4'S)-2-Hydroxy-6'-neopentyl-3', 4'dihydrospirorcyclobutane-1,2'-pyrano[2,3-b]pyridin-4'-amine and (1S,2R,4'S)-2-hydroxy-6'neopentyl-3',4'dihydrospiro[cyclobutane-1,2'-pyrano[2,3-b]pyridin-4'-amine To a solution of (1,2-cis,4'S)-2-benzyloxy-6'neopentyl-3', 4'dihydrospiro[cyclobutane-1,2'-pyrano[2,3-b]pyridin-4'-azide (1.320 g, 3.6 mmol) in MeOH (50 mL) under Ar is added Pd Black (76.7 mg, 720 µmol). $H_2$ gas was bubbled though the suspension for 15 min. The reaction was then stirred at rt under an atmosphere of $H_2$ (balloon) for 48 h. After 48 h, the $H_2$ atmosphere was replaced with $N_2$, and palladium hydroxide (506 mg, 720 mmol) was added, the reaction was sparged with $H_2$ and stirred for 24 h at rt. The $H_2$ atmosphere was replaced with $N_2$, and the suspension was filtered through a plug of Celite, washed with MeOH (3×50 mL), and the combined filtrates were concentrated in vacuo to give the crude product. Purification of the crude material by ISCO (120 g $SiO_2$, 0-30% MeOH/$CH_2Cl_2$ gradient elution) gave a mixture of (1R,2S,4'S)-2-hydroxy-6'-neopentyl-3', 4'dihydrospiro[cyclobutane-1,2'-pyrano[2,3-b]pyridin-4'-amine (415 mg, 41.7% yield) and (1S,2R,4'S)-2-hydroxy-6'neopentyl-3',4'dihydrospiro[cyclobutane-1,2'-pyrano[2,3-b]pyridin-4'-amine as a yellow solid.

Example 12

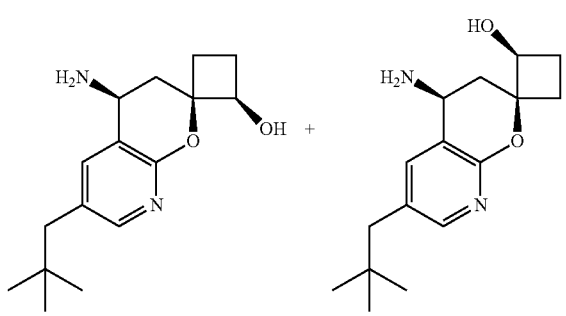 [SMILES: CC(C)(C)Cc1cnc2c(c1)[C@@H](N)C[C@@]1(CC[C@H]1O)O2 ; CC(C)(C)Cc1cnc2c(c1)[C@@H](N)C[C@]1(CC[C@@H]1O)O2]

(1R,2R,4'S)-2-Hydroxy-6'-neopentyl-3',4'dihydrospiro[cyclobutane-1,2'-pyrano[2,3-b]pyridin-4'-amine and (1S,2S,4'S)-2-hydroxy-6'neopentyl-3', 4'dihydrospiro[cyclobutane-1,2'-pyrano[2,3-b]pyridin-4'-amine The title compounds were prepared by a method analogous to that described in Example 11 above, starting with (trans)-1-allyl-2-(benzyloxy)cyclobutanol as the starting material.

Example 13

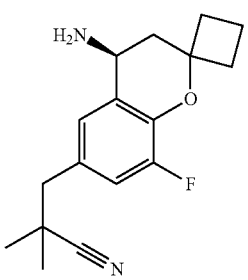 [SMILES: CC(C)(C#N)Cc1cc(F)c2c(c1)[C@@H](N)CC1(CCC1)O2]

(S)-3-(4-Amino-8-fluoro-2,2-spirocyclobutylchroman-6-yl)-2,2-dimethylpropanenitrile Step 1:
1-(5-Bromo-3-fluoro-2-hydroxyphenyl)ethanone 4-Bromo-2-fluorophenyl acetate (126 g, 540 mmol) in 1,2-dichlorobenzene (53 mL) was added dropwise to aluminum (III) chloride (72 g, 540 mmol) in 1,2-dichlorobenzene (64 mL) with vigorous stirring to give a red solution. The solution was heated to 120° C. for 60 hours, cooled, diluted with DCM, and added to 1N HCl at 0° C. The layers were separated and the aqueous layer was extracted with DCM. The combined organic layers were washed with 1N HCl, water, brine, and dried over sodium sulfate and concentrated. The crude material was taken up in hexanes and added to aqueous 1N NaOH at 0° C. The solid was collected and washed with hexanes. The aqueous filtrate and solid were acidified with concentrated HCl and extracted with ethyl acetate. The combined organic layers were washed with water, brine, dried over sodium sulfate, and concentrated. The crude solid was recrystallized from MeOH to afford the title compound (46 g, 37% yield).

Step 2:
6-Bromo-8-fluoro-2,2-spirocyclobutylchroman-4-one 1-(5-Bromo-3-fluoro-2-hydroxyphenyl)ethanone (15.00 g, 64 mmol), pyrrolidine (8 ml, 97 mmol), DIPEA (11 ml, 64 mmol), and cyclobutanone (9 ml, 129 mmol) were heated at 65° C. for 12 hours. After cooling, the reaction was diluted with EtOAc and washed with 1N HCl. The aqueous layer was extracted with EtOAc. The organic layers were combined, washed with water, brine, dried over sodium sulfate and concentrated. The residue was chromatographed on a silica gel column (10:1 Hexanes/Ether) to afford the title compound (9.73 g, 53% yield) as an orange solid. MS m/z: 285.0 (100%, M).

Step 3: (R)-6-Bromo-8-fluoro-2,2-spirocyclobutyl-chroman-4-ol (s)-2-Methyl-CBS-oxazaborolidine, 1M in toluene (3.41 ml, 3.41 mmol) was added to a solution of borane-dimethyl sulfide (4.86 ml, 51.2 mmol) in 74 mL of toluene at 0° C. After stirring 20 minutes, 6-Bromo-8-fluoro-2,2-spirocyclobutyl chroman-4-one (9.73 g, 34.1 mmol) was added via syringe pump in 106 mL of toluene over 1.5 hour at −5° C. After stirring an additional 30 minutes at −5° C. the reaction was quenched by the addition of methanol and then 1N HCl. The mixture was extracted with ethyl acetate and the combined organic layers were washed 2× with 50% saturated ammonium chloride, brine, and dried over sodium sulfate. Concentration of the filtered organic layer afforded the title compound as yellow oil.

Step 4:
(S)-4-Azido-6-bromo-8-fluoro-2,2-spirocyclobutyl chromane

Diphenyl azidophosphate (4.90 ml, 22.7 mmol) was added to a solution of 6-Bromo-8-fluoro-2,2-spirocyclobutyl chroman-4-one (4.35 g, 15.2 mmol) and DBU (3.43 ml, 22.7 mmol) in toluene (28 mL). The reaction was allowed to stir 48 hours and was filtered through a pad of silica gel and washed with EtOAc. Concentration of the EtOAc afforded the title compound.

Step 5: (S)-6-Bromo-8-fluoro-2,2-spirocyclobutyl-chroman-4-amine

Raney nickel (2800), slurry, in water (0.4 g, 6 mmol) was added to (S)-4-Azido-6-bromo-8-fluoro-2,2-spirocyclobutyl chromane (4.73 g, 15 mmol) dissolved in i-PrOH (150 mL). Hydrazine, monohydrate (5 ml, 76 mmol) was added and the reaction mixture was stirred 30 minutes before being filtered through a pad of Celite washing with ethanol. The EtOH solvent was concentrated, and the resulting crude material was purified by silica gel chromatography (20:1 DCM/MeOH (2M $NH_3$) to afford the title product. MS m/z: 269.0 (100%, M-17).

Step 6: (5)-tert-Butyl 6-bromo-8-fluoro-2,2-spirocyclobutylchroman-4-ylcarbamate (S)-6-Bromo-8-fluoro-2,2-spirocyclobutylchroman-4-amine (3.00 g, 10 mmol), TEA (2.2 ml, 16 mmol), and BOC-anhydride (3.0 g, 14 mmol) were stirred in DCM (30 mL) for 12 hrs and concentrated. The crude material was taken up in EtOAc and washed with saturated ammonium chloride, water, brine, dried over sodium sulfate and concentrated. The crude material was purified by recrystallization from methanol and water to afford the title product as a white solid.

Step 7: (S)-tert-Butyl allyl(6-bromo-8-fluoro-2,2-spirocyclobutylchroman-4-yl)carbamate (S)-tert-Butyl 6-bromo-8-fluoro-2,2-spirocyclobutylchroman-4-ylcarbamate (5.7 g, 15 mmol) was dissolved in DMF (70 mL) and cooled to 0° C. NaH (0.71 g, 18 mmol) was added carefully to the mixture and the solution was allowed to stir for 40 minutes. Allyl bromide (1.4 ml, 16 mmol) was added and the reaction mixture was stirred 45 minutes and then diluted with saturated aqueous ammonium chloride. Water was added and the solution was extracted with ether. The combined organic layers were washed with water, brine, dried over magnesium sulfate, filtered and concentrated to afford the title compound. MS m/z: 370.1 (100%, M-55).

Step 8: (5)-tert-Butyl allyl(8-fluoro-6-(hydroxymethyl)-2,2-spirocyclobutylchroman-4-yl)carbamate (S)-tert-Butyl allyl(6-bromo-8-fluoro-2,2-spirocyclobutylchroman-4-yl)carbamate (6.30 g, 15 mmol) was dissolved in diethyl ether (75 mL) and cooled to −78° C. tert-butyllithium (1.7 M) (19 ml, 33 mmol) was added dropwise to give a dark orange solution. After 20 minutes, DMF (13 ml, 163 mmol) was added and the solution was stirred for 45 minutes before being quenched by the addition of saturated ammonium chloride and water. The aqueous solution was extracted with EtOAc and the combined organic layers were washed with water, brine, dried over sodium sulfate and concentrated. The crude material was dissolved in 80 mL of MeOH, cooled to 0° C. and $NaBH_4$ (0.84 g, 22 mmol) was added to the cooled mixture. After stirring 40 minutes the reaction mixture and was quenched by addition of saturated ammonium chloride and water. The aqueous solution was extracted with EtOAc and the combined organic layers were washed with water, brine, dried over sodium sulfate and concentrated. The crude residue was purified by column chromatography (4:1 Hex/EtOAc) to give the title product.

Step 9: (S)-tert-Butyl allyl(6-(2-cyano-2-methylpropyl)-8-fluoro-2,2-spirocyclobutylchroman-4-yl)carbamate Dibromotriphenylphosphorane (4.28 g, 10.1 mmol) was added to a solution of (S)-tert-butyl allyl (8-fluoro-6-(hydroxymethyl)-2,2-spirocyclobutylchroman-4-yl)carbamate (3.48 g, 9.22 mmol) and N-ethyl-N-isopropylpropan-2-amine (1.61 ml, 9.22 mmol) in DCM (80 mL) at 0° C. After stirring 45 minutes at 0° C. and 30 minutes at ambient temperature, the reaction was concentrated and taken up in THF (40 mL). In a separate flask, diisopropylamine (8.21 ml, 58.1 mmol) was added to THF (90 mL) and the solution was cooled to −78° C. n-Butyllithium (22.1 ml, 55.3 mmol) was added and the solution was stirred 20 minutes at 0° C. Isobutyronitrile (4.96 ml, 55.3 mmol) was added and the yellow solution was stirred 40 minutes at 0° C. before the intermediate benzyl bromide described above in THF (40 mL) was added dropwise via addition funnel. The reaction was stirred at 0° C. and after 1 hour was complete. The reaction was quenched with saturated ammonium chloride and was extracted with EtOAc and the combined organic layers were washed with water, brine, dried over sodium sulfate and concentrated. The crude material was purified by silica gel chromatography (1.5:1 Hex/EtOAc) to afford the title product. MS m/z: 373.3 (100%, M-55).

Step 10: (S)-3-(4-(Allylamino)-8-fluoro-2,2-spirocyclobutylchroman-6-yl)-2,2-dimethylpropanenitrile (S)-tert-Butyl allyl (6-(2-cyano-2-methylpropyl)-8-fluoro-2,2-spirocyclobutylchroman-4-yl)carbamate (2.90 g, 6.8 mmol) and TFA (25 ml, 324 mmol) were stirred in DCM (50 mL) for 3 hours and concentrated. The crude product was taken up in DCM and 1 N NaOH and separated. The aqueous layer was extracted with DCM and the combined organic layers were washed with brine and dried over sodium sulfate. Concentration afforded the title product which was used without further purification. MS m/z: 329.3 (100%, M+1).

Step 11: (S)-3-(4-Amino-8-fluoro-2,2-spirocyclobutylchroman-6-yl)-2,2-dimethylpropanenitrile (S)-3-(4-(Allylamino)-8-fluoro-2,2-spirocyclobutylchroman-6-yl)-2,2-dimethylpropanenitrile was dissolved in degassed ($N_2$) DCM (40 mL) and 1,3-dimethylbarbituric acid (3.2 g, 20 mmol) was added. After two minutes, $Pd(PPh_3)_4$ (0.78 g, 0.68 mmol) was added and the reaction was stirred at ambient temperature for 12 hours. The reaction was diluted with DCM and 10% aqueous sodium carbonate and the layers were separated. The aqueous layer was extracted with DCM and the combined organic layers were washed with brine, dried over sodium sulfate and concentrated. The crude product was purified by silica gel chromatography (20:1 DCM/MeOH (2M $NH_3$)) to afford the title product. MS m/z: 289.2 (37%, M+1); 272.2 (100%, M−16).

Example 14

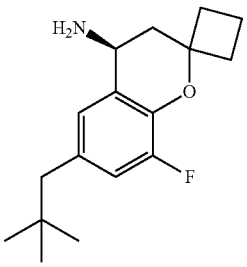 [SMILES: CC(C)(C)Cc1cc(F)c2c(c1)[C@@H](N)CC1(CCC1)O2]

(S)-8-Fluoro-2,2-spirocyclobutyl-6-neopentylchroman-4-yl-amine

To zinc(II) chloride (0.5 M THF) (50.3 ml, 25.1 mmol) was added neopentylmagnesium chloride (1.0 M ether) (39.6 ml, 39.6 mmol) in a sealed tube and stirred 20 minutes. 1,1'-bis(diphenylphosphino)ferrocene-palladium dichloride (0.557 g, 0.762 mmol) was added followed by (S)-6-bromo-8-fluoro-2,2-spirocyclobutylchroman-4-amine (2.18 g, 7.62 mmol) in THF (4 mL). The tube was sealed and heated to 70° C. for 12 h. The reaction was cooled and dilute with EtOAc and aqueous solution of a 9:1 saturated ammonium chloride/ammonium hydroxide solution (PH=9) and separated. The aqueous layer was extracted with EtOAc, and the combined organic layers were washed with a 9:1 saturated ammonium chloride/ammonium hydroxide solution (PH=9), water, brine, dried over sodium sulfate, and concentrated. Purification by silica gel chromatography (40:1 DCM/MeOH 2M $NH_3$) afforded the title product. MS m/z: 261.2 (100%, M−16).

Example 15

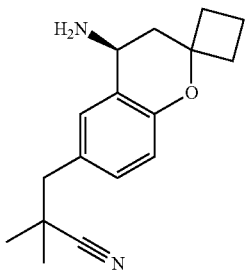 [SMILES: CC(C)(C#N)Cc1ccc2c(c1)[C@@H](N)CC1(CCC1)O2]

(S)-3-(4-Amino-2,2-spirocyclobutylchoman-6-yl)-2,2-dimethylpropanenitrile

The title compound was prepared according to steps 1-11 of the procedure described in Example 9 above.

Example 16

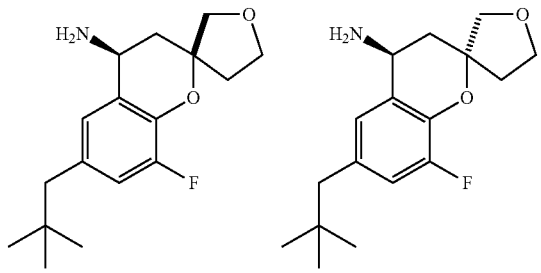

(S)-8-Fluoro-2,2-tetrahydrospirofuranyl-6-neopentylchroman-4-amine

Step 1: 6-Bromo-8-fluoro-2,2-tetrahydrospirofuranylchroman-4-one 1-(5-Bromo-3-fluoro-2-hydroxyphenyl)ethanone (0.200 g, 0.858 mmol), dihydrofuran-3(2H)-one (0.222 g, 2.57 mmol), and pyrrolidine (0.142 ml, 1.72 mmol) were dissolved in MeCN (0.5 mL) and heated in the microwave for 20 minutes fixed at 60° C. After cooling, the reaction was diluted with EtOAc and washed with 1N HCl. The aqueous layer was extracted with EtOAc. The organic layers were combined, washed with water, brine, dried over sodium sulfate, and concentrated. The crude product was purified by silica gel chromatography (1:4 EtOAc/hexanes) to afford the titled products. MS m/z: 301.0 (100%, M).

Step 2: (R)-6-Bromo-8-fluoro-2,2-tetrahydrospirofuranylchroman-4-ol (s)-2-Methyl-cbs-oxazaborolidine (0.767 ml, 0.767 mmol) was added to a solution of borane-methyl sulfide complex (1.09 ml, 11.5 mmol) in 16 mL of toluene at 0° C. After stirring 20 minutes, 6-bromo-8-fluoro-2,2-tetrahydrospirofuranylchroman-4-one (2.31 g, 7.67 mmol) was added via syringe pump in 23 mL of toluene over 1.5 hour at −5° C. After stirring an additional 30 minutes at −5° C. the reaction was quenched by the addition of MeOH and then 1N HCl. The mixture was extracted with ethyl acetate and the combined organic layers were washed twice with 50% saturated ammonium chloride, brine, and dried over sodium sulfate. Concentration of the filtered organic layer afforded the titled product as a yellow oil.

Step 3: (S)-4-Azido-6-bromo-8-fluoro-2,2-tetrahydrospirofuranylchroman

Diphenylphosphoryl azide (1.93 ml, 8.96 mmol) was added to a solution of (R)-6-bromo-8-fluoro-2,2-tetrahydrospirofuranylchroman-4-ol (1.81 g, 5.97 mmol) and DBU (1.35 ml, 8.96 mmol) in toluene (10 mL). The reaction was allowed to stir 48 hours and was filtered through a pad of silica gel with ethyl acetate. Concentration of the filtered organic layer afforded the titled products which were used without further purification.

Step 4. (S)-6-Bromo-8-fluoro-2,2-tetrahydrospirofuranylchroman-4-yl-amine

Raney nickel (2800, as a slurry in water) (0.19 g, 3.3 mmol) was added to (S)-4-azido-6-bromo-8-fluoro-2,2-tetrahydrospirofuranylchroman. (1.2 g, 3.7 mmol) dissolved in i-PrOH (50 mL). Hydrazine hydrate (1.1 ml, 18 mmol) was added and the reaction was stirred 30 minutes and then filtered through a pad of celite with ethanol, concentrated, and purified by silica gel chromatography (20:1 DCM/MeOH—$NH_3$) to afford the titled products. MS m/z: 302.1 (5%, M); 285.1 (100%, M−17).

Step 5: (S)-8-Fluoro-2,2-tetrahydrospirofuranyl-6-neopentylchroman-4-amine

To zinc chloride, 0.5M solution in THF (31 ml, 15 mmol) was added 2,2-dimethylpropylmagnesium chloride, 1.0 M solution in diethyl ether (25 ml, 25 mmol) in a sealed tube and stirred 20 minutes. 1,1'-Bis(diphenylphosphino)ferrocene-palladium dichloride (0.2 g, 0.3 mmol) was added to the mixture followed by (S)-6-bromo-8-fluoro-2,2-tetrahydrospirofuranylchroman-4-amine (0.932 g, 3 mmol) in THF (8 mL). The tube was sealed and heated to 70° C. for 12 h. The reaction was cooled and diluted with DCM and an aq. solution of a 9:1 saturated ammonium chloride/ammonium hydroxide and the layers were separated. The aqueous layer was extracted with DCM, and the combined organic layers were washed with a 9:1 saturated ammonium chloride/ammonium hydroxide solution, water, brine, dried over sodium sulfate, and concentrated. Purification of the crude concentrate by silica gel chromatography (20:1 DCM/MeOH—NH₃) afforded the title products.

Example 17

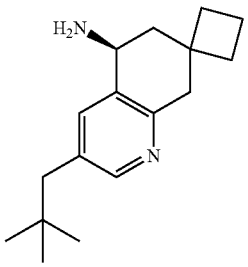 [SMILES: CC(C)(C)Cc1cnc2c(c1)[C@@H](N)CC1(CCC1)C2]

(S)-7,7-Spirocyclobutyl-3-neopentyl-5,6,7,8-tetrahydroquinolin-5-amine

Step 1:
3-Amino-5,5-spirocyclobutylcyclohex-2-enone 5,5-Spirocyclobutylcyclohexane-1,3-dione (15.2 g, 99.9 mmol), HOAc (5.15 ml, 89.9 mmol), and ammonium acetate (15.4 g, 200 mmol) were refluxed in benzene (250 mL) with a Dean-Stark trap for 5 hrs. After cooling, the product was filtered from the reaction mixture and the solid was taken up in EtOAc and washed with saturated sodium bicarbonate, brine, dried over sodium sulfate, and concentrated to afford the title product as a yellow solid.

Step 2: 4,4-Dimethylpentanal

DIBAL-H (1 M Hexanes)(80 ml, 80 mmol) was added to 4,4-dimethylpentanenitrile (5.9 g, 53 mmol) in DCM (200 mL) at 0° C. After stirring for 1.5 hrs the reaction was quenched with concentrated HCl and diluted with DCM. The aqueous layer was extracted with DCM and the combined organic layers were washed with concentrated HCl, water, brine, and dried over sodium sulfate. The organics were filtered and concentrated to afford the title compound which was used without further purification.

Step 3:
(Z)-2-(Ethoxymethylene)-4,4-dimethylpentanal 4,4-Dimethylpentanal (4.20 g, 36.8 mmol, Step 2) in 36 mL of THF was added over 4 hours by syringe pump to a solution of sodium methoxide, 25 wt. % in methanol (15.1 ml, 66.2 mmol), 15 mL of methanol, and methyl formate (166 ml, 2685 mmol). Following the addition, the reaction was diluted with benzene (50 mL) and DMF (40 mL). The solvents were distilled off at 90° C. leaving the DMF and residual benzene. Bromoethane (11.0 ml, 147 mmol) was added and the solution was heated at 40° C. for 48 hrs and then cooled. The solution was diluted with water, and the reaction was extracted with ether. The combined organic layers were washed with water, brine, and dried over magnesium sulfate, filtered and concentrated to afford the title compound.

Step 4: 7,7-Spirocyclobutyl-3-neopentyl-7,8-dihydroquinolin-5(6H)-one (Z)-2-(Ethoxymethylene)-4,4-dimethylpentanal (5.22 g, 31 mmol) and 3-amino-5,5-spirocyclobutylcyclohex-2-enone (4.6 g, 31 mmol) were heated to 140° C. in propionic acid (30 ml, 399 mmol) for 12 hours. After cooling, the reaction was diluted with ethyl acetate and washed 2× with 1N NaOH. The aqueous layer was extracted with ethyl acetate and the combined organic layers were washed with brine, dried over sodium sulfate, and concentrated. Purification of the crude by silica gel chromatography (3:1 Hexanes/EtOAc) afforded the titled product (3.1 g, 39% yield). MS m/z: 258.2 (100%, M+1).

Step 5: (R)-7,7-Spirocyclobutyl-3-neopentyl-5,6,7,8-tetrahydroquinolin-5-ol (s)-2-Methyl-cbs-oxazaborolidine, 1 M in toluene (1.2 ml, 1.2 mmol) was added to a solution of borane-dimethyl sulfide (1.7 ml, 18 mmol) in 26 mL of toluene at 0° C. After stirring 20 minutes, 7,7-spirocyclobutyl-3-neopentyl-7,8-dihydroquinolin-5(6H)-one (3.10 g, 12 mmol) was added to the mixture via syringe pump in 37 mL of toluene over 1.5 hour at −5° C. After stirring an additional 30 minutes at −5° C. the reaction was quenched by the addition of methanol and then 1N HCl. The mixture was extracted with ethyl acetate and the combined organic layers were washed 2 times with 50% saturated ammonium chloride, brine, and dried over sodium sulfate, filtered and concentrated to afford the titled product.

Step 6: (S)-5-Azido-7,7-spirocyclobutyl-3-neopentyl-5,6,7,8-tetrahydroquinoline

Diphenylphosphoryl azide (3.5 ml, 16 mmol) was added to a solution of (R)-7,7-spirocyclobutyl-3-neopentyl-5,6,7,8-tetrahydroquinolin-5-ol (2.8 g, 11 mmol) and DBU (2.4 ml, 16 mmol). The reaction was allowed to stir 24 hours and was filtered through a pad of silica gel washing and eluting with ethyl acetate. Concentration of the EtOAc afforded the titled product which was used without further purification.

Step 7: (S)-7,7-Spirocyclobutyl-3-neopentyl-5,6,7,8-tetrahydroquinolin-5-amine

A solution of (S)-5-azido-7,7-spirocyclobutyl-3-neopentyl-5,6,7,8-tetrahydroquinoline (1.21 g, 4 mmol) in ethanol (30 mL) was purged with nitrogen gas. Palladium, 5% on calcium carbonate, poisoned with lead (0.5 ml, 4 mmol) was added and the flask was flushed with a balloon of hydrogen gas. The reaction was allowed to stir under an atmosphere of hydrogen gas for 4 hours. After purging the reaction with nitrogen gas, the reaction was filtered through a pad of celite with ethanol. The reaction was concentrated and purified by

Example 18

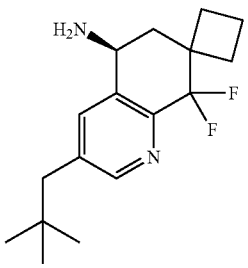 [SMILES: CC(C)(C)Cc1cnc2c(c1)[C@@H](N)CC1(CCC1)C2(F)F]

(S)-8,8-Difluoro-7,7-spirocyclobutyl-3-neopentyl-5,6,7,8-tetrahydroquinolin-5-amine

Step 1: (S)-tert-butyl 7,7-spirocyclobutyl-3-neopentyl-5,6,7,8-tetrahydroquinolin-5-ylcarbamate (S)-7,7-Spirocyclobutyl-3-neopentyl-5,6,7,8-tetrahydroquinolin-5-amine (3.47 g, 13.4 mmol), TEA (2.81 ml, 20.1 mmol), and di-tert-butyl dicarbonate (2.93 g, 13.4 mmol) were stirred in DCM (60 mL) for 12 hrs and concentrated. The crude material was taken up in ethyl acetate and washed with saturated ammonium chloride, water, brine, dried over sodium sulfate, and concentrated. The crude material was purified by column chromotography (10:1 to 1:1 Hexanes/EtOAc) to afford the titled product.

Step 2: N-oxide of (S)-tert-butyl 7,7-spirocyclobutyl-3-neopentyl-5,6,7,8-tetrahydroquinolin-5-ylcarbamate m-Chloroperbenzoic acid (0.662 g, 2.30 mmol) was added to a solution of (S)-tert-butyl 7,7-spirocyclobutyl-3-neopentyl-5,6,7,8-tetrahydroquinolin-5-ylcarbamate (0.688 g, 1.92 mmol) in DCM (20 mL) and the solution was stirred 12 hrs before being diluted with aqueous saturated sodium bicarbonate and aqueous sodium thiosulfate. The mixture was stirred vigorously for 1.5 hrs then separated. The aqueous layer was extracted with DCM and the combined organic layers were washed with aqueous sodium thiosulfate, 10% sodium carbonate, water, brine, and dried over sodium sulfate. The organic layer was filtered and concentrated to afford the title product.

Step 3: (S)-tert-Butyl 8-hydroxy-7,7-spirocyclobutyl-3-neopentyl-5,6,7,8-tetrahydroquinolin-5-ylcarbamate The N-oxide from above (0.719 g, 1.92 mmol, Step 2) was dissolved in DCM (9 mL). Trifluoroacetic anhydride (1.33 ml, 9.60 mmol) was added and the reaction was refluxed for 2 hours and concentrated. The crude product was dissolved in THF (4.5 mL) and aqueous saturated sodium bicarbonate was added by pipette in dropwise fashion until no further bubbling was observed. The reaction was diluted with ethyl acetate and water and the layers were separated. The aqueous layer was extracted with ethyl acetate and the combined organic layers were washed with water, brine, and dried over sodium sulfate, filtered and concentrated. The crude product was purified by silica gel column (20:1 DCM/MeOH 2N NH$_3$) to afford the titled product. MS m/z: 259.3 (100%, M+1).

silica gel chromatography (25:1 DCM/MeOH) to afford the titled product. MS m/z: 375.3 (100%, M+1).

Step 4: (S)-tert-Butyl 7,7-spirocyclobutyl-3-neopentyl-8-oxo-5,6,7,8-tetrahydroquinolin-5-ylcarbamate (S)-tert-Butyl 8-hydroxy-7,7-spirocyclobutyl-3-neopentyl-5,6,7,8-tetrahydroquinolin-5-ylcarbamate (0.285 g, 0.761 mmol) and Dess-Martin Periodinane (0.968 g, 2.28 mmol) were stirred 12 hrs in DCM (7 mL). The reaction was diluted with ether and aqueous sodium thiosulfate and saturated aqueous sodium bicarbonate and stirred vigorously. The layers were separated and the aqueous layers were extracted with ether and the combined organic layers were washed with saturated aqueous sodium bicarbonate and water and concentrated. The residue was taken up in ethyl acetate and washed with brine, dried over sodium sulfate, and concentrated. Purification by silica gel chromatography (1:1 Hexanes/EtOAc) afforded the titled product. MS m/z: 373.3 (100%, M+1).

Step 5: (S)-tert-Butyl 8,8-difluoro-7,7-spirocyclobutyl-3-neopentyl-5,6,7,8-tetrahydroquinolin-5-ylcarbamate (S)-tert-Butyl 7,7-spirocyclobutyl-3-neopentyl-8-oxo-5,6,7,8-tetrahydroquinolin-5-ylcarbamate (0.183 g, 0.491 mmol) was dissolved in DCM (1.5 mL) and cooled to −78° C. DAST (0.130 ml, 0.983 mmol) was added and the reaction mixture was allowed to warm to RT over 12 hrs and stirred for four additional days. The reaction was diluted with DCM and aqueous 10% sodium carbonate and separated. The aqueous layer was extracted with DCM and the combined organic layers were washed with water, brine, and dried over sodium sulfate. Concentration of the filtered organic solvent afforded the titled product. MS m/z: 395.2 (100%, M+1).

Step 6: (S)-8,8-Difluoro-7,7-spirocyclobutyl-3-neopentyl-5,6,7,8-tetrahydroquinolin-5-amine (S)-tert-Butyl 8,8-difluoro-7,7-spirocyclobutyl-3-neopentyl-5,6,7,8-tetrahydroquinolin-5-ylcarbamate (0.194 g, 0.49 mmol) was stirred in a 2:1 solution of DCM and TFA (4.5 mL) for 3 hours and concentrated. The crude product was taken up in chloroform and 1N aq. NaOH and the layers were separated. The aqueous layer was extracted with chloroform and the combined organic layers were washed with brine, dried over sodium sulfate, filtered and concentrated. The crude product was purified by silica gel chromatography (30:1 DCM/MeOH—NH$_3$) to afford the titled product. MS m/z: 295.2 (100%, M+1).

Example 19

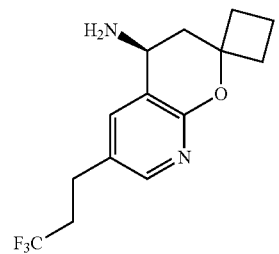 [SMILES: N[C@H]1CC2(CCC2)Oc2ncc(CCC(F)(F)F)cc21]

(S)-2,2-Spirocyclobutyl-6-(3,3,3-trifluoropropyl)-3,4-dihydro-2H-pyrano[2,3-b]pyridin-4-amine

Step 1: (1s,5s)-9-(3,3,3-Trifluoropropyl)-9-bora-bicyclo[3.3.1]nonane 3,3,3-Trifluoroprop-1-ene (2.9 g, 30 mmol) was condensed with a cold finger and the liquid was allowed to drop into a 500 mL RBF containing 9-BBN, 0.5M in THF (58 ml, 29 mmol) cooled in a dry ice/iPrOH bath. After the addition was complete the solution was allowed to stir under N₂ and slowly warm to RT.

Step 2: (S)-tert-butyl 2,2-spirocyclobutyl-6-(3,3,3-trifluoropropyl)-3,4-dihydro-2H-pyrano[2,3-b]pyridin-4-ylcarbamate To a 500 mL RBF containing (1s,5s)-9-(3,3,3-trifluoropropyl)-9-bora-bicyclo[3.3.1]nonane (6.3 g, 29 mmol, step 1) in THF (58 mL) was added, toluene:EtOH (110 mL, 10:1), (S)-tert-butyl 6-bromo-2,2-spirocyclobutyl-3,4-dihydro-2H-pyrano[2,3-b]pyridin-4-ylcarbamate (5.12 g, 14 mmol), sodium carbonate, 10% aqueous (28.0 ml, 26 mmol), and palladium tetrakis (790 mg, 0.68 mmol, Strem). The solution was stirred at 80° C. After 16 hours, LC-MS shows reaction to be ~20% complete and not progressing. The reaction was concentrated to half volume and the layers separated and the aqueous layer extracted with EtOAc (2×30 mL). The combined organic layers were concentrated in vacuo and adsorbed onto a plug of silica gel and chromatographed through a Redi-Sep® pre-packed silica gel column (120 g), eluting with 0% to 20% EtOAc in hexane, to provide (S)-tert-butyl 2,2-spirocyclobutyl-6-(3,3,3-trifluoropropyl)-3,4-dihydro-2H-pyrano[2,3-b]pyridin-4-ylcarbamate (1.01 g, 19% yield, 56% brsm) as a yellow oil that began to solidify upon standing under vacuum overnight.

Step 3: (S)-2,2-spirocyclobutyl-6-(3,3,3-trifluoropropyl)-3,4-dihydro-2H-pyrano[2,3-b]pyridin-4-amine To a 250 mL round bottomed flask containing (S)-tert-butyl 2,2-spirocyclobutyl-6-(3,3,3-trifluoropropyl)-3,4-dihydro-2H-pyrano[2,3-b]pyridin-4-ylcarbamate (1.00 g, 2588 mmol) in EtOAc (40 mL) was added HCl (4M in dioxane, 5 mL). The solution was stirred at RT. After 4 hours, another 5 mL of HCl was added to the mixture. After a further 16 hours, the reaction was poured into sat'd NaHCO₃. The aqueous layer was extracted with EtOAc and the combined organic layers washed with brine, dried over MgSO₄, and concentrated in vacuo to give (S)-2,2-spirocyclobutyl-6-(3,3,3-trifluoropropyl)-3,4-dihydro-2H-pyrano[2,3-b]pyridin-4-amine (700 mg, 94.5% yield), as a yellow oil. MS m/z: 287.2 (M+1).

Example 20

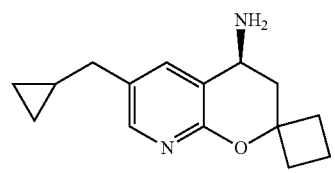 [SMILES: N[C@H]1CC2(CCC2)Oc2ncc(CC3CC3)cc21]

(S)-tert-Butyl 6-allyl-2,2-spirocyclobutyl-3,4-dihydro-2H-pyrano[2,3-b]pyridin-4-ylcarbamate

Step 1: (S)-tert-Butyl 6-allyl-2,2-spirocyclobutyl-3,4-dihydro-2H-pyrano[2,3-b]pyridin-4-ylcarbamate A solution of tris(dibenzylideneacetone)dipalladium (0) (0.186 g, 0.203 mmol), tri-t-butylphosphonium tetrafluoroborate (0.354 g, 1.22 mmol), cesium fluoride (3.09 g, 20.3 mmol), and (5)-tert-butyl 6-bromo-2,2-spirocyclobutyl-3,4-dihydro-2H-pyrano[2,3-b]pyridin-4-ylcarbamate (1.500 g, 4.06 mmol) in dioxane (12 mL) was thoroughly degassed then treated with allyltributylstannane (6.23 ml, 20.3 mmol). The reaction mixture was heated to 100° C. and allowed to stir 4 hours. The reaction mixture was then diluted with EtOAc, washed with saturated KF solution, water, and brine. The organic layer was dried over MgSO₄ and concentrated under reduced pressure. Purification of the crude residue by column chromatography gave (S)-tert-butyl 6-allyl-2,2-spirocyclobutyl-3,4-dihydro-2H-pyrano[2,3-b]pyridin-4-ylcarbamate (0.820 g, 61.1% yield) as a light yellow solid.

Step 2: (S)-tert-Butyl 6-(cyclopropylmethyl)-2,2-spirocyclobutyl-3,4-dihydro-2H-pyrano[2,3-b]pyridin-4-ylcarbamate A solution of (S)-tert-butyl 6-allyl-2,2-spirocyclobutyl-3,4-dihydro-2H-pyrano[2,3-b]pyridin-4-ylcarbamate (0.710 g, 2 mmol) in DCM (1.5 mL) was cooled to −10° C. and treated with diethylzinc 1M in hexanes (21 ml, 21 mmol), followed by dropwise addition of chloroiodomethane (3 ml, 43 mmol). After 1 hour an additional portion of diethylzinc and chloroiodomethane was added. After an additional hour at RT the reaction mixture was quenched with concentrated NH₄Cl solution and diluted with ether. The organic layer was washed with 2N NaOH, brine, dried over Na₂SO₄ and concentrated under reduced pressure. The crude residue was retreated with the reaction and work-up conditions three times. Purification of the crude residue by column chromatography gave (S)-tert-butyl 6-(cyclopropylmethyl)-2,2-spirocyclobutyl-3,4-dihydro-2H-pyrano[2,3-b]pyridin-4-ylcarbamate (0.300 g, 41% yield) as a clear oily solid with minor impurities.

Step 3: (S)-6-(Cyclopropylmethyl)-2,2-spirocyclobutyl-3,4-dihydro-2H-pyrano[2,3-b]pyridin-4-amine A solution of (S)-tert-Butyl 6-(cyclopropylmethyl)-2,2-spirocyclobutyl-3,4-dihydro-2H-pyrano[2,3-b]pyridin-4-ylcarbamate (0.300 g, 0.87 mmol) and DIEA (0.30 ml, 1.7 mmol) in DCM (2 mL) was treated with trimethylsilyltriflate (0.19 ml, 1.0 mmol) and was allowed to stir at RT overnight. An additional 4 equivalents of DIEA then 4 equivalents of trimethylsilyltriflate were then added. After an additional 2 hours of stirring the reaction mixture was quenched with 4N HCl in dioxane and allowed to stir for 1 hr. The reaction mixture was diluted with EtOAc, washed with 2N NaOH, water, and brine. The organics were dried over MgSO₄ and concentrated under reduced pressure. Purification of the crude residue by column chromatography gave (S)-6-(cyclopropylmethyl)-2,2-spirocyclobutyl-3,4-dihydro-2H-pyrano

[2,3-b]pyridin-4-amine as a 2:1 mixture an impurity. This material was used without further purification.

Example 21

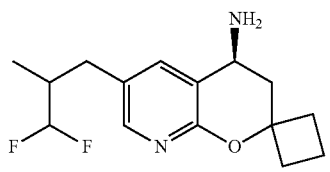 [SMILES: CC(Cc1cnc2c(c1)[C@@H](N)CC1(CCC1)O2)C(F)F]

tert-Butyl (S)-6-(3-hydroxy-2-methylpropyl)-2,2-spirocyclobutyl-3,4-dihydro-2H-pyrano[2,3-b]pyridin-4-ylcarbamate Step 1: tert-butyl (S)-6-(3-hydroxy-2-methylpropyl)-2,2-spirocyclobutyl-3,4-dihydro-2H-pyrano[2,3-b]pyridin-4-ylcarbamate A solution of tert-butyldimethyl(2-methylallyloxy)silane (9 g, 47 mmol) and 9-BBN 0.5M in THF (95 ml, 47 mmol) was degassed and allowed to stir at RT for 3 hours. A separate solution of palladium(II) acetate (0.2 g, 0.9 mmol) and S-Phos (1 g, 3 mmol) in THF (5 mL) and benzene (5 mL) was thoroughly degassed and allowed to stir at RT for one hour. The palladium solution was then added to the borane solution, followed by potassium phosphate (8 g, 38 mmol) and a solution of (S)-tert-butyl 6-bromo-2,2-spirocyclobutyl-3,4-dihydro-2H-pyrano[2,3-b]pyridin-4-ylcarbamate ((3.5 g, 9 mmol) in DMF (15 mL). The reaction mixture was degassed and heated to 100° C. 4 hours. Cesium fluoride (14 g, 95 mmol) was added followed by 1 mL water and the reaction mixture was heated to 100° C. overnight. The reaction mixture was decanted to a clean flask and concentrated. The crude residue was treated with TBAF 1M in THF (19 ml, 19 mmol) and was allowed to stir at RT for 2 hours. The reaction mixture was diluted with EtOAc, washed with saturated NH$_4$Cl solution, water, and brine. The organics were dried over MgSO$_4$ and concentrated under reduced pressure. Purification of the crude residue by column chromatography gave tert-butyl (S)-6-(3-hydroxy-2-methylpropyl)-2,2-spirocyclobutyl-3,4-dihydro-2H-pyrano[2,3-b]pyridin-4-ylcarbamate (1.444 g, 42% yield) as a yellow solid.

Step 2: tert-Butyl (S)-6-(2-methyl-3-oxopropyl)-2,2-spirocyclobutyl-3,4-dihydro-2H-pyrano[2,3-b]pyridin-4-ylcarbamate A solution of tert-butyl (S)-6-(3-hydroxy-2-methylpropyl)-2,2-spirocyclobutyl-3,4-dihydro-2H-pyrano[2,3-b]pyridin-4-ylcarbamate (2.290 g, 6.32 mmol) in wet DCM (20 mL) was treated with Dess-Martin periodinane (3.22 g, 7.58 mmol) and allowed to stir for 2 hours. The reaction mixture was diluted with 20 mL ether, treated with 1 mL saturated NaHCO$_3$ solution followed by sodium thiosulfate (4.99 g, 31.6 mmol) and was allowed to stir at RT for 1 hr. The reaction mixture was then diluted with EtOAc, washed with saturated NaHCO$_3$ solution, water, and brine. The organic layer was dried over MgSO$_4$ and concentrated under reduced pressure. Purification of the crude residue by column chromatography gave tert-butyl (S)-6-(2-methyl-3-oxopropyl)-2,2-spirocy- clobutyl-3,4-dihydro-2H-pyrano[2,3-b]pyridin-4-ylcarbamate (1.43 g, 62.8% yield) as a sticky white solid.

Step 3: tert-Butyl (S)-6-(3,3-difluoro-2-methylpropyl)-2,2-spirocyclobutyl-3,4-dihydro-2H-pyrano[2,3-b]pyridin-4-ylcarbamate A solution of tert-butyl (S)-6-(2-methyl-3-oxopropyl)-2,2-spirocyclobutyl-3,4-dihydro-2H-pyrano[2,3-b]pyridin-4-yl-carbamate (1.180 g, 3.27 mmol) in DCM (30 mL) was cooled to −78° C. and treated with deoxofluor (0.905 ml, 4.91 mmol). The solution was allowed to warm to RT and triethylamine trihydrofluoride (0.0534 ml, 0.327 mmol) was added. After 1.5 hours, so an additional equivalent of deoxofluor was added, and the reaction mixture was allowed to stir at RT for an additional hour. The reaction mixture was concentrated under reduced pressure, and the crude residue was purified by column chromatography yielding tert-butyl (S)-6-(3,3-difluoro-2-methylpropyl)-2,2-spirocyclobutyl-3,4-dihydro-2H-pyrano[2,3-b]pyridin-4-ylcarbamate (0.940 g, 75.1% yield) as a white solid.

Step 4: (4S)-6-(3,3-difluoro-2-methylpropyl)-2,2-spirocyclobutyl-3,4-dihydro-2H-pyrano[2,3-b]pyridin-4-amine A solution of tert-butyl (S)-6-(3,3-difluoro-2-methylpropyl)-2,2-spirocyclobutyl-3,4-dihydro-2H-pyrano[2,3-b]pyridin-4-ylcarbamate (1.015 g, 2.65 mmol) in DCM (10 mL) was treated with TFA (10.2 ml, 133 mmol) and allowed to stir overnight at RT. The reaction mixture was then concentrated under reduced pressure. The crude residue was dissolved in EtOAc, washed with 1N NaOH and brine. The organics were dried over MgSO$_4$ and concentrated under reduced pressure yielding (4S)-6-(3,3-difluoro-2-methylpropyl)-2,2-spirocyclobutyl-3,4-dihydro-2H-pyrano[2,3-b]pyridin-4-amine (0.720 g, 96.1% yield). The product was a mixture of diastereomers that was separated by chiral HPLC and the resulting single isomers were used for preparing compounds of Formulas I and II.

Example 22

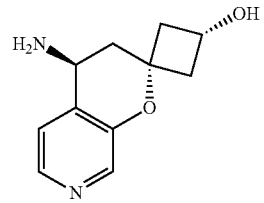 [SMILES: N[C@H]1C[C@]2(C[C@H](O)C2)Oc2cnccc21]

(1S,3S,4'S)-3-Hydroxy-3',4'-dihydrospiro[cyclobutane-1,2'-pyrano[2,3-c]pyridin-4'-amine Step 1: (1S,3S)-3-tert-Butyldimethylsiloxy-3',4'-dihydrospiro[cyclobutane-1,2'-pyrano[2,3-c]pyridin-4'-one; and (1S,3R)-3-tert-Butyldimethylsiloxy-3',4'-dihydrospiro[cyclobutane-1,2'-pyrano[2,3-c]pyridin-4'-one 3-(tert-Butyldimethylsilyloxy)cyclobutanone (15 g, 77 mmol), 1-(3-Hydroxypyridin-4-yl)ethanone (Example 37, 10.5 g, 77 mmol) and pyrrolidine (19 ml, 230 mmol) were dissolved in 500 ml CH₃CN and stirred at 65° C. for 2 h. TLC analysis revealed the disappearance of the SM and the formation of a single new spot. The mixture was evaporated (100 ml residue) and partitioned between water and EtOAc. The phases were separated and the aqueous was extracted 3× with EtOAc. The combined organic extracts were dried over MgSO₄ and evaporated and the mixture was purified via glass col. chromatography. The title compounds (8.500 g, 35% yield) were obtained as a yellow solid (1:1 mixture of stereo isomers)

Step 2: (1S,3S,4'R)-3-tert-Butyldimethylsiloxy-3',4'-dihydrospiro[cyclobutane-1,2'-pyrano[2,3-c]pyridin-4'-ol; (1S,3R,4'R)-3-tert-Butyldimethylsiloxy-3',4'-dihydrospiro[cyclobutane-1,2'-pyrano[2,3-c]pyridin-4'-ol (1S,3S)-3-tert-Butyldimethylsiloxy-3',4'-dihydrospiro[cyclobutane-1,2'-pyrano[2,3-c]pyridin-4'-one and (1S,3R)-3-tert-Butyldimethylsiloxy-3',4'-dihydrospiro[cyclobutane-1,2'-pyrano[2,3-c]pyridin-4'-one (1:1 mixture of stereo isomers) (8.5000 g, 26.61 mmol) were dissolved in 150 ml toluene and 50 ml water was added. Ar gas was bubbled through the mixture for 15 min. Tetrabutylammonium bromide (0.2573 g, 0.7982 mmol), sodium formate (18.09 g, 266.1 mmol) and TPAP (0.5190 g, 0.7982 mmol) were added and the mixture was stirred for 14 h under an Ar atmosphere. The mixture was partitioned between EtOAc and water and the phases were separated. The aqueous was extracted 3 times with EtOAc, dried over MgSO₄ and evaporated. Glass col. chrom (10-50% EtOAc in hex.) provided the title compounds (6.630 g, 77.51% yield) as yellow oil. (1:1 mixture of stereo isomers). MS m/z: 322.2 (M+1).

Step 3: (1S,3S,4'S)-3-tert-Butyldimethylsiloxy-3',4'-dihydrospiro[cyclobutane-1,2'-pyrano[2,3-c]pyridin-4'-azide; (1S,3R,4'S)-3-tert-Butyldimethylsiloxy-3',4'-dihydrospiro[cyclobutane-1,2'-pyrano[2,3-c]pyridin-4'-azide (1S,3S,4'R)-3-tert-Butyldimethylsiloxy-3',4'-dihydrospiro[cyclobutane-1,2'-pyrano[2,3-c]pyridin-4'-ol, (1S,3R,4'R)-3-tert-Butyldimethylsiloxy-3',4'-dihydrospiro[cyclobutane-1,2'-pyrano[2,3-c]pyridin-4'-ol (1:1 mixture of stereo isomers) (6.6300 g, 20.62 mmol), diphenyl azidophosphate (6.667 ml, 30.93 mmol) and DBU (4.626 ml, 30.93 mmol) were dissolved in 40 ml CH₂Cl₂ and stirred over the weekend. Monitoring revealed that the starting materials were almost consumed and product formed, but still a large portion of the phosphonate ester remained. 40 ml of Water was added and the mixture was extracted 3 times with Et₂O, dried over MgSO₄ and evaporated. The crude product was used w/o purification in the next step. MS m/z: 347.2 (M+1).

Step 4: (1S,3S,4'S)-3-tert-Butyldimethylsiloxy-3',4'-dihydrospiro[cyclobutane-1,2'-pyrano[2,3-c]pyridin-4'-amine; (1S,3R,4'S)-3-tert-Butyldimethylsiloxy-3',4'-dihydrospiro[cyclobutane-1,2'-pyrano[2,3-c]pyridin-4'-amine The crude (1S,3S,4'S)-3-tert-Butyldimethylsiloxy-3',4'-dihydrospiro[cyclobutane-1,2'-pyrano[2,3-c]pyridin-4'-azide and (1S,3R,4'S)-3-tert-Butyldimethylsiloxy-3',4'-dihydrospiro[cyclobutane-1,2'-pyrano[2,3-c]pyridin-4'-azide (1:1 mixture of stereo isomers) from the previous reaction (6.9 g, 20 mmol) was dissolved in 200 ml THF and lithium aluminum hydride, 2M in THF (30 ml, 60 mmol) was added at 0° C. The mixture was stirred for 60 min and hydrolyzed with Na₂SO₄-10H₂O until gas evolution had ceased. The mixture was filtered and evaporated and purified. (2-10% MeOH in CH₂Cl₂) glass col. chromatography provided the title compounds) as a yellow oil as a mixture of diastereomers. The diastereomers were separated by SFC. (1S,3S,4'S)-3-tert-Butyldimethylsiloxy-3',4'-dihydrospiro[cyclobutane-1,2'-pyrano[2,3-c]pyridin-4'-amine (1.200 g, 19% yield) and (1S,3R,4'S)-3-tert-Butyldimethylsiloxy-3',4'-dihydrospiro[cyclobutane-1,2'-pyrano[2,3-c]pyridin-4'-amine were obtained. MS m/z: 321.2 (M+1).

Example 23

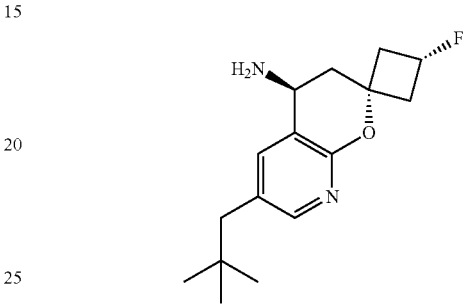

(1S,3S,4'S)-6'-(2,2-Dimethylpropyl)-3-fluoro-3',4'-dihydrospiro[cyclobutane-1,2'-pyrano[2,3-b]pyridin-4'-amine Step 1: (1S,3R,4'S)-tert-butyl 6'-(2,2-Dimethylpropyl)-3-hydroxy-3',4'-dihydrospiro[cyclobutane-1,2'-pyrano[2,3-b]pyridin-4'-carbamate (1S,3R,4'S)-6'-(2,2-Dimethylpropyl)-3-hydroxy-3',4'-dihydrospiro[cyclobutane-1,2'-pyrano[2,3-b]pyridin-4'-amine; (1S,3S,4'S)-6'-(2,2-Dimethylpropyl)-3-hydroxy-3',4'-dihydrospiro[cyclobutane-1,2'-pyrano[2,3-b]pyridin-4'-amine (mixture of stereoisomers) (7.5000 g, 21.472 mmol) was dissolved in 400 ml THF/H₂O (1:1) and carbonic acid monosodium salt (9.0189 g, 107.36 mmol) and di-tert-butylpyrocarbonate (9.3723 g, 42.944 mmol) were added. The mixture was stirred over night and 300 ml H₂O was added and the product was extracted out with EtOAc (3×800 ml). The combined organic phases were dried over MgSO₄ and evaporated and purified by chiral purification (SFC). MS m/z: 377.3 (M+1).

Alternatively, (1S,3S,4'S)-tert-butyl 6'-(2,2-Dimethylpropyl)-3-fluoro-3',4'-dihydrospiro[cyclobutane-1,2'-pyrano[2,3-b]pyridin-4'-carbamate can be made by: (1S,3R,4'S)-6'-(2,2-Dimethylpropyl)-3-hydroxy-3',4'-dihydrospiro[cyclobutane-1,2'-pyrano[2,3-b]pyridin-4'-(BOC)-amine (1.050 g, 2.789 mmol) was dissolved in 13 ml CH₂Cl₂ and DAST (0.4790 ml, 3.626 mmol) was added. The reaction was heated to 45° C. for 4 h and cooled to RT. The mixture was poured into 15 ml of sat. NaHCO₃ and extracted 3× with EtOAc (3×150 ml). The combined organic extracts were dried over MgSO4 and evaporated. The crude product was used without purification in the next step. MS m/z: 379.2 (M+1).

Step 2: (1S,3S,4'S)-6'-(2,2-Dimethylpropyl)-3-fluoro-3',4'-dihydrospiro[cyclobutane-1,2'-pyrano[2,3-b]pyridin-4'-amine The crude product from step 1 was dissolved in 5 ml MeOH and treated with 20 ml 4M HCl in dioxane. The mixture was stirred for 4 h at RT. and evaporated. The messy mixture was purified on HPLC. The combined HPLC fractions were basified (10% Na2CO3, aq.) and extracted with EtOAc (3×250 ml). The title compound (0.180 g) was obtained as a yellow solid, MS m/z: 279.2 (M+1).

Example 24

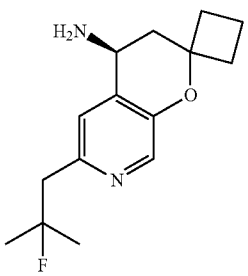 [SMILES: CC(C)(F)Cc1cc2c(cn1)OC1(CCC1)C[C@@H]2N]

(4'S)-6'-(2-Fluoro-2-methylpropyl)-3',4'-dihydrospiro[cyclobutane-1,2'-pyrano[2,3-c]pyridin-4' amine Step 1: 1-(5-(methoxymethoxy)pyridin-2-yl)-2-methylpropan-2-ol 5-(Methoxymethoxy)-2-methylpyridine (22.1500 g, 144.6 mmol) was dissolved in 1500 ml THF and cooled to −78° C. tert-Butyllithium (97.82 ml, 166.3 mmol) was added and the mixture was stirred for 15 min. Acetone, (42.52 ml, 578.4 mmol) was added and stirring of the mixture was continued for 15 min. The reaction was hydrolyzed with 300 ml H$_2$O and extracted with 4 L EtOAc (2×). The combined organic extracts were dried over MgSO$_4$ and evaporated. Glas col. chrom (20-100% EtOAc provided the 2 products: 1-(5-(methoxymethoxy)pyridin-2-yl)-2-methylpropan-2-ol (7.5000 g, 24.55% yield) and 2-(5-(methoxymethoxy)-2-methylpyridin-4-yl)propan-2-ol (15.00 g, 49.10% yield). MS m/z: 212.0 (M+1).

Step 2: 2-(2-fluoro-2-methylpropyl)-5-(methoxymethoxy)pyridine 1-(5-(methoxymethoxy)pyridin-2-yl)-2-methylpropan-2-ol (7.600 g, 36.0 mmol) was dissolved in 200 ml CH$_2$Cl$_2$ and cooled to −78° C. DAST (9.51 ml, 72.0 mmol) was added drop wise to the solution and stirring was continued for 30 min The mixture was allowed to warm up to 0° C. and was hydrolyzed with NaHCO$_3$ (200 ml). Stirring was continued in the cold until gas evolution had ceased and the phases were separated. The aqueous was extracted 2× with EtOAc and the combined organic layers were dried over MgSO$_4$ and evaporated. Glass col. Chromatography of the crude material provided 2-(2-fluoro-2-methylpropyl)-5-(methoxymethoxy)pyridine (5.80 g, 75.6% yield) as a pale yellow oil.

Step 3: 1-(2-(2-fluoro-2-methylpropyl)-5-(methoxymethoxy)pyridin-4-yl)ethanol 2,2,6,6-Tetramethylpiperidine (8.26 ml, 49.0 mmol) was dissolved with 270 ml THF and 1-butyllithium (14.1 ml, 35.4 mmol) was added at −78° C. The mixture was stirred for 10 min in an ice bath and cooled back to −78° C. A solution of 2-(2-fluoro-2-methylpropyl)-5-(methoxymethoxy)pyridine (5.8000 g, 27.2 mmol) in 20 ml THF was added dropwise and the reaction was stirred for 20 min. Acetylaldehyde (7.65 ml, 136 mmol) was added to the dark red solution and the color disappeared. Stirring was continued for 20 min and the mixture was hydrolyzed with 50 ml of water. The mixture was warmed to RT and extracted 3× with CH$_2$Cl$_2$ (300 ml each). The combined organic extracts were dried over MgSO$_4$ and evaporated and purified via glass col. chrom. (30-80% EtOAc in hex.) to provide 1-(2-(2-fluoro-2-methylpropyl)-5-(methoxymethoxy)pyridin-4-yl)ethanol a white solid. MS m/z: 258.2 (M+1).

Example 25

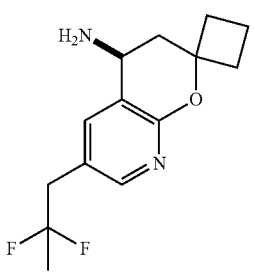 [SMILES: CC(F)(F)Cc1cnc2c(c1)[C@@H](N)CC1(CCC1)O2]

(4S)-6-(2,2-Difluoropropyl)-2,2-cyclobutyl-3,4-dihydro-2H-pyrano[2,3-b]pyridin-4-amine Step 1: (4S)-tert-Butyl 6-(2-oxopropyl)-1)-2,2-cyclobutyl-3,4-dihydro-2H-pyrano[2,3-b]pyridin-4-ylcarbamate Anhydrous, de-gassed THF (20 mL) was added to 2-(dicyclohexylphosphino)-2'-methylbiphenyl (1.2 g, 3.2 mmol) and tris(dibenzylideneacetone)dipalladium (0) chloroform adduct (1.4 g, 1.4 mmol), and the resulting solution was warmed to 45° C. and sparged with N$_2$. After 20 min, the reaction mixture was allowed to cool to RT, then added to a stirring, degassed mixture of (S)-tert-butyl 6-bromo-2,2-cyclobutyl-3,4-dihydro-2H-pyrano[2,3-b]pyridin-4-ylcarbamate (10 g, 27 mmol), finely ground potassium phosphate tribasic (14 g, 68 mmol), and acetone (100 mL, 1400 mmol) at RT, and the resulting mixture was sparged with N$_2$. After 20 min, the reaction mixture was heated at reflux for 24 h. The reaction mixture was allowed to cool to RT, filtered through a 0.45 µm Teflon filter, and the filtrate was concentrated. The residue was purified by flash chromatography on silica gel (gradient elution; 1:1→2:1 ethyl acetate-hexane) to afford 3.7 g (39%) of (S)-tert-butyl 6-(2-oxopropyl)-2,2-cyclobutyl-3,4-dihydro-2H-pyrano[2,3-b]pyridin-4-ylcarbamate as a yellow solid.

Step 2: (4S)-tert-Butyl 6-(2,2-difluoropropyl)-2,2-cyclobutyl-3,4-dihydro-2H-pyrano[2,3-b]pyridin-4-ylcarbamate Diethylaminosulfurtrifluoride (13 mL, 110 mmol) was added to a stirring solution of (S)-tert-butyl 6-(2-oxopropyl)-2,2-cyclobutyl-3,4-dihydro-2H-pyrano[2,3-b]pyridin-4-ylcarbamate (3.7 g, 11 mmol), ethanol (0.12 mL, 2.2 mmol), and CH$_2$Cl$_2$ (55 mL) at RT. After 24 h, the reaction mixture was added to a rapidly stirring solution of aqueous 10% Na$_2$CO$_3$. After 1 h, ethyl acetate was added, the layers were separated, the organic material was washed sequentially with aqueous 10% Na₂CO₃ and brine, dried (Na₂SO₄), filtered, and the filtrate was concentrated. The residue was purified by flash chromatography on silica gel (49:1 CH₂Cl₂-methanol) to afford 1.8 g (46%) of (S)-tert-butyl 6-(2,2-difluoropropyl)-2,2-cyclobutyl-3,4-dihydro-2H-pyrano[2,3-b]pyridin-4-ylcarbamate as a yellow solid.

Step 3: (S)-6-(2,2-Difluoropropyl)-2,2-cyclobutyl-3,4-dihydro-2H-pyrano[2,3-b]pyridin-4-amine Hydrogen chloride (12 mL of a 4.0 M solution with 1,4-dioxane, 49 mmol) was added to a stirring solution of (4S)-tert-butyl 6-(2,2-difluoropropyl)-2,2-cyclobutyl-3,4-dihydro-2H-pyrano[2,3-b]pyridin-4-ylcarbamate (1.8 g, 4.9 mmol) and CH₂Cl₂ (49 mL) at RT. After 24 h, the reaction mixture was concentrated, the residue was partitioned between aqueous 10% Na₂CO₃ and EtOAc, the layers were separated. The organic layer was washed with aqueous 10% Na₂CO₃, brine, dried (Na₂SO₄), filtered, and the filtrate was concentrated to afford (S)-6-(2,2-difluoropropyl)-2,2-cyclobutyl-3,4-dihydro-2H-pyrano[2,3-b]pyridin-4-amine as a yellow oil.

Example 26

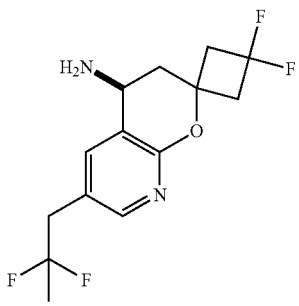 [SMILES: CC(F)(F)Cc1cnc2c(c1)[C@@H](N)CC1(CC(F)(F)C1)O2]

(S)-6-(2,2-Difluoropropyl)-2,2-(2',2'-difluorocyclobutyl)-3,4-dihydro-2H-pyrano[2,3-b]pyridin-4-amine Step 1: 1-(6-Fluoropyridin-3-yl)propan-2-one Anhydrous, de-gassed THF (20 mL) was added to 2-(dicyclohexylphosphino)-2'-methylbiphenyl (1.2 g, 3.2 mmol) and tris(dibenzylideneacetone)dipalladium (0) chloroform adduct (1.4 g, 1.4 mmol), and the resulting solution was warmed to 45° C. and sparged with N₂. After 20 min, the reaction mixture was allowed to cool to RT, then added to a stirring, degassed mixture of 5-bromo-2-fluoropyridine (4.8 g, 27 mmol), finely ground potassium phosphate tribasic (14 g, 68 mmol), and acetone (100 mL, 1400 mmol) at RT, and the resulting mixture was sparged with N₂. After 20 min, the reaction mixture was heated at reflux for 24 h, the reaction mixture was allowed to cool to room temperature, filtered through a 0.45 μm Teflon filter, and the filtrate was concentrated. The residue was purified by flash chromatography on silica gel (gradient elution; 4:1→2:1 hexane-ethyl acetate) to give 2.3 g (55%) of 1-(6-fluoropyridin-3-yl)propan-2-one as a brown oil.

Step 2: 5-(2,2-Difluoropropyl)-2-fluoropyridine

Diethylaminosulfurtrifluoride (9.8 mL, 75 mmol) was added to a stirring solution of 1-(6-fluoropyridin-3-yl)propan-2-one (2.3 g, 15 mmol), ethanol (0.18 mL, 3.0 mmol), and CH₂Cl₂ (60 mL) at RT. After 24 h, the reaction mixture was added to a rapidly stirring solution of aqueous 10% Na₂CO₃. After 1 h, ethyl acetate was added, the layers were separated, the organic layer was washed sequentially with aqueous 10% Na₂CO₃ and brine, dried (Na₂SO₄), filtered, and the filtrate was concentrated. The residue was purified by flash chromatography on silica gel (9:1 hexane-ethyl acetate) to afford 1.5 g (57%) of 5-(2,2-difluoropropyl)-2-fluoropyridine as a yellow-orange oil.

Step 3: (4S)-2-(1,3-Bis(tert-butyldimethylsiloxy)cyclobutyl)-1-(5-(2,2-difluoropropyl)-2-fluoropyridin-3-yl)-ethyl-((R)-tert-butylsulfinyl)amine Butyllithium (4.1 mL of a 2.5 M solution with toluene, 10 mmol) was added to a stirring solution of 2,2,6,6-tetramethylpiperidine (2.0 mL, 12 mmol) and THF (43 mL) at −78° C. After 5 min, the reaction mixture was raised above the cooling bath for 10 min, re-cooled to −78° C., and then a solution of 5-(2,2-difluoropropyl)-2-fluoropyridine (1.5 g, 8.6 mmol) and THF (8.6 mL) was added. After 30 min, a solution of 2-(1,3-bis(tert-butyldimethylsiloxy)cyclobutyl)acetaldehyde (R)-tert-butylsulfinylimine (4.4 g, 9.4 mmol) and THF (9.4 mL) was added. After 20 min, saturated aqueous NaHCO₃ was added, the reaction mixture was allowed to warm to RT, partitioned between saturated aqueous NaHCO₃ and ethyl acetate, the layers were separated, the organic layer was washed with saturated aqueous NaHCO₃, brine, dried (NaSO₄), filtered, and the filtrate was concentrated. The residue was purified by flash chromatography on silica gel (gradient elution; 4:1→3:1→2:1 hexane-ethyl acetate) to afford 2.9 g (53%) of (4S)-2-(1,3-bis(tert-butyldimethylsiloxy)cyclobutyl)-1-(5-(2,2-difluoropropyl)-2-fluoropyridin-3-yl)-ethyl-((R)-tert-butylsulfinyl)amine as a yellow solid.

Step 4: (S)-6-(2,2-difluoropropyl)-2,2-((R)-2'-hydroxy)cyclobutyl-3,4-dihydro-2H-pyrano[2,3-b]pyridin-4-amine and (S)-6-(2,2-difluoropropyl)-2,2-((S)-2'-hydroxy)cyclobutyl-3,4-dihydro-2H-pyrano[2,3-b]pyridin-4-amine Hydrogen fluoride (24 mL of a 70 wt % solution with pyridine, 1300 mmol) was added to (S)-2-(1,3-bis(tert-butyldimethylsiloxy)cyclobutyl)-1-(5-(2,2-difluoropropyl)-2-fluoropyridin-3-yl)-ethyl-((R)-tert-butylsulfinyl) amine (1.7 g, 2.7 mmol) in Teflon™ reaction vessel, and the reaction mixture was heated at 80° C. After 48 h, the reaction mixture was added to aqueous 10% Na₂CO₃, the mixture was stirred vigorously for 2 h, ethyl acetate was added, the layers were separated, the organic material was washed with aqueous 10% Na₂CO₃, brine, dried (Na₂SO₄), filtered, and the filtrate was concentrated to afford 0.64 g (84%) of a mixture of (S)-6-(2,2-difluoropropyl)-2,2-((R)-2'-hydroxy)cyclobutyl-3,4-dihydro-2H-pyrano[2,3-b]pyridin-4-amine and (S)-6-(2,2-difluoropropyl)-2,2-((S)-2'-hydroxy)cyclobutyl-3,4-dihydro-2H-pyrano[2,3-b]pyridin-4-amine as a yellow solid.

Step 5: (S)-tert-butyl 6-(2,2-difluoropropyl)-2,2-((R)-2'-hydroxy)cyclobutyl-3,4-dihydro-2H-pyrano[2,3-b]pyridin-4-ylcarbamate and (S)-tert-butyl 6-(2,2-difluoropropyl)-2,2-((S)-2'-hydroxy)cyclobutyl-3,4-dihydro-2H-pyrano[2,3-b]pyridin-4-ylcarbamate Di-tert-butyl dicarbonate (0.64 g, 2.9 mmol) was added to a stirring solution of the (S)-6-(2,2-difluoropropyl)-2,2-((R)-2'-hydroxy)cyclobutyl-3,4-dihydro-2H-pyrano[2,3-b]pyridin-4-amine and (S)-6-(2,2-difluoropropyl)-2,2-((S)-2'-hydroxy)cyclobutyl-3,4-dihydro-2H-pyrano[2,3-b]pyridin-4-amine mixture (0.64 g, 2.3 mmol), CH$_2$Cl$_2$ (23 mL), and diisopropyethylamine (2.0 mL, 11 mmol) at RT. After 24 h, aqueous 10% Na$_2$CO$_3$ was added, the mixture was stirred vigorously for 1 h, EtOAc was added, the layers were separated, the organic layer was washed with aqueous 10% Na$_2$CO$_3$, brine, dried (Na$_2$SO$_4$), filtered, and the filtrate was concentrated. The residue was purified by flash chromatography on silica gel (19:1 CH$_2$Cl$_2$-methanol) to afford 0.32 g (37%) of a mixture of (S)-tert-butyl 6-(2,2-difluoropropyl)-2,2-((R)-2'-hydroxy)cyclobutyl-3,4-dihydro-2H-pyrano[2,3-b]pyridin-4-ylcarbamate and (S)-tert-butyl 6-(2,2-difluoropropyl)-2,2-((S)-2'-hydroxy)cyclobutyl-3,4-dihydro-2H-pyrano[2,3-b]pyridin-4-ylcarbamate as a yellow-brown solid.

Step 6: (S)-tert-butyl 6-(2,2-difluoropropyl)-2,2-cyclobutan-2'-one-3,4-dihydro-2H-pyrano[2,3-b]pyridin-4-ylcarbamate Dess-Martin periodinane (0.49 g, 1.2 mmol) was added to a mixture of (S)-tert-butyl 6-(2,2-difluoropropyl)-2,2-((R)-2'-hydroxy)cyclobutyl-3,4-dihydro-2H-pyrano[2,3-b]pyridin-4-ylcarbamate and (S)-tert-butyl 6-(2,2-difluoropropyl)-2,2-((S)-2'-hydroxycyclobutyl)-3,4-dihydro-2H-pyrano[2,3-b]pyridin-4-ylcarbamate (0.32 g, 0.83 mmol), CH$_2$Cl$_2$ (8.3 mL), and NaHCO$_3$ (0.21 g, 2.5 mmol) at RT. After 2 h, the reaction mixture was purified by flash chromatography on silica gel (1:1 hexane-ethyl acetate) to afford 0.24 g (75%) of (S)-tert-butyl 6-(2,2-difluoropropyl)-2,2-cyclobutan-2'-one-3,4-dihydro-2H-pyrano[2,3-b]pyridin-4-ylcarbamate as a colorless solid.

Step 7: (S)-tert-butyl 6-(2,2-difluoropropyl)-2,2-(2',2'-difluorocyclobutyl)-3,4-dihydro-2H-pyrano[2,3-b]pyridin-4-ylcarbamate Diethylaminosulfur trifluoride (0.41 mL, 3.1 mmol) was added to a stirring solution of (S)-tert-butyl 6-(2,2-difluoropropyl)-2,2-cyclobutan-2'-one-3,4-dihydro-2H-pyrano[2,3-b]pyridin-4-ylcarbamate (0.24 g, 0.63 mmol), CH$_2$Cl$_2$ (6.3 mL), and ethanol (7.3 L, 0.13 mmol) at RT. After 24 h, the reaction mixture was added to a stirring solution of aqueous 10% Na$_2$CO$_3$, the mixture was stirred for 1 h, partitioned between EtOAc and aqueous 10% Na$_2$CO$_3$, the layers were separated, the organic layer was washed with aqueous 10% Na$_2$CO$_3$, brine, dried (Na$_2$SO$_4$), filtered, and the filtrate was concentrated. The residue was purified by flash chromatography on silica gel (2:1 hexane-ethyl acetate) to give 0.15 g (59%) of (S)-tert-butyl 6-(2,2-difluoropropyl)-2,2-(2',2'-difluorocyclobutyl)-3,4-dihydro-2H-pyrano[2,3-b]pyridin-4-ylcarbamate as a colorless solid.

Step 8: (4S)-6-(2,2-difluoropropyl)-2,2-(2',2'-difluorocyclobutyl)-3,4-dihydro-2H-pyrano[2,3-b]pyridin-4-amine Hydrogen chloride (0.93 mL of a 4.0 M solution with 1,4-dioxane, 3.7 mmol) was added to a stirring solution of (S)-tert-butyl 6-(2,2-difluoropropyl)-2,2-(2',2'-difluorocyclobutyl)-3,4-dihydro-2H-pyrano[2,3-b]pyridin-4-ylcarbamate (0.15 g, 0.37 mmol) and CH$_2$Cl$_2$ (3.7 mL) at RT. After 24 h, the reaction mixture was concentrated, the residue was partitioned between aqueous 10% Na$_2$CO$_3$ and ethyl acetate, the layers were separated, the organic material was washed with aqueous 10% Na$_2$CO$_3$, brine, dried (Na$_2$SO$_4$), filtered, and the filtrate was concentrated to afford (S)-6-(2,2-difluoropropyl)-2,2-(2',2'-difluorocyclobutyl)-3,4-dihydro-2H-pyrano[2,3-b]pyridin-4-amine as a yellow solid.

Example 27

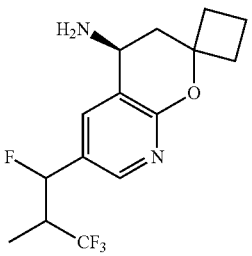 [SMILES: CC(C(F)c1cnc2c(c1)[C@@H](N)CC1(CCC1)O2)C(F)(F)F]

(4S)-2,2-Spirocyclobutyl-6-(1,3,3,3-tetrafluoro-2-methylpropyl)-3,4-dihydro-2H-pyrano(2,3-b)pyridine-4-amine Step 1: tert-Butyl allyl((S)-2,2-spirocyclobutyl-6-(3,3,3-trifluoro-1-hydroxy-2-methylpropyl)-3,4-dihydro-2H-pyrano(2,3-b)pyridine-4-yl)carbamate To a cooled (−78° C.) solution of (5)-tert-butyl allyl(6-bromo-2,2-spirocyclobutyl-3,4-dihydro-2H-pyrano(2,3-b)pyridine-4-yl)carbamate (8.70 g, 21 mmol) in diethylether was added tert-butyllithium (25 ml, 43 mmol) dropwise. After stirred for 15 min, the fresh distilled 3,3,3-trifluoro-2-methylpropanal (5.8 ml, 53 mmol) was added, and the reaction was stirred for 30 min, and then quenched with saturated NH$_4$Cl. The resulted mixture was allowed to warm to RT and extracted with EtOAc (3×). The organic layers were combined, dried over Na$_2$SO$_4$, filtered and concentrated. The residue was purified on silica gel column to afford the title compound as a mixture of isomers (4.5 g, 46% yield) as light yellow oil. MS m/z: 457 (M+1).

Step 2: tert-Butyl allyl((S)-2,2-spirocyclobutyl-6-(1,3,3,3-tetrafluoro-2-methylpropyl)-3,4-dihydro-2H-pyrano(2,3-b)pyridine-4-yl)carbamate To a cooled (−78° C.) solution of tert-butyl allyl((S)-2,2-spirocyclobutyl-6-(3,3,3-trifluoro-1-hydroxy-2-methylpropyl)-3,4-dihydro-2H-pyrano(2,3-b)pyridine-4-yl)carbamate (1.24 g, 2.7 mmol) in toluene was added (diethylamino)sulfur trifluoride (0.54 ml, 4.1 mmol) via a syringe. The reaction was stirred for 50 min, then quenched with saturated NH$_4$Cl (10 ml) and warmed to RT. The layers were separated. The aqueous layer was extracted with EtOAc (2×20 ml). The organic layers were combined, dried over Na$_2$SO$_4$, filtered and concentrated. The crude residue was purified on a silica gel column (10-15% EtOAc/hexane) to afford the title compound as a mixture of isomers as colorless oil. MS m/z: 459 (M+1).

Step 3: (4S)-N-Allyl-2,2-spirocyclobutyl-6-(1,3,3,3-tetrafluoro-2-methylpropyl)-3,4-dihydro-2H-pyrano(2,3-b)pyridine-4-amine To a solution of tert-butyl allyl((S)-2,2-spirocyclobutyl-6-(1,3,3,3-tetrafluoro-2-methylpropyl)-3,4-dihydro-2H-pyrano(2,3-b)pyridine-4-yl)carbamate (430 mg, 938 μmol) in MeOH was added hydrogen chloride 4.0m in 1,4-dioxane (2.0 ml, 8000 μmol). The reaction was stirred for 2 days (over the weekend) at RT, then concentrated and neutralized with 10% Na₂CO₃ and extracted with DCM (3×). The organic layers were combined, dried over Na₂SO₄ and filtered. The filtrate was concentrated and dried in vacuum to afford the title compound as a mixture of isomers as a light yellow oil. MS+m/z: 359 (M+1).

Step 4: (4S)-2,2-Spirocyclobutyl-6-(1,3,3,3-tetrafluoro-2-methylpropyl)-3,4-dihydro-2H-pyrano(2,3-b)pyridine-4-amine The crude product from step 3 above was dissolved in CH₂Cl₂ (10 ml) to which 1,3-dimethylpyrimidine-2,4,6(1H,3H,5H)-trione (439 mg, 2814 mmol) was added. The mixture was purged with N₂ gas for 10 min and tetrakis(triphenylphosphine)palladium (0) (54 mg, 47 mmol) was added. The reaction was heated at 40° C. for 3 h, then cooled and diluted with DCM and washed with 10% Na₂CO₃ (2×). The aqueous layer was back extracted with EtOAc (2×). The organic layers were combined, dried over Na₂SO₄, filtered and concentrated. The residue was dried in vacuum to afford the title compound as mixture of isomers as a yellow oil. MS m/z: 319 (M+1).

Example 28

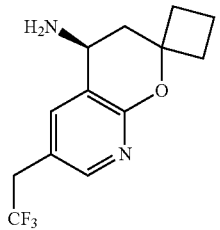 [SMILES: N[C@H]1CC2(CCC2)Oc2ncc(CC(F)(F)F)cc21]

(S)-2,2-Spirocyclobutyl-6-(2,2,2-trifluoroethyl)-3,4-dihydro-2H-pyrano(2,3-b)pyridine-4-amine Step 1: (5)-tert-Butyl allyl(2,2-spirocyclobutyl-6-(2,2,2-trifluoroacetyl)-3,4-dihydro-2H-pyrano(2,3-b)pyridine-4-yl)carbamate To a cooled (−78° C.) solution of (5)-tert-butyl allyl(6-bromo-2,2-spirocyclobutyl-3,4-dihydro-2H-pyrano(2,3-b)pyridine-4-yl)carbamate (19.85 g, 48 mmol) in THF (400 ml) was added butyllithium solution, ~2.5 m in toluene (21 ml, 53 mmol) dropwise via a syringe. After the addition was completed, the mixture was stirred 15 min. At this point, methyl trifluoroacetate (5.4 ml, 53 mmol) was added, and the reaction mixture was stirred for 60 min at the same temperature, then quenched by addition of saturated NH₄Cl (250 ml). The resulted mixture was allowed to warm to RT and the layers were separated. The aqueous layer was back extracted with EtOAc (3×). The organic layers were combined, dried over Na₂SO₄, filtered and concentrated. The residue was purified on a silica gel column (5-35% EtOAc/hexane) to afford the title compound as light yellow oil. MS+m/z: 445 (M+18).

Step 2: tert-Butyl allyl((S)-2,2-spirocyclobutyl-6-(2,2,2-trifluoro-1-hydroxyethyl)-3,4-dihydro-2H-pyrano(2,3-b)pyridine-4-yl)carbamate To a solution of (S)-tert-butyl allyl(2,2-spirocyclobutyl-6-(2,2,2-trifluoroacetyl)-3,4-dihydro-2H-pyrano(2,3-b)pyridine-4-yl)carbamate (20.0 g, 46.9 mmol) in EtOH (400 ml) was added sodium tetrahydroborate (1.77 g, 46.9 mmol). The mixture was stirred at RT for 15 h, and then quenched with water. The resulted mixture was concentrated under reduced pressure. The aqueous residue was diluted with water and extracted with EtOAc (3×). The organic layers were combined, washed with brine, dried over Na₂SO₄, and filtered. The filtrate was concentrated and dried in vacuum to afford the title compound as a mixture of isomers as brown oil. MS m/z: 429 (M+1).

Step 3: 1-((S)-4-(Allylamino)-2,2-spirocyclobutyl-3,4-dihydro-2H-pyrano(2,3-b)pyridine-6-yl)-2,2,2-trifluoroethanol The title compound was prepared by a method analogous to that described in step 3 of Example 27 above. MS m/z: 329 (M+1).

Step 4: 1-((S)-4-amino-2,2-spirocyclobutyl-2H-pyrano(2,3-b)pyridine-6-yl)-2,2,2-trifluoroethanol The title compound was prepared by a method analogous to that described in step 4 of Example 27 above. MS m/z: 289 (M+1)

Step 5: tert-butyl (S)-2,2-spirocyclobutyl-6-(2,2,2-trifluoro-1-hydroxyethyl)-3,4-dihydro-2H-pyrano(2,3-b)pyridine-4-yl)carbamate To a solution of 1-((S)-4-amino-2,2-spirocyclobutyl-2H-pyrano(2,3-b)pyridine-6-yl)-2,2,2-trifluoroethanol (10.3 g, 35.7 mmol) in DCM (450 ml) was added diisopropylethylamine (6.22 ml, 35.7 mmol) followed by di-tert-butyl dicarbonate (7.80 g, 35.7 mmol). The mixture was stirred at RT for 15 h, the resulted suspension was filtered, and the solid was rinsed with DCM to afford the title compound as a white solid. MS m/z: 389 (M+1). The filtrate was washed with 2 N HCl (2×). The organic layer was concentrated and a precipitation was occurred. The resulted suspension was filtered. The solid was dried in vacuum to afford an additional amount of the title compound as a white solid. The filtrate was concentrated and purified on a silica gel column (30-35% EtOAc/hexane) to provide another crop of the title compound as a light yellow solid.

Step 6: tert-Butyl (S)-6-(1-chloro-2,2,2-trifluoroethyl)-2,2-spirocyclobutyl-3,4-dihydro-2H-pyrano(2,3-b)pyridine-4-yl)carbamate To a solution of tert-butyl (S)-2,2-spirocyclobutyl-6-(2,2,2-trifluoro-1-hydroxyethyl)-3,4-dihydro-2H-pyrano(2,3-b)pyridine-4-yl)carbamate (5.00 g, 12.9 mmol) in toluene (120 ml) was added pyridine (1.04 ml, 12.9 mmol) at RT. Sulfuryl dichloride (1.31 ml, 18.0 mmol) was then added to the reaction slowly via a syringe. After the addition was completed, the reaction was stirred at RT for 15 h, then heated at 45° C. for another 3 h. The resulted brown solution was cooled to RT and diluted with water and EtOAc. The aqueous layer was back extracted with EtOAc (2×). The organic layers were combined, washed with brine, dried over Na₂SO₄, and filtered. The filtrate was concentrated and purified on a silica gel column (5-25% EtOAc/hexane) to afford the title compound as a mixture of isomers. MS m/z: 407 (M+1)

Step 7: (S)-tert-Butyl 2,2-spirocyclobutyl-6-(2,2,2-trifluoroethyl)-3,4-dihydro-2H-pyrano(2,3-b)pyridine-4-ylcarbamate A mixture of tert-butyl (S)-6-(1-chloro-2,2,2-trifluoroethyl)-2,2-spirocyclobutyl-3,4-dihydro-2H-pyrano(2,3-b)pyridine-4-yl)carbamate (1.3 g, 4.9 mmol) and Palladium on carbon (0.7 g, 10% on carbon) in ethanol (100 ml) was stirred under $H_2$ atmosphere ($H_2$ balloon) for 18 h. The reaction mixture was then filtered through celite. The filtrate was concentrated and dried in vacuum to afford the title compound as light yellow solid. MS m/z: 373 (M+1).

Step 8: (S)-2,2-Spirocyclobutyl-6-(2,2,2-trifluoroethyl)-3,4-dihydro-2H-pyrano(2,3-b)pyridine-4-amine To a solution of (S)-tert-butyl 2,2-spirocyclobutyl-6-(2,2,2-trifluoroethyl)-3,4-dihydro-2H-pyrano(2,3-b)pyridine-4-ylcarbamate (1.0 g, 3.0 mmol) in methanol was added hydrogen chloride 4.0m in 1,4-dioxane (5.0 ml, 20 mmol). After stirred for 3 h at RT, the reaction was concentrated and dried in vacuum to afford the title compound as an off-white solid. MS m/z: 273 (M+1).

Example 29

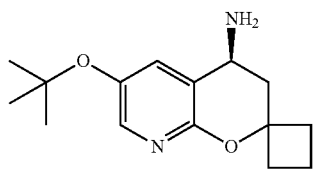 [SMILES: CC(C)(C)Oc1cnc2c(c1)[C@@H](N)CC1(CCC1)O2]

(S)-6-tert-Butoxy-2,2-spirocyclobutyl-3,4-dihydro-2H-pyrano[2,3-b]pyridin-4-amine

Step 1: (S)-4-Azido-2,2-spirocyclobutyl-3,4-dihydro-2H-pyrano[2,3-b]pyridin-6-ol A 25-mL RBF was charged with (S)-4-azido-6-bromo-2,2-spirocyclobutyl-3,4-dihydro-2H-pyrano[2,3-b]pyridine (0.100 g, 0.34 mmol), and the solid was dissolved in THF (3.0 mL). The solution was cooled to −78° C., and a solution of butyllithium (2.50 M, 0.20 ml, 0.51 mmol) in hexane was added, followed immediately by triisopropyl borate (0.079 ml, 0.34 mmol After 45 minutes, the reaction solution was warmed to 0° C. After 30 minutes, a mixture of aqueous 30% hydrogen peroxide (0.35 ml, 3.4 mmol), and sodium hydroxide (2.50 M, 0.81 ml, 2.0 mmol) was added, and the mixture was warmed to ambient temperature. After 30 minutes the mixture was concentrated, the crude residue was taken up in half-saturated $NH_4Cl$ (10 mL) and extracted with DCM (3×20 mL). The organic layers were combined, dried over sodium sulfate and concentrated. The crude material was purified through silica gel (25 mL) using 50% EtOAc-hexane to afford the title compound. MS m/z 233 (M+1).

Step 2: (S)-4-Azido-6-tert-butoxy-2,2-spirocyclobutyl-3,4-dihydro-2H-pyrano[2,3-b]pyridine In a microwave vessel, the (S)-4-azido-2,2-spirocyclobutyl-3,4-dihydro-2H-pyrano[2,3-b]pyridin-6-ol (0.024 g, 0.10 mmol) was suspended in DCM (2 mL), and trifluoromethanesulfonic acid (0.011 ml, 0.12 mmol) was added to the mixture, The reaction mixture was cooled to −78° C. 2-Methylprop-1-ene (0.97 ml, 10 mmol) was separately liquefied at −78° C. and added to the reaction mixture via a pipet. The reaction vessel was sealed and allowed to warm to RT while stirring overnight. The reaction was diluted with DCM (60 mL), and the organic phase was extracted with dilute sodium carbonate (2×6 mL), then with dilute brine (6 mL). The organic phase was dried over sodium sulfate, filtered and concentrated, and the crude residue was purified through silica gel (20 mL) using 38% EtOAc-hexane to afford the title compound (15 mg, 0.052 mmol, 50%) as a white solid. MS m/z 289 (M+1).

Step 3: (S)-6-tert-Butoxy-2,2-spirocyclobutyl-3,4-dihydro-2H-pyrano[2,3-b]pyridin-4-amine In a 25-mL RBF, the (S)-4-azido-6-tert-butoxy-2,2-spirocyclobutyl-3,4-dihydro-2H-pyrano[2,3-b]pyridine (0.036 g, 0.12 mmol) and Pd/C (10%, 0.0036 g) were taken up in EtOAc (2.5 mL), and the mixture was stirred at ambient temperature under an atmosphere of hydrogen. After 16 h, the mixture was filtered through Celite, and the filtrate was concentrated. Purification of the concentrate through silica gel (20 mL), which had been deactivated with triethylamine (2 mL) using 0.5% MeOH-DCM, afforded the title compound. MS m/z 263 (M+1).

Example 30

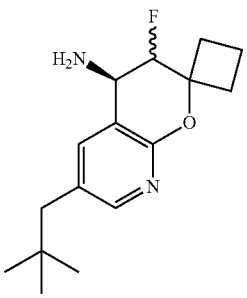 [SMILES: CC(C)(C)Cc1cnc2c(c1)[C@@H](N)C(F)C1(CCC1)O2]

6-(2',2'-Dimethylpropyl)-2,2-spirocyclobutyl-3-fluoro-3,4-dihydro-2H-pyrano[2,3-b]pyridin-4-amine

Step 1: (±) 6-Bromo-2,2-spirocyclobutyl-3-fluoro-3,4-dihydro-2H-pyrano[2,3-b]pyridin-4-one A mixture of 6-bromo-2,2-spirocyclobutyl-3,4-dihydro-2H-pyrano[2,3-b]pyridin-4-one (4.9 g, 18 mmol) and SLECTFLUOR (7.1 g, 20 mmol) in 40 ml of anhydrous MeOH was heated at 110-130° C. in a pressure bottle for 16 h. The mixture was cooled down and the solids were filtered off The filtrate was concentrated to give an oil which was purified by silica gel chromatography using EtOAc-Hexanes (0-12%) to give the tile compound as a clear oil which solidified upon drying.

Step 2: (±) 6-Bromo-2,2-spirocyclobutyl-3-fluoro-3,4-dihydro-2H-pyrano[2,3-b]pyridin-4-yl-(S)-tert-butylsulfinylimine A solution of (±) 6-Bromo-2,2-spirocyclobutyl-3-fluoro-3,4-dihydro-2H-pyrano[2,3-b]pyridin-4-one (3.0 g, 10 mmol) and (S)-2-methylpropane-2-sulfinamide (2.5 g, 21 mmol) in 5 ml of THF was treated with tetraethoxytitanium (8.7 ml, 42 mmol) at rt for 18 h. The reaction mixture was diluted with 100 ml of EtOAc and the resulting solution was added dropwise to 150 ml of sat. aq. NaHCO$_3$. White precipiates formed, and the mixture was stirred at rt vigorously for 1 h. The EtOAc layer was carefully decanted; the rest of mixture was filtered through a celite pad with Na$_2$SO$_4$. The celite pad was washed with 150 ml of EtOAc. The filtrates were combined and the EtOAc layer was separated. All organic layers were combined, dried (Na$_2$SO$_4$) and concentrated to give an oil that was purified by Isco (0-30% EtOAc in hexanes) to give the title compound as a yellow foam.

Step 3: (4R)-6-Bromo-2,2-spirocyclobutyl-3-fluoro-3,4-dihydro-2H-pyrano[2,3-b]pyridin-4-amine A solution of (±) 6-Bromo-2,2-spirocyclobutyl-3-fluoro-3,4-dihydro-2H-pyrano[2,3-b]pyridin-4-yl-(S)-tert-butyl-sulfinylimine from Step 2 (2.55 g, 6.6 mmol) in 20 ml of THF:H$_2$O (98:2) at −50° C. was treated with sodium borohydride (0.74 g, 20 mmol) and the resulting mixture was stirred and warmed up to rt over 2 h, and then stirred overnight. The solvents were then removed, The crude residue was triturated with DCM, washed with sat. aq. NaHCO$_3$ (2×75 ml), dried over Na$_2$SO$_4$ and concentrated to give the title compound as an oil.

Step 4: (4R)-tert Butyl 6-Bromo-2,2-spirocyclobutyl-3-fluoro-3,4-dihydro-2H-pyrano[2,3-b]pyridin-4-carbamate A solution of (4R)-6-Bromo-2,2-spirocyclobutyl-3-fluoro-3,4-dihydro-2H-pyrano[2,3-b]pyridin-4-amine (1.23 g, 4.3 mmol) in 15 ml of dry DCM was treated with Boc anhydride (4.3 ml, 4.3 mmol) at rt overnight. The reaction solvent was removed and the resulting crude residue was purified by ISCO (0-20% EtOAc on hexanes) to give the titled compound.

Step 5: (4R)-6-(2'2'-dimethylpropyl)-2,2-spirocyclobutyl-3-fluoro-3,4-dihydro-2H-pyrano[2,3-b]pyridin-4-amine To a 50 mL RBF was added (4R)-tert butyl 6-bromo-2,2-spirocyclobutyl-3-fluoro-3,4-dihydro-2H-pyrano[2,3-b]pyridin-4-carbamate (580 mg, 1498 µmol), dioxane (10 mL). The solution was degassed with N$_2$ for 10 minutes, and Pd catalyst (53 mg, 75 µmol) was added to the solution. A solution of neopentylzinc(II) iodide, in THF (8.0 ml, 4000 µmol) was then added and the reaction mixture was stirred at RT under N$_2$ for 16 hours. The reaction mixture was quenched with water (20 mL) and acidified to pH 2 with 1N HCl. The mixture was extracted with EtOAc (2×40 mL). The combined organic layers were washed with brine and concentrated in vacuo to give a dark brown oil, which was then treated with MeOH (30 mL) and HCl (4M in dioxane, 10 mL) and stirred overnight. The material was concentrated in vacuo and taken up in DCM (5% MeOH was added to improve solubility), and extracted with 1N HCl (2×20 mL). The combined acidic aqueous layers were washed with DCM (20 mL), neutralized with sat'd NaHCO$_3$ and extracted with DCM (3×20 mL). The combined organic layers were concentrated in vacuo to give the title compound.

Example 31

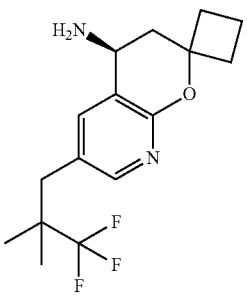 [SMILES: CC(C)(Cc1cnc2c(c1)[C@@H](N)CC1(CCC1)O2)C(F)(F)F]

(4S)-6-(2',2'-Dimethyl-3',3',3'-trifluoro-propyl)-2,2-spirocyclobutyl-3,4-dihydro-2H-pyrano[2,3-b]pyridin-4-amine Step 1: 1,1,1-Trifluoro-2-(4-methoxyphenyl)propan-2-ol A solution of 1-bromo-4-methoxybenzene (19 ml, 150 mmol) in 300 ml of dry THF at −78° C. was treated with n-butyllithium (96 ml, 154 mmol) (1.6 M or 15% in hexanes, Strem). The resulting mixture was stirred for an additional 30 min. At −78° C., 1,1,1-trifluoropropan-2-one (16 ml, 180 mmol) was added and the mixture was stirred −78° C. and slowly warmed up overnight. The reaction mixture was treated with 100 ml of 5N HCl and concentrated. The layers were separated. The bottom layer (organic) was diluted with 50 ml of DCM, washed with 1×100 ml of H$_2$O, and dried (MgSO$_4$) and concentrated to give an oil which was purified by silica gel chromatography eluting with 0-5% EtOAc in hexanes to provide the title compound.

Step 2: 1-(2-chloro-1,1,1-trifluoropropan-2-yl)-4-methoxybenzene

A solution of 1,1,1-trifluoro-2-(4-methoxyphenyl)propan-2-ol (22.5 g, 102 mmol) in 150 ml of anhydrous toluene was treated sequentially with pyridine (8.26 ml, 102 mmol) and dropwise sulfuryl dichloride (11.2 ml, 153 mmol) at 0° C. The resulting mixture was then heated at 55° C. for 18 h. The reaction was diluted with 100 ml of EtOAc, washed with 100 ml of H$_2$O and 100 ml of 1N HCl, dried over Na$_2$SO$_4$, and concentrated to give an oil which was filtered through a silca gel pad eluting with 0-5% EtOAc in hexanes to afford the title compound.

Step 3: 1-Methoxy-4-(1,1,1-trifluoro-2-methylpropan-2-yl)benzene

A solution of 1-(2-chloro-1,1,1-trifluoropropan-2-yl)-4-methoxybenzene (18.0 g, 75 mmol) in 400 ml of hexanes was treated with trimethylaluminum (151 ml, 302 mmol) (2.0 M in heptane) at rt and the resulting mixture was heated at 95° C. overnight. The reaction mixture was cooled in an ice-water bath, conc. HCl was added to the reaction mixture dropwise. Fumes were generated. After about 10 ml of conc. HCl was added, more rapid addition of acid was possible due to the near complete quenching of the unreacted AlMe₃. After addition of 100 ml of conc. HCl, 250 ml of H₂O was added and the mixture was stirred vigorously for 1 h. The layers were separated. The org layer was dried (Na₂SO₄) and concentrated to give the title compound as an oil, which solidified upon drying on the vac line.

Step 4: 3,3,3-Trifluoro-2,2-dimethylpropanoic acid

To a biphasic mixture of 1-methoxy-4-(1,1,1-trifluoro-2-methylpropan-2-yl)benzene (10.0 g, 45.8 mmol) and sodium periodate (137 g, 642 mmol) in a mixture solvent of CCl₄:CH₃CN:H₂O (2:2:3, 550 ml) was added slowly ruthenium (III) chloride hydrate (0.517 g, 2.29 mmol) (black powder) while the reaction flask was kept in an ice-water bath. The mixture turned yellow rapidly then red after 5 minutes, ans was stirred for 0.5 h. The ice-water bath was removed and the reaction mixture was stirred vigorously, via a mechanical stirrer, overnight. The solids were filtered off, washed with 100 ml of DCM, 100 ml of H₂O. The filtrate (pH ~1) was basified with 10 N NaOH to pH>11, and the layers were separated, and the aq. layer was extracted with 130 ml of DCM. The aq. layer was then acidified carefully with conc. HCl to pH ~1, extracted with 3×150 ml of DCM. The org layers were combined, dried (Na₂SO₄), and concentrated to give the title compound as an oil, which became a semi-solid upon drying on the vac line.

Step 5: Naphthalen-2-ylmethyl 3,3,3-trifluoro-2,2-dimethylpropanoate

A mixture of 3,3,3-trifluoro-2,2-dimethylpropanoic acid (2.96 g, 19.0 mmol), 2-(bromomethyl)naphthalene (4.19 g, 19.0 mmol), and potassium carbonate (7.86 g, 56.9 mmol) in 50 ml of anhydrous DMF was stirred at 30° C. overnight. Diluted with 150 ml of EtOAc, washed with 150 ml of H₂O, 2×100 ml of 1N NaOH, 2×100 ml of 1N HCl, diced (Na₂SO₄) and concentrated to give an oil that was purified by ISCO using EtOAc in hexanes (5%) as eluents to provide the title compound as an oil.

Step 6: (4S)-6-(2',2'-dimethyl-3',3',3'-trifluoro-propyl)-2,2-spirocyclobutyl-3,4-dihydro-2H-pyrano[2,3-b]pyridin-4-amine The title compound was obtained by a method analogous to the method of the last step described in Example 28 above.

Example 32

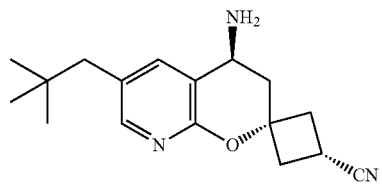 [SMILES: CC(C)(C)Cc1cnc2c(c1)[C@@H](N)C[C@]1(C[C@H](C#N)C1)O2]

(4S)-6-Neopenyl-[(2,2-spirocyclobutyl)-3'-cis-cyano)]-2,3-dihydropyrano[2,3-b-]pyridin-4-amine Step 1: 3-Cyanocyclobutanone To a stirred mixture of 3-methylenecyclobutanecarbonitrile (5.0 g, 54 mmol) and ruthenium trichloride hydrate (0.086 ml, 1.2 mmol) in DCM/MeCN/H₂O (215/215/315 ml) was added sodium meta periodate (12 ml, 225 mmol) in several portions (30 min.). The reaction mixture was slowly warmed to RT and stirred in 3 h. The precipitated solid was filtered off. The filtrate was extracted with DCM (3×); dried over MgSO₄, concentrated and filtered through a short plug of silical gel, concentrated, to give the title compound as a light brown oil, which solidified upon standing at rt.

Step 2: 3-(2-(5-Bromo-2-methoxypyridin-3-yl)-2-oxoethylidene)cyclobutanecarbonitrile A mixture of lithium (Z)-1-(5-bromo-2-methoxypyridin-3-yl)-2-(dimethoxyphosphoryl)ethenolate (2.0 g, 5.8 mmol) and 3-oxocyclobutanecarbonitrile (1.1 g, 12 mmol) in p-dioxane (6 ml) was heated at 120° C. by Microwave in 1 h. The mixture was cooled, taken up in H₂O, extracted with EtOAc (3×), dried over MgSO₄, concentrated to provide the title compound. MS (m+1): 307.0.

Step 3: 6-Bromo-[(2,2-spirocyclobutyl)-3'-cyano)]-2,3-dihydropyrano[2,3-b-]pyridine-4-one A mixture of 3-(2-(5-bromo-2-methoxypyridin-3-yl)-2-oxoethylidene)cyclobutanecarbonitrile (3.4 g, 11 mmol), sodium iodide (1.8 ml, 44 mmol), and chlorotrimethyl silane (5.6 ml, 44 mmol) in MeCN (40 ml) was stirred at rt for 24 h, concentrated, taken up in H₂O, extracted with DCM (3×), washed with saturated NH₄Cl, brine, dried over MgSO₄, concentrated and purified by ISCO (20% EtOAc/Hexanes) to give the title compound as a yellow solid.

Step 4: (4R)-6-Bromo-[(2,2-spirocyclobutyl)-3'-cyano)]-2,3-dihydropyrano[2,3-b-]pyridine-4-ol To a stirred solution of (S)-2-methyl-CBS-oxazaborolidine (1M in toluene; 1.0 ml, 1.0 mmol) in toluene (5 ml) was added a solution of borane-methyl sulfide complex (0.5 ml, 5 mmol) in toluene (20 ml) and a solution of 6-bromo-[(2,2-spirocyclobutyl)-3'-cyano)]-2,3-dihydropyrano[2,3-b-]pyridine-4-one (1.40 g, 5 mmol) in toluene (20 ml) in 30 min at 0° C. The reaction mixture was stirred for another 15 min. then slowly quenched with 10% aq. HCl, extracted with EtOAc (3×), washed with NaHCO₃, brine, dried over MgSO₄, concentrated to give the title compound as a light yellow solid. MS (m+1): 296.1

Step 5: (4R)-6-Bromo-4-tert-butyldimethylsilyloxo-[(2,2-spirocyclobutyl)-3'-cyano)]-2,3-dihydropyrano[2,3-b-]pyridine To a stirred mixture of (4R)-6-bromo-[(2,2-spirocyclobutyl)-3'-cyano)]-2,3-dihydropyrano[2,3-b]pyridine-4-ol (5.7 g, 19 mmol) and 1H-imidazole (22 ml, 193 mmol) in DMF (70 ml) was added tert-butylchlorodimethylsilane (15 g, 97 mmol). The reaction mixture was stirred at rt in 24 h, added water, extracted with ether (3×), dried over MgSO₄, concentrated and purified by ISCO (15% EtOAc/Hexanes) to give the title compound. MS (m+1): 410.4.

Step 6: (4R)-6-(2'2-dimethylpropyl)-4-tert-butyldimethylsilyloxo-[(2,2-spirocyclobutyl)-3'-cyano)]-2,3-dihydropyrano[2,3-b-]pyridine To a stirred solution of neopentylmagnesium chloride (1M, 15 ml, 15 mmol) at 0° C. was added dropwise a solution of zinc(II) chloride (8 ml, 8 mmol). The mixture was gradually warmed to rt in 30 min. PdCl$_2$(dppf)$_2$ (0.2 g, 0.2 mmol) and a solution of (4R)-6-bromo-4-tert-butyldimethylsilyloxo-[(2,2-spirocyclobutyl)-3'-cyano)]-2,3-dihydropyrano[2,3-b-]pyridine (1.56 g, 4 mmol) in THF (20 ml) were successively added to the mixture. The reaction mixture was stirred at 40° C. overnight, then cooled, quenched with saturated NH$_4$Cl, extracted with EtOAc, dried over MgSO$_4$, concentrated to provide the title compound. MS (m+1): 401.6.

Step 7: (4R)-6-Neopenyl-[(2,2-spirocyclobutyl)-3'-cis-cyano)]-2,3-dihydropyrano[2,3-b-]pyridine-4-ol and (4R)-6-neopenyl-[(2,2-spirocyclobutyl)-3'-trans-cyano)]-2,3-dihydropyrano[2,3-b-]pyridine-4-ol To a stirred solution of (4R)-6-neopentyl-4-tert-butyldimethylsilyloxo-[(2,2-spirocyclobutyl)-3'-cyano)]-2,3-dihydropyrano[2,3-b]pyridine (1.5 g, 4 mmol) in THF (10 ml) was added tetrabutylammonium fluoride, 1.0M in THF (7 ml, 7 mmol). The reaction mixture was stirred in 2 h, quenched with H$_2$O, extracted with EtOAc, dried over MgSO$_4$, concentrated and purified by ISCO (40% EtOAc/Hexanes with 120 g column) to separate the cis- and trans-isomers of the title compound. MS (m+1): 287.4.

Step 8: (4S)-4-Azido-6-neopenyl-[(2,2-spirocyclobutyl)-3'-cis-cyano)]-2,3-dihydropyrano[2,3-b-]pyridine To a stirred solution of (4R)-6-neopenyl-[(2,2-spirocyclobutyl)-3'-cis-cyano)]-2,3-dihydropyrano[2,3-b]pyridine-4-ol (1.05 g, 3.67 mmol) in toluene (30 ml) was added DPPA (1.03 ml, 4.77 mmol) dropwise. After stirring for 15 min., DBU (0.713 ml, 4.77 mmol) was slowly added, and the reaction mixture was stirred at RT for 16 h. H$_2$O was added and the mixture was extracted with EtOAc (3×), washed with brine, dried over MgSO$_4$, concentrated to give the title compound as a brown oil. MS (m+1): 312.4.

Step 9: (4S)-6-Neopenyl-[(2,2-spirocyclobutyl)-3'-cis-cyano)]-2,3-dihydropyrano[2,3-b-]pyridin-4-amine A mixture of (4S)-4-azido-6-neopenyl-[(2,2-spirocyclobutyl)-3'-cis-cyano)]-2,3-dihydropyrano[2,3-b-]pyridine (3 g, 10 mmol) and triphenylphosphine (3 g, 10 mmol) in THF (20 ml) was stirred at RT in 2 h, 3 ml of H$_2$O was added and heated at 80° C. in 4 h. 40 ml of 10% aq. HCl was added and the mixture was heated for 10 min. at 80° C., then cooled and extracted with toluene, (discarded). The acidic aqueous layer was neutralized with solid Na$_2$CO$_3$, extracted with DCM (3×), dried over MgSO$_4$, purified by ISCO (3% MeOH/DCM) to give the title compound as a yellow foam. MS (m+1): 286.4.

Example 33

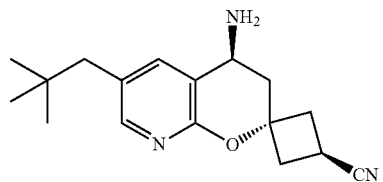 [SMILES: CC(C)(C)Cc1cnc2c(c1)[C@@H](N)C[C@]1(C[C@@H](C#N)C1)O2]

(4S)-6-Neopenyl-[(2,2-spirocyclobutyl)-3'-trans-cyano)]-2,3-dihydropyrano[2,3-b-]pyridin-4-amine Step 1: (4S)-4-Azido-6-neopenyl-[(2,2-spirocyclobutyl)-3'-trans-cyano)]-2,3-dihydropyrano[2,3-b-]pyridine To a stirred solution of (4R)-6-neopenyl-[(2,2-spirocyclobutyl)-3'-trans-cyano)]-2,3-dihydropyrano[2,3-b-]pyridine-4-ol (2.6 g, 9.1 mmol) in toluene (50 ml) was added diphenylphosphoryl azide (2.9 ml, 14 mmol) dropwise. After the addition, the mixture was stirred for 15 min., cooled in an ice bath and DBU (2.0 ml, 14 mmol) was added thereto dropwise. The reaction mixture was stirred at RT overnight, quenched with H$_2$O, extracted with ether (3×), dried over MgSO$_4$, concentrated to give the title compound as a brown oil. MS (m+1): 312.4.

Step 2: (4S)-6-neopenyl-[(2,2-spirocyclobutyl)-3'-trans-cyano)]-2,3-dihydropyrano[2,3-b-]pyridin-4-amine To a stirred solution of (45)-4-azido-6-neopenyl-[(2,2-spirocyclobutyl)-3'-trans-cyano)]-2,3-dihydropyrano[2,3-b-]pyridine (3 g, 10 mmol) in THF (50 ml) was added triphenylphosphine (3 g, 10 mmol). The mixture was stirred at RT in 1 h, 10 ml of H$_2$O was added and stirred at 85° C. for 24 h, added 10% aq. HCl, stirred, cooled, extracted with toluene (discarded). The aqueous layer was neutralized with solid Na$_2$CO$_3$, extracted with DCM (3×), dried over MgSO$_4$, concentrated, purified by ISCO (3% MeOH/DCM) to give the title compound as a light yellow solid. MS (m+1): 286.4.

Example 34

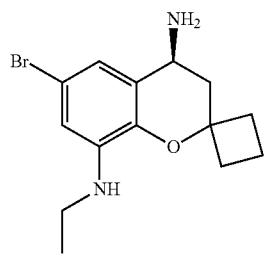 [SMILES: CCNc1cc(Br)cc2c1OC1(CCC1)C[C@@H]2N]

(S)-6-Bromo-N$^8$-ethyl-2,2,-spirocyclobutyl-3,4-dihydro-2H-chromene-4,8-diamine Step 1: 1-(3-amino-5-bromo-2-hydroxyphenyl)ethanone A mixture of 1-(5-bromo-2-hydroxy-3-nitrophenyl)ethanone (25 g, 96 mmol), iron (27 g, 481 mmol), and NH$_4$Cl (5.1 g, 96 mmol) in EtOH/H$_2$O (5:1, 300 ml) was heated at reflux in 2 h, the mixture was cooled filtered the solid, the filtrate was concentrated, taken up in H$_2$O, extracted with DCM (3×), dried over MgSO$_4$, concentrated and purified by ISCO (10% EtOAc/Hexanes) to give the title compound as a yellow solid. MS (m+2): 232.1.

Step 2: 8-Amino-6-bromo-2,2-spirocyclobutyl-2,3-dihydrochromen-4-one

A mixture of 1-(3-amino-5-bromo-2-hydroxyphenyl)ethanone (4.5 g, 20 mmol), cyclobutanone (3 ml, 39 mmol), and pyrrolidine (5 ml, 59 mmol) in p-dioxane (80 ml) was heated at 65° C. for 24 h. The mixture was cooled, taken up in dilute acid, stirred, extracted with EtOAc (3×), dried over MgSO$_4$, concentrated and purified by ISCO (0-20% in 30 min.) to give the title compound as an orange solid. MS (m+2): 284.1.

Step 3: (4R)-8-Amino-6-bromo-2,2-spirocyclobutyl-2,3-dihydrochromen-4-ol

To a stirred solution of (s)-2-methyl-CBS-oxazaborolidine, 1M in toluene (1 ml, 1 mmol) in toluene (2 ml) was added a solution of borane-methyl sulfide complex (5 ml, 11 mmol) in toluene (20 ml) followed by addition of a solution of 8-amino-6-bromo-2,2-spirocyclobutyl-2,3-dihydrochromen-4-one (3 g, 11 mmol) in toluene (40 ml) dropwise. After the reaction was complete as monitored by TLC, it was quenched with 10% aq. HCl (40 ml), stirred for 15 min., extracted with EtOAc (3×), washed with brine, dried over MgSO$_4$, filtered and concentrated to give the title compound as a purple foam. MS (M+1): 285.2.

Step 4: (4R)-8-Amino-6-bromo-4-tertbutyldimethylsilyloxo-2,2-spirocyclobutyl-2,3-dihydrochromene A mixture of 8-amino-6-bromo-2,2-spirocyclobutyl-2,3-dihydrochromen-4-ol (3.2 g, 11 mmol) and imidazole (1 ml, 12 mmol) in DCM (30 ml) was added tert-butylchlorodimethylsilane (2 g, 12 mmol). The mixture was stirred for 3 h, then H$_2$O was added and the layers were separated, dried over MgSO$_4$, concentrated and the crude was purified by ISCO (5% EtOAc/Hexanes) to give the title compound as a colorless oil. MS (M+1): 399.4.

Step 5: (4R)-8-ethylamino-6-bromo-4-tertbutyldimethylsilyloxo-2,2-spirocyclobutyl-2,3-dihydrochromene A mixture of (4R)-8-amino-6-bromo-4-tertbutyldimethylsilyloxo-2,2-spirocyclobutyl-2,3-dihydrochromene (2 g, 5 mmol), acetaldehyde (0.3 ml, 5 mmol), and trimethyl orthoformate (4 ml, 40 mmol) in DCE (20 ml) was stirred at RT in 30 min. Sodium triacetoxyborohydride (5 g, 25 mmol) was added and stirred in 3 h, quenched with diluted aq. HCl, extracted with DCM (3×), dried over MgSO$_4$, concentrated and purified by ISCO (5% EtOAc/Hexanes) to give the title compound as a light yellow oil. MS (M+1): 428.4.

Step 6: (4R)-6-Bromo-8-(ethylamino)-2,2-spirocyclobutyl-3,4-dihydro-2H-chromen-4-ol To a mixture of (4R)-8-ethylamino-6-bromo-4-tertbutyldimethylsilyloxo-2,2-spirocyclobutyl-2,3-dihydrochromene (0.900 g, 2.2 mmol) in THF (15 ml) was added tetrabutylammonium fluoride (2.6 ml, 2.6 mmol). The reaction mixture was stirred at RT for about 2 h. H$_2$O was added and the mixture was extracted with EtOAc (3×), dried over MgSO$_4$, concentrated to give the title compound as a brown oil. MS (M+1): 304.4.

Step 7: (S)-6-Bromo-N$^8$-ethyl-2,2,-spirocyclobutyl-3,4-dihydro-2H-chromene-4,8-diamine The title compound was obtained as a white foam, by a method analogous to that described in Steps 7-8 of Example 9 above. MS (M+1): 312.2.

Example 35

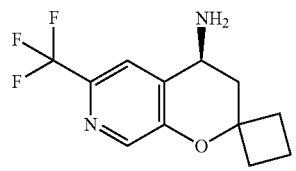 [SMILES: N[C@H]1CC2(CCC2)Oc2cnc(C(F)(F)F)cc21]

(S)-2,2-Spirocyclobutyl-6-trifluoromethyl-3,4-dihydro-2H-pyrano[2,3-c]pyridine-4-amine

Step 1: 5-Methoxymethoxy)-2-(trifluoromethyl)pyridine

To a stirred suspension of NaH (3.1 ml, 74 mmol) in DMF (100 ml) was added 6-(trifluoromethyl)pyridin-3-ol (10 g, 61 mmol) in several portions. The mixture was stirred for 30 min., then chlorodimethyl ether (5.0 ml, 64 mmol) was added dropwise and stirring was continued for 3 h. The reaction was cooled to 0° C. and quenched slowly by addition of H$_2$O. The solution was extracted with ether (3×), the organic layers were dried over MgSO$_4$, filtered and concentrated to give the title compound as a yellow oil. MS (M+1): 208.2.

Step 2: 1-(5-(Methoxymethoxy)-2-(trifluoromethyl)pyridine-4-yl)ethanol

To a stirred solution of piperidine, 2,2,6,6-tetramethyl—(9.2 ml, 54 mmol) in THF (400 ml) at −78° C. was added butyllithium (−2.5 m in toluene; 18 ml, 45 mmol) dropwise. The reaction was then stirred at 0° C. for 5 min at −78° C., and a solution of 5-(methoxymethoxy)-2-(trifluoromethyl)pyridine (7.5 g, 36 mmol) in THF (100 ml) was added dropwise. The mixture was stirred for an additional 10 min, then acetaldehyde (20 ml, 362 mmol) was added and stirring continued for 15 min. the reaction was slowly quenched with H$_2$O, warmed to RT, extracted with EtOAc (3×), combine organic layers were dried over MgSO$_4$, filtered, concentrated and the crude product was purified by ISCO (20% EtOAc/Hexanes) to give the title compound as a light yellow solid. MS (m+1): 252.2.

Step 3: 1-(5-(methoxymethoxy)-2-(trifluoromethyl)pyridin-4-yl)ethanone

To a stirred mixture of 1-(5-(methoxymethoxy)-2-(trifluoromethyl)pyridin-4-yl)ethanol (3.2 g, 13 mmol) and NaHCO$_3$ (3.2 g, 38 mmol) in DCM (100 ml) was added Dess Martin Periodinane (5.9 g, 14 mmol). The reaction mixture was stirred at rt in 16 h, the solid was filtered, the filtrate was concentrated, then taken up and stirred in ether/EtOAc. The precipitated white solids were filtered and discarded. The filtrate was concentrated to give the title compound as a light yellow oil. MS (m+1): 250.2.

Step 4: 1-(5-hydroxy-2-(trifluoromethyl)pyridin-4-yl)ethanone

A mixture of 1-(5-(methoxymethoxy)-2-(trifluoromethyl)pyridin-4-yl)ethanone (3.2 g, 13 mmol) and 5N (40 ml) in i-PrOH/THF (1:1, 40 ml) was stirred at 45° C. overnight. The mixture was cooled, concentrated, taken up in H₂O, neutralized with saturated NaHCO₃, and extracted with DCM (3×). The organic layers were combined, dried over Na₂SO₄, and concentrated to give the title compound as a tan solid. MS (m+1): 206.2

Step 5: (S)-2,2-Spirocyclobutyl-6-trifluoromethyl-3,4-dihydro-2H-pyrano[2,3-c]pyridine-4-amine The title compound was obtained by a method analogous to that described in Steps 6-8 of Example 9 above. MS (m+1): 259.2.

Example 36

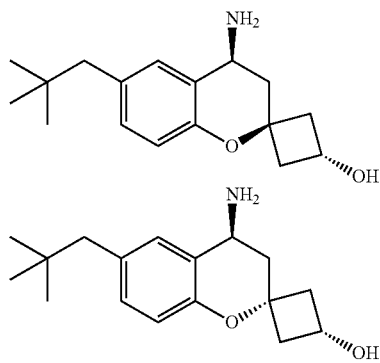

(4S)-[(2,2-Spirocyclobutyl-3'(trans)-hydroxyl)]-6-neopentyl-3,4-dihydro-2H-chromen-4-amine and (4S)-[(2,2-Spirocyclobutyl-3'(cis)-hydroxyl)]-6-neopentyl-3,4-dihydro-2H-chromen-4-amine

Step 1: 2,2-Dichloro-3-oxocyclobutyl pivalate

To a stirred mixture of vinyl pivalate (30 g, 234 mmol) and zinc (31 g, 468 mmol) in ether (300 ml) was added a solution of 2,2,2-trichloroacetyl chloride (55 g, 304 mmol) in ether (300 ml) dropwise (2-3 h) in a water bath. (Note: fast addition causes the reaction temp. to elevate) while maintaining the reaction temperature between 15-30° C. After the reaction was done (stained with KMnO₄ solution), it was filtered through Celite. The filtrate was washed with cold water, brine, dried over MgSO₄ and concentrated to give the title compound as an orange solid.

Step 2: 3-Oxocyclobutyl pivalate

To a stirred suspension of zinc dust (103 g, 1568 mmol) in HOAc (200 ml) was added a solution of 2,2-dichloro-3-oxocyclobutyl pivalate (75 g, 314 mmol) in HOAc (400 ml) dropwise in an ice bath. The reaction mixture was stirred for 1 h, filtered the solid through celite and washed with DCM. The DCM layer was washed with H₂O, NaHCO₃, brine, dried over MgSO₄, filtered and concentrated. The crude material was purified by ISCO (10% EtOAc/Hexanes) to give the title compound as a light yellow oil.

Step 3: 3-Hydroxylcyclobutyl pivalate

To a stirred solution of 3-oxocyclobutyl pivalate (15.1 g, 88.7 mmol) in ethanol (100 ml) at 0° C. was added sodium borohydride (4.69 ml, 133 mmol) in several portions. The reaction was stirred for 30 min, slowly quenched with 10% aqueous HCl and concentrated to remove ethanol. The solution was taken up with more 10% HCl, extracted with DCM (3×), washed with brine, dried over MgSO₄ and concentrated to give the title compound as a light yellow oil.

Step 4: 3-(tert-Butyldimethylsilyloxy)cyclobutyl pivalate

To a stirred mixture of 3-hydroxycyclobutyl pivalate (16.60 g, 96.4 mmol) and diea (25.2 ml, 145 mmol) in DCM (100 ml) at 0° C. was added tert-butyldimethylsilyl triflate (31.0 ml, 135 mmol) dropwise. The reaction was stirred for 2 h, then quenched with H₂O. The layers were separated, and the organic layer was washed with saturated NaHCO₃, brine, dried over MgSO₄ and concentrated to give the title compound as a light brown oil.

Step 5: 3-(tert-butyldimethylsilyloxy)cyclobutanol

To a stirred solution of 3-(tert-butyldimethylsilyloxy)cyclobutyl pivalate (4.32 g, 15 mmol) in THF (20 ml) at 0° C. was added diisobutylaluminum hydride, 1.0m solution in hexanes (48 ml, 48 mmol) dropwise. The reaction was stirred in 1 h, then slowly quenched with Rochelle's salt. The quenched mixture was stirred and layers were separated. The organic layer was dried over MgSO₄ and concentrated to give the title compound as a colorless oil.

Step 6: 3-(tert-butyldimethylsilyloxy)cyclobutanone

A mixture of 3-(tert-butyldimethylsilyloxy)cyclobutanol (2.59 g, 13 mmol), sodium bicarbonate (3 ml, 38 mmol), and Reactant 1 [?] (7 g, 15 mmol) in DCM (40 ml) was stirred at RT in 4 h, the solid was filtered; the filtrated was purified by ISCO (5% EtOAc/Hexanes) to give the title compound as a colorless oil.

Step 7: (4S)-[(2,2-Spirocyclobutyl-3'(trans)-hydroxyl)]-6-neopentyl-3,4-dihydro-2H-chromen-4-amine and (4S)-[(2,2-Spirocyclobutyl-3'(cis)-hydroxyl)]-6-neopentyl-3,4-dihydro-2H-chromen-4-amine The title compounds were obtained, by a method analogous to that described in Steps 6-8 of Example 9 above, after separation of the cis- and trans-isomers by reverse phase HPLC. MS (m+1): 261.2.

Example 37

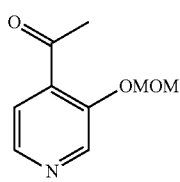

1-(3-(Methoxymethoxy)pyridin-4-yl)ethanone

Step 1: 3-(methoxymethoxy)pyridine

Pyridin-3-ol (25 g, 260 mmol) was added to a stirring mixture of NaH (11 g of a 60 wt % dispersion with mineral oil, 260 mmol) and DMF (350 mL) at 0° C. After 30 min, the reaction mixture was allowed to warm to RT, stirred for 90 min, and then chloromethoxymethane (20 mL, 260 mmol) was added. After 18 h, the reaction mixture was partitioned between ethyl acetate and saturated aqueous $NaHCO_3$, the layers were separated, the organic layer was washed with saturated aqueous $NaHCO_3$, brine, dried ($Na_2SO_4$), filtered, and the filtrate was concentrated. The residue was dissolved with $CH_2Cl_2$, the solution was filtered through a plug of silica gel (sequential elution; 9:1→1:1 hexane-ethyl acetate), and the second filtrate was concentrated to give 10 g (27%) of 3-(methoxymethoxy)pyridine as a clear yellow oil.

Step 2: 1-(3-(methoxymethoxy)pyridin-4-yl)ethanol

A solution of 3-(methoxymethoxy)pyridine (9.8 g, 70 mmol) and THF (40 mL) was added to a stirring mixture of tert-butyllithium (91 mL of a 1.7 M solution with pentane, 160 mmol) and THF (100 mL) at −78° C. After 1 h, acetaldehyde (9.9 mL, 180 mmol) was added, and the reaction mixture was stirred for 3 h and then warmed to RT. After 21 h, the reaction mixture was partitioned between ethyl acetate and saturated aqueous $NaHCO_3$, the layers were separated, the organic material was washed with saturated aqueous $NaHCO_3$, brine, dried ($Na_2SO_4$), filtered, and the filtrate was concentrated. The residue was purified by flash chromatography on silica gel (1:1 hexane-ethyl acetate) to afford 4.6 g (36%) of 1-(3-(methoxymethoxy)pyridin-4-yl)ethanol as a colorless solid.

Step 3: 1-(3-(methoxymethoxy)pyridin-4-yl)ethanone

Dess-Martin periodinane (18 g, 43 mmol) was added to a stirring mixture of 1-(3-(methoxymethoxy)pyridin-4-yl)ethanol (4.6 g, 25 mmol), $NaHCO_3$ (6.3 g, 75 mmol), and $CHCl_3$ (75 mL) at RT. After 24 h, 1.0 M aqueous $Na_2S_2O_3$ was added, the reaction mixture was stirred for 90 min, partitioned between ethyl acetate and 1.0 M aqueous $Na_2S_2O_3$, the layers were separated, the organic layer was washed with 1.0 M aqueous $Na_2S_2O_3$, water, brine, dried ($Na_2SO_4$), and the filtrate was concentrated. The residue was purified by flash chromatography on silica gel (gradient elution; 2:1→1:1 hexane-ethyl acetate) to give 3.9 g (86%) of 1-(3-(methoxymethoxy)pyridin-4-yl)ethanone as a clear yellow-orange oil.

Example 38

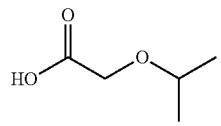

2-Isopropoxyacetic acid

Step 1: tert-Butyl 2-isopropoxyacetate

In a 250-mL flask, 35% aqueous sodium hydroxide (29.3 g, 256 mmol), propan-2-ol (0.785 ml, 10.3 mmol) tetrabutylammonium chloride (0.214 g, 0.769 mmol), and tert-butyl 2-bromoacetate (1.00 g, 5.13 mmol) were taken up in benzene (25 mL). The mixture was stirred at ambient temperature overnight. The reaction was concentrated to remove most of the benzene. The aqueous residue was diluted further with water (100 mL) and the aqueous phase was extracted with 75% ether-hexane (3×33 mL). The organics were combined, washed with water (10 mL) then with saturated brine (10 mL). The organics were dried over magnesium sulfate, filtered, and concentrated to afford the title compound (119 mg, 0.683 mmol, 13%).

Step 2: 2-Isopropoxyacetic acid

In a 25-mL RBF, the tert-butyl 2-isopropoxyacetate (0.120 g, 0.69 mmol) was dissolved in DCM (1.5 mL). The solution was cooled to 0° C. TFA (0.53 ml, 6.9 mmol) was added, and the solution was stirred at 0° C. for 30 min. Then the ice bath was removed and the mixture was stirred at ambient temperature overnight. The mixture was then concentrated to afford the title compound.

Example 39

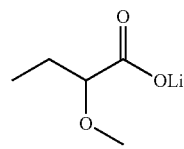

Lithium 2-methoxybutanoate

Step 1: Methyl 2-methoxybutanoate

A 250-mL RBF was charged with DMSO (15 mL). n-Butyllithium (2.50 M, 8.45 ml, 21.1 mmol) was added to the mixture as a solution in hexane. A solution of 2-hydroxybutanoic acid (1.00 g, 9.61 mmol) was dissolved in DMSO (15 mL). The solution was transferred via cannula into the dimsyl anion reaction mixture. The resulting mixture was stirred at ambient temperature for 2.5 h. Iodomethane (1.44 ml, 23.1 mmol) was added and the reaction mixture was stirred overnight. The mixture was diluted with water (125 mL) and the aqueous layer was extracted with ether (50 mL). The organic layer was washed with water (2×5 mL), then with saturated brine (5 mL), then was dried over magnesium sulfate, filtered, and concentrated to afford the title compound.

Step 2: Lithium 2-methoxybutanoate

In a 15-mL RBF was dissolved methyl 2-methoxybutanoate (0.027 g, 0.20 mmol) in methanol (0.75 mL). A solution of lithium hydroxide monohydrate (0.0086 g, 0.20 mmol) in water (0.75 mL) was added, and the mixture was stirred overnight. The mixture was concentrated to afford the title compound.

Example 40

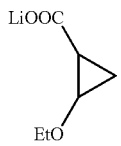

Lithium 2-ethoxycyclopropanecarboxylate (as a mixture of enantiomers and cis- and trans-isomers)

In a 250 mL RBF, ethyl vinyl ether (4.2 ml, 44 mmol) was dissolved in DCM (20 mL). Rhodium (II) acetate dimer (0.019 g, 0.044 mmol) was added as a green powder, and ethyl diazoacetate (0.91 ml, 8.8 mmol) was added as a solution in DCM (4 mL) to the reaction mixture. The mixture was stirred overnight and concentrated. The crude mixture was dissolved in MeOH (0.75 mL), and lithium hydroxide hydrate (0.014 g, 0.34 mmol) was added as a solution in water (0.75 mL). The reaction mixture was stirred overnight, then concentrated and the title compound was used without purification.

Example 41

N-((1S,2R)-3-(((4'S)-6'-(acetylamino)-3',4'-dihydrospiro[cyclobutane-1,2'-pyrano[2,3-b]pyridin]-4'-yl]amino)-1-((4-fluorophenyl)methyl)-2-hydroxypropyl)acetamide To a microwave vial was added N-((2S,3R)-4-(S)-6-bromo-3,4-dihydrospiro[cyclobutane-1,2H-pyrano[2,3-b]pyridin-4-ylamino)-1-(4-fluorophenyl)-3-hydroxybutan-2-yl]acetamide (0.050 g, 0.10 mmol), followed by cuprous iodide (0.00097 g, 0.0051 mmol), acetamide (0.0066 g, 0.11 mmol), POTASSIUM CARBONATE (0.028 g, 0.21 mmol), trans-1,3-cyclohexanebis(methylamine) (0.0016 ml, 0.010 mmol) and toluene (1 mL). The mixture was heated to 150° C. in the microwave for 1 hour. The reaction was cooled to RT and diluted with EtOAc. The solution was concentrated on silica gel and purified using an ISCO chromatography system eluting with a solvent gradient of 0-100% DCM to DCM/MeOH/NH4OH (90:10:1). Collected product fractions and concentrated in vaccuo to afford a yellow oil. A minimal amount of MeOH was added to the oil followed by water. The solution was frozen and lypholized overnight to yield the title compound as a white solid. Found MS m/z: 471.1 (M+1).

Example 42

N-((1S,2R)-1-fluoro-3-hydroxy-4-((S)-6-neopentyl-3',4'-dihydrospiro[cyclobutane-1,2'-pyrano[2,3-b]pyridin-4-ylamino)-1-phenylbutan-2-yl]acetamide Step 1: Methyl 2-fluoro-2-phenylacetate To a 1.0 L RBF containing NaHMDS (5.16 g, 28.1 mmol) was added THF (100 mL) and the mixture was allowed to stir at −78° C. for 10 min. At this time, methyl 2-phenylacetate (3.25 g, 21.6 mmol) was taken up in THF (15 ml) and added dropwise to the reaction, which was then placed in a 0° C. bath for 40 min before being rechilled to −78° C. for 10 min. At this time, NFSI (8.87 g, 28.1 mmol) was added in THF (930 ml) and the flask was placed in a 0° C. bath. The reaction was allowed to stir for 30 min when a white solid appeared. The reaction was allowed to stir for an additional 20 min and then poured into ammonium chloride (200 ml) and extracted with EtOAc (3×100 ml). The combined organics were washed with sodium carbonate (10%, 3×100 ml) and brine. The solution was dried with sodium sulfate, filtered and concentrated to give 6.7 g of a yellow oil. A white solid formed upon storage on the bench. The crude mixture was purified on a 330 g ISCO column (gradient of 20 to 50% EtOAc in hexanes) to give pure methyl 2-fluoro-2-phenylacetate as a pale yellow oil. (3.10 g, 85.2% yield).

Step 2: 2-Fluoro-2-phenylacetaldehyde

To a 500 mL RBF containing 2-fluoro-2-phenylethanol (440.00 mg, 3139 μmol) was added DCM (30 mL) and the mixture was allowed to stir at 23° C. for 5 min. At this time, sodium bicarbonate (343 mg, 4081 μmol) and Dess-Martin-Periodinane (1731 mg, 4081 μmol) were added in one portion and the reaction mixture was allowed to stir for 15 min before the reaction was quenched by the addition of sodium thiosulfate (2482 mg, 15697 μmol) in water (50 ml) and sodium bicarbonate (sat, 50 ml) and diethyl ether (100 ml). The quenched reaction was allowed to stir for 20 min and the organic layer was washed with sodium bicarbonate (sat., 3×75 ml) and brine. The organic layer was dried over magnesium sulphate, filtered and concentrated to give the title compound (385 mg) as a pale yellow oil.

Step 3: (R,E)-N-(2-fluoro-2-phenylethylidene)-2-methylpropane-2-sulfinamide

To a 500 mL RBF containing 2-fluoro-2-phenylacetaldehyde (320.00 mg, 2316.5 μmol) was added DCM (10 mL) and the mixture was allowed to stir at 23° C. for 2 min. At this time, (R)-2-methylpropane-2-sulfinamide (364.99 mg, 3011.5 μmol) was added in one portion to the mixture followed by copper(II) chloride (856.51 mg, 6370.4 μmol) at 5:30 pm. The reaction was allowed to stir overnight and then filtered through a plug of celite over silica gel. The solvent was removed and the crude residue was purified on a silica gel column (15 to 35% EtOAc in hexanes) to give the product (168 mg, 30%).

Step 4: (R)-N-((R)-1-fluoro-1-phenylbut-3-en-2-yl)-2-methylpropane-2-sulfinamide To a 250 mL RBF containing (1 0R,E)-N-(2-fluoro-2-phenylethylidene)-2-methylpropane-2-sulfinamide (672.00 mg, 2785 μmol) was added THF (15 mL) and the mixture was allowed to stir at −78° C. for 10 min. At this time, BF3.OEt2

(706 μl, 5569 μmol) was added via syringe and the reaction was allowed to stir for 5 min before adding to it vinylmagnesium bromide (2785 μl, 2785 μmol) dropwise via syringe. The reaction was allowed to stir for 30 min and then quenched with ammonium chloride (sat, 120 ml). The aqueous layer was extracted with EtOAc (3×75 ml). The combined organics were washed with brine, dried over sodium sulfate, filtered and concentrated to give 800 mg of crude oil that was purified on a silica gel column. The following product fractions were isolated: Fraction 1: slightly higher, 104 mg, one diasteromer only. Rf=0.30 in 35% EtOAc in hexanes, UV active, stains brown to anisaldehyde. Fraction 2: the rest, a mixture of diastereomers, 425 mg. The lower Rf diasteromer is just below the higher Rf diasteromer spot. Interestingly, the lower Rf spot is UV active and stains yellow to anisaldehyde and not brown.

Step 5: (R)-Tert-butyl 1-fluoro-1-phenylbut-3-en-2-ylcarbamate

To a 150 mL RBF containing (R)—N-((1S,2R)-1-fluoro-1-phenylbut-3-en-2-yl)-2-methylpropane-2-sulfinamide (107.00 mg, 397 μmol) was added methanol (5 mL) and the mixture was allowed to stir at 0° C. for 10 min. At this time, HCl (4N) (993 μl, 3972 μmol) was added and the reaction was allowed to stir for 30 min. Then TEA (1384 μl, 9930 μmol) was added to the mixture followed by DCM (2 ml) and BOC$_2$O (173 mg, 794 μmol) in one portion. The reaction was allowed to stir overnight and then the bulk of the methanol was removed by evaporation. The residue was dissolved in EtOAc and washed with HCL (0.5 N, 2×40 ml). The combined aqueous layers were back extacted with EtOAc. The combined organics were washed with sodium bicarbonate (1×50 ml, sat) and brine and then dried with sodium sulfate. The dried solution was passed though a plug of silica gel to give tert-butyl (1S,2R)-1-fluoro-1-phenylbut-3-en-2-ylcarbamate (111.0 mg). Rf=0.45 in 20% EtOAc in hexanes, UV active and stain yellow to anisaldehyde. LC/MS give an ionization for eliminated product (mass=190).

Step 6: (R)-tert-butyl 1-fluoro-3,4-dihydroxy-1-phenylbutan-2-ylcarbamate

To a 250 mL RBF containing tert-butyl (1S,2R)-1-fluoro-1-phenylbut-3-en-2-ylcarbamate (105.00 mg, 396 mmol) (mixture of diasteromers at benzylic fluoride stereocenter) was added tert-butanol (3 mL) and water (1 ml). The mixture was allowed to stir at 23° C. for 2 min, then NMO (139 mg, 1187 mmol) and osmium tetraxide (124 μA, 396 mmol) were added and the reaction was allowed to stir for another 48 h. before the reaction was quenched with water and sodium sulfite (1496 mg, 11872 mmol). The reaction was allowed to stir for 15 min and then extracted with EtOAc (3×). The combined organics were washed with HCl (1 N), sodium bicarbonate, brine and dried over sodium sulfate. The dried solution was passed through a plug of silica gel and concentrated to give 102 mg of a colorless oil Step 7: (R)-tert-butyl 3,4-bis(tert-butyldimethylsilyloxy)-1-fluoro-1-phenylbutan-2-ylcarbamate To a 500 mL RBF containing tert-butyl (1S,2R)-1-fluoro-3,4-dihydroxy-1-phenylbutan-2-ylcarbamate (98.00 mg, 327 mmol) was added DCM (5 mL) and the mixture was allowed to stir at 0° C. for 5 min. At this time, TEA (274 μA, 1964 mmol) and tert-butyldimethylsilyl triflate (188 μl, 818 μmol) was added to the mixture via syringe. The reaction was allowed to stir for 30 min and then quenched with sodium bicarbonate (50 ml, sat). The aq. layer was extracted with DCM (3×25 ml). The combined organics were washed with brine, dried with sodium sulfate and passed through a plug of silica gel and concentrated to give 203 mg of a yellow oil that was taken directly to the next step.

Step 8: (R)-tert-butyl 3-(tert-butyldimethylsilyloxy)-1-fluoro-4-hydroxy-1-phenylbutan-2-ylcarbamate To a plastic bottle containing (R)-tert-butyl 3,4-bis(tert-butyldimethylsilyloxy)-1-fluoro-1-phenylbutan-2-ylcarbamate was added 10 ml THF, 3 ml pyridine, 1 ml HF-pyr at 0° C. The mixture was stirred for 6 h and then carefully quench with sodium bicarbonate. The aq. layer was extracted with DCM (4×25 ml). The combined organics were washed with brine, dried with sodium sulfate, filtered, concentrated and the crude purified on a 40 g ISCO column to give 225 mg of the title compound.

Step 9: N-((1S,2R)-1-fluoro-3-hydroxy-4-((S)-6-neopentyl-3',4'-dihydrospiro[cyclobutane-1,2'-pyrano[2,3-b]pyridin-4-ylamino)-1-phenylbutan-2-yl)acetamide The title compound was prepared using procedures analogous to those disclosed in U.S. patent application Ser. No. 11/595,187 which disclosure is hereby incorporated by reference herein in its entirety. More particularly, the title compound was prepared using the Dess-Martin oxidation, reductive amination, deprotection and amide formation procedures described both therein and herein.

Example 43

N-((1S,2R)-3-(((4'S)-6'-(2,2-dimethylpropyl)-3',4'-dihydrospiro[cyclobutane-1,2'-pyrano[3,2-b]pyridin]-4'-yl]amino)-1-((4-fluorophenyl)methyl)-2-hydroxypropyl)-2-(methyloxy)acetamide The title compound was prepared according to a procedure analogous to that described in Example 42 above. MS m/z: 514.2 (M+H).

Example 44

N-((1S,2R)-3-(((4'S)-6'-((1,1-difluoroethyl)oxy)-3',4'-dihydrospiro[cyclobutane-1,2'-pyrano[2,3-b]pyridin]-4'-yl]amino)-1-[((3-fluorophenyl)methyl)-2-hydroxypropyl]acetamide The title compound was prepared according to a procedure analogous to that described in Example 42 above. MS m/z: 494.4 (M+H).

Example 45

N-((1S,2R)-3-(((4'S)-8'-amino-6'-(2,2-dimethylpropyl)-3',4'-dihydrospiro[cyclobutane-1,2'-pyrano[2,3-c]pyridin]-4'-yl)amino)-1-(1,3-benzodioxol-5-ylmethyl)-2-hydroxypropyl)-2-(methyloxy)acetamide To a flame-dried microwave vial under Ar gas was added 'N-((1S,2R)-1-(1,3-benzodioxol-5-ylmethyl)-3-(4'S)-8'-chloro-6'-(2,2-dimethylpropyl)-3',4'-dihydrospiro[cyclobutane-1,2'-pyrano[2,3-c]pyridin]-4'-yl)amino)-2-hydroxypropyl)-2-(methyloxy)acetamide (350 mg, 610 μmol), Pd2 dba3

(112 mg, 122 μmol), and DavePhos (106 mg, 268 μmol). The vial was purged with N₂ 5×, then THF (5.0 mL), and LiHMDS (5487 μl, 5487 μmol) were added. The vial was sealed and heated in a microwave at 110° C. for 10 min. The mixture was quenched with H₂O (8 mL), and extracted with CH₂Cl₂ (3×20 mL). The combined organic layers were dried (MgSO₄), and concentrated to give a brown oil. The crude product was purified by reverse phase HPLC to give the title compound as an amorphous off-white solid. MS m/z: 555.2 (M+1).

Example 46

N-((1S,2R)-3-(((4'S)-6'-(2,2-dimethylpropyl)-8'-((2,2,2-trifluoroethyl)oxy)-3',4'-dihydrospiro[cyclobutane-1,2'-pyrano[2,3-c]pyridin]-4'-yl]amino)-1-((3-fluorophenyl)methyl)-2-hydroxypropyl)-2-(methyloxy)acetamide

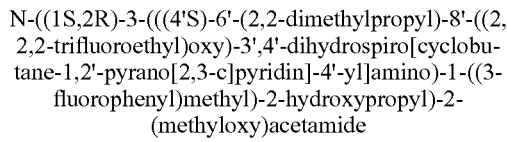

To a flame-dried microwave vial under Ar gas was added N-((1S,2R)-1-[((3-fluorophenyl)methyl)-3-(((4'S)-8'-chloro-6'-(2,2-dimethylpropyl)-3',4'-dihydrospiro[cyclobutane-1,2'-pyrano[2,3-c]pyridin]-4'-yl)amino)-2-hydroxypropyl)-2-(methyloxy)acetamide (100 mg, 182 μmol), cesium carbonate (357 mg, 1095 μmol), DavePhos (79 mg, 201 μmol), palladium(II) acetate (41 mg, 182 μmol) were added and vial was flushed with N₂ 5×, then 2,2,2-trifluoroethanol (332 μl, 4561 μmol) and toluene (1 mL) were added simultaneously. The reaction was heated in the microwave at 110° C. for 30 min. The reaction mixture was filtered through a small plug of silica gel, and the residue purified by reverse phase HPLC to give the title compound as a tan amorphous solid. MS m/z: 612.0 (M+1).

Example 47

(2R)-N-((1S,2R)-3-(((4'S)-6'-(2,2-dimethylpropyl)-8'-((2,2,2-trifluoroethyl)amino)-3',4'-dihydrospiro[cyclobutane-1,2'-pyrano[2,3-c]pyridin]-4'-yl]amino)-1-[((4-fluorophenyl)methyl)-2-hydroxypropyl)-2-(methyloxy)propanamide

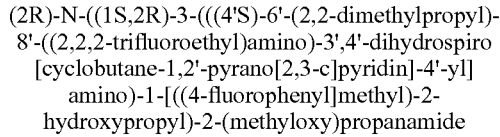

To a flame-dried microwave vial under Ar gas was added (2R)-N-((1S,2R)-1-(4-fluorophenyl)methyl)-3-(((4'S)-8'-chloro-6'-(2,2-dimethylpropyl)-3',4'-dihydrospiro[cyclobutane-1,2'-pyrano[2,3-c]pyridin]-4'-yl)amino)-2-hydroxypropyl)-2-(methyloxy)propanamide (140 mg, 249 μmol), Pd₂dba₃ (45.6 mg, 49.8 μmol), and DavePhos (43.1 mg, 110 μmol). The vial was purged with N₂ 5×, then THF (1 mL), 2,2,2-trifluoroethanamine (98.7 μl, 996 μmol), and LiHMDS (2242 μl, 2242 μmol) were added. The vial was sealed and heated in a microwave at 110° C. for 10 min. The mixture was quenched with H₂O (8 mL), and extracted with CH₂Cl₂ (3×20 mL). The combined organic layers were dried (MgSO₄), and concentrated to give a brown oil. The crude product was by reverse phase HPLC to give the title compound as an amorphous off-white solid. MS m/z: 625.2 (M+1).

Example 48

N-((1S,2R)-3-(((4'S)-6'-(2,2-dimethylpropyl)-8'-((2-(methyloxy)ethyl)amino)-3',4'-dihydrospiro[cyclobutane-1,2'-pyrano[2,3-c]pyridin]-4'-yl]amino)-1-((4-fluorophenylmethyl)-2-hydroxypropyl)acetamide

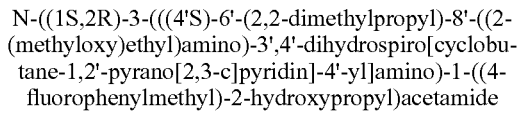

To a flame-dried microwave vial under Ar gas was added N-((1S,2R)-1-(4-fluorophenyl)methyl)-3-(((4'S)-8'-chloro-6'-(2,2-dimethylpropyl)-3',4'-dihydrospiro[cyclobutane-1, 2'-pyrano[2,3-c]pyridin]-4'-yl)amino)-2-hydroxypropyl)acetamide (200 mg, 386 mmol), Pd2 dba3 (35.4 mg, 38.6 μmol), and DavePhos (33.4 mg, 84.9 μmol). The vial was purged with N₂ 5×, then THF (1 mL), 2-methoxyethanamine (133 μl, 1544 μmol), and LiHMDS (3474 μl, 3474 μmol) were added. The vial was sealed and heated in a microwave at 110° C. for 10 min. The mixture was quenched with H₂O (1 mL), and filtered through a 0.2 um syringe filter. The filtrate was purified by reverse phase HPLC to give the title compound as an amorphous off-white solid. MS m/z: 557.2 (M+1).

Example 49

N-((1S,2R)-1-((3-Bromo-4-fluorophenyl)methyl)-3-(((4'S)-6'-((1,1-dimethylethyl)oxy)-3',4'-dihydrospiro[cyclobutane-1,2'-pyrano[2,3-b]pyridin]-4'-yl)amino)-2-hydroxypropyl)acetamide

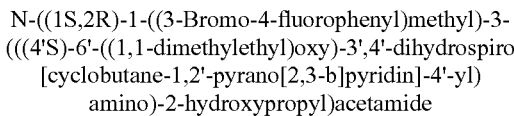

Step 1: (9H-Fluoren-9-yl)methyl (2S,3R)-1-(3-bromo-4-fluorophenyl)-4-((S)-6-tert-butoxy-2,2-spirocyclobutyl-3,4-dihydro-2H-pyrano[2,3-b]pyridin-4-ylamino)-3-(tert-butyldimethylsilyloxy)butan-2-ylcarbamate In a 25-mL RBF, (S)-6-tert-butoxy-2,2-spirocyclobutyl-3,4-dihydro-2H-pyrano[2,3-b]pyridin-4-amine (0.038 g, 0.14 mmol) and (9H-fluoren-9-yl)methyl (2S,3S)-1-(3-bromo-4-fluorophenyl)-3-(tert-butyldimethylsilyloxy)-4-oxobutan-2-ylcarbamate (prepared analogously to the corresponding N-Boc compound, except using Fmoc-Cl and Et₃N instead of Boc₂O, 0.089 g, 0.14 mmol) were dissolved in DCM (2.0 mL). Trimethoxymethane (0.40 ml, 3.6 mmol) was added, and the solution was stirred at ambient temperature for 1 hr. Sodium triacetoxyborohydride (0.12 g, 0.58 mmol) was added, and the resulting suspension was stirred at ambient temperature overnight. The mixture was quenched with 10% aqueous sodium carbonate (8 mL). After 2 h, the aqueous phase was extracted with DCM (3×20 mL). The organic layers were dried over sodium sulfate and concentrated. The crude material was purified through silica gel (20 mL) using 33% EtOAc-hexane to afford the title compound as a white foam. Found MS m/z 858/860 (M+1).

Step 2: N-((2S,3R)-1-(3-Bromo-4-fluorophenyl)-4-(S)-6-tert-butoxy-2,2-spirocyclobutyl-3,4-dihydro-2H-pyrano[2,3-b]pyridin-4-ylamino)-3-(tert-butyldimethylsilyloxy)butan-2-yl)acetamide In a 25-mL RBF, the (9H-fluoren-9-yl)methyl (2S,3R)-1-(3-bromo-4-fluorophenyl)-4-((S)-6-tert-butoxy-2,2-spirocyclobutyl-3,4-dihydro-2H-pyrano[2,3-b]pyridin-4-ylamino)-3-(tert-butyldimethylsilyloxy)butan-2-ylcarbamate (0.073 g, 0.085 mmol) was dissolved in DMF (1.5 mL). The solution was cooled to 0° C. Pyrrolidine (0.018 ml, 0.21 mmol) was added and the reaction solution was warmed to ambient temperature. The reaction was concentrated on a rotovap, the crude residue was diluted with DMF (0.25 mL), to which Hunig's base (0.060 mL, 0.34 mmol), and N-acetylimidazole (38 mg, 0.34 mmol) were added. The mixture was stirred at ambient temperature overnight and concentrated. The residue was diluted with aqueous sodium bicarbonate (10 mL) and the aqueous phase was extracted with EtOAc (3×20 mL). The organic phase was dried over sodium sulfate and concentrated. The crude material was purified by passing through silica gel (20 g; deactivated with TEA (2.0 mL)), eluting with DCM to afford the title compound. MS m/z 678/680 (M+1).

Step 3: N-((1S,2R)-1-((3-Bromo-4-fluorophenyl)methyl)-3-(((4'S)-6'-((1,1-dimethylethyl)oxy)-3',4'-dihydrospiro[cyclobutane-1,2'-pyrano[2,3-b]pyridin]-4'-yl)amino)-2-hydroxypropyl)acetamide In a 25-mL RBF, the N-((2S,3R)-1-(3-bromo-4-fluorophenyl)-4-(S)-6-tert-butoxy-2,2-spirocyclobutyl-3,4-dihydro-2H-pyrano[2,3-b]pyridin-4-ylamino)-3-(tert-butyldimethylsilyloxy)butan-2-yl)acetamide (0.050 g, 0.074 mmol) was dissolved in THF (2.0 mL). TBAF (1.0 M in THF, 0.074 ml, 0.074 mmol) was added. After 1 h, the reaction was concentrated. The residue was purified by passing through silica gel (20 g; deactivated with triethylamine (2.0 mL)), eluting with methanol-DCM (2.0 to 2.5%) to afford the title compound. MS m/z 564/566 (M+1).

Example 50

N-((1S,2R)-1-((3-Bromo-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)(methyl)amino)-2-hydroxypropyl)acetamide In a 15-mL RB flask, N-((1S,2R)-1-((3-bromo-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide (0.027 g, 0.048 mmol) was dissolved in DCM (1.5 mL). Trimethyl orthoformate (0.13 ml, 1.2 mmol) was added, followed by addition of Formaldehyde (37%, 0.0089 ml, 0.12 mmol) as an aqueous solution. The mixture was stirred at ambient temperature for 2 h. Then sodium triacetoxyborohydride (0.036 g, 0.17 mmol) was added, and the mixture was stirred at ambient temperature overnight. The reaction mixture was quenched with 10% aqueous sodium carbonate (5 mL), stirred vigorously for 2 h, and diluted with DCM (60 mL). The organic layer was separated and extracted with dilute brine (5 mL), dried over sodium sulfate and concentrated. The residue was purified by passing it through silica gel (20 g; deactivated with triethylamine (2.0 mL)), eluting with 95% EtOAc-hexane to provide the title compound. MS m/z 576/578 (M+1).

Example 51

N-((1S,2R)-3-(((1s,3R,4'S)-6'-(2,2-Dimethylpropyl)-3-(hydroxymethyl)-3',4'-dihydrospiro[cyclobutane-1,2'-pyrano[2,3-b]pyridin]-4'-yl)amino)-1-((4-fluorophenyl)methyl)-2-hydroxypropyl)acetamide Step 1: (S)-N-((2R,3S)-3-Amino-2-(tert-butyldimethylsilyloxo)-4-(4-fluorophenyl)butyl)-[(2,2-spirocyclobutyl-3'-cis-hydroxymethyl)]-6-neopentyl-3,4-dihydro-2H-pyrano[2,3-b]pyridine-4-amine To a stirred solution of (S)-N-((2R,3S)-3-amino-2-(tert-butyldimethylsilyloxo)-4-(4-fluorophenyl)butyl)-[(2,2-spirocyclobutyl-3'-cis-methoxycarbonyl)]-6-neopentyl-3,4-dihydro-2H-pyrano[2,3-b]pyridine-4-amine (0.28 g, 0.5 mmol) in THF (5 ml) was added diisobutylaluminum hydride, 1.0m solution in hexanes (2 ml, 2 mmol) dropwise. The reaction mixture was stirred at RT for about 2 h, then slowly quenched with Rochelle's salt and vigorously stirred in 2 h. The reaction mixture was extracted with DCM (3×), dried over MgSO$_4$, concentrated to give the title compound as a yellow oil. MS (m+1): 586.8).

Step 2: N-((1S,2R)-3-(((1s,3R,4'S)-6'-(2,2-dimethylpropyl)-3-(hydroxymethyl)-3',4'-dihydrospiro[cyclobutane-1,2'-pyrano[2,3-b]pyridin]-4'-yl)amino)-1-((4-fluorophenyl)methyl)-2-hydroxypropyl)acetamide The title compound was prepared by a procedure analogous to that described in Steps 2-3 of Example 49 above. MS: refer to Table I herein.

The following examples in Table I were prepared by methods and Steps analogous to those described in Examples 41-51 above. Provided also is the mass spectral data and BACE enzyme and cell-based assay data (IC$_{50}$'s in uM) for each example, where available.

TABLE 1

| Ex. No. | Compound Name | Observed MS | BACE1 FRET assay (uM) | HEK cell assay (uM) |
|---|---|---|---|---|
| 52 | N-((1S,2R)-1-(1,3-benzodioxol-5-ylmethyl)-3-(((4'S)-6'-(2,2-dimethylpropyl)-3,3-difluoro-3',4'-dihydrospiro[cyclobutane-1,2'-pyrano[2,3-b]pyridin]-4'-yl)amino)-2-hydroxypropyl)-2-(methyloxy)acetamide | 576.3 | 0.042 | 0.103 |
| 53 | N-((1S,2R)-3-((6'-(2,2-dimethylpropyl)-3,3-difluoro-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)acetamide | 550.3 | 0.011 | 0.065 |
| 54 | N-((1S,2R)-3-((6'-(2,2-dimethylpropyl)-3,3-difluoro-3',4'-dihydrospiro[cyclobutane-1,2'-pyrano[2,3-b]pyridin]-4'-yl)amino)-1-((phenyl)methyl)-2-hydroxypropyl)-2-(methyloxy)acetamide | 532.3 | 0.003 | 0.066 |
| 55 | N-((1S,2R)-1-(1,3-benzodioxol-5-ylmethyl)-3-(((4'S)-6'-(2,2-dimethylpropyl)-3,3-difluoro-3',4'-dihydrospiro[cyclobutane-1,2'-pyrano[2,3-b]pyridin]-4'-yl)amino)-2-hydroxypropyl)acetamide | 546.3 | 0.02359 | 0.08303 |

TABLE 1-continued

| Ex. No. | Compound Name | Observed MS | BACE1 FRET assay (uM) | HEK cell assay (uM) |
|---|---|---|---|---|
| 56 | (2R)-N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)propanamide | 535.4 | 0.00263 | 0.00305 |
| 57 | N-((1S,2R)-1-((3-cyanophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)-2-(methyloxy)acetamide | 525.3 | 0.00294 | 0.0053 |
| 58 | (2R)-N-((1S,2R)-1-((3-cyanophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)-2-(methyloxy)propanamide | 539.3 | 0.00575 | 0.00678 |
| 59 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3,3,3-trifluoro-2-(methyloxy)propanamide | 582.4 | 0.36433 | 0.17123 |
| 60 | N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-1-cyclobutyl-4,4-dimethyl-5-oxo-3-pyrrolidinecarboxamide | 624.4 | 0.02106 | 0.06315 |
| 61 | (2S)-N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-3,3,3-trifluoro-2-hydroxypropanamide | 575.3 | 0.00323 | 0.00965 |
| 62 | (2R)-N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-3,3,3-trifluoro-2-hydroxypropanamide | 575.3 | 0.00401 | 0.00983 |
| 63 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3,3,3-trifluoro-2-(methyloxy)propanamide | 582.4 | 0.25803 | 0.12846 |
| 64 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3,3,3-trifluoro-2-(methyloxy)propanamide | 582.4 | 0.61719 | 0.07965 |
| 65 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)-3,3,3-trifluoro-2-(methyloxy)propanamide | 582.4 | 0.03426 | 0.12727 |
| 66 | 1-cyclobutyl-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)-4,4-dimethyl-5-oxo-3-pyrrolidinecarboxamide | 635.4 | 0.04358 | 1.10647 |
| 67 | 1-cyclobutyl-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-5-oxo-3-pyrrolidinecarboxamide | 635.4 | 0.4709 | 0.06253 |
| 68 | (2S)-N-((1S,2R)-3-(((4'S)-6'-(2,2-dimethylpropyl)-3',4'-dihydrospiro[cyclobutane-1,2'-pyrano[2,3- | 568.3 | 0.04862 | 0.05526 |

TABLE 1-continued

| Ex. No. | Compound Name | Observed MS | BACE1 FRET assay (uM) | HEK cell assay (uM) |
|---|---|---|---|---|
|  | b]pyridin]-4'-yl)amino)-1-((4-fluorophenyl)methyl)-2-hydroxypropyl)-3,3,3-trifluoro-2-hydroxypropanamide | | | |
| 69 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-3,3,3-trifluoro-2-hydroxypropanamide | 568.3 | 0.03363 | 0.07835 |
| 70 | (2R)-N-((1S,2R)-1-((4-chloro-3-fluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)-2-(methyloxy)propanamide | 566.3 | 0.05582 | 0.13796 |
| 71 | (2R)-N-((1S,2R)-1-((2,3-difluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)-2-(methyloxy)propanamide | 550.3 | 0.0339 | 0.09268 |
| 72 | (2R)-N-((1S,2R)-1-((3-chloro-4-fluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)-2-(methyloxy)propanamide | 566.3 | 0.02907 | 0.06051 |
| 73 | N-((1S,2R)-1-((3-fluorophenyl)methyl)-2-hydroxy-3-(((4'S)-6'-(3,3,3-trifluoro-2,2-dimethylpropyl)-3',4'-dihydrospiro[cyclobutane-1,2'-pyrano[2,3-b]pyridin]-4'-yl)amino)propyl)-2-(methyloxy)acetamide | 568.3 | 0.01604 | 0.05314 |
| 74 | (2R)-N-((1S,2R)-1-((3-fluorophenyl)methyl)-2-hydroxy-3-(((4'S)-6'-(3,3,3-trifluoro-2,2-dimethylpropyl)-3',4'-dihydrospiro[cyclobutane-1,2'-pyrano[2,3-b]pyridin]-4'-yl)amino)propyl)-2-(methyloxy)propanamide | 582.3 | 0.03045 | 0.09487 |
| 75 | (2R)-N-((1S,2R)-1-((4-fluorophenyl)methyl)-2-hydroxy-3-(((4'S)-6'-(3,3,3-trifluoro-2,2-dimethylpropyl)-3',4'-dihydrospiro[cyclobutane-1,2'-pyrano[2,3-b]pyridin]-4'-yl)amino)propyl)-2-(methyloxy)propanamide | 582.3 | 0.00668 | 0.01988 |
| 76 | N-((1S,2R)-1-((4-fluorophenyl)methyl)-2-hydroxy-3-(((4'S)-6'-(3,3,3-trifluoro-2,2-dimethylpropyl)-3',4'-dihydrospiro[cyclobutane-1,2'-pyrano[2,3-b]pyridin]-4'-yl)amino)propyl)-2-(methyloxy)acetamide | 568.3 | 0.00368 | 0.01084 |
| 77 | N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-((4-fluoro-3-((trifluoromethyl)oxy)phenyl)methyl)-2-hydroxypropyl)acetamide | 572.3 | 0.00488 | 0.01597 |
| 78 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluoro-3-(methyloxy)phenyl)methyl)-2-hydroxypropyl)acetamide | 514.3 | 0.00449 | 0.00763 |
| 79 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluoro-3-(methyloxy)phenyl)methyl)-2-hydroxypropyl)-2-(methyloxy)acetamide | 544.3 | 0.00637 | 0.01477 |
| 80 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluoro-3- | 568.2 | 0.01231 | 0.12547 |

TABLE 1-continued

| Ex. No. | Compound Name | Observed MS | BACE1 FRET assay (uM) | HEK cell assay (uM) |
|---|---|---|---|---|
| | (methyloxy)phenyl)methyl)-2-hydroxypropyl)-2,2,2-trifluoroacetamide | | | |
| 81 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluoro-3-((trifluoromethyl)oxy)phenyl)methyl)-2-hydroxypropyl)-2-(methyloxy)acetamide | 598.2 | 0.00251 | 0.01399 |
| 82 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluoro-3-((trifluoromethyl)oxy)phenyl)methyl)-2-hydroxypropyl)-2,2,2-trifluoroacetamide | 622.2 | 0.00283 | 0.52314 |
| 83 | N-((1S,2R)-3-(((4'S)-6'-(acetylamino)-3',4'-dihydrospiro[cyclobutane-1,2'-pyrano[2,3-b]pyridin]-4'-yl)amino)-1-((4-fluorophenyl)methyl)-2-hydroxypropyl)acetamide | 471.1 | 0.59327 | 10 |
| 84 | N-((4'S)-4'-(((2R,3S)-3-(acetylamino)-4-(4-fluorophenyl)-2-hydroxybutyl)amino)-3',4'-dihydrospiro[cyclobutane-1,2'-pyrano[2,3-b]pyridin]-6'-yl)-2,2-dimethylpropanamide | 513.1 | 4.86752 | 10 |
| 85 | N-((4'S)-4'-(((2R,3S)-3-(acetylamino)-4-(4-fluorophenyl)-2-hydroxybutyl)amino)-3',4'-dihydrospiro[cyclobutane-1,2'-pyrano[2,3-b]pyridin]-6'-yl)propanamide | 485.2 | 0.88988 | 10 |
| 86 | N-((4'S)-4'-(((2R,3S)-3-(acetylamino)-4-(4-fluorophenyl)-2-hydroxybutyl)amino)-3',4'-dihydrospiro[cyclobutane-1,2'-pyrano[2,3-b]pyridin]-6'-yl)-2-methylpropanamide | 499.1 | 7.46555 | 9.73297 |
| 87 | N-((1S,2R)-1-(1,3-benzodioxol-5-ylmethyl)-3-(((4'S)-6'-(2-cyano-2-methylpropyl)-3',4'-dihydrospiro[cyclobutane-1,2'-pyrano[2,3-b]pyridin]-4'-yl)amino)-2-hydroxypropyl)-2-(methyloxy)acetamide | 551.1 | 0.11727 | 0.0828 |
| 88 | N-((1S,2R)-1-(1,3-benzodioxol-5-ylmethyl)-3-(((4'S)-6'-(2-cyano-2-methylpropyl)-3',4'-dihydrospiro[cyclobutane-1,2'-pyrano[2,3-b]pyridin]-4'-yl)amino)-2-hydroxypropyl)acetamide | 521.2 | 0.04846 | 0.01605 |
| 89 | N-((1S,2R)-1-((3,5-difluorophenyl)methyl)-3-(((4'S)-6'-(2,2-dimethylpropyl)-1'-oxo-3',4'-dihydro-1'H-spiro[cyclopentane-1,2'-naphthalen]-4'-yl)amino)-2-hydroxypropyl)-2-(methyloxy)acetamide | 557.2 | 0.00495 | 0.05857 |
| 90 | N-((1S,2R)-1-((3,5-difluorophenyl)methyl)-3-(((4'S)-6'-(2,2-dimethylpropyl)-1'-oxo-3',4'-dihydro-1'H-spiro[cyclopentane-1,2'-naphthalen]-4'-yl)amino)-2-hydroxypropyl)acetamide | 527.2 | 0.01035 | 0.07474 |
| 91 | N-((1S,2R)-3-(((4'S)-6'-(2-cyano-2-methylpropyl)-3',4'-dihydrospiro[cyclobutane-1,2'-pyrano[2,3-b]pyridin]-4'-yl)amino)-1-((3,5-difluorophenyl)methyl)-2-hydroxypropyl)acetamide | 513.2 | 0.00442 | 0.00646 |
| 92 | N-((1S,2R)-3-(((4'S)-6'-(2-cyano-2-methylpropyl)-3',4'-dihydrospiro[cyclobutane-1,2'-pyrano[2,3-b]pyridin]-4'-yl)amino)-1-((3,5-difluorophenyl)methyl)-2-hydroxypropyl)-2-(methyloxy)acetamide | 543.1 | 0.00325 | 0.00621 |
| 93 | 1,3-thiazol-5-ylmethyl ((1S,2R)-1-((3,5-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)carbamate | 601.3 | 0.00495 | 0.0792 |

TABLE 1-continued

| Ex. No. | Compound Name | Observed MS | BACE1 FRET assay (uM) | HEK cell assay (uM) |
|---|---|---|---|---|
| 94 | N-((1S,2R)-1-((3,5-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-((1,3-thiazol-5-ylmethyl)oxy)acetamide | 615.2 | 0.003 | 0.01707 |
| 95 | 2,2-dichloro-N-((1S,2R)-1-((3,5-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 571.2 | 0.00043 | 0.01667 |
| 96 | 2-chloro-N-((1S,2R)-1-((3,5-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2,2-difluoroacetamide | 573.2 | 0.00023 | 0.04322 |
| 97 | 2,2-dichloro-N-((1S,2R)-1-((3,5-difluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)propanamide | 585.3 | 0.01378 | 0.38469 |
| 98 | N-((2S,3R)-1-(benzo[d][1,3]dioxol-5-yl)-3-hydroxy-4-((S)-6-neopentyl-3,4-dihydrospiro[cyclobutane-1,2H-pyrano[2,3-b]pyridin-4-ylamino)butan-2-yl)-2,2-dichloropropanamide | 593 | 0.54043 | 0.76738 |
| 99 | N-((2S,3R)-1-(benzo[d][1,3]dioxol-5-yl)-3-hydroxy-4-((S)-6-neopentyl-3,4-dihydrospiro[cyclobutane-1,2H-pyrano[2,3-b]pyridin-4-ylamino)butan-2-yl)-2-chloro-2,2-difluoroacetamide | 581.2 | 0.05934 | 0.31692 |
| 100 | N-((2S,3R)-1-(benzo[d][1,3]dioxol-5-yl)-3-hydroxy-4-((S)-6-neopentyl-3,4-dihydrospiro[cyclobutane-1,2H-pyrano[2,3-b]pyridin-4-ylamino)butan-2-yl)-2,2-dichloroacetamide | 579.1 | 0.01269 | 0.07141 |
| 101 | thiazol-5-ylmethyl (2S,3R)-1-(benzo[d][1,3]dioxol-5-yl)-3-hydroxy-4-((S)-6-neopentyl-3,4-dihydrospiro[cyclobutane-1,2H-pyrano[2,3-b]pyridin-4-ylamino)butan-2-ylcarbamate | 609.1 | 0.15924 | 1.85082 |
| 102 | (R)-N-((2S,3R)-1-(3,5-difluorophenyl)-3-hydroxy-4-((S)-6-neopentyl-3,4-dihydrospiro[cyclobutane-1,2H-pyrano[2,3-b]pyridin-4-ylamino)butan-2-yl)-2-methoxypropanamide | 546.2 | 0.0053 | 0.01063 |
| 103 | (S)-N-((2S,3R)-1-(3,5-difluorophenyl)-3-hydroxy-4-((S)-6-neopentyl-3,4-dihydrospiro[cyclobutane-1,2H-pyrano[2,3-b]pyridin-4-ylamino)butan-2-yl)-2-methoxypropanamide | 546.2 | 0.0101 | 0.02684 |
| 104 | 2-chloro-N-((2S,3R)-1-(3,5-difluorophenyl)-3-hydroxy-4-((S)-6-neopentyl-3,4-dihydrospiro[cyclobutane-1,2H-pyrano[2,3-b]pyridin-4-ylamino)butan-2-yl)acetamide | 537.1 | 0.00369 | 0.01875 |
| 105 | 2,2-dichloro-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide | 553.2 | 0.00406 | 0.02948 |
| 106 | 2,2-dichloro-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)propanamide | 567.2 | 0.06691 | 0.83427 |
| 107 | 2-chloro-N-((1S,2R)-3-(((4'S)-6'-(2,2-dimethylpropyl)-3',4'-dihydrospiro[cyclobutane-1,2'-pyrano[2,3- | 519.2 | 0.00507 | 0.02243 |

TABLE 1-continued

| Ex. No. | Compound Name | Observed MS | BACE1 FRET assay (uM) | HEK cell assay (uM) |
|---|---|---|---|---|
| | b]pyridin]-4'-yl)amino)-1-((3-fluorophenyl)methyl)-2-hydroxypropyl)acetamide | | | |
| 108 | 2-chloro-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)-2,2-difluoroacetamide | 555.1 | 0.00506 | 0.09061 |
| 109 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluoro-2-methylphenyl)methyl)-2-hydroxypropyl)acetamide | 498.2 | 0.07235 | 0.3186 |
| 110 | N-((1S,2R)-1-fluoro-3-hydroxy-4-((S)-6-neopentyl-3',4'-dihydrospiro[cyclobutane-1,2'-pyrano[2,3-b]pyridin-4-ylamino)-1-phenylbutan-2-yl)acetamide | 484.2 | 0.89655 | 0.8038 |
| 111 | N-((1S,2R,3R)-1-fluoro-3-hydroxy-4-((S)-6-neopentyl-3',4'-dihydrospiro[cyclobutane-1,2'-pyrano[2,3-b]pyridin-4-ylamino)-1-phenylbutan-2-yl)acetamide | 484.2 | 0.01118 | 0.01586 |
| 112 | N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-2-hydroxy-1-(phenylmethyl)propyl)-2-(methyloxy)acetamide | 525.4 | 0.03043 | 0.00893 |
| 113 | N-((1S,2R)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)-2-(methyloxy)acetamide | 539.4 | 0.02646 | 0.49651 |
| 114 | N-((1S,2R)-3-((((1R,2S,4'S)-6'-(2,2-dimethylpropyl)-2-hydroxy-3',4'-dihydrospiro[cyclobutane-1,2'-pyrano[2,3-b]pyridin]-4'-yl)amino)-1-((4-fluorophenyl)methyl)-2-hydroxypropyl)acetamide | 500.0 | 1.5759 | 0.90893 |
| 115 | N-((1S,2R)-3-((((1S,2R,4'R)-6'-(2,2-dimethylpropyl)-2-hydroxy-3',4'-dihydrospiro[cyclobutane-1,2'-pyrano[2,3-b]pyridin]-4'-yl)amino)-1-((4-fluorophenyl)methyl)-2-hydroxypropyl)acetamide | 500.0 | 6.88019 | 5.4962 |
| 116 | N-((1S,2R)-3-((((1R,2R,4'S)-6'-(2,2-dimethylpropyl)-2-hydroxy-3',4'-dihydrospiro[cyclobutane-1,2'-pyrano[2,3-b]pyridin]-4'-yl)amino)-1-((4-fluorophenyl)methyl)-2-hydroxypropyl)acetamide | 500.0 | 0.11718 | 0.14811 |
| 117 | N-((1S,2R)-3-((((1S,2S,4'S)-6'-(2,2-dimethylpropyl)-2-hydroxy-3',4'-dihydrospiro[cyclobutane-1,2'-pyrano[2,3-b]pyridin]-4'-yl)amino)-1-((4-fluorophenyl)methyl)-2-hydroxypropyl)acetamide | 500.0 | 0.00785 | 0.03362 |
| 118 | N-((1S,2R)-3-((((1S,2R,4'S)-6'-(2,2-dimethylpropyl)-2-hydroxy-3',4'-dihydrospiro[cyclobutane-1,2'-pyrano[2,3-b]pyridin]-4'-yl)amino)-1-((4-fluorophenyl)methyl)-2-hydroxypropyl)acetamide | 500.0 | 0.00911 | 0.028 |
| 119 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-c]pyridin]-4'-yl)amino)-2-hydroxypropyl)-2-(methyloxy)acetamide | 540.2 | 0.20318 | 0.12701 |
| 120 | N-((1S)-1-((1R)-2-(((4'S)-6'-(2,2-dimethylpropyl)-3',4'-dihydrospiro[cyclobutane-1,2'-pyrano[2,3- | 446.3 | 0.74455 | 0.34266 |

TABLE 1-continued

| Ex. No. | Compound Name | Observed MS | BACE1 FRET assay (uM) | HEK cell assay (uM) |
|---|---|---|---|---|
| | c]pyridin]-4'-yl)amino)-1-hydroxyethyl)-3-buten-1-yl)-2-(methyloxy)acetamide | | | |
| 121 | N-((1S,2R)-3-(((4'S)-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)-2-(methyloxy)acetamide | 496.4 | 0.02213 | 0.10212 |
| 122 | N-((1S,2R)-3-(((4'S)-6'-(2,2-dimethylpropyl)-3',4'-dihydrospiro[cyclobutane-1,2'-pyrano[2,3-c]pyridin]-4'-yl)amino)-1-((3-fluorophenyl)methyl)-2-hydroxypropyl)-2-(methyloxy)acetamide | 514.3 | 0.00754 | 0.02305 |
| 123 | N-((1S,2R)-3-(((4'S)-6'-(2,2-dimethylpropyl)-3',4'-dihydrospiro[cyclobutane-1,2'-pyrano[3,2-b]pyridin]-4'-yl)amino)-1-((4-fluorophenyl)methyl)-2-hydroxypropyl)-2-(methyloxy)acetamide | 514.2 | 3.71536 | 3.80719 |
| 124 | N-((1S,2R)-1-(1,3-benzodioxol-5-ylmethyl)-3-(((4'S)-8'-chloro-6'-(2,2-dimethylpropyl)-3',4'-dihydrospiro[cyclobutane-1,2'-pyrano[2,3-c]pyridin]-4'-yl)amino)-2-hydroxypropyl)acetamide | 544.3 | 0.02863 | 0.11446 |
| 125 | N-((1S,2R)-1-(1,3-benzodioxol-5-ylmethyl)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-2-hydroxypropyl)-2-(methyloxy)acetamide | 569.4 | 0.05703 | 0.01327 |
| 126 | N-((1S,2R)-1-(1,3-benzodioxol-5-ylmethyl)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-2-hydroxypropyl)acetamide | 539.4 | 0.04841 | 0.0091 |
| 127 | N-((1S,2R)-1-(1,3-benzodioxol-5-ylmethyl)-3-(((4'S)-8'-chloro-6'-(2,2-dimethylpropyl)-3',4'-dihydrospiro[cyclobutane-1,2'-pyrano[2,3-c]pyridin]-4'-yl)amino)-2-hydroxypropyl)-2-(methyloxy)acetamide | 574.3 | 0.02552 | 0.06784 |
| 128 | N-((1S,2R)-3-(((4'S)-8'-(1-azetidinyl)-6'-(2,2-dimethylpropyl)-3',4'-dihydrospiro[cyclobutane-1,2'-pyrano[2,3-c]pyridin]-4'-yl)amino)-2-hydroxy-1-(phenylmethyl)propyl)acetamide | 521.4 | 0.03316 | 0.016 |
| 129 | N-((1S,2R)-3-(((4'S)-8'-amino-6'-(2,2-dimethylpropyl)-3',4'-dihydrospiro[cyclobutane-1,2'-pyrano[2,3-c]pyridin]-4'-yl)amino)-1-(1,3-benzodioxol-5-ylmethyl)-2-hydroxypropyl)-2-(methyloxy)acetamide | 555.2 | 0.119 | 0.03089 |
| 130 | N-((1S,2R)-1-(1,3-benzodioxol-5-ylmethyl)-3-(((4'S)-6'-(2,2-dimethylpropyl)-8'-(1-pyrrolidinyl)-3',4'-dihydrospiro[cyclobutane-1,2'-pyrano[2,3-c]pyridin]-4'-yl)amino)-2-hydroxypropyl)-2-(methyloxy)acetamide | 609.2 | 0.05413 | 0.05504 |
| 131 | (2R)-N-((1S,2R)-1-(1,3-benzodioxol-5-ylmethyl)-3-(((4'S)-8'-chloro-6'-(2,2-dimethylpropyl)-3',4'-dihydrospiro[cyclobutane-1,2'-pyrano[2,3-c]pyridin]-4'-yl)amino)-2-hydroxypropyl)-2-(methyloxy)propanamide | 588.0 | 0.02679 | 0.37595 |
| 132 | N-((1S,2R)-1-(1,3-benzodioxol-5-ylmethyl)-2-hydroxy-3-(((1s,3R,4'S)-3-methyl-6'-(2-methylpropyl)-3',4'-dihydrospiro[cyclobutane-1,2'-pyrano[2,3-b]pyridin]-4'-yl)amino)propyl)acetamide | 510.0 | 0.02519 | 0.06605 |
| 133 | N-((1S,2R)-1-(1,3-benzodioxol-5-ylmethyl)-2-hydroxy-3-(((1s,3R,4'S)-3-methyl-6'-(2-methylpropyl)-3',4'- | 540.0 | 0.03976 | 0.14283 |

TABLE 1-continued

| Ex. No. | Compound Name | Observed MS | BACE1 FRET assay (uM) | HEK cell assay (uM) |
|---|---|---|---|---|
| | dihydrospiro[cyclobutane-1,2'-pyrano[2,3-b]pyridin]-4'-yl)amino)propyl)-2-(methyloxy)acetamide | | | |
| 134 | (2R)-N-((1S,2R)-1-(1,3-benzodioxol-5-ylmethyl)-2-hydroxy-3-(((1s,3R,4'S)-3-methyl-6'-(2-methylpropyl)-3',4'-dihydrospiro[cyclobutane-1,2'-pyrano[2,3-b]pyridin]-4'-yl)amino)propyl)-2-(methyloxy)propanamide | 554.0 | 0.02719 | 0.1923 |
| 135 | (2R)-N-((1S,2R)-1-(1,3-benzodioxol-5-ylmethyl)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxypropyl)-2-(methyloxy)propanamide | 597.2 | 0.06466 | 0.17531 |
| 136 | (2R)-N-((1S,2R)-1-(1,3-benzodioxol-5-ylmethyl)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-2-hydroxypropyl)-2-(methyloxy)propanamide | 583.4 | 0.04114 | 0.01626 |
| 137 | (2R)-N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-1-((4-fluorophenyl)methyl)-2-hydroxypropyl)-2-(methyloxy)propanamide | 557.4 | 0.082 | 0.05753 |
| 138 | (2R)-N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)(methyl)amino)-1-((4-fluorophenyl)methyl)-2-hydroxypropyl)-2-(methyloxy)propanamide | 571.2 | 0.1777 | 0.16206 |
| 139 | (2R)-N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-1-((3-fluorophenyl)methyl)-2-hydroxypropyl)-2-(methyloxy)propanamide | 557.4 | 0.04204 | 0.00899 |
| 140 | N-((1S,2R)-3-(((4'S)-6'-(2,2-dimethylpropyl)-8'-((2,2,2-trifluoroethyl)oxy)-3',4'-dihydrospiro[cyclobutane-1,2'-pyrano[2,3-c]pyridin]-4'-yl)amino)-1-((3-fluorophenyl)methyl)-2-hydroxypropyl)-2-(methyloxy)acetamide | 612.0 | 0.00775 | 0.11452 |
| 141 | (2R)-N-((1S,2R)-3-(((4'S)-6'-(2,2-dimethylpropyl)-8'-((2,2,2-trifluoroethyl)amino)-3',4'-dihydrospiro[cyclobutane-1,2'-pyrano[2,3-c]pyridin]-4'-yl)amino)-1-((4-fluorophenyl)methyl)-2-hydroxypropyl)-2-(methyloxy)propanamide | 625.2 | 0.31918 | 2.83803 |
| 142 | N-((1S,2R)-1-(1,3-benzodioxol-5-ylmethyl)-3-(((4'S)-6'-(2,2-dimethylpropyl)-8'-((2,2,2-trifluoroethyl)amino)-3',4'-dihydrospiro[cyclobutane-1,2'-pyrano[2,3-c]pyridin]-4'-yl)amino)-2-hydroxypropyl)-2-(methyloxy)acetamide | 637.2 | 0.35042 | 1.94821 |
| 143 | N-((1S,2R)-3-(((4'S)-6'-(2,2-dimethylpropyl)-8'-((2,2,2-trifluoroethyl)amino)-3',4'-dihydrospiro[cyclobutane-1,2'-pyrano[2,3-c]pyridin]-4'-yl)amino)-1-((3-fluorophenyl)methyl)-2-hydroxypropyl)-2-(methyloxy)acetamide | 611.4 | 0.01952 | 0.31407 |
| 144 | N-((1S,2R)-3-(((4'S)-6'-(2,2-dimethylpropyl)-8'-((2,2,2-trifluoroethyl)amino)-3',4'-dihydrospiro[cyclobutane-1,2'-pyrano[2,3-c]pyridin]-4'-yl)amino)-1-((4-fluorophenyl)methyl)-2-hydroxypropyl)acetamide | 581.4 | 0.09436 | 0.63375 |

TABLE 1-continued

| Ex. No. | Compound Name | Observed MS | BACE1 FRET assay (uM) | HEK cell assay (uM) |
|---|---|---|---|---|
| 145 | (2R)-N-((1S,2R)-1-(1,3-benzodioxol-5-ylmethyl)-3-(((4'S)-6'-(2,2-dimethylpropyl)-8'-(methylamino)-3',4'-dihydrospiro[cyclobutane-1,2'-pyrano[2,3-c]pyridin]-4'-yl)(methyl)amino)-2-hydroxypropyl)-2-(methyloxy)propanamide | 597.2 | 0.29755 | 0.77684 |
| 146 | N-((1S,2R)-3-(((4'S)-6'-((1,1-difluoroethyl)oxy)-3',4'-dihydrospiro[cyclobutane-1,2'-pyrano[2,3-b]pyridin]-4'-yl)amino)-1-((4-fluorophenyl)methyl)-2-hydroxypropyl)acetamide | 494.3 | 0.42141 | 1.25253 |
| 147 | N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-1-((4-fluorophenyl)methyl)-2-hydroxypropyl)-2-(methyloxy)acetamide | 543.2 | 0.04953 | 0.02315 |
| 148 | N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-1-((3-fluorophenyl)methyl)-2-hydroxypropyl)-2-(methyloxy)acetamide | 543.2 | 0.03868 | 0.00654 |
| 149 | N-((1S,2R)-3-(((4'S)-6'-(2,2-dimethylpropyl)-8'-((2-(methyloxy)ethyl)amino)-3',4'-dihydrospiro[cyclobutane-1,2'-pyrano[2,3-c]pyridin]-4'-yl)amino)-1-((4-fluorophenyl)methyl)-2-hydroxypropyl)acetamide | 557.2 | 0.04789 | 0.02717 |
| 150 | N-((1S,2R)-3-(((4'S)-6'-(2,2-dimethylpropyl)-8'-((2-(methyloxy)ethyl)amino)-3',4'-dihydrospiro[cyclobutane-1,2'-pyrano[2,3-c]pyridin]-4'-yl)amino)-1-((4-fluorophenyl)methyl)-2-hydroxypropyl)-2-(methyloxy)acetamide | 587.2 | 0.04793 | 0.02261 |
| 151 | N-((1S,2R)-3-(((4'S)-6'-((1,1-difluoroethyl)oxy)-3',4'-dihydrospiro[cyclobutane-1,2'-pyrano[2,3-b]pyridin]-4'-yl)amino)-1-((3-fluorophenyl)methyl)-2-hydroxypropyl)acetamide | 494.4 | 0.02047 | 0.08406 |
| 152 | (2S)-N-((1S,2R)-3-(((4'S)-6'-((1,1-difluoroethyl)oxy)-3',4'-dihydrospiro[cyclobutane-1,2'-pyrano[2,3-b]pyridin]-4'-yl)amino)-1-((3-fluorophenyl)methyl)-2-hydroxypropyl)-5-oxotetrahydro-2-furancarboxamide | 564.4 | 0.01064 | 0.0336 |
| 153 | N-((1S,2R)-3-(((4'S)-6'-(2,2-dimethylpropyl)-8'-methyl-3',4'-dihydrospiro[cyclobutane-1,2'-pyrano[2,3-c]pyridin]-4'-yl)amino)-1-((4-fluorophenyl)methyl)-2-hydroxypropyl)-2-(methyloxy)acetamide | 528.2 | 0.1996 | 0.15319 |
| 154 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)propanamide | 528 | 0.01324 | 0.02805 |
| 155 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)propanamide | 528 | 0.04013 | 0.07595 |
| 156 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-hydroxypropanamide | 514 | 0.0277 | 0.04533 |

TABLE 1-continued

| Ex. No. | Compound Name | Observed MS | BACE1 FRET assay (uM) | HEK cell assay (uM) |
|---|---|---|---|---|
| 157 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-hydroxypropanamide | 514 | 0.01515 | 0.02168 |
| 158 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2,3,3,3-tetrafluoropropanamide | 570 | 0.05043 | 0.24094 |
| 159 | N-((1S,2R)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 520.3 | 0.01915 | 0.03628 |
| 160 | N-((1S,2R)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)acetamide | 550.3 | 0.00884 | 0.03915 |
| 161 | N-((1S,2R)-3-(((4S)-6-(2-cyano-2-methylpropyl)-3,4-dihydrospiro[chromene-2,1'-cyclobutan]-4-yl)amino)-1-((4-fluorophenyl)methyl)-2-hydroxypropyl)acetamide | 494.2 | 0.01125 | 0.01738 |
| 162 | N-((1S,2R)-3-(((4S)-6-(2-cyano-2-methylpropyl)-3,4-dihydrospiro[chromene-2,1'-cyclobutan]-4-yl)amino)-1-((4-fluorophenyl)methyl)-2-hydroxypropyl)-2-(methyloxy)acetamide | 524.3 | 0.04458 | 0.03105 |
| 163 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-(trifluoromethyl)-4-pyridinyl)methyl)propyl)-2-(methyloxy)acetamide | 565.3 | 0.0269 | 0.03586 |
| 164 | N-((1S,2R)-3-(((5'S)-3'-(2,2-dimethylpropyl)-5',8'-dihydro-6'H-spiro[cyclobutane-1,7'-quinolin]-5'-yl)amino)-1-((4-fluorophenyl)methyl)-2-hydroxypropyl)acetamide | 482.3 | 0.06229 | 0.02051 |
| 165 | N-((1S,2R)-3-(((5'S)-3'-(2,2-dimethylpropyl)-8',8'-difluoro-5',8'-dihydro-6'H-spiro[cyclobutane-1,7'-quinolin]-5'-yl)amino)-1-((4-fluorophenyl)methyl)-2-hydroxypropyl)acetamide | 518.3 | 0.10721 | 0.10928 |
| 166 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-((2,2,2-trifluoroethyl)oxy)-4-pyridinyl)methyl)propyl)-2-(methyloxy)acetamide | 595.3 | 0.01084 | 0.00985 |
| 167 | N-((1S,2R)-1-(1,3-benzodioxol-5-ylmethyl)-3-(((5'S)-3'-(2,2-dimethylpropyl)-5',8'-dihydro-6'H-spiro[cyclobutane-1,7'-quinolin]-5'-yl)amino)-2-hydroxypropyl)acetamide | 508.4 | 0.1248 | 0.06837 |
| 168 | N-((1S,2R)-1-(1,3-benzodioxol-5-ylmethyl)-3-(((5'S)-3'-(2,2-dimethylpropyl)-5',8'-dihydro-6'H-spiro[cyclobutane-1,7'-quinolin]-5'-yl)amino)-2-hydroxypropyl)-2-(methyloxy)acetamide | 538.4 | 0.14886 | 0.21117 |
| 169 | N-((1S,2R)-3-(((2R,4S)-6-(2,2-dimethylpropyl)-8-fluoro-3,4,4',5'-tetrahydrospiro[chromene-2,3'-furan]-4-yl)amino)-1-((4-fluorophenyl)methyl)-2- | 517.3 | 0.01961 | 0.04544 |

TABLE 1-continued

| Ex. No. | Compound Name | Observed MS | BACE1 FRET assay (uM) | HEK cell assay (uM) |
|---|---|---|---|---|
| | hydroxypropyl)acetamide N-((1S,2R)-3-(((2S,4S)-6-(2,2-dimethylpropyl)-8-fluoro-3,4,4',5'-tetrahydrospiro[chromene-2,3'-furan]-4-yl)amino)-1-((4-fluorophenyl)methyl)-2-hydroxypropyl)acetamide | | | |
| 170 | N-((1S,2R)-1-(1,3-benzodioxol-5-ylmethyl)-3-(((4S)-6-(2,2-dimethylpropyl)-8-fluoro-3,4-dihydrospiro[chromene-2,1'-cyclobutan]-4-yl)amino)-2-hydroxypropyl)acetamide | 527.3 | 0.01249 | 0.05351 |
| 171 | N-((1S,2R)-3-(((4S)-6-(2-cyano-2-methylpropyl)-8-fluoro-3,4-dihydrospiro[chromene-2,1'-cyclobutan]-4-yl)amino)-1-((4-fluorophenyl)methyl)-2-hydroxypropyl)acetamide | 512.3 | 0.01585 | 0.02819 |
| 172 | N-((1S,2R)-3-(((4S)-6-(2-cyano-2-methylpropyl)-8-fluoro-3,4-dihydrospiro[chromene-2,1'-cyclobutan]-4-yl)amino)-1-((4-fluorophenyl)methyl)-2-hydroxypropyl)-2-(methyloxy)acetamide | 542.3 | 0.0186 | 0.04327 |
| 173 | (2S)-N-((1S,2R)-3-(((4S)-6-(2-cyano-2-methylpropyl)-8-fluoro-3,4-dihydrospiro[chromene-2,1'-cyclobutan]-4-yl)amino)-1-((4-fluorophenyl)methyl)-2-hydroxypropyl)-2-(methyloxy)propanamide | 556.3 | 0.03635 | 0.0546 |
| 174 | N-((1S,2R)-3-(((4S)-6-(2,2-dimethylpropyl)-8-fluoro-3,4-dihydrospiro[chromene-2,1'-cyclobutan]-4-yl)amino)-1-((4-fluorophenyl)methyl)-2-hydroxypropyl)acetamide | 501.3 | 0.0072 | 0.05264 |
| 175 | (2S)-N-((1S,2R)-3-(((4S)-6-(2,2-dimethylpropyl)-8-fluoro-3,4-dihydrospiro[chromene-2,1'-cyclobutan]-4-yl)amino)-1-((4-fluorophenyl)methyl)-2-hydroxypropyl)-2-(methyloxy)propanamide | 545.3 | 0.01725 | 0.22914 |
| 176 | N-((1S,2R)-1-(4-thiazolylmethyl)-3-(((5'S)-3'-(2,2-dimethylpropyl)-5',8'-dihydro-6'H-spiro[cyclobutane-1,7'-quinolin]-5'-yl)amino)-2-hydroxypropyl)-2-(methyloxy)acetamide | 503.3 | 0.01054 | 0.01696 |
| 177 | N-((1S,2R)-1-((3,4-difluorophenyl)methyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)acetamide | 520.3 | 0.00217 | 0.00934 |
| 178 | N-((1S,2R)-1-(1,3-benzodioxol-5-ylmethyl)-3-(((4'S)-6'-(3-fluoro-2,2-dimethylpropyl)-3',4'-dihydrospiro[cyclobutane-1,2'-pyrano[2,3-b]pyridin]-4'-yl)amino)-2-hydroxypropyl)acetamide | 528.3 | 0.00839 | 0.01752 |
| 179 | N-((1S,2R)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)acetamide | 532.3 | 0.00549 | 0.01855 |
| 180 | N-((1S,2R)-3-(((4'S)-6'-(3-fluoro-2,2-dimethylpropyl)-3',4'-dihydrospiro[cyclobutane-1,2'-pyrano[2,3-b]pyridin]-4'-yl)amino)-2-hydroxy-1-(phenylmethyl)propyl)acetamide | 484.3 | 0.00232 | 0.007 |
| 181 | N-((1S,2R)-1-(1,3-benzodioxol-5-ylmethyl)-3-(((4'S)-6'-(3-fluoro-2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 558.3 | 0.01548 | 0.01757 |
| 182 | N-((1S,2R)-1-(1,3-benzodioxol-5-ylmethyl)-3-(((4'S)-6'-((1R)-1-fluoro-2,2- | 528.3 | 0.00701 | 0.01598 |

TABLE 1-continued

| Ex. No. | Compound Name | Observed MS | BACE1 FRET assay (uM) | HEK cell assay (uM) |
|---|---|---|---|---|
| | dimethylpropyl)-3',4'-dihydrospiro[cyclobutane-1,2'-pyrano[2,3-b]pyridin]-4'-yl)amino)-2-hydroxypropyl)acetamide | | | |
| 183 | N-((1S,2R)-1-(1,3-benzodioxol-5-ylmethyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 558.3 | 0.00863 | 0.01782 |
| 184 | N-((1S,2R)-3-(((4'S)-6'-(3-fluoro-2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-2-(methyloxy)acetamide | 514.3 | 0.00246 | 0.00645 |
| 185 | N-((1S,2R)-1-(1,3-benzodioxol-5-ylmethyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)-2-fluoroacetamide | 546.3 | 0.01849 | 0.02644 |
| 186 | (2R)-N-((1S,2R)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)propanamide | 546.3 | 0.00776 | 0.0265 |
| 187 | N-((1S,2R)-1-(1,3-benzodioxol-5-ylmethyl)-3-(((4S)-2-(2,2-dimethylpropyl)-6,6-dimethyl-4,5,6,7-tetrahydro-1-benzothien-4-yl)amino)-2-hydroxypropyl)-2-(methyloxy)acetamide | 531.4 | 0.02015 | 0.06346 |
| 188 | N-((1S,2R)-1-((4-fluorophenyl)methyl)-2-hydroxy-3-(((4'S)-6'-((1R)-1-hydroxy-2,2-dimethylpropyl)-3',4'-dihydrospiro[cyclobutane-1,2'-pyrano[2,3-b]pyridin]-4'-yl)amino)propyl)-2-(methyloxy)acetamide | 530.3 | 0.06116 | 1.65509 |
| 189 | N-((1S,2R)-1-((4-fluorophenyl)methyl)-2-hydroxy-3-(((4'S)-6'-((1S)-1-hydroxy-2,2-dimethylpropyl)-3',4'-dihydrospiro[cyclobutane-1,2'-pyrano[2,3-b]pyridin]-4'-yl)amino)propyl)-2-(methyloxy)acetamide | 530.3 | 0.87987 | 1.0028 |
| 190 | (2R)-N-((1S,2R)-1-(1,3-benzodioxol-5-ylmethyl)-3-(((4'S)-6'-(3-fluoro-2,2-dimethylpropyl)-3',4'-dihydrospiro[cyclobutane-1,2'-pyrano[2,3-b]pyridin]-4'-yl)amino)-2-hydroxypropyl)-2-(methyloxy)propanamide | 572.4 | 0.02384 | 0.04323 |
| 191 | (2R)-N-((1S,2R)-1-((3-fluorophenyl)methyl)-2-hydroxy-3-(((4'S)-6'-(3,3,3-trifluoropropyl)-3',4'-dihydrospiro[cyclobutane-1,2'-pyrano[2,3-b]pyridin]-4'-yl)amino)propyl)-2-(methyloxy)propanamide (2S)-N-((1S,2R)-1-((3-fluorophenyl)methyl)-2-hydroxy-3-(((4'S)-6'-(3,3,3-trifluoropropyl)-3',4'-dihydrospiro[cyclobutane-1,2'-pyrano[2,3-b]pyridin]-4'-yl)amino)propyl)-2-(methyloxy)propanamide | 554.3 | 0.12732 | 0.28135 |
| 192 | (2R)-N-((1S,2R)-1-((4-fluorophenyl)methyl)-2-hydroxy-3-(((4'S)-6'-(3,3,3-trifluoropropyl)-3',4'-dihydrospiro[cyclobutane-1,2'-pyrano[2,3-b]pyridin]-4'-yl)amino)propyl)-2-(methyloxy)propanamide '(2S)-N-((1S,2R)-1-((4-fluorophenyl)methyl)-2-hydroxy-3-(((4'S)-6'-(3,3,3-trifluoropropyl)-3',4'-dihydrospiro[cyclobutane-1,2'-pyrano[2,3-b]pyridin]-4'-yl)amino)propyl)-2-(methyloxy)propanamide | 554.3 | 1.01716 | 2.02629 |

TABLE 1-continued

| Ex. No. | Compound Name | Observed MS | BACE1 FRET assay (uM) | HEK cell assay (uM) |
|---|---|---|---|---|
| 193 | N-((1S,2R)-1-((4-fluorophenyl)methyl)-2-hydroxy-3-(((4'S)-6'-(3,3,3-trifluoropropyl)-3',4'-dihydrospiro[cyclobutane-1,2'-pyrano[2,3-b]pyridin]-4'-yl)amino)propyl)-2-(methyloxy)acetamide | 540.3 | 0.20159 | 0.51799 |
| 194 | (2R)-N-((1S,2R)-1-(1,3-benzodioxol-5-ylmethyl)-2-hydroxy-3-(((4'S)-6'-(3,3,3-trifluoropropyl)-3',4'-dihydrospiro[cyclobutane-1,2'-pyrano[2,3-b]pyridin]-4'-yl)amino)propyl)-2-(methyloxy)propanamide | 580.3 | 1.07076 | 1.52482 |
| 195 | N-((1S,2R)-1-(1,3-benzodioxol-5-ylmethyl)-2-hydroxy-3-(((4'S)-6'-(3,3,3-trifluoropropyl)-3',4'-dihydrospiro[cyclobutane-1,2'-pyrano[2,3-b]pyridin]-4'-yl)amino)propyl)-2-(methyloxy)acetamide | 566.3 | 0.75439 | 0.62097 |
| 196 | N-((1S,2R)-1-(1,3-benzodioxol-5-ylmethyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-(methyloxy)propyl)-2-(methyloxy)acetamide | 572.4 | 2.63943 | 3.9904 |
| 197 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-3-(methyloxy)propanamide | 554.2 | 0.0209 | 0.02185 |
| 198 | N-((1S,2R)-3-(((4'S)-6'-((2S)-3,3-difluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 506 | 0.02896 | 0.03211 |
| 199 | N-((1S,2R)-3-(((4'S)-6'-((2R)-3,3-difluoro-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 506 | 0.04516 | 0.05906 |
| 200 | N-((1S,2R)-3-(((4S)-6-(2-fluoro-2-methylpropyl)-3,4-dihydrospiro[chromene-2,1'-cyclobutan]-4-yl)amino)-1-((4-fluorophenyl)methyl)-2-hydroxypropyl)acetamide | 487.1 | 0.20616 | 0.37547 |
| 201 | N-((1S,2R)-3-(((4S)-6-(2-fluoro-2-methylpropyl)-3,4-dihydrospiro[chromene-2,1'-cyclobutan]-4-yl)amino)-1-((3-fluorophenyl)methyl)-2-hydroxypropyl)acetamide | 467.2 | 0.02011 | 0.07676 |
| 202 | N-((1S,2R)-3-(((4'S)-6'-(cyclopropylmethyl)-3',4'-dihydrospiro[cyclobutane-1,2'-pyrano[2,3-b]pyridin]-4'-yl)amino)-2-hydroxy-1-(phenylmethyl)propyl)acetamide | 450.1 | 0.03417 | 0.06594 |
| 203 | N-((1S,2R)-1-((7-bromo-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 589.2 | 0.00284 | 0.02108 |
| 204 | N-((1S,2R)-1-((7-bromo-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 619.6 | 0.09558 | 0.08245 |
| 205 | N-((1S,2R)-1-(2,3-dihydro-1,4-benzodioxin-6-ylmethyl)-3-(((4'S)-6'-(2,2-dimethylpropyl)-3',4'-dihydrospiro[cyclobutane-1,2'-pyrano[2,3- | 524.2 | 0.02289 | 0.02294 |

TABLE 1-continued

| Ex. No. | Compound Name | Observed MS | BACE1 FRET assay (uM) | HEK cell assay (uM) |
|---|---|---|---|---|
| | b]pyridin]-4'-yl)amino)-2-hydroxypropyl)acetamide | | | |
| 206 | N-((1S,2R)-1-(2,3-dihydro-1,4-benzodioxin-6-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 554.2 | 0.02268 | 0.04249 |
| 207 | N-((1S,2R)-1-((7-chloro-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 544.2 | 0.00663 | 0.01422 |
| 208 | N-((1S,2R)-1-((7-chloro-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 574.2 | 0.00641 | 0.00996 |
| 209 | (2R)-N-((1S,2R)-1-((7-chloro-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)propanamide | 588.3 | 0.01217 | 0.01815 |
| 210 | (2R)-N-((1S,2R)-1-((7-bromo-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)propanamide | 631.6 | 0.16337 | 0.22406 |
| 211 | N-((1S,2R)-1-((7-bromo-1,3-benzodioxol-5-yl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)-2-(methyloxy)acetamide | 623.6 | 0.42345 | 0.31174 |
| 212 | N-((1S,2R)-1-((4-chlorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 530.2 | 0.00215 | 0.0314 |
| 213 | N-((1S,2R)-1-(cyclopropylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 460.3 | 0.05695 | 0.07873 |
| 214 | N-((1S,2R)-1-((3-((difluoromethyl)oxy)-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 580.2 | 0.00877 | 0.00903 |
| 215 | N-((1S,2R)-1-((3-chloro-4-fluorophenyl)methyl)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-2-hydroxypropyl)acetamide | 554.2 | 0.00705 | 0.02642 |
| 216 | N-((1S,2R)-1-((4-chloro-3-(methyloxy)phenyl)methyl)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-2-hydroxypropyl)acetamide | 566.2 | 0.016 | 0.02485 |
| 217 | N-((1S,2R)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide | 520.2 | 0.00292 | 0.00298 |
| 218 | N-((1S,2R)-3-(((4'S)-6'-(3,3-difluoro-2,2-dimethylpropyl)-3',4'-dihydrospiro[cyclobutane-1,2'-pyrano[2,3- | 550.2 | 0.00438 | 0.00525 |

TABLE 1-continued

| Ex. No. | Compound Name | Observed MS | BACE1 FRET assay (uM) | HEK cell assay (uM) |
|---|---|---|---|---|
| | b]pyridin]-4'-yl)amino)-1-((3-fluorophenyl)methyl)-2-hydroxypropyl)-2-(methyloxy)acetamide | | | |
| 219 | (2R)-N-((1S,2R)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)-2-(methyloxy)propanamide | 564.2 | 0.00508 | 0.00599 |
| 220 | N-((1S,2R)-3-(((4S)-6-(2,2-dimethylpropyl)-8-fluoro-3,4-dihydrospiro[chromene-2,1'-cyclobutan]-4-yl)amino)-1-((3-fluorophenyl)methyl)-2-hydroxypropyl)acetamide | 501.2 | 0.00405 | 0.01159 |
| 221 | N-((1S,2R)-3-(((4S)-6-(2,2-dimethylpropyl)-8-fluoro-3,4-dihydrospiro[chromene-2,1'-cyclobutan]-4-yl)amino)-1-((3-fluorophenyl)methyl)-2-hydroxypropyl)-2-(methyloxy)acetamide | 531.2 | 0.01374 | 0.04442 |
| 222 | (2R)-N-((1S,2R)-3-(((4S)-6-(2,2-dimethylpropyl)-8-fluoro-3,4-dihydrospiro[chromene-2,1'-cyclobutan]-4-yl)amino)-1-((3-fluorophenyl)methyl)-2-hydroxypropyl)-2-(methyloxy)propanamide | 545.2 | 0.00445 | 0.01273 |
| 223 | N-((1S,2R)-1-((2-((2,2-difluoroethyl)oxy)-4-pyridinyl)methyl)-3-(((4S)-6-(2,2-dimethylpropyl)-8-fluoro-3,4-dihydrospiro[chromene-2,1'-cyclobutan]-4-yl)amino)-2-hydroxypropyl)acetamide | 564.2 | 0.00969 | 0.02979 |
| 224 | N-((1S,2R)-1-((3,5-difluorophenyl)methyl)-3-(((4S)-6-(2,2-dimethylpropyl)-8-fluoro-3,4-dihydrospiro[chromene-2,1'-cyclobutan]-4-yl)amino)-2-hydroxypropyl)acetamide | 519.2 | 0.00467 | 0.01935 |
| 225 | N-((1S,2R)-1-((4-chloro-3-fluorophenyl)methyl)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-2-hydroxypropyl)acetamide | 554.2 | 0.00922 | 0.02393 |
| 226 | N-((1S,2R)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-1-((3,5-difluorophenyl)methyl)-2-hydroxypropyl)acetamide | 538.2 | 0.00415 | 0.00527 |
| 227 | (2R)-N-((1S,2R)-1-((4-chloro-3-fluorophenyl)methyl)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-2-hydroxypropyl)-2-(methyloxy)propanamide | 598.1 | 0.01509 | 0.03136 |
| 228 | (2R)-N-((1S,2R)-3-(((4'S)-6'-(3,3-difluoro-2,2-dimethylpropyl)-3',4'-dihydrospiro[cyclobutane-1,2'-pyrano[2,3-b]pyridin]-4'-yl)amino)-1-((3,5-difluorophenyl)methyl)-2-hydroxypropyl)-2-(methyloxy)propanamide | 582.2 | 0.00615 | 0.00756 |
| 229 | N-((1S,2R)-3-(((4S)-6-(2,2-dimethylpropyl)-8-fluoro-3,4-dihydrospiro[chromene-2,1'-cyclobutan]-4-yl)amino)-1-((4-fluorophenyl)methyl)-2-hydroxypropyl)-2-(methyloxy)acetamide | 531.2 | 0.00819 | 0.08555 |
| 230 | N-((1S,2R)-3-(((1s,3S,4'S)-6'-(2,2-dimethylpropyl)-3-hydroxy-3',4'-dihydrospiro[cyclobutane-1,2'-pyrano[2,3-b]pyridin]-4'-yl)amino)-1-((4-fluorophenyl)methyl)-2-hydroxypropyl)-2-fluoroacetamide | 518 | 0.00424 | 0.01003 |
| 231 | N-((1S,2R)-3-(((1s,3S,4'S)-6'-(2,2-dimethylpropyl)-3-hydroxy-3',4'-dihydrospiro[cyclobutane-1,2'-pyrano[2,3- | 500.3 | 0.00404 | 0.00304 |

TABLE 1-continued

| Ex. No. | Compound Name | Observed MS | BACE1 FRET assay (uM) | HEK cell assay (uM) |
|---|---|---|---|---|
| | b]pyridin]-4'-yl)amino)-1-((3-fluorophenyl)methyl)-2-hydroxypropyl)acetamide | | | |
| 232 | N-((1S,2R)-3-(((1s,3S,4'S)-6'-(2,2-dimethylpropyl)-3-hydroxy-3',4'-dihydrospiro[cyclobutane-1,2'-pyrano[2,3-b]pyridin]-4'-yl)amino)-1-((3-fluorophenyl)methyl)-2-hydroxypropyl)-2-(methyloxy)acetamide | 530.3 | 0.00234 | 0.00327 |
| 233 | N-((1S,2R)-1-((3,4-difluorophenyl)methyl)-3-(((1s,3S,4'S)-6'-(2,2-dimethylpropyl)-3-hydroxy-3',4'-dihydrospiro[cyclobutane-1,2'-pyrano[2,3-b]pyridin]-4'-yl)amino)-2-hydroxypropyl)-2-(methyloxy)acetamide | 548.3 | 0.00724 | 0.00733 |
| 234 | N-((1S,2R)-1-((4-chlorophenyl)methyl)-3-(((1s,3S,4'S)-6'-(2,2-dimethylpropyl)-3-hydroxy-3',4'-dihydrospiro[cyclobutane-1,2'-pyrano[2,3-b]pyridin]-4'-yl)amino)-2-hydroxypropyl)-2-(methyloxy)acetamide | 546.3 | 0.00404 | 0.01349 |
| 235 | N-((1S,2R)-1-((3-fluorophenyl)methyl)-2-hydroxy-3-(((1s,3S,4'S)-3-hydroxy-3',4'-dihydrospiro[cyclobutane-1,2'-pyrano[2,3-c]pyridin]-4'-yl)amino)propyl)-2-(methyloxy)acetamide | 460 | 0.58114 | 0.45239 |
| 236 | N-((1S,2R)-1-((3-fluorophenyl)methyl)-2-hydroxy-3-(((1r,3R,4'S)-3-hydroxy-3',4'-dihydrospiro[cyclobutane-1,2'-pyrano[2,3-c]pyridin]-4'-yl)amino)propyl)-2-(methyloxy)acetamide | 460 | 5.1754 | 0.27036 |
| 237 | N-((1S,2R)-1-((3-fluorophenyl)methyl)-2-hydroxy-3-(((1r,3R,4'S)-3-hydroxy-3',4'-dihydrospiro[cyclobutane-1,2'-pyrano[2,3-c]pyridin]-4'-yl)amino)propyl)acetamide | 430 | 6.41509 | 2.4457 |
| 238 | N-((1S,2R)-1-(1,3-benzodioxol-5-ylmethyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)-2-(methyloxy)acetamide | 554 | 0.01841 | 0.03274 |
| 239 | (2R)-N-((1S,2R)-1-(1,3-benzodioxol-5-ylmethyl)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-2-hydroxypropyl)-2-(methyloxy)propanamide | 568 | 0.01785 | 0.03459 |
| 240 | N-((1S,2R)-1-(1,3-benzodioxol-5-ylmethyl)-3-(((1s,3S,4'S)-6'-(2,2-dimethylpropyl)-3-fluoro-3',4'-dihydrospiro[cyclobutane-1,2'-pyrano[2,3-b]pyridin]-4'-yl)amino)-2-hydroxypropyl)-2-(methyloxy)acetamide | 558 | 0.087 | 0.10808 |
| 241 | (2R)-N-((1S,2R)-1-(1,3-benzodioxol-5-ylmethyl)-3-(((1s,3S,4'S)-6'-(2,2-dimethylpropyl)-3-fluoro-3',4'-dihydrospiro[cyclobutane-1,2'-pyrano[2,3-b]pyridin]-4'-yl)amino)-2-hydroxypropyl)-2-(methyloxy)propanamide | 572 | 0.00628 | 0.03357 |
| 242 | N-((1S,2R)-1-(1,3-benzodioxol-5-ylmethyl)-2-hydroxy-3-(((1s,3S,4'S)-3-hydroxy-3',4'-dihydrospiro[cyclobutane-1,2'-pyrano[2,3-c]pyridin]-4'-yl)amino)propyl)-2-(methyloxy)acetamide | 486 | 23.885 | 1.16302 |
| 243 | (2R)-N-((1S,2R)-1-(1,3-benzodioxol-5-ylmethyl)-2-hydroxy-3-(((1s,3S,4'S)-3-hydroxy-3',4'-dihydrospiro[cyclobutane-1,2'-pyrano[2,3-c]pyridin]-4'-yl)amino)propyl)-2-(methyloxy)propanamide | 500 | 36.0611 | 3.33333 |
| 244 | N-((1S,2R)-1-(1,3-benzodioxol-5-ylmethyl)-2-hydroxy-3-(((1r,3R,4'S)-3-hydroxy-3',4'-dihydrospiro[cyclobutane-1,2'-pyrano[2,3-c]pyridin]-4'-yl)amino)propyl)-2-(methyloxy)acetamide | 500.3 | 40 | 10 |

TABLE 1-continued

| Ex. No. | Compound Name | Observed MS | BACE1 FRET assay (uM) | HEK cell assay (uM) |
|---|---|---|---|---|
| 245 | (2R)-N-((1S,2R)-1-(1,3-benzodioxol-5-ylmethyl)-2-hydroxy-3-(((1r,3R,4'S)-3-hydroxy-3',4'-dihydrospiro[cyclobutane-1,2'-pyrano[2,3-c]pyridin]-4'-yl)amino)propyl)-2-(methyloxy)propanamide | 500.3 | 40 | 10 |
| 246 | N-((1S,2R)-1-(1,3-benzodioxol-5-ylmethyl)-2-hydroxy-3-(((1s,3S,4'S)-3-hydroxy-6'-(2-methylpropyl)-3',4'-dihydrospiro[cyclobutane-1,2'-pyrano[2,3-b]pyridin]-4'-yl)amino)propyl)-2-(methyloxy)acetamide | 542 | 0.01347 | 0.01643 |
| 247 | N-((1S,2R)-1-(1,3-benzodioxol-5-ylmethyl)-2-hydroxy-3-(((1s,3S,4'S)-3-hydroxy-6'-(2-methylpropyl)-3',4'-dihydrospiro[cyclobutane-1,2'-pyrano[2,3-b]pyridin]-4'-yl)amino)propyl)acetamide | 512 | 0.00677 | 0.01323 |
| 248 | (2R)-N-((1S,2R)-1-(1,3-benzodioxol-5-ylmethyl)-2-hydroxy-3-(((1s,3S,4'S)-3-hydroxy-6'-(2-methylpropyl)-3',4'-dihydrospiro[cyclobutane-1,2'-pyrano[2,3-b]pyridin]-4'-yl)amino)propyl)-2-(methyloxy)propanamide | 556 | 0.0172 | 0.03497 |
| 249 | N-((1S,2R)-1-((4-fluorophenyl)methyl)-2-hydroxy-3-(((1s,3S,4'S)-3-hydroxy-6'-(2-methylpropyl)-3',4'-dihydrospiro[cyclobutane-1,2'-pyrano[2,3-b]pyridin]-4'-yl)amino)propyl)-2-(methyloxy)acetamide | 516.3 | 0.0065 | 0.01127 |
| 250 | (2R)-N-((1S,2R)-1-((4-fluorophenyl)methyl)-2-hydroxy-3-(((1s,3S,4'S)-3-hydroxy-6'-(2-methylpropyl)-3',4'-dihydrospiro[cyclobutane-1,2'-pyrano[2,3-b]pyridin]-4'-yl)amino)propyl)-2-(methyloxy)propanamide | 530 | 0.01281 | 0.02733 |
| 251 | N-((1S,2R)-1-((4-fluorophenyl)methyl)-2-hydroxy-3-(((1s,3S,4'S)-3-hydroxy-6'-(2-methylpropyl)-3',4'-dihydrospiro[cyclobutane-1,2'-pyrano[2,3-b]pyridin]-4'-yl)amino)propyl)acetamide | 486.3 | 0.00634 | 0.01179 |
| 252 | N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-((3-fluorophenyl)methyl)-2-hydroxypropyl)-2-(methyloxy)acetamide | 518.3 | 0.02365 | 0.05381 |
| 253 | (2R)-N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-((3-fluorophenyl)methyl)-2-hydroxypropyl)-2-(methyloxy)propanamide | 532.3 | 0.03616 | 0.07442 |
| 254 | N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide | 488 | 0.17778 | 0.15184 |
| 255 | N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-((4-fluorophenyl)methyl)-2-hydroxypropyl)-2-(methyloxy)acetamide | 518.3 | 0.18995 | 0.21603 |
| 256 | (2R)-N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-((4-fluorophenyl)methyl)-2-hydroxypropyl)-2-(methyloxy)propanamide | 532 | 0.22592 | 0.27359 |
| 257 | methyl (1s,3R,4'S)-4'-(((2R,3S)-3-(acetylamino)-4-(4-fluorophenyl)-2-hydroxybutyl)amino)-6'-(2,2-dimethylpropyl)-3',4'- | 542.6 | 0.27072 | 0.37163 |

TABLE 1-continued

| Ex. No. | Compound Name | Observed MS | BACE1 FRET assay (uM) | HEK cell assay (uM) |
|---|---|---|---|---|
| | dihydrospiro[cyclobutane-1,2'-pyrano[2,3-b]pyridine]-3-carboxylate | | | |
| 258 | methyl (1r,3S,4'S)-4'-(((2R,3S)-3-(acetylamino)-4-(4-fluorophenyl)-2-hydroxybutyl)amino)-6'-(2,2-dimethylpropyl)-3',4'-dihydrospiro[cyclobutane-1,2'-pyrano[2,3-b]pyridine]-3-carboxylate | 542.6 | 0.0389 | 0.09286 |
| 259 | N-((1S,2R)-3-(((1s,3R,4'S)-6'-(2,2-dimethylpropyl)-3-(hydroxymethyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 514.6 | 15.9694 | 3.33333 |
| 260 | N-((1S,2R)-3-(((1s,3R,4'S)-3-cyano-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 509.6 | 0.09867 | 0.07023 |
| 261 | N-((1S,2R)-3-(((1r,3S,4'S)-3-cyano-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)acetamide | 539.6 | 0.03891 | |
| 262 | N-((1S,2R)-3-(((1r,3S,4'S)-3-cyano-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 509.6 | 0.04654 | |
| 263 | (1s,3R,4'S)-4'-(((2R,3S)-3-(acetylamino)-4-(4-fluorophenyl)-2-hydroxybutyl)amino)-6'-(2,2-dimethylpropyl)-3',4'-dihydrospiro[cyclobutane-1,2'-pyrano[2,3-b]pyridine]-3-carboxylic acid | 528.6 | 0.01072 | 0.97615 |
| 264 | N-((1S,2R)-1-(1,3-benzodioxol-5-ylmethyl)-3-(((1r,3R,4'S)-6'-(2,2-dimethylpropyl)-3-hydroxy-3',4'-dihydrospiro[cyclobutane-1,2'-pyrano[2,3-c]pyridin]-4'-yl)amino)-2-hydroxypropyl)acetamide N-((1S,2R)-1-(1,3-benzodioxol-5-ylmethyl)-3-(((1s,3S,4'S)-6'-(2,2-dimethylpropyl)-3-hydroxy-3',4'-dihydrospiro[cyclobutane-1,2'-pyrano[2,3-c]pyridin]-4'-yl)amino)-2-hydroxypropyl)acetamide | 525.4 | 0.04223 | 0.06884 |
| 265 | N-((1S,2R)-1-(1,3-benzodioxol-5-ylmethyl)-2-hydroxy-3-(((4'S)-6'-(trifluoromethyl)-3',4'-dihydrospiro[cyclobutane-1,2'-pyrano[2,3-c]pyridin]-4'-yl)amino)propyl)acetamide | 508.4 | 9.60035 | 0.38833 |
| 266 | N-((1S,2R)-1-(1,3-benzodioxol-5-ylmethyl)-2-hydroxy-3-(((4'S)-6'-(trifluoromethyl)-3',4'-dihydrospiro[cyclobutane-1,2'-pyrano[2,3-c]pyridin]-4'-yl)amino)propyl)-2-(methyloxy)acetamide | 538.4 | 7.47346 | 1.25325 |
| 267 | N-((1S,2R)-1-(1,3-benzodioxol-5-ylmethyl)-3-(((2s,3'S,4S)-6-(2,2-dimethylpropyl)-3'-hydroxy-3,4-dihydrospiro[chromene-2,1'-cyclobutan]-4-yl)amino)-2-hydroxypropyl)-2-(methyloxy)acetamide | 555.6 | 0.03178 | 0.03142 |
| 268 | (2R)-N-((1S,2R)-1-(1,3-benzodioxol-5-ylmethyl)-3-(((2s,3'S,4S)-6-(2,2-dimethylpropyl)-3'-hydroxy-3,4-dihydrospiro[chromene-2,1'-cyclobutan]-4-yl)amino)-2-hydroxypropyl)-2-(methyloxy)propanamide | 569.4 | 0.01872 | 0.01511 |
| 269 | (2R)-N-((1S,2R)-1-(1,3-benzodioxol-5-ylmethyl)-3-(((2r,3'R,4S)-6-(2,2- | 569.4 | 0.24224 | 0.10268 |

TABLE 1-continued

| Ex. No. | Compound Name | Observed MS | BACE1 FRET assay (uM) | HEK cell assay (uM) |
|---|---|---|---|---|
| | dimethylpropyl)-3'-hydroxy-3,4-dihydrospiro[chromene-2,1'-cyclobutan]-4-yl)amino)-2-hydroxypropyl)-2-(methyloxy)propanamide | | | |
| 270 | N-((1S,2R)-3-(((4S)-6-bromo-8-(ethylamino)-3,4-dihydrospiro[chromene-2,1'-cyclobutan]-4-yl)amino)-1-((3-fluorophenyl)methyl)-2-hydroxypropyl)-2-(methyloxy)acetamide | 565.4 | 0.44787 | 0.15734 |
| 271 | N-((1S,2R)-3-(((4'S)-6'-(2,2-difluoropropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)acetamide | 522.2 | 0.03867 | 0.10003 |
| 272 | N-((1S,2R)-3-(((4'S)-6'-(2,2-difluoropropyl)-3',4'-dihydrospiro[cyclobutane-1,2'-pyrano[2,3-b]pyridin]-4'-yl)amino)-2-hydroxy-1-(phenylmethyl)propyl)acetamide | 474.3 | 0.01508 | 0.01471 |
| 273 | N-((1S,2R)-3-(((4'S)-6'-(2,2-difluoropropyl)-3',4'-dihydrospiro[cyclobutane-1,2'-pyrano[2,3-b]pyridin]-4'-yl)amino)-2-hydroxy-1-(phenylmethyl)propyl)-2-(methyloxy)acetamide | 504.3 | 0.01494 | 0.02648 |
| 274 | N-((1S,2R)-3-(((4'S)-6'-(2,2-difluoropropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 492.2 | 0.02969 | 0.07265 |
| 275 | N-((1S,2R)-1-(1,3-benzodioxol-5-ylmethyl)-3-(((4'S)-6'-(2,2-difluoropropyl)-3',4'-dihydrospiro[cyclobutane-1,2'-pyrano[2,3-b]pyridin]-4'-yl)amino)-2-hydroxypropyl)acetamide | 518.2 | 0.08205 | 0.06383 |
| 276 | N-((1S,2R)-1-(1,3-benzodioxol-5-ylmethyl)-3-(((4'S)-6'-(2,2-difluoropropyl)-3',4'-dihydrospiro[cyclobutane-1,2'-pyrano[2,3-b]pyridin]-4'-yl)amino)-2-hydroxypropyl)-2-(methyloxy)acetamide | 548.2 | 0.07601 | 0.08724 |
| 277 | N-((1S,2R)-3-(((4'S)-6'-(2,2-difluoropropyl)-3',4'-dihydrospiro[cyclobutane-1,2'-pyrano[2,3-b]pyridin]-4'-yl)amino)-1-((3-fluorophenyl)methyl)-2-hydroxypropyl)acetamide | 492.3 | 0.00613 | 0.00936 |
| 278 | N-((1S,2R)-3-(((4'S)-6'-(2,2-difluoropropyl)-3',4'-dihydrospiro[cyclobutane-1,2'-pyrano[2,3-b]pyridin]-4'-yl)amino)-1-((3-fluorophenyl)methyl)-2-hydroxypropyl)-2-(methyloxy)acetamide | 522.2 | 0.00676 | 0.00822 |
| 279 | (2R)-N-((1S,2R)-1-(1,3-benzodioxol-5-ylmethyl)-3-(((4'S)-6'-(2,2-difluoropropyl)-3',4'-dihydrospiro[cyclobutane-1,2'-pyrano[2,3-b]pyridin]-4'-yl)amino)-2-hydroxypropyl)-2-(methyloxy)propanamide | 562.3 | 0.12609 | 0.10816 |
| 280 | N-((1S,2R)-3-(((4'S)-6'-(2,2-difluoropropyl)-3,3-difluoro-3',4'-dihydrospiro[cyclobutane-1,2'-pyrano[2,3-b]pyridin]-4'-yl)amino)-1-((3-fluorophenyl)methyl)-2-hydroxypropyl)-2-(methyloxy)acetamide | 558.2 | 0.01895 | 0.17452 |
| 281 | N-((1S,2R)-1-(1,3-benzodioxol-5-ylmethyl)-3-(((4S)-6-(2,2-dimethylpropyl)-3,4-dihydrospiro[chromene-2,1'-cyclobutan]-4-yl)amino)-2-hydroxypropyl)acetamide | 509.3 | 0.01125 | 0.05969 |
| 282 | N-((1S,2R)-1-(1,3-benzodioxol-5-ylmethyl)-3-(((4'S)-6'-(2,2- | 540.3 | 0.00613 | 0.01682 |

TABLE 1-continued

| Ex. No. | Compound Name | Observed MS | BACE1 FRET assay (uM) | HEK cell assay (uM) |
|---|---|---|---|---|
| | dimethylpropyl)-3',4'-dihydrospiro[cyclobutane-1,2'-pyrano[2,3-b]pyridin]-4'-yl)amino)-2-hydroxypropyl)-2-(methyloxy)acetamide | | | |
| 283 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-fluoroacetamide | 528.1 | 0.00751 | 0.019 |
| 284 | N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-((3-fluorophenyl)methyl)-2-hydroxypropyl)-2-(methyloxy)acetamide | 518.1 | 0.00265 | 0.00477 |
| 285 | N-((1S,2R)-1-(1,3-benzodioxol-5-ylmethyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)-2-(methyloxy)acetamide | 544.2 | 0.05699 | 0.07385 |
| 286 | N-((1S,2R)-1-((3,5-difluorophenyl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)-2-(methyloxy)acetamide | 536.2 | 0.00332 | 0.00599 |
| 287 | (2R)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)propanamide | 554.2 | 0.0181 | 0.01414 |
| 288 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2,2,2-trifluoroacetamide | 564.1 | 0.05394 | 0.4552 |
| 289 | methyl ((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)carbamate | 526.2 | 0.07753 | 0.19605 |
| 290 | N-((1S,2R)-1-(1,3-benzodioxol-5-ylmethyl)-3-(((4S)-6-(2,2-dimethylpropyl)-3,4-dihydrospiro[chromene-2,1'-cyclobutan]-4-yl)amino)-2-hydroxypropyl)-2-(methyloxy)acetamide | 539.3 | 0.02313 | 0.05487 |
| 291 | N-((1S,2R)-1-((2,2-difluoro-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 576.2 | 0.04141 | 0.38249 |
| 292 | N-((1S,2R)-1-((2,2-difluoro-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)acetamide | 546.3 | 0.03249 | 0.15887 |
| 293 | N-((1S,2R)-1-((2,2-dimethyl-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 568.3 | 0.48381 | 0.33262 |
| 294 | (2S)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3- | 554.2 | 0.03349 | 0.06655 |

TABLE 1-continued

| Ex. No. | Compound Name | Observed MS | BACE1 FRET assay (uM) | HEK cell assay (uM) |
|---|---|---|---|---|
|  | b]pyridin]-4'-yl)amino)-2-hydroxypropyl)-2-(methyloxy)propanamide |  |  |  |
| 295 | (2R)-N-((1S,2R)-1-((2,2-difluoro-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)propanamide | 590.2 | 0.09688 | 1.33365 |
| 296 | (2S)-N-((1S,2R)-1-((2,2-difluoro-1,3-benzodioxol-5-yl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)propanamide | 590.2 | 0.10198 | 0.57544 |
| 297 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)acetamide N-((1S,2S)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)acetamide | 528.3 | 0.00778 | 0.00853 |
| 298 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)-2-(methyloxy)acetamide N-((1S,2S)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)-2-(methyloxy)acetamide | 558.3 | 0.00917 | 0.0071 |
| 299 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)-2-(methyloxy)propanamide (2R)-N-((1S,2S)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)-2-(methyloxy)propanamide | 572.2 | 0.015 | 0.01219 |
| 300 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)-2-(methyloxy)propanamide (2S)-N-((1S,2S)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)-2-(methyloxy)propanamide | 572.2 | 0.0571 | 0.13704 |
| 301 | (2R)-N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-((3-fluorophenyl)methyl)-2-hydroxypropyl)-2-(methyloxy)propanamide | 532.2 | 0.00781 | 0.00699 |
| 302 | N-((1S,2R)-3-(((4'S)-6'-(2,2-dimethylpropyl)-3',4'-dihydrospiro[cyclobutane-1,2'-pyrano[2,3- | 558.1 | 0.00573 | 0.01152 |

TABLE 1-continued

| Ex. No. | Compound Name | Observed MS | BACE1 FRET assay (uM) | HEK cell assay (uM) |
|---|---|---|---|---|
| | b]pyridin]-4'-yl)amino)-1-((7-fluoro-1,3-benzodioxol-5-yl)methyl)-2-hydroxypropyl)-2-(methyloxy)acetamide | | | |
| 303 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)-2-(methyloxy)propanamide | 572.2 | 0.00901 | 0.02137 |
| 304 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)-2-(methyloxy)propanamide | 572.2 | 0.0376 | 0.08825 |
| 305 | N-((1S,2S)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)acetamide | 528.3 | 0.03789 | 0.05795 |
| 306 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((7-fluoro-1,3-benzodioxol-5-yl)methyl)-2-hydroxypropyl)acetamide | 528.3 | 0.00428 | 0.00747 |
| 307 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-oxopropanamide | 537.7 | 0.03131 | 0.06832 |
| 308 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-3-oxobutanamide | 551.8 | 0.02438 | 0.02091 |
| 309 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-chloroacetamide | 544.2 | 0.02056 | 0.03996 |
| 310 | N-((1S,2R)-1-((4-fluorophenyl)methyl)-2-hydroxy-3-(((4'S)-6'-((1-(trifluoromethyl)cyclopropyl)methyl)-3',4'-dihydrospiro[cyclobutane-1,2'-pyrano[2,3-b]pyridin]-4'-yl)amino)propyl)acetamide | 536.3 | 0.05051 | 0.16554 |
| 311 | N-((1S,2R)-1-((4-fluorophenyl)methyl)-2-hydroxy-3-(((4'S)-6'-((1-(trifluoromethyl)cyclopropyl)methyl)-3',4'-dihydrospiro[cyclobutane-1,2'-pyrano[2,3-b]pyridin]-4'-yl)amino)propyl)-2-(methyloxy)acetamide | 566.3 | 0.05155 | 0.30733 |
| 312 | N-((1S,2R)-1-(1,3-benzodioxol-5-ylmethyl)-2-hydroxy-3-(((4'S)-6'-((1-(trifluoromethyl)cyclopropyl)methyl)-3',4'-dihydrospiro[cyclobutane-1,2'-pyrano[2,3-b]pyridin]-4'-yl)amino)propyl)acetamide | 562.3 | 0.06168 | 0.19674 |
| 313 | N-((1S,2R)-1-(1,3-benzodioxol-5-ylmethyl)-2-hydroxy-3-(((4'S)-6'-((1-(trifluoromethyl)cyclopropyl)methyl)-3',4'-dihydrospiro[cyclobutane-1,2'-pyrano[2,3-b]pyridin]-4'-yl)amino)propyl)-2-(methyloxy)acetamide | 592.3 | 0.15114 | 0.32669 |
| 314 | N-((1S,2R)-1-((3-fluorophenyl)methyl)-2-hydroxy-3-(((4'S)-6'-((2S)-3,3,3-trifluoro-2-methylpropyl)-3',4'- | 524.3 | 0.00419 | 0.0113 |

TABLE 1-continued

| Ex. No. | Compound Name | Observed MS | BACE1 FRET assay (uM) | HEK cell assay (uM) |
|---|---|---|---|---|
| | dihydrospiro[cyclobutane-1,2'-pyrano[2,3-b]pyridin]-4'-yl)amino)propyl)acetamide | | | |
| 315 | N-((1S,2R)-1-((3-fluorophenyl)methyl)-2-hydroxy-3-(((4'S)-6'-((2R)-3,3,3-trifluoro-2-methylpropyl)-3',4'-dihydrospiro[cyclobutane-1,2'-pyrano[2,3-b]pyridin]-4'-yl)amino)propyl)acetamide | 524.3 | 0.00611 | 0.00943 |
| 316 | N-((1S,2R)-2-hydroxy-1-(phenylmethyl)-3-(((4'S)-6'-((2S)-3,3,3-trifluoro-2-methylpropyl)-3',4'-dihydrospiro[cyclobutane-1,2'-pyrano[2,3-b]pyridin]-4'-yl)amino)propyl)acetamide | 506.3 | 0.01363 | 0.04971 |
| 317 | N-((1S,2R)-2-hydroxy-1-(phenylmethyl)-3-(((4'S)-6'-((2R)-3,3,3-trifluoro-2-methylpropyl)-3',4'-dihydrospiro[cyclobutane-1,2'-pyrano[2,3-b]pyridin]-4'-yl)amino)propyl)acetamide | 506.3 | 0.01969 | 0.02779 |
| 318 | N-((1S,2R)-2-hydroxy-1-(phenylmethyl)-3-(((4'S)-6'-((1-(trifluoromethyl)cyclopropyl)methyl)-3',4'-dihydrospiro[cyclobutane-1,2'-pyrano[2,3-b]pyridin]-4'-yl)amino)propyl)acetamide | 518.3 | 0.03468 | 0.08501 |
| 319 | N-((1S,2R)-2-hydroxy-1-(phenylmethyl)-3-(((4'S)-6'-((1-(trifluoromethyl)cyclopropyl)methyl)-3',4'-dihydrospiro[cyclobutane-1,2'-pyrano[2,3-b]pyridin]-4'-yl)amino)propyl)-2-(methyloxy)acetamide | 548.3 | 0.05579 | 0.30864 |
| 320 | N-((1S,2R)-1-(1,3-benzodioxol-5-ylmethyl)-2-hydroxy-3-(((4'S)-6'-((2S)-3,3,3-trifluoro-2-methylpropyl)-3',4'-dihydrospiro[cyclobutane-1,2'-pyrano[2,3-b]pyridin]-4'-yl)amino)propyl)acetamide | 550.3 | 0.15511 | 0.12046 |
| 321 | N-((1S,2R)-1-(1,3-benzodioxol-5-ylmethyl)-2-hydroxy-3-(((4'S)-6'-((2R)-3,3,3-trifluoro-2-methylpropyl)-3',4'-dihydrospiro[cyclobutane-1,2'-pyrano[2,3-b]pyridin]-4'-yl)amino)propyl)acetamide | 550.3 | 0.1339 | 0.06456 |
| 322 | N-((1S,2R)-1-((3-fluorophenyl)methyl)-2-hydroxy-3-(((4'S)-6'-((1R,2S)-1,3,3,3-tetrafluoro-2-methylpropyl)-3',4'-dihydrospiro[cyclobutane-1,2'-pyrano[2,3-b]pyridin]-4'-yl)amino)propyl)acetamide | 542.3 | 0.01089 | 0.03989 |
| 323 | N-((1S,2R)-1-((3-fluorophenyl)methyl)-2-hydroxy-3-(((4'S)-6'-((1S,2S)-1,3,3,3-tetrafluoro-2-methylpropyl)-3',4'-dihydrospiro[cyclobutane-1,2'-pyrano[2,3-b]pyridin]-4'-yl)amino)propyl)acetamide | 542.3 | 0.36519 | |
| 324 | N-((1S,2R)-1-((3-fluorophenyl)methyl)-2-hydroxy-3-(((4'S)-6'-((1R,2R)-1,3,3,3-tetrafluoro-2-methylpropyl)-3',4'-dihydrospiro[cyclobutane-1,2'-pyrano[2,3-b]pyridin]-4'-yl)amino)propyl)acetamide N-((1S,2R)-1-((3-fluorophenyl)methyl)-2-hydroxy-3-(((4'S)-6'-((1S,2R)-1,3,3,3-tetrafluoro-2-methylpropyl)-3',4'-dihydrospiro[cyclobutane-1,2'-pyrano[2,3-b]pyridin]-4'-yl)amino)propyl)acetamide | 542.3 | 0.01373 | 0.06325 |
| 325 | N-((1S,2R)-1-((3-fluorophenyl)methyl)-2-hydroxy-3-(((4'S)-6'-((2S)-3,3,3-trifluoro-2-methylpropyl)-3',4'-dihydrospiro[cyclobutane-1,2'-pyrano[2,3-b]pyridin]-4'-yl)amino)propyl)-2-(methyloxy)acetamide | 554.3 | 0.00371 | 0.01366 |
| 326 | N-((1S,2R)-1-((3-fluorophenyl)methyl)-2-hydroxy-3-(((4'S)-6'-((2R)-3,3,3-trifluoro-2-methylpropyl)-3',4'-dihydrospiro[cyclobutane-1,2'-pyrano[2,3-b]pyridin]-4'-yl)amino)propyl)-2-(methyloxy)acetamide | 554.3 | 0.00777 | 0.02709 |
| 327 | N-((1S,2R)-1-((3-fluorophenyl)methyl)-2-hydroxy-3-(((4'S)-6'-((1-(trifluoromethyl)cyclopropyl)methyl)-3',4'-dihydrospiro[cyclobutane-1,2'- | 566.3 | 0.00985 | 0.06044 |

TABLE 1-continued

| Ex. No. | Compound Name | Observed MS | BACE1 FRET assay (uM) | HEK cell assay (uM) |
|---|---|---|---|---|
| | pyrano[2,3-b]pyridin]-4'-yl)amino)propyl)-2-(methyloxy)acetamide | | | |
| 328 | N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(phenylmethyl)propyl)-2-(methyloxy)acetamide | 482.3 | 0.00919 | 0.02298 |
| 329 | N-((1S,2R)-1-((3-fluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-(methyloxy)acetamide | 500.3 | 0.00326 | 0.00601 |
| 330 | (2R)-N-((1S,2R)-1-(1,3-benzodioxol-5-ylmethyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)-2-(methyloxy)propanamide | 572.4 | 0.02213 | 0.04392 |
| 331 | (2S)-N-((1S,2R)-1-(1,3-benzodioxol-5-ylmethyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)-2-(methyloxy)propanamide | 572.4 | 0.05146 | 0.04463 |
| 332 | N-((1S,2R)-1-((4-fluorophenyl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-(methyloxy)acetamide | 500.3 | 0.01087 | 0.01894 |
| 333 | (2R)-N-((1S,2R)-1-((4-fluorophenyl)methyl-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-(methyloxy)propanamide | 514.3 | 0.02895 | 0.04792 |
| 334 | N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-(methyloxy)acetamide | 526.3 | 0.04803 | 0.06717 |
| 335 | (2R)-N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-(methyloxy)propanamide | 540.3 | 0.03827 | 0.07651 |
| 336 | (2R)-N-((1S,2R)-1-(1,3-benzodioxol-5-ylmethyl)-3-(((4'S)-7'-fluoro-6'-(2-methylpropyl)-3',4'-dihydrospiro[cyclobutane-1,2'-pyrano[2,3-b]pyridin]-4'-yl)amino)-2-hydroxypropyl)-2-(methyloxy)propanamide | 558.3 | 0.13482 | 0.40409 |
| 337 | N-((1S,2R)-1-(1,3-benzodioxol-5-ylmethyl)-3-(((4'S)-7'-fluoro-6'-(2-methylpropyl)-3',4'-dihydrospiro[cyclobutane-1,2'-pyrano[2,3-b]pyridin]-4'-yl)amino)-2-hydroxypropyl)-2-(methyloxy)acetamide | 544.3 | 0.12042 | 0.53058 |
| 338 | N-((1S,2R)-1-(1,3-benzodioxol-5-ylmethyl)-3-(((4'S)-7'-fluoro-6'-(2-methylpropyl)-3',4'-dihydrospiro[cyclobutane-1,2'-pyrano[2,3-b]pyridin]-4'-yl)amino)-2-hydroxypropyl)acetamide | 514.3 | 0.10901 | 0.25233 |
| 339 | N-((1S,2R)-1-(1,3-benzodioxol-5-ylmethyl)-2-hydroxy-3-(((4'S)-6'-((2S)-3,3,3-trifluoro-2-methylpropyl)-3',4'-dihydrospiro[cyclobutane-1,2'-pyrano[2,3-b]pyridin]-4'-yl)amino)propyl)-2-(methyloxy)acetamide | 580.3 | 0.0437 | 0.12558 |
| 340 | (2R)-N-((1S,2R)-1-(1,3-benzodioxol-5-ylmethyl)-2-hydroxy-3-(((4'S)-6'-((2S)-3,3,3-trifluoro-2-methylpropyl)-3',4'- | 594.3 | 0.14791 | 0.09058 |

TABLE 1-continued

| Ex. No. | Compound Name | Observed MS | BACE1 FRET assay (uM) | HEK cell assay (uM) |
|---|---|---|---|---|
| | dihydrospiro[cyclobutane-1,2'-pyrano[2,3-b]pyridin]-4'-yl)amino)propyl)-2-(methyloxy)propanamide | | | |
| 341 | N-((1S,2R)-1-(1,3-benzodioxol-5-ylmethyl)-2-hydroxy-3-(((4'S)-6'-((2R)-3,3,3-trifluoro-2-methylpropyl)-3',4'-dihydrospiro[cyclobutane-1,2'-pyrano[2,3-b]pyridin]-4'-yl)amino)propyl)-2-(methyloxy)acetamide | 580.3 | 0.0595 | 0.1378 |
| 342 | (2R)-N-((1S,2R)-1-(1,3-benzodioxol-5-ylmethyl)-2-hydroxy-3-(((4'S)-6'-((2R)-3,3,3-trifluoro-2-methylpropyl)-3',4'-dihydrospiro[cyclobutane-1,2'-pyrano[2,3-b]pyridin]-4'-yl)amino)propyl)-2-(methyloxy)propanamide | 594.3 | 0.1754 | 0.34293 |
| 343 | (2R)-N-((1S,2R)-1-((7-fluoro-1,3-benzodioxol-5-yl)methyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-(methyloxy)propanamide | 558.3 | 0.03441 | 0.04171 |
| 344 | (2R)-N-((1S,2R)-1-((3-fluorophenyl)methyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)-2-(methyloxy)propanamide | 540.3 | 0.00894 | 0.0442 |
| 345 | (2R)-N-((1S,2R)-1-((3-cyanophenyl)methyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)-2-(methyloxy)propanamide | 547.3 | 0.02656 | 0.06089 |
| 346 | (2R)-N-((1S,2R)-1-((3,5-difluorophenyl)methyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)-2-(methyloxy)propanamide | 558.3 | 0.01019 | 0.0471 |
| 347 | N-((1S,2R)-1-((3-cyanophenyl)methyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)-2-(methyloxy)acetamide | 533.3 | 0.01036 | 0.01923 |
| 348 | N-((1S,2R)-1-((3,5-difluorophenyl)methyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)-2-(methyloxy)acetamide | 544.3 | 0.00688 | 0.01817 |
| 349 | N-((1S,2R)-1-((3,5-difluorophenyl)methyl)-2-hydroxy-3-(((4'S)-6'-((1R)-2,2,2-trifluoro-1-hydroxyethyl)-3',4'-dihydrospiro[cyclobutane-1,2'-pyrano[2,3-b]pyridin]-4'-yl)amino)propyl)-2-(methyloxy)acetamide N-((1S,2R)-1-((3,5-difluorophenyl)methyl)-2-hydroxy-3-(((4'S)-6'-((1S)-2,2,2-trifluoro-1-hydroxyethyl)-3',4'-dihydrospiro[cyclobutane-1,2'-pyrano[2,3-b]pyridin]-4'-yl)amino)propyl)-2-(methyloxy)acetamide | 560.3 | 0.16608 | 0.1393 |
| 350 | N-((1S,2R)-1-((3-fluorophenyl)methyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)-2-(methyloxy)acetamide | 526.3 | 0.00909 | 0.02453 |
| 351 | N-((1S,2R)-1-((3-chloro-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 548 | 0.00275 | 0.01233 |

TABLE 1-continued

| Ex. No. | Compound Name | Observed MS | BACE1 FRET assay (uM) | HEK cell assay (uM) |
|---|---|---|---|---|
| 352 | N-((1S,2R)-1-((3-bromo-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(methyloxy)acetamide | 592/594 | 0.00371 | 0.0176 |
| 353 | N-((1S,2R)-1-((3-bromo-4-fluorophenyl)methyl)-3-(((4'S)-6'-((1,1-dimethylethyl)oxy)-3',4'-dihydrospiro[cyclobutane-1,2'-pyrano[2,3-b]pyridin]-4'-yl)amino)-2-hydroxypropyl)acetamide | 564/566 | 0.12045 | 0.42392 |
| 354 | N-((1S,2R)-1-((3-bromo-4-fluorophenyl)methyl)-3-(((4'S)-6'-(2,2-dimethylpropyl)-3',4'-dihydrospiro[cyclobutane-1,2'-pyrano[2,3-b]pyridin]-4'-yl)(methyl)amino)-2-hydroxypropyl)acetamide | 576/578 | 4.77544 | 3.48843 |
| 355 | N-((1S,2R)-3-((6'-(2,2-dimethylpropyl)-3'-fluoro-3',4'-dihydrospiro[cyclobutane-1,2'-pyrano[2,3-b]pyridin]-4'-yl)amino)-1-((4-fluorophenyl)methyl)-2-hydroxypropyl)acetamide | 502.2 | 0.11726 | 0.11347 |
| 356 | N-((1S,2R)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxy-1-(phenylmethyl)propyl)-2-(methyloxy)acetamide | 514 | 0.00317 | 0.00646 |
| 357 | N-((1S,2R)-3-(((3'S,4'R)-6'-(2,2-dimethylpropyl)-3'-fluoro-3',4'-dihydrospiro[cyclobutane-1,2'-pyrano[2,3-b]pyridin]-4'-yl)amino)-1-((4-fluorophenyl)methyl)-2-hydroxypropyl)acetamide | 502.3 | 13.2666 | 10 |
| 358 | N-((1S,2R)-3-(((3'R,4'R)-6'-(2,2-dimethylpropyl)-3'-fluoro-3',4'-dihydrospiro[cyclobutane-1,2'-pyrano[2,3-b]pyridin]-4'-yl)amino)-1-((4-fluorophenyl)methyl)-2-hydroxypropyl)acetamide | 502.3 | 0.02239 | 0.35305 |
| 359 | methyl ((1S,2R)-1-(1,3-benzodioxol-5-ylmethyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-hydroxypropyl)carbamate | 544.3 | 0.19857 | 0.2082 |
| 360 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)-2-(methyloxy)propanamide | 528.4 | 0.00311 | 0.00482 |
| 361 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)-2-(methyloxy)propanamide | 528.4 | 0.00658 | 0.00923 |
| 362 | N-((1S,2R)-1-(1,3-benzodioxol-5-ylmethyl)-2-hydroxy-3-(((4'S)-6'-(3,3,3-trifluoro-2,2-dimethylpropyl)-3',4'-dihydrospiro[cyclobutane-1,2'-pyrano[2,3-b]pyridin]-4'-yl)amino)propyl)-2-(methyloxy)acetamide | 594.3 | 0.06014 | 0.12297 |
| 363 | (2R)-N-((1S,2R)-1-(1,3-benzodioxol-5-ylmethyl)-2-hydroxy-3-(((4'S)-6'-(3,3,3-trifluoro-2,2-dimethylpropyl)-3',4'-dihydrospiro[cyclobutane-1,2'-pyrano[2,3-b]pyridin]-4'-yl)amino)propyl)-2-(methyloxy)propanamide | 608.3 | 0.04901 | 0.1597 |

The following compounds in Tables 2 and 3 are additional representative examples of Formulas I-IV provided by the present invention.

TABLE 2

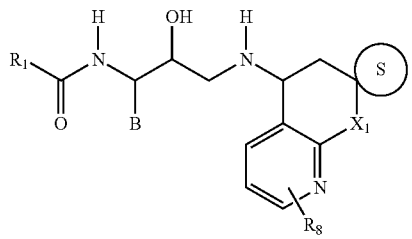

| Ex. No. | R¹ | B | R⁸ | X¹ | S |
|---|---|---|---|---|---|
| 364 | CH₃—O—CH₂— | benzyl-O— | neopentyl | NH | cyclobutyl |
| 365 | CH₃—S—CH₂— | benzyl-S— | isopropyl | S | cyclobutyl |
| 366 | CH₃—NH—CH₂— | benzyl-NH— | hydroxypropyl | O | cyclobutyl |
| 367 | CH₃—N(CH₃)—CH₂— | benzyl-O— | ethyl | NH | cyclopentyl |
| 368 | CH₃CH₂—O—CH₂— | benzyl-S— | butyl | S | cyclopentyl |
| 369 | CH₃—O—CH₂CH₂— | benzyl-NH— | pentyl | O | cyclopentyl |
| 370 | CH₃—O—CH(CF₃)— | 3,5-dioxolylPh—CH₂— | Cyclopropylmethyl- | SO₂ | cyclopropyl |
| 371 | CH₂(CF₃)—O—CH₂— | 3,5-difluoroPh—CH₂— | neopentyl | N—Me | cyclopropyl |
| 372 | CH₃—S—CH₂— | 3,5-dimethylPh—CH₂— | isopropyl | S | cyclopropyl |
| 373 | CH₃CH₂—S—CH₂— | 3,5-dihydroxyPh—CH₂— | hydroxypropyl | O | cyclohexyl |
| 374 | CH₃CH₂—NH—CH₂— | 3,5-dioxolylPh—CH₂— | pentyl | SO₂ | cyclohexyl |
| 375 | (CH₃)₂NCH₂—O—CH₂— | 3,5-difluoroPh—CH₂— | Cyclopropylmethyl- | N—Et | cyclohexyl |
| 376 | CH₃—O—CH₂— | 3,5-dioxolylPh—CH₂— | neopentyl | NH | cyclobutyl |
| 377 | CH₃—S—CH₂— | 3,5-difluoroPh—CH₂— | isopropyl | S | cyclopentyl |
| 378 | CH₃—NH—CH₂— | 3,5-dimethylPh—CH₂— | hydroxypropyl | O | cyclopentyl |
| 379 | CH₃—N(CH₃)—CH₂— | 3,5-dihydroxyPh—CH₂— | ethyl | SO₂ | cyclopentyl |
| 380 | CH₃CH₂—O—CH₂— | 3,5-dioxolylPh—CH₂— | butyl | N—Me | cyclopropyl |
| 381 | CH₃—O—CH₂CH₂— | 3,5-difluoroPh—CH₂— | pentyl | S | cyclopropyl |
| 382 | CH₃—O—CH(CF₃)— | 3,5-dioxolylPh—CH₂— | Cyclopropylmethyl- | O | cyclopropyl |

TABLE 3

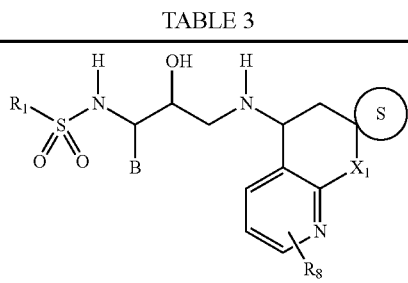

| Ex. No. | R¹ | B | R⁸ | X¹ | S |
|---|---|---|---|---|---|
| 384 | CH₃—O—CH₂— | benzyl-O— | neopentyl | NH | |
| 385 | CH₃—S—CH₂— | benzyl-S— | isopropyl | S | cyclobutyl |
| 386 | CH₃—NH—CH₂— | benzyl-NH— | hydroxypropyl | O | cyclobutyl |
| 387 | CH₃—N(CH₃)—CH₂— | benzyl-O— | ethyl | NH | cyclobutyl |
| 388 | CH₃CH₂—O—CH₃— | benzyl-S— | butyl | S | cyclopentyl |
| 389 | CH₃—O—CH₂CH₂— | benzyl-NH— | pentyl | O | cyclopentyl |
| 390 | CH₃—O—CH(CF₃)— | 3,5-dioxolylPh—CH₂— | Cyclopropylmethyl- | SO₂ | cyclopentyl |
| 391 | CH₂(CF₃)—O—CH₂— | 3,5-difluoroPh—CH₂— | neopentyl | N—Me | cyclopropyl |
| 392 | CH₃—S—CH₂— | 3,5-dimethylPh—CH₂— | isopropyl | S | cyclopropyl |
| 393 | CH₃CH₂—S—CH₂— | 3,5-dihydroxyPh—CH₂— | hydroxypropyl | O | cyclopropyl |
| 394 | CH₃CH₂—NH—CH₂— | 3,5-dioxolylPh—CH₂— | pentyl | SO₂ | cyclohexyl |
| 395 | (CH₃)₂NCH₂—O—CH₂— | 3,5-difluoroPh—CH₂— | Cyclopropylmethyl- | N—Et | cyclohexyl |
| 396 | CH₃—O—CH₂— | 3,5-dioxolylPh—CH₂— | neopentyl | NH | cyclohexyl |
| 397 | CH₃—S—CH₂— | 3,5-difluoroPh—CH₂— | isopropyl | S | cyclobutyl |
| 398 | CH₃—NH—CH₂— | 3,5-dimethylPh—CH₂— | hydroxypropyl | O | cyclopentyl |
| 399 | CH₃—N(CH₃)—CH₂— | 3,5-dihydroxyPh—CH₂— | ethyl | SO₂ | cyclopentyl |
| 400 | CH₃CH₂—O—CH₂— | 3,5-dioxolylPh—CH₂— | butyl | N—Me | cyclopentyl |
| 401 | CH₃—O—CH₂CH₂— | 3,5-difluoroPh—CH₂— | pentyl | S | cyclopropyl |
| 402 | CH₃—O—CH(CF₃)— | 3,5-dioxolylPh—CH₂— | Cyclopropylmethyl- | O | cyclopropyl |
| 403 | CH₂(CF₃)—O—CH₂— | 4-CH₃-phenyl | neopentyl | NH | cyclopropyl |

TABLE 3-continued

| Ex. No. | R¹ | B | R⁸ | X¹ | S |
|---|---|---|---|---|---|
| 404 | CH₃—S—CH₂— | phenyl | isopropyl | S | cyclohexyl |
| 405 | CH₃—S—CH₂— | phenyl | isopropyl | S | cyclobutyl |

The following examples provide a further understanding and appreciation of compounds of the present invention.

Example 406

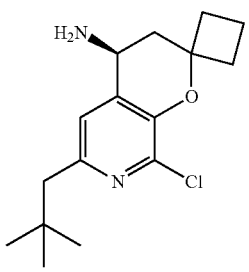 [SMILES: CC(C)(C)Cc1cc2c(c(Cl)n1)OC1(CCC1)C[C@@H]2N]

Synthesis of (S)-8-chloro-2,2-spirocyclobutyl-6-neopentyl-3,4-dihydro-2H-pyrano[2,3-c]pyridin-4-amine

Step 1: 2-bromo-5-(methoxymethoxy)pyridine

To a solution of 6-bromopyridin-3-ol (25 g, 144 mmol) in DMF (300 mL) at 0° C. under $N_2$ is added portionwise NaH (5.7 g, 144 mmol) over 5 min. The reaction was stirred 1 h, then chloro(methoxy)methane (12 g, 144 mmol) was added and the reaction stirred an additional 1 h at 0° C. Saturated sodium bicarbonate (500 mL) was added slowly and the suspension stirred 30 min and warmed to rt. The solution was extracted with EtOAc (3×400 mL), the combined organic layers washed with $H_2O$ (500 mL), saturated NaCl (500 mL), dried ($Na_2SO_4$), and concentrated in vacuo to give the title compound as a brown oil.

Step 2: 5-(methoxymethoxy)-2-neopentylpyridine

To a solution of 2-bromo-5-(methoxymethoxy)pyridine (30.5 g, 140 mmol) in THF (5 mL) at 0° C. under $N_2$ is added dichloro-((bis-diphenylphosphino)ferrocenyl)-palladium (11)(4.88 g, 5.5 mmol) followed by dropwise addition of neopentylmagnesium chloride (155 mL, 155 mmol) over 2 min. After addition, the cooling bath was removed and the reaction stirred 3 h at rt. The reaction was cooled to 0° C. and saturated $NH_4Cl$ (500 mL) was added, and the aqueous layers extracted with EtOAc (3×200 mL). The combined organic layers were washed with saturated NaCl, dried ($Na_2SO_4$) and concentrated to give a red oil. Purification by vacuum filtration through a silica plug (9×7 cm, dry load, 10-20%% EtOAc/Hexanes) gives 5-(methoxymethoxy)-2-neopentylpyridine as a light yellow oil.

Step 3: 1-(5-(methoxymethoxy)-2-neopentylpyridin-4-yl)ethanol

To a solution of 5-(methoxymethoxy)-2-neopentylpyridine (16.5 g, 79 mmol) and in THF (200 mL)-78° C. is added tert-butyllithium (46 ml, 79 mmol) (1.7 M in pentane) over 2 min via cannula. The reaction was stirred at -78° C. 30 min, and acetaldehyde (11 ml, 197 mmol) was added. The reaction was stirred at -78° C. 10 min, then the reaction was warmed to rt and stirred 3 h. The reaction was quenched by addition of saturated aqueous $NH_4Cl$ (400 mL), extracted with EtOAc (3×200 mL), the combined organic layers washed with saturated NaCl (10 mL), dried ($Na_2SO_4$), and concentrated to give a orange oil, which was purified by chromatography on an ISCO (330 g $SiO_2$, 10%-50% EtOAc/Hexane) gives 1-(5-(methoxymethoxy)-2-neopentylpyridin-4-yl)ethanol as a clear, light yellow oil.

Step 4: 1-(5-(methoxymethoxy)-2-neopentylpyridin-4-yl)ethanone

To a solution of 1-(5-(methoxymethoxy)-2-neopentylpyridin-4-yl)ethanol (24.4 g, 96.3 mmol) and sodium bicarbonate (32.4 g, 385 mmol) in $CHCl_3$ (500 mL) at 0° C. was added Dess-Martin Periodinane (53.1 g, 125 mmol). The reaction was stirred 5 h, quenched with saturated aqueous $Na_2SO_3$ (300 mL), extracted with $CH_2Cl_2$ (3×250 mL), the combined organic layers washed with saturated NaCl (300 mL), dried ($Na_2SO_4$), and concentrated to give a yellow oil. Purification by ISCO (330 g $SiO_2$, 20% EtOAc/Hexane) gives 1-(5-(methoxymethoxy)-2-neopentylpyridin-4-yl)ethanone as a clear, colorless oil.

Step 5: 1-(5-hydroxy-2-neopentylpyridin-4-yl)ethanone

A solution of 1-(5-(methoxymethoxy)-2-neopentylpyridin-4-yl)ethanone (21.6 g, 86 mmol) in (2:1:1) 5 M HCl:i-PrOH:THF (800 mL) was stirred 4 h at rt. The mixture was concentrated to remove the THF and i-PrOH. The resulting solution consisting of the product in aqueous HCl was quenched by slow addition to a solution of saturated aqueous $NaHCO_3$ (500 mL) containing excess solid $NaHCO_3$ (50 g).

The aqueous layer was extracted with $CH_2Cl_2$ (3×250 mL), the organic layers combined and washed with saturated aqueous NaCl (250 mL), dried ($MgSO_4$), and concentrated to give 1-(5-hydroxy-2-neopentylpyridin-4-yl)ethanone as a brown oil.

Step 6: 2,2-spirocyclobutyl-6-neopentyl-2,3-dihydropyrano[2,3-c]pyridin-4-one

A mixture of 1-(5-hydroxy-2-neopentylpyridin-4-yl]ethanone (14.8 g, 71 mmol) (76894-11), Hünig's base (12 ml, 71 mmol), pyrrolidine (8.9 ml, 107 mmol), and cyclobutanone (13 ml, 179 mmol) in toluene (300 mL) with a Dean-Stark trap was heated in a 140° C. oil bath for 2 h. The mixture was cooled to rt, then diluted with EtOAc (25 mL), washed with $H_2O$, saturated aqueous $NH_4Cl$, saturated aqueous NaCl, dried ($MgSO_4$), and concentrated. Purification by ISCO (120 g $SiO_2$, 10-20% EtOAc/Hexane) gives the title compound as a yellow solid.

Step 7: 2,2-spirocyclobutyl-6-neopentyl-7-oxo-2,3-dihydropyrano[2,3-c]pyridin-4-one 2,2-spirocyclobutyl-6-neopentyl-2,3-dihydropyrano[2,3-c]pyridin-4-one (5.00 g, 19 mmol) was dissolved in 100 ml $CHCl_3$ and cooled to 0° C., mCPBA (10.0 g, 58 mmol) was added portionwise and the reaction was stirred under $N_2$ and allowed to warm slowly to rt; stirring was continued for 17 h. The mixture was then cooled to 0° C., 1M NaOH (100 mL) was added, and stirring was continued vigorously for 10 min. The mixture was extracted with $CH_2Cl_2$ (3×100 mL), the combined organic layers washed with saturated sodium chloride (100 mL), dried ($Na_2SO_4$) and evaporated to give the title compound as a white solid.

Step 8: 8-chloro-2,2-spirocyclobutyl-6-neopentyl-2,3-dihydro pyrano[2,3-c]pyridin-4-one 2,2-spirocyclobutyl-6-neopentyl-7-oxo-2,3-dihydropyrano[2,3-c]pyridin-4-one. (5.3 g, 19 mmol) was taken up in phosphoryl trichloride (20 mL, 218 mmol) and the mixture was heated to 80° C. for 2 h under $N_2$. The reaction mixture was quenched by slow addition to vigorously stirred cold 10% aqueous $NaCO_3$ (300 mL), extracted with EtOAc (3×200 mL), the combined organic layers were washed with saturated NaCl (200 mL), dried ($Na_2SO_4$), and concentrated to give a brown oil. Purification by ISCO (120 g $SiO_2$, 10% EtOAc/Hexane) gives the title compound as a light yellow solid.

Step 9: (R)-8-chloro-2,2-spirocyclobutyl-6-neopentyl-3,4-dihydro-2H-pyrano[2,3-c]pyridin-4-ol To a stirred solution of (s)-2-methyl-cbs-oxazaborolidine (1.7 ml, 1.7 mmol) in THF (20 mL) at 0° C. is added borane-methyl sulfide complex (14 ml, 28 mmol) followed by a solution of 8-chloro-2,2-spirocyclobutyl-6-neopentyl-2,3-dihydropyrano[2,3-c]pyridin-4-one (4.90 g, 17 mmol) in THF (40 mL) dropwise via syringe pump over 2.8 h. The reaction was stirred an additional 30 min, then was quenched by dropwise addition (1 drop/10 sec) of 5 M HCl (25 mL) at 0° C., after 15 mL HCl was added, bubbling had ceased and the addition rate was increased as the ice bath was removed. The reaction was stirred an additional 2 h at rt. The reaction was recooled to 0° C. and neutralized with 5 M NaOH (27 mL). The mixture was then extracted with EtOAc (2×150 mL), washed with saturated aqueous NaCl (200 mL), dried ($MgSO_4$), and concentrated in vacuo. Purification by ISCO (120 g $SiO_2$, 20% EtOAc/Hexane) gives the title compound as a white foam.

Step 10: (S)-4-azido-8-chloro-2,2-spirocyclobutyl-6-neopentyl-3,4-dihydro-2H-pyrano[2,3-c]pyridine To a solution of (R)-8-chloro-2,2-spirocyclobutyl-6-neopentyl-3,4-dihydro-2H-pyrano[2,3-c]pyridin-4-ol (2.33 g, 7.9 mmol) in toluene (43 mL) is added diphenylphosphoryl azide (2.4 ml, 11 mmol) then 1,8-diazabicyclo(5.4.0)-7-undecene (1.6 ml, 11 mmol). The reaction was stirred under $N_2$ at rt 4 days. The clear, light yellow solution first turned into a yellow cloudy/opaque solution after 10 min. Water (100 mL) was added and the reaction mixture extracted with EtOAc (3×100 mL). The combined organic layers were washed with saturated NaCl (150 mL), dried ($MgSO_4$), and concentrated to give the title compound as a brown oil which was used in the next step without purification.

Step 11: (S)-8-chloro-2,2-spirocyclobutyl-6-neopentyl-3,4-dihydro-2H-pyrano[2,3-c]pyridin-4-amine To a solution of (S)-4-azido-8-chloro-2,2-spirocyclobutyl-6-neopentyl-3,4-dihydro-2H-pyrano[2,3-c]pyridine (2.21 g, 6.9 mmol) in 10:1 $THF/H_2O$ (44 mL) at 0° C. is added NaOH (3.0 ml, 15 mmol) (5 N). After 5 min, trimethylphosphine (2.4 ml, 28 mmol) was added dropwise over 4 min. The reaction went from brown to pink to purple as $N_2$ evolution occurred. The ice bath was allowed to melt as the reaction warmed to rt and stirred a total of 15 h. The mixture was re-cooled to 0° C. and 5 N HCl (25 mL) was added. The resulting mixture was extracted with EtOAc (3×50 mL), the combined organic layers were washed with 2.5 N HCl (2×25 mL). The combined aqueous layers were cooled to 0° C. and basified to pH 14 with 5 N NaOH (100 mL). The aqueous layer was extracted with EtOAc (3×50 mL) the combined organic layers dried ($Na_2SO_4$), and concentrated to give the crude product as a viscous yellow oil. The combined organic layers were combined with the crude product from above and concentrated to give a crude yellow oil. Purification of the crude oil by flash chromatography (5×15 cm $SiO_2$, 0-10% $MeOH/CH_2Cl_2$ gradient elution) gave the title compound as a yellow oil.

Example 407

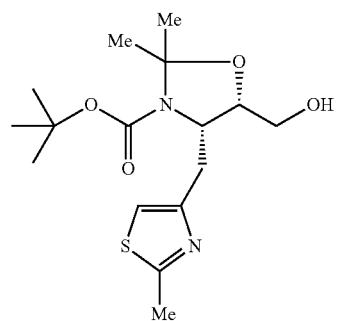 [SMILES: Cc1nc(C[C@H]2[C@@H](CO)OC(C)(C)N2C(=O)OC(C)(C)C)cs1]

Synthesis of (4S,5S)-tert-butyl 5-(hydroxymethyl)-2,2-dimethyl-4-((2-methylthiazol-4-yl)methyl)oxazolidine-3-carboxylate Step 1: (4S,5S)-tert-butyl 5-((tert-butyldimethylsilyloxy)methyl)-2,2-dimethyl-4-(thiazol-4-ylmethyl)oxazolidine-3-carboxylate (4S,5S)-Tert-butyl 5-(hydroxymethyl)-2,2-dimethyl-4-(thiazol-4-ylmethyl)oxazolidine-3-carboxylate (0.096 g, 0.29 mmol) was dissolved in DMF (1 mL) with 1H-imidazole (0.026 g, 0.38 mmol) and tert-butylchlorodimethylsilane (0.053 g, 0.35 mmol). The reaction was stirred 2 hrs, diluted with diethyl ether and washed twice with water and once with brine. The organic layer was dried over magnesium sulfate and concentrated to furnish the title compound, which was used for the next step without purification.

Step 2: (4S,5S)-tert-butyl 5-((tert-butyldimethylsilyloxy)methyl)-2,2-dimethyl-4-((2-methylthiazol-4-yl)methyl)oxazolidine-3-carboxylate (4S,5S)-Tert-butyl 5-((tert-butyldimethylsilyloxy)methyl)-2,2-dimethyl-4-(thiazol-4-ylmethyl)oxazolidine-3-carboxylate (0.100 g, 0.23 mmol) was dissolved in THF (2.5 mL) and cooled to −78° C. n-Butyllithium (0.12 ml, 0.29 mmol) was added and the reaction was stirred at −50° C. for 40 minutes followed by the addition of iodomethane (0.018 ml, 0.29 mmol). After stirring 40 minutes the reaction was quenched with saturated ammonium chloride and extracted with ethyl acetate. The combined organic layers were washed with water, brine, and dried over sodium sulfate to afford the title compound. MS m/z: 457.3 (M+1).

Step 3: (4S,5S)-tert-butyl 5-(hydroxymethyl)-2,2-dimethyl-4-((2-methylthiazol-4-yl)methyl)oxazolidine-3-carboxylate (4S,5S)-Tert-butyl 5-((tert-butyldimethylsilyloxy)methyl)-2,2-dimethyl-4-((2-methylthiazol-4-yl)methyl)oxazolidine-3-carboxylate (0.100 g, 0.219 mmol) was dissolved in THF (4 mL) and cooled to 0° C. Next, TBAF (0.547 ml, 0.547 mmol) was added dropwise and the reaction was stirred 1 hr. and then quenched with saturated ammonium chloride and diluted with EtOAc. The layers were separated and the aqueous layer was extracted with ethyl acetate. The combined organic layers were washed with water, brine, dried over sodium sulfate, and concentrated. Purification by column chromatography (2.5:1 Hexanes/EtOAc) afforded the title compound.

Example 408

Step 1: (S)-methyl 2-(tert-butoxycarbonyl)-3-(4-(trifluoromethyl)phenyl)propanoate Iodine (0.0140 g, 0.0553 mmol) was added to zinc (0.542 g, 8.29 mmol) and the solid mixture was heated under vacuum for 10 minutes. The flask was flushed with nitrogen three times and allowed to cool. DMF (0.5 mL, degassed with nitrogen) was added and the suspension was cooled to 0° C. and stirred while (R)-methyl 2-(tert-butoxycarbonyl)-3-iodopropanoate (1.82 g, 5.53 mmol) in DMF (2.8 mL) was added dropwise. The mixture was stirred for 30 minutes at 0° C. and then allowed to come to RT for 30 minutes. 1-Iodo-4-(trifluoromethyl)benzene (1.50 g, 5.53 mmol), tris(dibenzylideneacetone)dipalladium (0.101 g, 0.111 mmol), and dicyclohexylphosphino-2',6'-dimethoxy-1,1'-biphenyl (S-Phos) (0.182 g, 0.442 mmol) were added. The flask was purged with nitrogen and heated at 40° C. After 3 hours the reaction was allowed to cool and partitioned between EtOAc and an aqueous solution of ~9:1 saturated ammonium chloride/ammonium hydroxide. The aqueous layer was extracted with EtOAc and the combined organic layers were washed with water, brine, and dried over sodium sulfate. Concentration and purification by silica gel chromatography (6:1 Hexanes/EtOAc) afforded (S)-methyl 2-(tert-butoxycarbonyl)-3-(4-(trifluoromethyl)phenyl)propanoate.

Step 2: (S)-2-(tert-butoxycarbonyl)-3-(4-(trifluoromethyl)phenyl)propanoic acid (S)-Methyl 2-(tert-butoxycarbonyl)-3-(4-(trifluoromethyl)phenyl)propanoate (6.20 g, 17.9 mmol) was dissolved in THF (180 mL) and cooled to 0° C. A 0.2 M of aq. LiOH (89.3 ml, 17.9 mmol) was added dropwise and stirred 20 minutes before TLC analysis (2:1 Hexanes/EtOAc) showed no starting material. The PH of the reaction was carefully adjusted to PH=8 with 1 N HCl. The aqueous layer was washed with diethyl ether and the organics were back extracted with 1% aqueous sodium bicarbonate and the combined aqueous layers were carefully brought to a PH=4 and extracted with EtOAc. The combined organic layers were washed with brine, dried over sodium sulfate, and concentrated to afford (S)-2-(tert-butoxycarbonyl)-3-(4-(trifluoromethyl)phenyl)propanoic acid, which was used without further purification.

Example 409

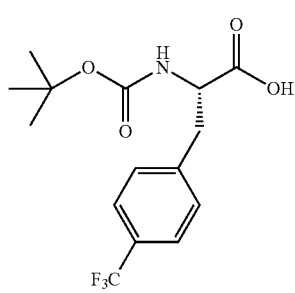 [SMILES: CC(C)(C)OC(=O)N[C@@H](Cc1ccc(C(F)(F)F)cc1)C(=O)O]

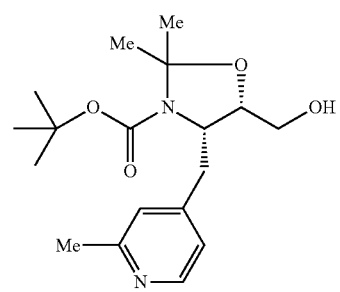 [SMILES: Cc1cc(C[C@H]2[C@@H](CO)OC(C)(C)N2C(=O)OC(C)(C)C)ccn1]

(4S,5S)-tert-Butyl 5-(hydroxymethyl)-2,2-dimethyl-4-((2-methylpyridin-4-yl)methyl)oxazolidine-3-carboxylate Step 1: (4S,5S)-tert-Butyl 5-((tert-butyldimethylsilyloxy)methyl)-2,2-dimethyl-4-(pyridin-4-ylmethyl)oxazolidine-3-carboxylate The title compound was synthesized in manner analogous to that described in Example 407, using (4S,5S)-tert-butyl 5-(hydroxymethyl)-2,2-dimethyl-4-(pyridin-4-ylmethyl)oxazolidine-3-carboxylate in the presence of TBSCl and imidazole, and was used without further purification.

Step 2: (4S,5S)-tert-butyl 5-((tert-butyldimethylsilyloxy)methyl)-2,2-dimethyl-4-((2-methylpyridin-4-yl)methyl)oxazolidine-3-carboxylate (4S,5S)-Tert-butyl 5-((tert-butyldimethylsilyloxy)methyl)-2,2-dimethyl-4-(pyridin-4-ylmethyl)oxazolidine-3-carboxylate (0.150 g, 0.344 mmol) was dissolved in THF (3.5 mL) and cooled to 0° C. Acetyl chloride (0.0256 ml, 0.361 mmol) was added and the reaction was stirred 30 minutes before METHYLMAGNESIUM BROMIDE (0.294 ml, 0.412 mmol) was added. The reaction was stirred 1 hr. at 0° C. and then warmed to RT and quenched with saturated ammonium chloride and diluted with EtOAc and water. The layers were separated and the aqueous layer was extracted with EtOAc. The combined organic layers were washed with a 9:1 aqueous solution of saturated ammonium chloride/ammonium hydroxide, water, brine, and dried over sodium sulfate. The crude product was dissolved in isopropylacetate (4 mL) and heated to 50° C. before DDQ (0.117 g, 0.515 mmol) was added. After 30 minutes the reaction was cooled and diluted with ethyl acetate and washed twice with saturated sodium bicarbonate, once with water, brine, and dried over sodium sulfate. The mixture was passed through a plug of silica gel with 2:1 Hexanes/EtOAc and concentrated to afford the title compound, MS m/z: 451.3 (100%, M+1)).

Step 3: (4S,5S)-tert-butyl 5-(hydroxymethyl)-2,2-dimethyl-4-((2-methylpyridin-4-yl)methyl)oxazolidine-3-carboxylate (4S,5S)-Tert-butyl 5-((tert-butyldimethylsilyloxy)methyl)-2,2-dimethyl-4-((2-methylpyridin-4-yl)methyl)oxazolidine-3-carboxylate (0.083 g, 0.18 mmol) was dissolved in THF (2 mL) and cooled to 0° C. Next, TBAF (0.28 ml, 0.28 mmol) was added dropwise and the reaction was stirred 1 hr. and then quenched with saturated ammonium chloride and diluted with ethyl acetate. The layers were separated and the aqueous layer was extracted with EtOAc. The combined organic layers were washed with water, brine, dried over sodium sulfate, and concentrated. Purification by column chromatography (19:1 DCM/MeOH) afforded the title compound, MS m/z: 337.2 (100%, M+1).

Example 410

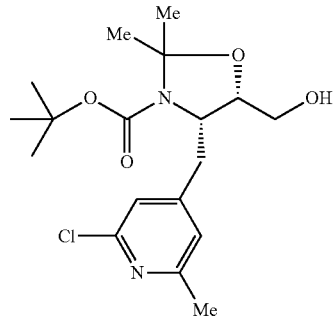 [SMILES: Cc1cc(C[C@H]2[C@@H](CO)OC(C)(C)N2C(=O)OC(C)(C)C)cc(Cl)n1]

Step 1: (4S,5S)-Tert-butyl 5-((tert-butyldimethylsilyloxy)methyl)-4-(2-chloropyridin-4-yl)methyl)-2,2-dimethyloxazolidine-3-carboxylate. The title compound was synthesized in a manner analogous to Example 407, step 1 via (4S,5S)-tert-butyl 4-((2-chloropyridin-4-yl)methyl)-5-(hydroxymethyl)-2,2-dimethyloxazolidine-3-carboxylate in the presence of TBSCl and imidazole and was used without further purification.

Step 2: (4S,5S)-tert-butyl 5-((tert-butyldimethylsilyloxy)methyl)-4-((2-chloro-6-methylpyridin-4-yl)methyl)-2,2-dimethyloxazolidine-3-carboxylate Dimethylethanolamine (0.128 ml, 1.27 mmol) was added to anhydrous hexanes (1.4 L) and cooled to 0° C. N-BUTYL-LITHIUM (2.5 M in hexanes)(1.02 ml, 2.55 mmol) was added dropwise and stirred for 30 minutes before being cooled to −78° C. (4S,5S)-Tert-butyl 5-((tert-butyldimethylsilyloxy)methyl)-4-(2-chloropyridin-4-yl)methyl)-2,2-dimethyloxazolidine-3-carboxylate (0.200 g, 0.425 mmol) in hexanes (1 mL) was added dropwise and the solution was stirred for 1 hour at −78° C. to give a dark orange solution. MeI (0.106 ml, 1.70 mmol) in THF (3.2 mL) was added dropwise and the reaction was allowed to slowly warm to 0° C. and was quenched with saturated aqueous ammonium chloride. The reaction was diluted with ethyl acetate and water and separated. The aqueous layer was extracted with ethyl acetate and the combined organic layers were washed with water, brine, dried over sodium sulfate, and concentrated to give the titled compound which was used directly for the next step without purification.

Step 3: (4S,5S)-tert-butyl 4-((2-chloro-6-methylpyridin-4-yl)methyl)-5-(hydroxymethyl)-2,2-dimethyloxazolidine-3-carboxylate (4S,5S)-Tert-butyl 5-((tert-butyldimethylsilyloxy)methyl)-4-((2-chloro-6-methylpyridin-4-yl)methyl)-2,2-dimethyloxazolidine-3-carboxylate (0.206 g, 0.425 mmol) was dissolved in THF (4 mL) and cooled to 0° C. TBAF (0.637 ml, 0.637 mmol) was added to the mixture dropwise and the reaction was stirred 1 hr and then quenched with saturated ammonium chloride and diluted with EtOAc. The layers were separated and the aqueous layer was extracted with EtOAc. The combined organic layers were washed with water, brine, dried over sodium sulfate, and concentrated. The crude material was purified by silica column chromatography (19:1 DCM/MeOH) and then reverse phase HPLC to give the title compound. MS m/z: 371.3 (100%, M+1).

Example 411

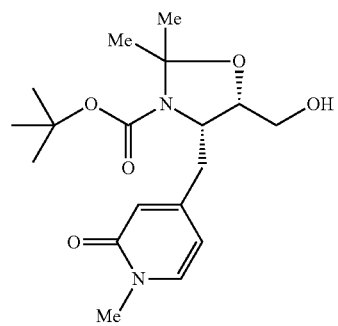 [SMILES: Cn1ccc(C[C@H]2[C@@H](CO)OC(C)(C)N2C(=O)OC(C)(C)C)cc1=O]

(4S,5S)-tert-butyl 5-(hydroxymethyl)-2,2-dimethyl-4-((1-methyl-2-oxo-1,2-dihydropyridin-4-ylmethyl)oxazolidine-3-carboxylate (4S,5S)-Tert-butyl 5-(hydroxymethyl)-4-(2-methoxypyridin-4-yl)methyl)-2,2-dimethyloxazolidine-3-carboxylate (0.281 g, 0.797 mmol) was refluxed in methanol (17 mL) with MeI (0.0798 ml, 1.28 mmol) for 48 hrs. Concentration and purification by silica gel chromotography (20:1 DCM/MeOH) afforded the titled compound along with recovered starting material.

Example 412

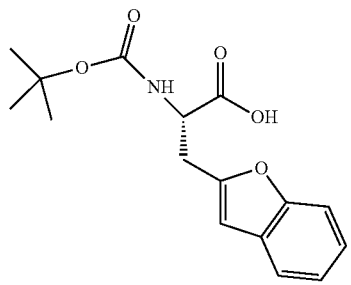 [SMILES: CC(C)(C)OC(=O)N[C@@H](Cc1cc2ccccc2o1)C(=O)O]

(S)-methyl 3-(benzofuran-2-yl)-2-(tert-butoxycarbonyl)propanoate

The title compound was synthesized in a manner analogous to that described Example 408, using (R)-methyl 2-(tert-butoxycarbonyl)-3-iodopropanoate and 2-bromobenzofuran. (MS m/z: 220.1 (100%, M-99).

Example 413

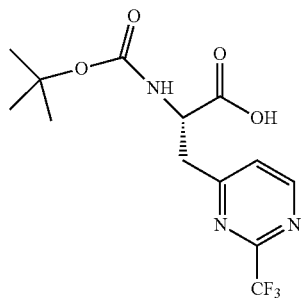 [SMILES: CC(C)(C)OC(=O)N[C@@H](Cc1ccnc(C(F)(F)F)n1)C(=O)O]

(S)-methyl 2-(tert-butoxycarbonyl)-3-(2-(trifluoromethyl)pyrimidin-4-yl)propanoate The title compound was synthesized in a manner analogous to that described Example 408, using (R)-methyl 2-(tert-butoxycarbonyl)-3-iodopropanoate and 4-chloro-2-(trifluoromethyl)pyrimidine.

Example 414

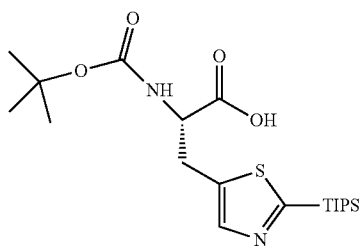

(S)-methyl 2-(tert-butoxycarbonyl)-3-(2-(triisopropylsilyl)thiazol-5-yl)propanoate The title compound was synthesized in a manner analogous to that described Example 408, using (R)-methyl 2-(tert-butoxycarbonyl)-3-iodopropanoate and 5-bromo-2-(triisopropylsilyl)thiazole (prepared according to Stangeland, Eric L.; Sammakia, Tarek, Use of Thiazoles in the Halogen Dance Reaction: Application to the Total Synthesis of WS75624 B, Journal of Organic Chemistry (2004), 69(7), 2381-2385). MS m/z: 443.3 (100%, M+1).

Example 415

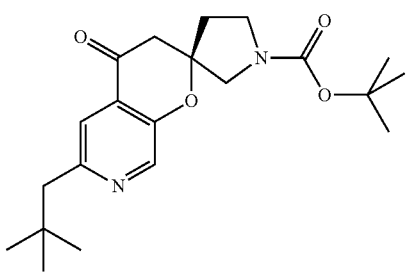

Tert-butyl 3-oxopyrrolidine-1-carboxylate (20.0 g, 108 mmol) was added to a solution of 1-(5-hydroxy-2-neopentylpyridin-4-yl)ethanone (7.58 g, 37 mmol) (prepared according to a procedure described in WO2007061670), pyrrolidine (9.1 ml, 110 mmol), and HOAc (6.3 ml, 110 mmol) in ACN (131 mL) and the reaction was heated to 75° C. After 12 hrs, the reaction was allowed to cool. After diluting the reaction with ethyl acetate and 10% sodium carbonate, the layers were separated and the aqueous layer was extracted with ethyl acetate. The combined organic layers were washed with water, saturated ammonium chloride, brine, and dried over sodium sulfate. The crude product was purified through a plug of silica gel (4:1 Hexanes/EtOAc) to afford the compounds above, as illustrated, as an approximate 1:1 mixture of diastereomers. MS m/z: 375.2 (100%, M+1).

Example 416

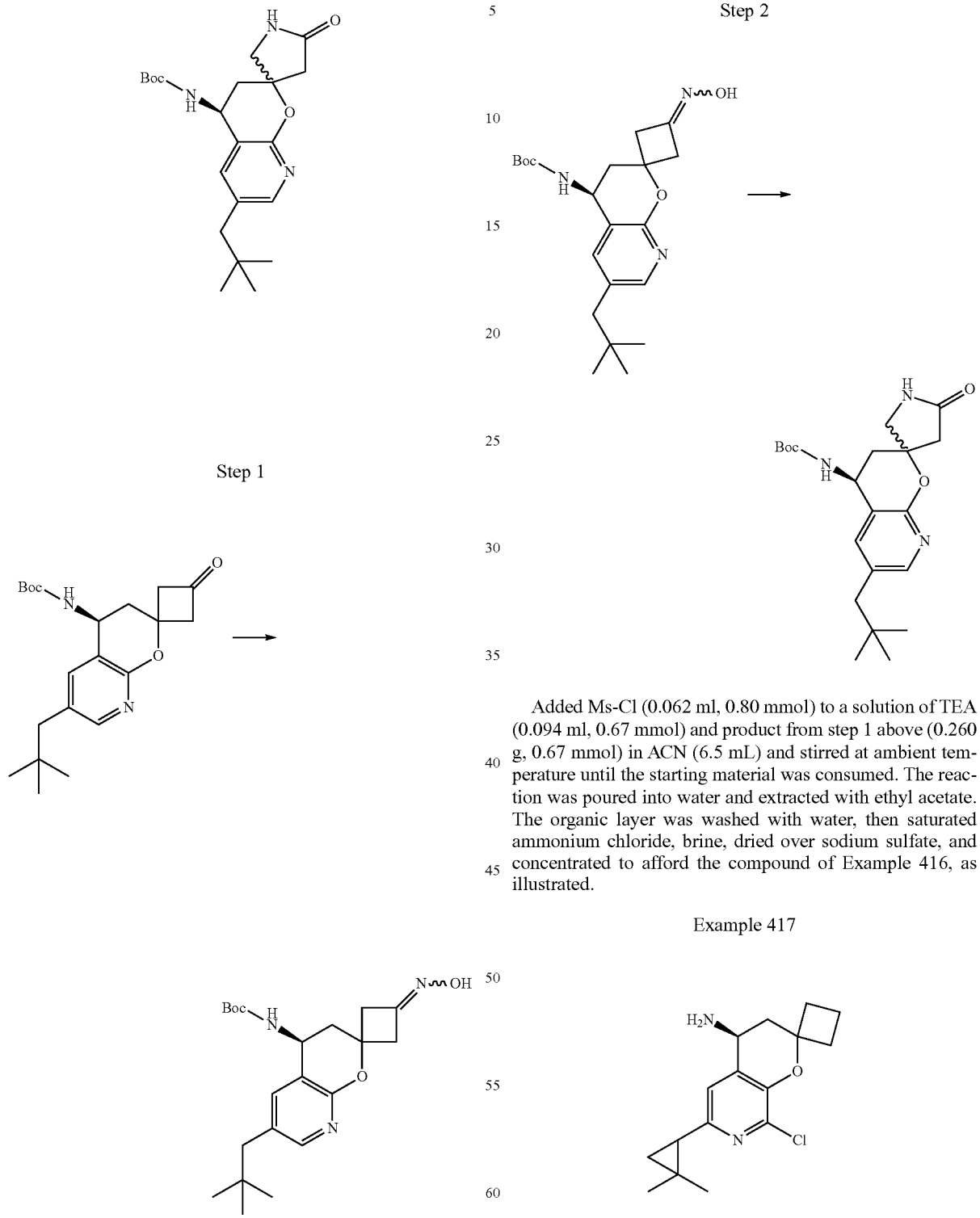

Step 1

Hydroxylamine hydrochloride (0.900 g, 13.0 mmol) and Ketone (0.680 g, 1.82 mmol) (prepared according to a procedure described in WO2007061670) were stirred in pyridine (15 mL) for 2 hours and then poured into water and extracted with ether. The combined organic layers were washed with water, brine, dried over magnesium sulfate, and concentrated to afford the title compound.

Step 2

Added Ms-Cl (0.062 ml, 0.80 mmol) to a solution of TEA (0.094 ml, 0.67 mmol) and product from step 1 above (0.260 g, 0.67 mmol) in ACN (6.5 mL) and stirred at ambient temperature until the starting material was consumed. The reaction was poured into water and extracted with ethyl acetate. The organic layer was washed with water, then saturated ammonium chloride, brine, dried over sodium sulfate, and concentrated to afford the compound of Example 416, as illustrated.

Example 417

Step 1:
5-(Methoxymethoxy)-2-(2-methylprop-1-enyl)pyridine

A solution of 2-chloro-5-(methoxymethoxy)pyridine (0.620 g, 3.6 mmol) and 1,1'-bis(diphenylphosphino)ferrocene-palladium dichloride (0.13 g, 0.18 mmol) in THF (7 mL) was cooled to 0° C. 2-methyl-1-propenylmagnesium bromide, (0.5 M in THF) (9.3 ml, 4.6 mmol) was added slowly and the reaction was allowed to stir 12 hrs at RT. The reaction was quenched by the addition of a 10:1 aqueous sat ammonium chloride/ammonium hydroxide solution and extracted into ethyl acetate. The combined organic layers were washed with 10:1 aqueous sat. ammonium chloride/ammonium hydroxide solution, water, brine, dried over sodium sulfate and concentrated. The crude product was purified by filtration through a plug of silica gel (2:1 Hexanes/EtOAc) to afford the title product. MS m/z: 194.1 (100%, M+1).

Step 2: 2-(2,2-Dimethylcyclopropyl)-5-(methoxymethoxy)pyridine

Diiodomethane (24.8 ml, 308 mmol) was added dropwise to a solution of diethylzinc (200 ml, 220 mmol) 1.1 M in toluene at 0° C. After the addition, the solution was stirred at RT for 40 minutes and then recooled to 0° C. when 5-(methoxymethoxy)-2-(2-methylprop-1-enyl)pyridine (21.3 g, 110 mmol) in toluene (150 mL) was added dropwise through an addition funnel. The reaction was allowed to come to RT and was stirred 12 hrs before being quenched at 0° C. by the addition of a 10:1 saturated ammonium chloride/ammonium hydroxide aqueous solution. The layers were separated and the aqueous layer was diluted with water and extracted into ethyl acetate. The combined organic layers were washed with 10:1 saturated ammonium chloride/ammonium hydroxide aqueous solution, water, brine, dried over sodium sulfate, and concentrated. The crude product was purified through a plug of silica (10:1 Hexanes/EtOAc) to afford the titled compound. MS m/z: 208.2 (100%, M+1).

Step 3

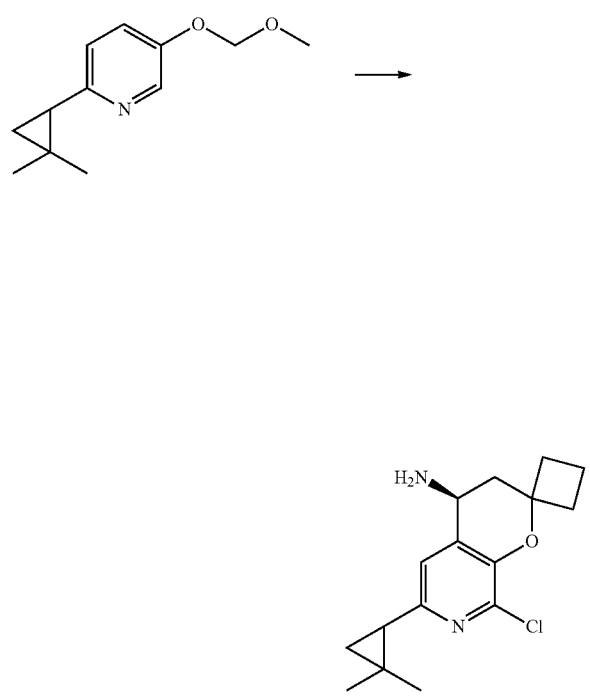

The above depicted conversion of 2-(2,2-dimethylcyclopropyl)-5-(methoxymethoxy)pyridine to the desired depicted amine was prepared by a procedure analogous to that described in WO2007061670.

Example 418

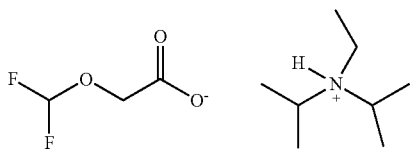

Synthesis of N-ethyl-N-isopropylpropan-2-aminium 2-(difluoromethoxy)acetate

Benzyl 2-hydroxyacetate (3.2 ml, 22.2 mmol), sodium sulfate (0.63 g, 4.4 mmol), and MeCN (34 ml) were placed in a 100 ml two-necked RBF fitted with a magnetic stirrer, a dropping funnel and a refluxing condenser. 2,2-Difluoro-2-(fluorosulfonyl)acetic acid (9.18 ml, 89 mmol) was then added with stirring at 45° C. After addition, the mixture was further stirred for 1 h at this temperature. The reaction mixture was poured into 10% aqueous sodium carbonate and was extracted with diethyl ether, the combined extracts were washed with 10% aqueous sodium carbonate, water, brine, dried over sodium sulfate, and concentrated. The crude material was purified by column chromatography (4:1 Hexanes/EtOAc) to afford the intermediate benzyl 2-(difluoromethoxy)acetate which was dissolved in EtOAc (34 mL). N-Ethyl-N-isopropylpropan-2-amine (0.561 ml, 3.2 mmol) was added and after degassing with nitrogen, palladium on carbon (0.680 g, 0.64 mmol) was added. The reaction was purged with hydrogen and stirred under 50 PSI of hydrogen for 24 hours. The degassed reaction was filtered through a pad of Celite and concentrate to afford the titled product as the amine salt which was used directly for subsequent reaction steps without further purification.

Example 419

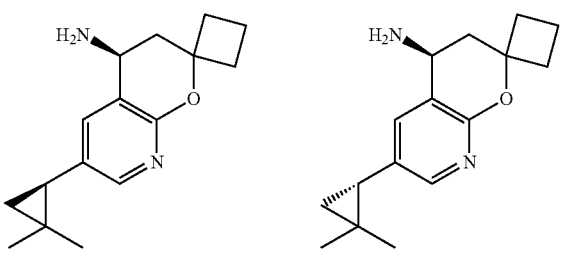 [SMILES: CC1(C)C[C@H]1c1cnc2c(c1)[C@@H](N)CC1(CCC1)O2 ; CC1(C)C[C@@H]1c1cnc2c(c1)[C@@H](N)CC1(CCC1)O2]

Synthesis of N-[(4'S)-6'-((R)-2,2-Dimethylcyclopropyl)-3',4'-dihydrospiro[cyclobutane-1,2'-[2H]pyrano[2,3-b]pyridin]-4'-yl]-4-amine and N-[(4'S)-6'-((S)-2,2-dimethylcyclopropyl)-3',4'-dihydrospiro[cyclobutane-1,2'-[2H]pyrano[2,3-b]pyridin]-4'-yl]-4-amine

Step 1: 2,2-Dimethylcyclopropylboronic acid

Sodium periodate (2.23 g, 10.4 mmol) was added to a RT solution of 2-(2,2-dimethylcyclopropyl)-4,4,5,5-tetramethyl-1,3,2-dioxaborolane (0.680 g, 3.47 mmol) (Prepared according to a procedure described in *Synthesis*, 8, pg 605-609, 1991) in THF/H$_2$O (4:1, 30 mL). The mixture was stirred 5 minutes when HCl (2N) (1.14 ml, 2.29 mmol) was added. After stirring for 12 h the reaction was diluted with water and extracted with ethyl acetate. The combined organic extracts were washed with water, brine, dried over sodium sulfate, and concentrated in vacuo to afford the title compound which was used without further purification.

Step 2

N-[(4'S)-6'-((R)-2,2-Dimethylcyclopropyl)-3',4'-dihydrospiro[cyclobutane-1,2'-[2H]pyrano[2,3-b]pyridin]-4'-yl]-N$^2$-propen-1-yl-, 1,1-dimethylethyl ester carbamic acid and N-[(4'S)-6'-((S)-2,2-dimethylcyclopropyl)-3',4'-dihydrospiro[cyclobutane-1,2'-[2H]pyrano[2,3-b]pyridin]-4'-yl]-N$^2$-propen-1-yl-, 1,1-dimethylethyl ester carbamic acid and Pd(OAc)$_2$ (0.428 g, 1.91 mmol) and tricyclohexylphosphine (1.07 g, 3.81 mmol) were added to a solution of 2,2-dimethylcyclopropylboronic acid (3.26 g, 28.6 mmol), N-[(4'S)-6'-bromo-3',4'-dihydrospiro[cyclobutane-1,2'42H]pyrano[2,3-b]pyridin]-4'-yl]-, 1,1-dimethylethyl ester carbamic acid (7.04 g, 19.1 mmol) (prepared by a procedure analogous to that described in WO2007061670), and potassium phosphate (14.2 g, 66.8 mmol) in 10:1 toluene/water (132 mL). The reaction was refluxed for 18 hours, cooled, diluted with ethyl acetate and washed with 10:1 saturated ammonium chloride/ammonium hydroxide and water. The aqueous layer was back extracted with ethyl acetate and the combined organic layers were washed with water, brine, dried over sodium sulfate, and concentrated. The crude material was purified by silica gel chromatography with 4:1 Hexanes/EtOAc to afford the title compound as a 1:1 mixture of diastereomers. MS m/z: 359.3 (100%, M+1). The diastereomers were further separated by HPLC to afford each individual diastereomer.

Step 3: (S)-6-(R)-2,2-dimethylcyclopropyl)-3',4'-dihydrospiro[cyclobutane-1,2'-pyrano[2,3-b]pyridin-4-amine The (R) diastereomer Boc protected product from step 2 (10.7 g, 29.8 mmol) was stirred in a solution of TFA (46.0 ml, 597 mmol) and DCM (100 mL) until LC/MS showed complete conversion to product. The solution was concentrated and the crude material was taken up in DCM and free-based by washing with 1 N NaOH. Concentration of the organics after brine wash and drying (sodium sulfate) afforded the titled compound. MS m/z: 259.2 (100%, M+1).

Example 420

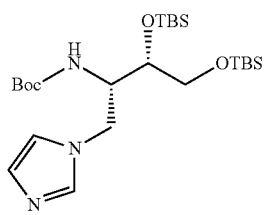 [SMILES: CC(C)(C)OC(=O)N[C@@H](Cn1ccnc1)[C@@H](CO[Si](C)(C)C(C)(C)C)O[Si](C)(C)C(C)(C)C]

Synthesis of tert-butyl (2S,3S)-3,4-bis(tert-butyldimethylsilyloxy)-1-(1H-imidazol-1-yl)butan-2-ylcarbamate Step 1: (S)-N-((1R,2S)-2,3-bis(tert-butyldimethylsilyloxy)-1-thiazol-2-yl)propyl)-2-methylpropane-2-sulfinamide A solution of 2-bromothiazole (7.9 ml, 89 mmol) in 200 mL ether was cooled to −78° C. and treated with a solution of n-butyllithium (36 ml, 89 mmol) (2.5N in hexanes). After stirring for 30 minutes the reaction mixture was slowly added to a cooled (−78° C.) suspension of (S,E)-N-((S)-2,3-bis(tert-butyldimethylsilyloxy)propylidene)-2-methylpropane-2-sulfinamide (25.000 g, 59 mmol) in 100 mL ether. The reaction mixture was allowed to stir at −78° C. for one hour. The reaction mixture was quenched with MeOH and saturated NH$_4$Cl solution. The organic solution was washed with water, brine, dried over MgSO4 and concentrated in vacuo. Purification of the crude residue by column chromatography gave (S)-N-((1R,2S)-2,3-bis(tert-butyldimethylsilyloxy)-1-(thiazol-2-yl)propyl)-2-methylpropane-2-sulfinamide (24.81 g, 83% yield).

Step 2: tert-butyl (1R,2S)-2,3-bis(tert-butyldimethylsilyloxy)-1-(thiazol-2-yl)propylcarbamate A solution of (S)-N-((1R,2S)-2,3-bis(tert-butyldimethylsilyloxy)-1-(thiazol-2-yl)propyl)-2-methylpropane-2-sulfinamide (16.000 g, 32 mmol) in 32 mL THF was cooled to −10° C. and was treated with a solution of HCl (4N in dioxane) (12 ml, 47 mmol). Almost immediately a white solid precipitated, and an additional 32 mL of THF was added to solubilize the solid. The reaction mixture was allowed to stir at −10° C. for 2 hours then was allowed to slowly warm to RT overnight. N,N-diisopropylethylamine (17 ml, 95 mmol) was added, and the reaction mixture was allowed to stir for 20 minutes. A solution of di-tert-butyldicarbonate (1N in THF) (35 ml, 35 mmol) was added, and the reaction mixture was allowed to warm to RT and stir overnight. The reaction mixture was quenched with 6N NaOH and was allowed to stir for 30 minutes. The reaction mixture was then diluted with ether, washed with water then brine. The organics were dried over MgSO4 and concentrated. Purification of the crude residue by column chromatography gave tert-butyl (1R,2S)-2,3-bis(tert-butyldimethylsilyloxy)-1-(thiazol-2-yl)propylcarbamate (6.15 g, 39% yield).

Step 3: Tert-butyl (2S,3S)-3,4-bis(tert-butyldimethylsilyloxy)-1-hydroxybutan-2-ylcarbamate A solution of tert-butyl (1R,2S)-2,3-bis(tert-butyldimethylsilyloxy)-1-(thiazol-2-yl)propylcarbamate (6.150 g, 12.2 mmol) in 120 mL MeCN was treated with 4A mol. sieves and was allowed to stir at room temperature for 10 minutes. Methyl trifluoromethylsulfonate (1.62 ml, 14.7 mmol) was added, and the reaction mixture was allowed to stir for an additional 30 minutes. The reaction mixture was then concentrated in vacuo. The crude residue was dissolved in 100 mL MeOH, cooled to 0° C., and treated with NaBH$_4$ (1.39 g, 36.7 mmol). The reaction mixture was allowed to warm to RT and stir for an additional 20 minutes. The reaction mixture was then concentrated, diluted with EtOAc, filtered through celite and again concentrated in vacuo. The residue was dissolved in 100 mL ACN and 20 mL water and was treated with mercury(II)chloride (3.32 g, 12.2 mmol). After stirring for 30 minutes, an additional portion of NaBH$_4$ (1.39 g, 36.7 mmol)

was added, and the reaction mixture was allowed to stir for another 30 minutes. The reaction mixture was quenched with saturated NaHCO$_3$ solution and diluted with EtOAc. The crude reaction mixture was then washed with water then brine. The organic layer was dried over MgSO$_4$ and concentrated in vacuo. The crude residue was forced through a short plug of silica eluting with ether. The filtrate was again concentrated in vacuo yielding tert-butyl (2S,3S)-3,4-bis(tert-butyldimethylsilyloxy)-1-hydroxybutan-2-ylcarbamate (5.33 g, 96.9% yield) with minor impurities.

Step 4: (5)-Tert-butyl 2-((S)-1,2-bis(tert-butyldimethylsilyloxy)ethyl)aziridine-1-carboxylate A solution of tert-butyl (2S,3S)-3,4-bis(tert-butyldimethylsilyloxy)-1-hydroxybutan-2-ylcarbamate (1.025 g, 2.3 mmol) in 20 mL DCM was cooled to 0° C., treated with N,N-DIPEA (0.60 ml, 3.4 mmol) followed by Ms-Cl (0.18 ml, 2.3 mmol). After stirring at 0° C. for 2 hours, the reaction mixture was concentrated in vacuo and the crude residue was dissolved in 20 mL THF. KOt-Bu (0.51 g, 4.6 mmol) was added, and the reaction mixture was allowed to stir at RT for 10 minutes. The reaction mixture was then diluted with EtAOc, washed with water then brine. The organics dried over MgSO$_4$ and concentrated in vacuo. Purification of the crude residue by column chromatography gave (5)-tert-butyl 2-((S)-1,2-bis(tert-butyldimethylsilyloxy)ethyl)aziridine-1-carboxylate as a clear oil.

Step 5: Tert-butyl (2S,3S)-3,4-bis(tert-butyldimethylsilyloxy)-1-(1H-imidazol-1-yl)butan-2-ylcarbamate A solution of (5)-tert-butyl 2-((S)-1,2-bis(tert-butyldimethylsilyloxy)ethyl)aziridine-1-carboxylate (0.740 g, 1.7 mmol) and 1H-imidazole (0.35 g, 5.1 mmol) in 3 mL toluen was thoroughly degassed and treated with tributylphosphine (0.42 ml, 1.7 mmol). The reaction mixture was heated to reflux and allowed to stir for 3 hours. NaH (60% dispersion in mineral oil) (0.069 g, 2.9 mmol) was added and the reaction mixture was allowed to stir at 110° C. overnight. The reaction mixture was quenched with saturated NH$_4$Cl solution and diluted with EtOAc. The reaction mixture was washed with water then brine. The organics were dried over MgSO4 and concentrated in vacuo. Purification of the crude residue by column chromatography gave tert-butyl (2S,3S)-3,4-bis(tert-butyldimethylsilyloxy)-1-(1H-imidazol-1-yl)butan-2-ylcarbamate with tributylphosphine oxide as the major impurity. This material was used without further purification.

Example 421

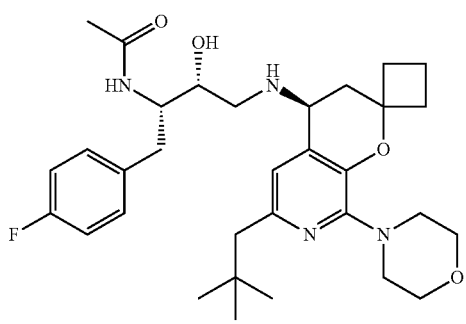 [SMILES: CC(=O)N[C@@H](Cc1ccc(F)cc1)[C@H](O)CN[C@H]1CC2(CCC2)Oc2c1cc(CC(C)(C)C)nc2N1CCOCC1]

Synthesis of N-((2S,3R)-4-((S)-2,2-spirocyclobutyl-8-morpholino-6-neopentyl-3,4-dihydro-2H-pyrano [2,3-c]pyridin-4-ylamino)-1-(4-fluorophenyl)-3-hydroxybutan-2-yl]acetamide A glass microwave reaction vessel was charged with N-((2S,3R)-4-((S)-2,2-spirocyclobutyl-8-chloro-6-neopentyl-3,4-dihydro-2H-pyrano[2,3-c]pyridin-4-ylamino)-1-(4-fluorophenyl)-3-hydroxybutan-2-yl)acetamide (118 mg, 228 μmol), Pd$_2$(dba)$_3$ (17.5 mg, 19 μmol), and DavePhos (26.9 mg, 68 μmol). The vessel was purged with N$_2$ for 5 minutes, then THF (1 mL), LHMDS (2.0 ml, 2050 μmol), and morpholine (0.10 ml, 1148 μmol) were added. The reaction mixture was stirred and heated in a Biotage Initiator at 100° C. for 10 minutes. The reaction was filtered through a 0.2 multipor nylon membrane and purified by reverse-phase preparative HPLC (Shimadzu) on a Phenomenex Gemini column (10 micron, C18, 110 Å, Axia, 100×50 mm) eluting at 100 mL/min with a linear gradient of 10% (v/v) to 60% MeCN (0.1% v/v TFA) in water (0.1% TFA) over 30 minutes. The desired fractions were poured into 10% Na$_2$CO$_3$ and extracted with CH$_2$Cl$_2$ (3×20 mL) to give the titled compound as a light yellow solid. MS m/z: 569.2 (M+1).

Example 422

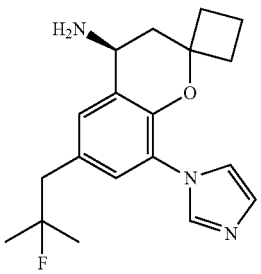 [SMILES: CC(C)(F)Cc1cc2c(c(-n3ccnc3)c1)OC1(CCC1)C[C@@H]2N]

Synthesis of (4S)-6-(2-fluoro-2-methylpropyl)-8-(1H-imidazol-1-yl)-2,2-spirocyclobutylchroman-4-amine Step 1: (R)-(6-Bromo-2,2-spirocyclobutyl-3,4-dihydro-2H-chromen-4-yloxy)(tert-butyl)dimethylsilane To a round bottomed flask was added (R)-6-bromo-2,2-spirocyclobutyl-3,4-dihydro-2H-chromen-4-ol (37.7 g, 140 mmol), CH$_2$Cl$_2$ (600 mL), DIPEA (39.0 ml, 210 mmol) and an ice bath. After cooling for 20 minutes, TBS triflate (32.0 ml, 139 mmol) was added. After stirring for 45 minutes, the ice bath was removed and an additional 6 mL of TBS triflate were added. After stirring for a further 30 minutes, the reaction was washed with water (100 mL), HCl (1M, 200 mL), and sat'd NaHCO$_3$ (100 mL). The organic layer was concentrated in vacuo. The crude orange oil was taken up in hexane (100 mL) and eluted through a plug of silica gel (600 mL Frit) using 2% EtOAc/hexane to give (R)-(6-bromo-2,2-spirocyclobutyl-3,4-dihydro-2H-chromen-4-yloxy)(tert-butyl)dimethylsilane (51.05 g, 95.1% yield), as a colorless oil. The material was carried forward without further characterization. MS m/z: 253.1 (M−H−OTBS).

Step 2: (R)-1-(4-(Tert-butyldimethylsilyloxy)-2,2-spirocyclobutyl-3,4-dihydro-2H-chromen-6-yl)propan-2-one To a RBF was added MePhos (1.7 g, 4.7 mmol), dichloro [1,1'-bis(diphenylphosphino)ferrocene]palladium (II) (1.4 g, 2.0 mmol), and THF (29 mL). The solution was degassed with N$_2$ for 20 minutes. The solution was heated to 45° C. for 20 minutes, then allowed to cool to RT. To a separated 500 mL RBF was added (R)-(6-bromo-2,2-spirocyclobutyl-3,4-dihydro-2H-chromen-4-yloxy)(tert-butyl)dimethylsilane (15.0 g, 39 mmol), potassium phosphate (21.77 g, 103 mmol) (freshly ground) and degassed acetone, 99% (140 ml, 1904 mmol). The solution of catalyst and ligand were cannulated into the acetone solution and the entire reaction further degassed with N$_2$ for 20 minutes. The solution was then stirred at reflux. After 24 hours, the reaction was allowed to cool to RT and filtered through a cartridge of celite. The filtrate was concentrated in vacuo and adsorbed onto a plug of silica gel and chromatographed through a Redi-Sep® pre-packed silica gel column (120 g), eluting with 0% to 5% EtOAc in hexane, to provide (R)-1-(4-(tert-butyldimethylsilyloxy)-2,2-spirocyclobutyl-3,4-dihydro-2H-chromen-6-yl)propan-2-one as a light yellow oil. MS m/z: 229.1 (M–H-OTBS).

Step 3: (R)-1-(4-(Tert-butyldimethylsilyloxy)-2,2-spirocyclobutyl-3,4-dihydro-2H-chromen-6-yl)-2-methylpropan-2-ol To a RBF was added (R)-1-(4-(tert-butyldimethylsilyloxy)-2,2-spirocyclobutyl-3,4-dihydro-2H-chromen-6-yl) propan-2-one (4.97 g, 13.8 mmol) and THF (60 mL, anhydrous). The solution was cooled to 0° C. and treated with methylmagnesium chloride (5.50 ml, 16.5 mmol). The solution was allowed to warm to RT over 1 hour, then stirred at RT for 2 hours. The reaction was then partitioned between EtOAc:water and the resulting aqueous layer extracted with EtOAc (50 mL). The combined organic layers were washed with brine, dried over MgSO$_4$, and concentrated in vacuo to give (R)-1-(4-(tert-butyldimethylsilyloxy)-2,2-spirocyclobutyl-3,4-dihydro-2H-chromen-6-yl)-2-methylpropan-2-ol as a yellow oil that solidified. MS m/z: 245.2 (M–H-OTBS).

Step 4: (R)-1-(8-Bromo-4-(tert-butyldimethylsilyloxy)-2,2-spirocyclo-butyl-3,4-dihydro-2H-chromen-6-yl)-2-methylpropan-2-ol To a RBF was added (R)-1-(4-(tert-butyldimethylsilyloxy)-2,2-spirocyclobutyl-3,4-dihydro-2H-chromen-6-yl)-2-methylpropan-2-ol (5.04 g, 13.4 mmol), sodium bromide (2.75 g, 26.8 mmol), acetone:water (1:1, 160 mL), and Oxone (8.23 g, 13.4 mmol). The reaction warmed about 10° C. After 6 hours, the reaction was filtered and the filtrate extracted with EtOAc (2×50 mL). The combined organic layers were concentrated in vacuo and adsorbed onto a plug of silica gel and chromatographed through a Redi-Sep® pre-packed silica gel column (80 g), eluting with 0% to 10% EtOAc in hexane, to provide (R)-1-(8-bromo-4-(tert-butyldimethylsilyloxy)-2,2-spirocyclo-butyl-3,4-dihydro-2H-chromen-6-yl)-2-methylpropan-2-ol as a light yellow oil. MS m/z: 325.0 (M–H-OTBS).

Step 5: 1-((4R)-4-(Tert-butyldimethylsilyloxy)-8-(1H-imidazol-1-yl)-2,2-spirocyclobutyl-chroman-6-yl)-2-methylpropan-2-ol A glass microwave reaction vessel was charged with (R)-1-(8-bromo-4-(tert-butyldimethylsilyloxy)-2,2-spirocyclobutyl-3,4-dihydro-2H-chromen-6-yl)-2-methylpropan-2-ol (1.30 g, 2.9 mmol), DMF:Water (9:1, 20 mL), cesium carbonate (4.6 g, 14 mmol), copper(I) iodide (0.54 g, 2.9 mmol), 1H-imidazole (0.97 g, 14 mmol), and N,N'-dimethylethane-1,2-diamine (0.31 ml, 2.9 mmol). The reaction mixture was stirred and heated in a Biotage Initiator at 180° C. for 40 minutes. The reaction was set up in triplicate. The vials were all poured into 150 mL of water. The aqueous solution was extracted with EtOAc (4×40 mL). The combined organic layers were filtered through a celite cartridge to remove an emulsion. The filtrate was washed with water, brine, and concentrated in vacuo to give a brown oil. The oil was adsorbed onto a plug of silica gel and chromatographed through a Redi-Sep® pre-packed silica gel column (40 g), eluting with 0% to 5% MeOH in CH$_2$Cl$_2$, to provide 1-((4R)-4-(tert-butyldimethylsilyloxy)-8-(1H-imidazol-1-yl)-2,2-spirocyclobutyl-chroman-6-yl)-2-methylpropan-2-ol as a brown solid. MS m/z: 443.3 (M+1).

Step 6: 1-((4R)-4-(Tert-butyldimethylsilyloxy)-6-(2-fluoro-2-methylpropyl)-2,2-spirocyclobutyl-3,4-dihydro-2H-chromen-8-yl)-1H-imidazole To a RBF was added 1-((4R)-4-(tert-butyldimethylsilyloxy)-8-(1H-imidazol-1-yl)-2,2-spirocyclobutyl-chroman-6-yl)-2-methylpropan-2-ol (2.94 g, 6.64 mmol), CH$_2$Cl$_2$ (80 mL), and a dry ice/iPrOH bath. After stirring for 15 minutes, DAST (1.75 ml, 13.3 mmol) was added. After 30 minutes, TLC shows complete conversion. The cooling bath was removed and the material poured into sat'd NaHCO$_3$ (25 mL). The aqueous layer was extracted with CH$_2$Cl$_2$ (5 mL) and the combined organic layers were concentrated in vacuo. The crude product was adsorbed onto a plug of silica gel and chromatographed through a Redi-Sep® pre-packed silica gel column (12 g), eluting with 0% to 20% EtOAc in CH$_2$Cl$_2$, to provide 1-((4R)-4-(tert-butyldimethylsilyloxy)-6-(2-fluoro-2-methylpropyl)-2,2-spirocyclobutyl-3,4-dihydro-2H-chromen-8-yl)-1H-imidazole as a brown oil, that solidified upon standing. MS m/z: 445.3 (M+1).

Step 7: (4R)-6-(2-Fluoro-2-methylpropyl)-8-(1H-imidazol-1-yl)-2,2-spiro-cyclobutylchroman-4-ol To a RBF was added 1-((4R)-4-(tert-butyldimethylsilyloxy)-6-(2-fluoro-2-methylpropyl)-2,2-spiro-cyclobutyl-3,4-dihydro-2H-chromen-8-yl)-1H-imidazole (1.6 g, 3.6 mmol), THF (40 mL), and an ice bath. After stirring for 15 minutes, TBAF (4.0 ml, 4.0 mmol) was added. After 3 hours, LC-MS shows complete conversion. The reaction was poured on to a plug of silica gel and eluted with 50% EtOAc in CH2Cl2, to provide (4R)-6-(2-fluoro-2-methylpropyl)-8-(1H-imidazol-1-yl)-2,2-spiro-cyclobutylchroman-4-ol as a light yellow solid. This material was carried forward as is. MS m/z: 331.2 (M+1).

Step 8: 1-((4S)-4-Azido-6-(2-fluoro-2-methylpropyl)-2,2-spirocyclobutyl-3,4-dihydro-2H-chromen-8-yl)-1H-imidazole To RBF was added (4R)-6-(2-fluoro-2-methylpropyl)-8-(1H-imidazol-1-yl)-2,2-spiro-cyclobutylchroman-4-ol (1.18 g, 3.57 mmol), toluene (4 mL), and an ice bath. After stirring for 15 minutes, DPPA (1.08 ml, 5.00 mmol) was added, then DBU (0.748 ml, 5.00 mmol). After 24 hours, LC-MS shows complete conversion. The reaction was diluted with water (100 mL) and extracted with EtOAc (3×40 mL). The combined organic layers were concentrated in vacuo and adsorbed onto a plug of silica gel and chromatographed through a Redi-Sep® pre-packed silica gel column (12 g), eluting with 0% to 40% EtOAc in hexane, to provide 1-((4S)-

4-azido-6-(2-fluoro-2-methylpropyl)-2,2-spirocyclobutyl-3,4-dihydro-2H-chromen-8-yl)-1H-imidazole as a light golden oil. MS m/z: 356.4 (M+1).

Step 9: (4S)-6-(2-Fluoro-2-methylpropyl)-8-(1H-imidazol-1-yl)-2,2-spirocyclobutylchroman-4-amine To RBF was added 1-((4S)-4-azido-6-(2-fluoro-2-methylpropyl)-2,2-spirocyclobutyl-3,4-dihydro-2H-chromen-8-yl)-1H-imidazole (1.11 g, 3.1 mmol), THF (100 mL), and a dry ice/iPrOH bath. After stirring for 15 minutes, LAH (12 ml, 12 mmol) was added over 30 minutes. LC-MS showed no progress. The solution was warmed to 0° C. via an ice bath. After a further 30 min, the reaction is ~75% complete (via LC-MS). After another hour, the reaction was cautiously quenched with sat'd Rochelle's salt and the organic layer separated. The aqueous layer was extracted with EtOAc (2×30 mL). The combined organic layers were washed with brine, concentrated in vacuo, and adsorbed onto a plug of silica gel and chromatographed through a Redi-Sep® prepacked silica gel column (12 g), eluting with 0% to 5% MeOH in CH$_2$Cl$_2$, to provide (4S)-6-(2-fluoro-2-methylpropyl)-8-(1H-imidazol-1-yl)-2,2-spirocyclobutylchroman-4-amine as a light yellow oil. MS m/z: 330.4 (M+1).

Example 423

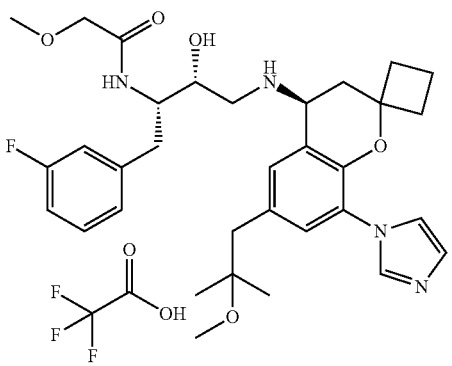

The amine chroman precursor of this compound was isolated as a byproduct during the synthesis of Example 422 above. The compound depicted above was made from this amine using procedures as described in WO2007061670.

Example 424

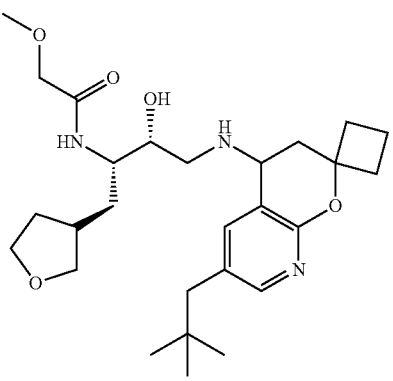

N-((2S,3S)-4-(2,2-spirocyclobutane-6-neopentyl-3,4-dihydro-2H-pyrano[2,3-b]pyridine-4-ylamino)-3-hydroxy-1-((S)-tetrahydrofuran-3-yl)butan-2-yl)-2-methoxyacetamide Step 1: (S)-N-((2S,3S)-3,4-bis(tert-butyldimethylsilyloxy)-1-(tetrahydrofuran-3-yl)butan-2-yl)-2-methylpropane-2-sulfinamide A solution of azeotropically dried (S,E)-N-((S)-2,3-bis(tert-butyldimethylsilyloxy)propylidene)-2-methylpropane-2-sulfinamide (2.3 g, 5 mmol) and 3-(iodomethyl)-THF (1 g, 7 mmol) in dry THF (10 mL) was brought to −78° C. followed by the dropwise addition of tert-butyllithium (6 mL, 11 mmol). A white precipitate was formed. The resulting solution was stirred at −78° C. for 40 min, quenched with sat NH$_4$Cl and extracted with EtOAc. The combined organics were washed with brine, dried over Na$_2$SO$_4$, filtered, concentrated, and chromatographed on silica gel using 0-5% EtOAc/hexanes to afford a colorless oil as (S)-N-((2S,3S)-3,4-bis(tert-butyldimethylsilyloxy)-1-(tetrahydrofuran-3-yl)butan-2-yl)-2-methylpropane-2-sulfinamide.

Step 2: Tert-butyl(2S,3S)-3(tert-butyldimethylsilyloxy)-4-hydroxy-1-((S)-tetrahydrofuran-3-yl)butan-2-ylcarbamate and Tert-butyl(2S,3S)-3(tert-butyldimethylsilyloxy)-4-hydroxy-1-((R)-tetrahydrofuran-3-yl)butan-2-ylcarbamate A solution of (S)-N-((2S,3S)-3,4-bis(tert-butyldimethylsilyloxy)-1-(tetrahydrofuran-3-yl)butan-2-yl)-2-methylpropane-2-sulfinamide (1.5 g, 3.0 mmol) in dry MeOH (30 mL) was brought to −20° C. followed by the addition of 10% HCl (100 mL, MeOH/acetyl chloride) and the resulting mixture was stirred at −20 C for 1 h. The mixture was quenched with 10% Na$_2$CO$_3$ and extracted with DCM (8×). The combined organics were dried over Na$_2$CO$_4$, filtered, concentrated and colorless oil obtained was dissolved in DCM (30 mL) followed by the addition of TEA (1.2 mL, 8.9 mmol) and di-tert-butyldicarbonate (1.0 mL, 4.4 mmol). The reaction was stirred at RT for 17 h. The mixture was concentrated and chromatographed on silica gel using 4:1 to 1:1 EtOAc/hexanes to afford a colorless oil as tert-butyl(2S,3S)-3(tert-butyldimethylsilyloxy)-4-hydroxy-1-((S)-tetrahydrofuran-3-yl)butan-2-ylcarbamate AND Tert-butyl(2S,3S)-3 (tert-butyldimethylsilyloxy)-4-hydroxy-1-((R)-tetrahydrofuran-3-yl)butan-2-ylcarbamate.

Step 3: N-((2S,3S)-4-(2,2-spirocyclobutane-6-neopentyl-3,4-dihydro-2H-pyrano[2,3-b]pyridine-4-ylamino)-3-hydroxy-1-((S)-tetrahydrofuran-3-yl)butan-2-yl)-2-methoxyacetamide The titled compound was prepared from the product of step 2 according to the procedure described in Example 42 herein.

Example 425

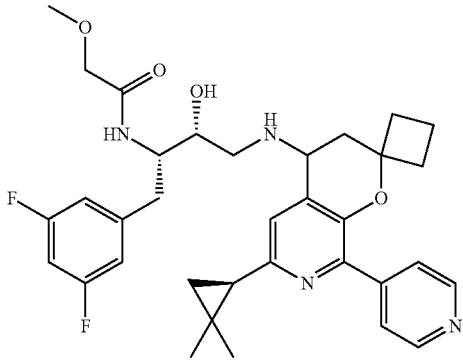 [SMILES: COCC(=O)N[C@@H](Cc1cc(F)cc(F)c1)[C@H](O)CNC1CC2(CCC2)Oc2c1cc([C@@H]1CC1(C)C)nc2-c1ccncc1]

N-((2S,3R)-1-(3,5-difluorophenyl)-4-(6-((R)-2,2-dimethylcyclopropyl)-2,2-spirocyclobutane-8-(pyridine-4-yl)-3,4-dihydro-2H-pyrano[2,3-c]pyridine-4-ylamino)-3-hydroxybutan-2-yl)-2-methoxyacetamide To a microwave vial were added N-((2S,3R)-4-(8-chloro-6-((R)-2,2-dimethylcyclopropy)-2,2-spirocyclobutane-3,4-dihydro-2H-pyrano[2,3-c]pyridine-4-ylamino)-1-(3,5-fidluorophenyl)-3-hydroxybutan-2-yl)-2-methoxyacetamide (0.43 g, 0.76 mmol), 4-pyridylboronic acid (0.14 g, 1.1 mmol), tetrakis(triphenylphosphine)palladium (0.13 g, 0.11 mmol), and potassium carbonate (0.14 ml, 2.3 mmol) and the mixture was purged with $N_2$ followed by the addition of 1,4-dioxane (6 mL) and water (0.6 mL). The mixture was again purged with $N_2$ and heated in a microwave oven at 140° C. for 30 min. The mixture was filtered through celite, concentrated, and purified by HPLC to afford N-((2S,3R)-1-(3,5-difluorophenyl)-4-(6-((R)-2,2-dimethylcyclopropyl)-2,2-spirocyclobutane-8-(pyridine-4-yl)-3,4-dihydro-2H-pyrano[2,3-c]pyridine-4-ylamino)-3-hydroxybutan-2-yl)-2-methoxyacetamide as a light yellow solid. MS m/z: 607.2 (M+1).

Example 426

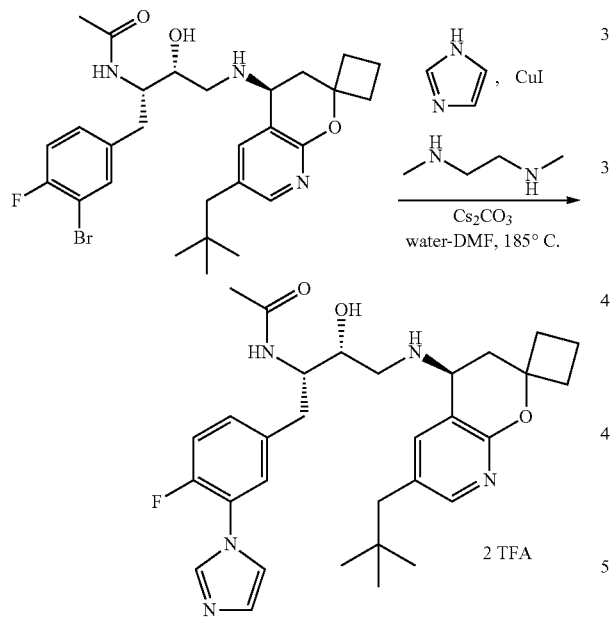

N-((1S,2R)-3-(((4'S)-6'-(2,2-Dimethylpropyl)-3',4'-dihydrospiro[cyclobutane-1,2'-pyrano[2,3-b]pyridin]-4'-yl)amino)-1-(4-fluoro-3-(1H-imidazol-1-yl)benzyl)-2-hydroxypropyl)acetamide A 2-5 mL microwave vial was charged with N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-bromo-4-fluoro-3-benzyl)-2-hydroxypropyl)acetamide (199 mg, 353 μmol), cesium carbonate (575 mg, 177 μmol), imidazole (360 mg, 529 μmol), and copper iodide (67.0 mg, 353 μmol). The vial was capped, and 10:1 dimethylformamide/water (2 mL) and N,N'-dimethylethane-1,2-diamine (38 μl, 35 μmol) were added in sequence. The vial was heated to 185° C. in a Biotage Initiator microwave reactor for 30 min. The reaction mixture was cooled and filtered through celite. The filter pad was washed with dichloromethane (3×5 mL), and the filtrate was evaporated. The residue was subjected to reverse-phase HPLC (0.1% TFA, 10-90% acetonitrile in water) to give the product (120 mg, bis-trifluoroacetate salt, 53% yield) as a clear glass. MS m/z=550.2 [M+H]$^+$. Calc'd for $C_{31}H_{41}FN_5O_3$: 550.3.

Example 427

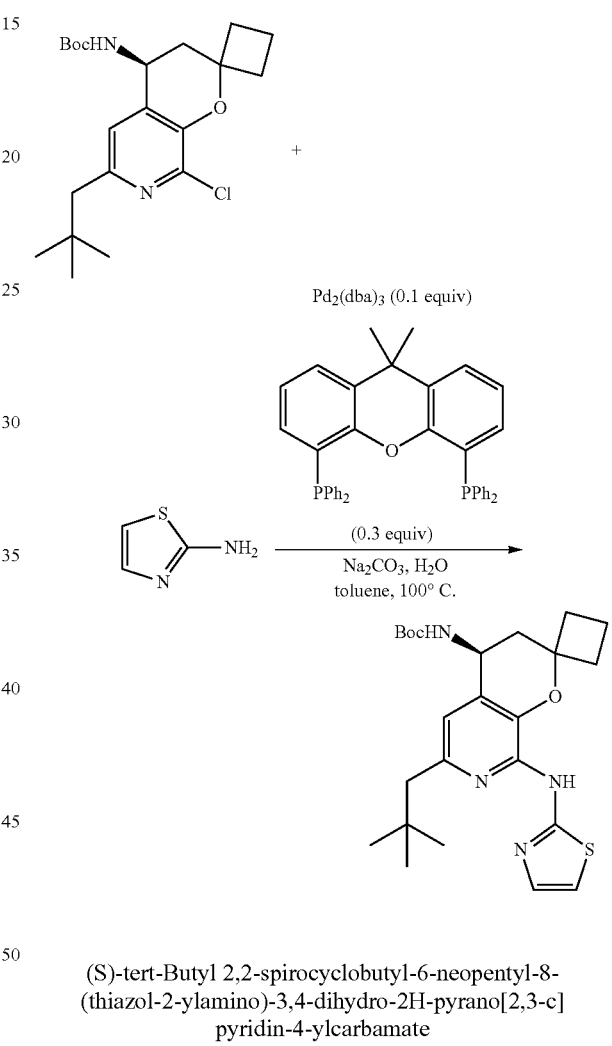

(S)-tert-Butyl 2,2-spirocyclobutyl-6-neopentyl-8-(thiazol-2-ylamino)-3,4-dihydro-2H-pyrano[2,3-c]pyridin-4-ylcarbamate A 25-mL Schlenk flask was charged with (S)-tert-butyl 8-chloro-2,2-spirocyclobutyl-6-neopentyl-3,4-dihydro-2H-pyrano[2,3-c]pyridin-4-ylcarbamate (266 mg, 674 μmol), thiazol-2-amine (202 mg, 202 μmol), sodium carbonate (100 mg, 943 μmol), tris(dibenzylideneacetone)dipalladium (62 mg, 67 μmol), and 4,5-bis(diphenylphosphino)-9,9-dimethyl-9H-xanthene (117 mg, 202 μmol). The flask was evacuated and refilled with $N_2$ (g). This process was repeated twice. Ar (g)-degassed toluene (3.4 mL) was added, and the resulting solution was stirred for 10 min. Water (12 μl, 67 μmol) was added, and the reaction vessel was sealed and heated in a 100° C. oil bath for 24 h. The mixture was then cooled to RT, diluted with THF (5 mL), filtered through celite, and concentrated under reduced pressure. The residue was purified by chromatography on a 40-g Redi Sep silica gel column with 5-50% EtOAc/hexanes to give the product as a clear oil. MS m/z=459.3 [M+H]$^+$. Calc'd for $C_{24}H_{35}N_4O_3S$: 459.2.

Examples 428 and 429

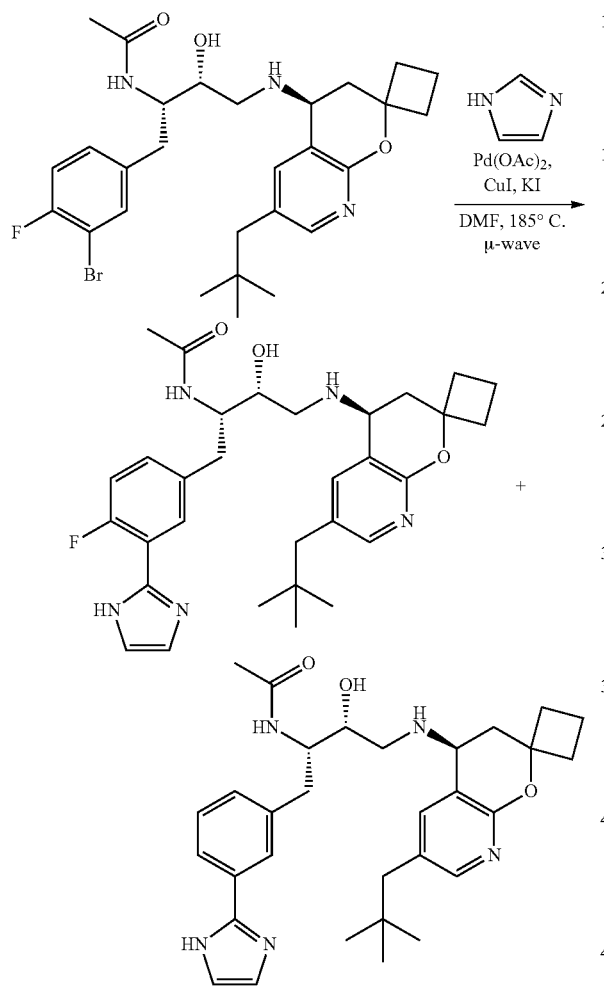

Synthesis of N-((2S,3R)-4-((S)-2,2-spirocyclobutyl-6-neopentyl-3,4-dihydro-2H-pyrano[2,3-b]pyridin-4-ylamino)-1-(4-fluoro-3-(1H-imidazol-2-yl)phenyl)-3-hydroxybutan-2-yl]acetamide (428) and N-((2S,3R)-1-(3-(1H-imidazol-2-yl)phenyl)-4-(S)-2,2-spirocyclobutyl-6-neopentyl-3,4-dihydro-2H-pyrano[2,3-b]pyridin-4-ylamino)-3-hydroxybutan-2-yl) acetamide (429)

Two dry microwave vials were each charged separately with N-((2S,3R)-1-(3-bromo-4-fluorophenyl)-4-((S)-2,2-spirocyclobutyl-6-neopentyl-3,4-dihydro-2H-pyrano[2,3-b]pyridin-4-ylamino)-3-hydroxybutan-2-yl)acetamide (78.0 mg, 139 µmol), imidazole (142 mg, 2.08 mmol), KI (46.0 mg, 277 µmol), palladium acetate (6.2 mg, 28 µmol), copper iodide (53.0 mg, 277 µmol), and DMF (0.75 mL). Each vial was capped and evacuated until the mixture bubbled, then was refilled with N$_2$ (g). This process was repeated two additional times. The vials were sonicated until the solids had dissolved (3-5 min), resulting in a deep blue solution. Each vial was heated to 185° C. for 10 min in a Biotage Initiator Microwave Reactor. The reaction mixtures were cooled to RT, combined, and filtered through a pad of celite. The filter pad was washed with DCM (4×5 mL), and the filtrate was evaporated. The residue was purified first by reverse-phase HPLC (0.1% TFA in 10-90% ACN/water), then by supercritical-CO$_2$ chromatography to give product 1 and product 2 as white powders. MS for Product 1 (Example 428) m/z=550.2 [M+H]$^+$. Calc'd for $C_{31}H_{41}FN_5O_3$: 550.3. MS for Product 2 (Example 429) m/z=532.2 [M+1]$^+$Calc'd for $C_{31}H_{42}N5O_3$: 532.3.

Example 430

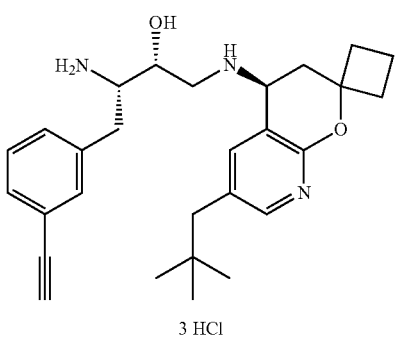 [SMILES: C#Cc1cccc(C[C@H](N)[C@H](O)CN[C@H]2CC3(CCC3)Oc3ncc(CC(C)(C)C)cc32)c1]

3 HCl

Synthesis of (2R,3S)-3-Amino-1-((S)-2,2-spirocyclobutyl-6-neopentyl-3,4-dihydro-2H-pyrano[2,3-b] pyridin-4-ylamino)-4-(3-ethynylphenyl)butan-2-ol trihydrochloride Step 1: tert-Butyl (2S,3S)-3-(tert-butyldimethylsilyloxy)-4-hydroxy-1-(3-(2-(trimethylsilyl)ethynyl) phenyl)butan-2-ylcarbamate Tert-Butyl (2S,3S)-1-(3-bromophenyl)-3-(tert-butyldimethylsilyloxy)-4-hydroxybutan-2-ylcarbamate (2.09 g, 4.40 mmol) was concentrated under reduced pressure from DCM in a 50-mL RBF. The flask was filled with N$_2$ (g), then PdCl$_2$ (PhCN)$_2$ (0.101 g, 0.264 mmol), tri-tert-butylphosphonium tetrafluoroborate (0.153 g, 0.529 mmol), and copper iodide (33.6 mg, 0.176 mmol) were added. The flask was evacuated and refilled with N$_2$ (g). This process was repeated 3×, then a rubber septum was attached. Ar (g)-degassed dioxane (10 mL) was added, and the flask was sonicated for 5 min to dissolve the starting materials. Ethynyltrimethylsilane (0.915 ml, 6.61 mmol) and diisopropylamine (0.942 ml, 6.61 mmol) were added in sequence, and the resulting black solution was stirred at RT for 4 h. The reaction mixture was diluted with EtOAc and filtered through a pad of celite. The filtrate was evaporated, and the crude product was purified by chromatography on a 120-g Redi-Sep silica gel column, eluting with 5-40% ethyl acetate/hexanes to give tert-butyl (2S,3S)-3-(tert-butyldimethylsilyloxy)-4-hydroxy-1-(3-(2-(trimethylsilyl)ethynyl)phenyl)butan-2-ylcarbamate as a brown oil.

Step 2: tert-Butyl (2S,3S)-3-(tert-butyldimethylsilyloxy)-4-oxo-1-(3-(2-(trimethylsilyl)ethynyl)phenyl) butan-2-ylcarbamate A RBF containing a solution of tert-butyl (2S,3S)-3-(tert-butyldimethylsilyloxy)-4-hydroxy-1-(3-(2-(trimethylsilyl)

ethynyl)phenyl)butan-2-ylcarbamate (2.04 g, 4.15 mmol) in DCM (30 mL) was placed in an ice-bath for 10 min. Sodium bicarbonate (1.05 g, 12.4 mmol) and Dess-Martin Periodinane (2.29 g, 5.39 mmol) were added in sequence, the ice-bath was removed, and the reaction was stirred for 2 h. The reaction mixture was diluted with a 1:1 mixture of saturated sodium thiosulfate solution and brine (60 mL), and the resulting biphasic mixture was stirred vigorously for 2 min. The mixture was then extracted with DCM (3×30 mL), and the combined organic extracts were dried over sodium sulfate, filtered, and evaporated. The residue was purified by chromatography on a 120-g Redi-Sep column, eluting with 5-30% EtOAc/Hexanes to give tert-butyl (2S,3S)-3-(tert-butyldimethylsilyloxy)-4-oxo-1-(3-(2-(trimethylsilyl)ethynyl)phenyl)butan-2-ylcarbamate as a pale yellow oil.

Step 3: tert-Butyl (2S,3R)-4-(S)-2,2-spirocyclobutyl-6-neopentyl-3,4-dihydro-2H-pyrano[2,3-b]pyridin-4-ylamino)-1-(3-ethynylphenyl)-3-hydroxybutan-2-ylcarbamate Trimethyl orthoformate (708 µl, 6.40 mmol) was added to a mixture of tert-butyl (2S,3S)-3-(tert-butyldimethylsilyloxy)-4-oxo-1-(3-(2-(trimethylsilyl)ethynyl)phenyl)butan-2-ylcarbamate (392 mg, 800 µmol) and (S)-2,2-spirocyclobutyl-6-neopentyl-3,4-dihydro-2H-pyrano[2,3-b]pyridin-4-amine (219 mg, 840 µmol) in DCM (16.0 mL, 800 µmol). The resulting mixture was stirred for 40 min, then sodium triacetoxyborohydride (678 mg, 3.20 mmol) was added and stirring was continued for 2 h. A saturated aqueous solution of Rochelle's salt (55 mL) was added, and the resulting biphasic mixture was stirred vigorously for 2 h. The reaction mixture was extracted with DCM (3×25 mL), and the combined organic extracts were washed with brine, dried over sodium sulfate, filtered, and evaporated. The residue was dissolved in THF (5 mL), and tetrabutylammonium fluoride (2.00 mL of a 1.0 M solution, 2.00 mmol) was added. The resulting orange solution was stirred at RT for 16 h. The reaction mixture was then partitioned between water (15 mL) and ethyl acetate (10 mL). The layers were separated, and the aqueous layer was extracted with ethyl acetate (2×10 mL). The combined organic extracts were dried over sodium sulfate, filtered, and evaporated. The crude product was purified by chromatography on an 80-g Redi-Sep silica gel column, eluting with 0-5% methanol/DCM to give tert-Butyl (2S,3R)-4-(S)-2,2-spirocyclobutyl-6-neopentyl-3,4-dihydro-2H-pyrano[2,3-b]pyridin-4-ylamino)-1-(3-ethynylphenyl)-3-hydroxybutan-2-ylcarbamate as a white foam. MS m/z=548.4 [M+H]⁺. Calc'd for $C_{33}H_{46}N_3O_4$: 548.4.

Step 4: (2R,3S)-3-Amino-1-((S)-2,2-spirocyclobutyl-6-neopentyl-3,4-dihydro-2H-pyrano[2,3-b]pyridin-4-ylamino)-4-(3-ethynylphenyl)butan-2-ol trihydrochloride To an ice-cold (0° C.) solution of tert-butyl (2S,3R)-4-(S)-2,2-spirocyclobutyl-6-neopentyl-3,4-dihydro-2H-pyrano[2,3-b]pyridin-4-ylamino)-1-(3-ethynylphenyl)-3-hydroxybutan-2-ylcarbamate (385 mg, 703 µmol) in MeOH (3.5 mL) was added HCl (8.79 mL of a 4.0 M solution in dioxane, 35.1 mmol) over 2 min. The resulting yellow solution was warmed to RT and stirred for 45 min. After this time, the solution was concentrated under reduced pressure to give (2R,3S)-3-Amino-1-((S)-2,2-spirocyclobutyl-6-neopentyl-3,4-dihydro-2H-pyrano[2,3-b]pyridin-4-ylamino)-4-(3-ethynylphenyl)butan-2-ol trihydrochloride as a white solid. MS m/z=448.3 [M+H]⁺. Calc'd for $C_{28}H_{38}N_3O_2$: 448.2.

Example 431

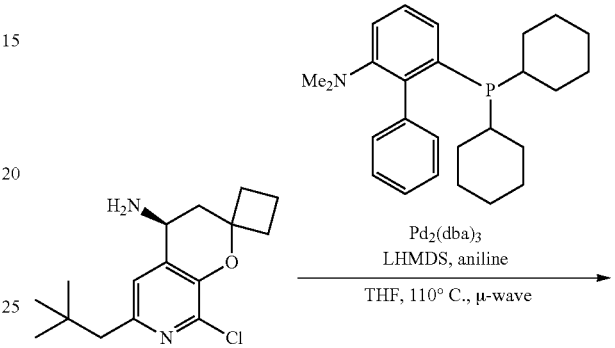

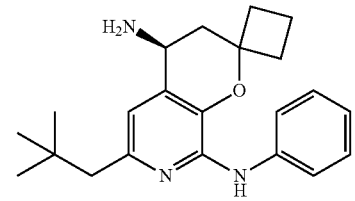

(S)-2,2-Spirocyclobutyl-6-neopentyl-N-8-phenyl-3,4-dihydro-2H-pyrano[2,3-c]pyridine-4,8-diamine A dry 2-mL microwave vial was charged with (S)-8-chloro-2,2-spirocyclobutyl-6-neopentyl-3,4-dihydro-2H-pyrano[2,3-c]pyridin-4-amine (186 mg, 631 µmol), DavePhos (109 mg, 278 µmol), and tris(dibenzylideneacetone)dipalladium(0) (116 mg, 126 µmol). The vessel was sealed and purged with N₂(g). THF (3 mL) was added, followed by aniline (345 µl, 3785 µmol). Lithium bis(trimethylsilyl)amide (3785 µl, of 1.0 M solution in THF, 3785 µmol) was added dropwise over 25 seconds to give a dark purple solution. This mixture was heated in a Biotage Initiator microwave reactor at 110° C. for 10 min. The reaction mixture was diluted with 2N HCl solution (aq., 20 mL) and washed with DCM (1×20 mL, 2×10 mL). The DCM layers were combined and extracted with water (10 mL). The aqueous layers were combined and treated with 1N NaOH solution (to pH 13) and extracted with ethyl acetate (3×30 mL). The combined organic extracts were dried over MgSO₄, filtered, and evaporated. The residue was purified by chromatography using a 40 g Redi-Sep column eluting with DCM (2 min), then a gradient of 8% MeOH/0.8% NH₄OH/DCM over 15 min, then 8%

MeOH/0.8% NH₄OH/DCM for 2 min to give desired product (179.5 mg, 81%) as a tan foam. MS m/z=352.2 [M+H]⁺. Calc'd for $C_{22}H_{30}N_3O$: 352.2.

Example 432

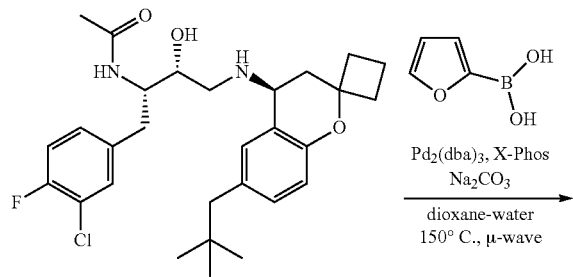

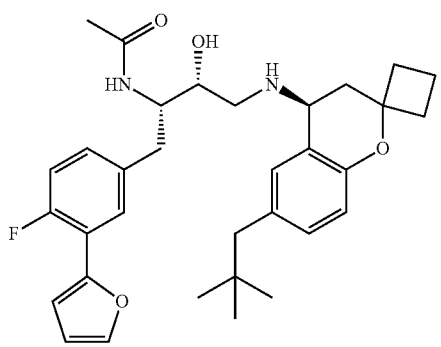

N-((2S,3R)-4-[((S)-2,2-Spirocyclobutyl-6-neopentyl-3,4-dihydro-2H-chromen-4-ylamino)-1-(4-fluoro-3-(furan-2-yl)phenyl)-3-hydroxybutan-2-yl]acetamide A microwave vial was charged with N-((2S,3R)-1-(3-chloro-4-fluorophenyl)-4-(S)-2,2-spirocyclobutyl-6-neopentyl-3,4-dihydro-2H-chromen-4-ylamino)-3-hydroxybutan-2-yl)acetamide (151 mg, 292 mmol), X-Phos (28 mg, 58 mmol), tris(dibenzylideneacetone)dipalladium(0) (27 mg, 29 mmol), 2-furanboronic acid (49 mg, 438 mmol), and sodium carbonate (186 mg, 1752 mmol). The vessel was capped, evacuated, and refilled with N₂(g). This process was repeated 3×, then dioxane (2 mL) and water (2 mL) were added in sequence. The vessel was capped again and heated in a Biotage Initiator microwave reactor at 150° C. for 30 min. The reaction mixture was diluted with DCM (20 mL) and water (10 mL). The layers were separated and the aqueous layer was extracted with DCM (10 mL). The organic layers were combined, washed with 0.5 N NaOH solution (aq., 20 mL), washed with brine, dried over sodium sulfate, filtered, and evaporated. The residue was purified by reverse-phase HPLC (10-90% CH₃CN/H₂O with 0.1% TFA) to give the product TFA-salt as a white foam. MS m/z=549.2 [M+H]⁺. Calc'd for $C_{33}H_{42}FN_2O_4$: 549.3.

Example 433

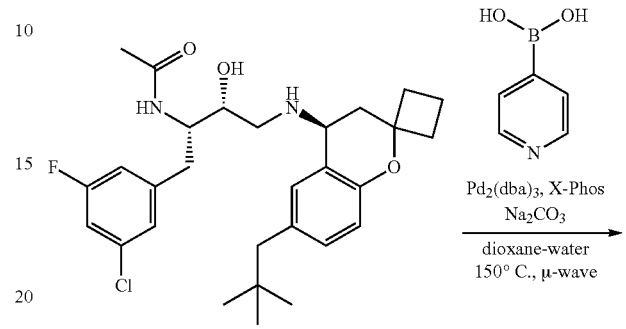

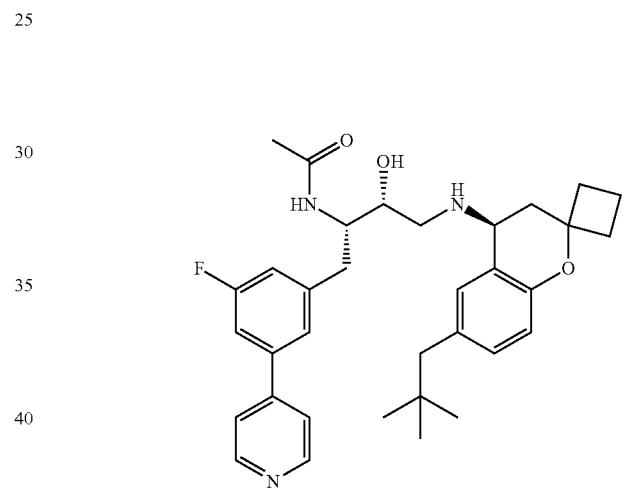

N-((2S,3R)-4-[((S)-2,2-Spirocyclobutyl-6-neopentyl-3,4-dihydro-2H-chromen-4-ylamino)-1-(3-fluoro-5-(pyridin-4-yl)phenyl)-3-hydroxybutan-2-yl]acetamide A microwave vial was charged with N-((2S,3R)-1-(3-chloro-5-fluorophenyl)-4-(S)-2,2-spirocyclobutyl-6-neopentyl-3,4-dihydro-2H-chromen-4-ylamino)-3-hydroxybutan-2-yl)acetamide (170 mg, 329 μmol), sodium carbonate (209 mg, 1973 μmol), 4-pyridineboronic acid (61 mg, 493 μmol), X-Phos (31 mg), and tris(dibenzylideneacetone)dipalladium(0) (30 mg, 33 μmol). Dioxane (2 mL) and water (2 mL) were added, the flask was stoppered, and the vial was heated in a Biotage Initiator microwave reactor at 150° C. for 30 min. The mixture was diluted with DCM (25 mL) and water (10 mL), and the layers were separated. The aqueous layer was extracted with DCM (10 mL), and the organic layers were combined. The combined organic layers were washed with water (10 mL), washed with brine, dried over sodium sulfate, filtered, and evaporated to give an orange residue. The residue was purified by reverse-phase HPLC (10-90% CH₃CN/H₂O with 0.1% TFA) to give the product TFA-salt (228.9 mg, 88% yield) as a white foam. MS m/z=560.2 [M+H]⁺. Calc'd for $C_{34}H_{43}FN_3O_3$: 560.3.

Example 434

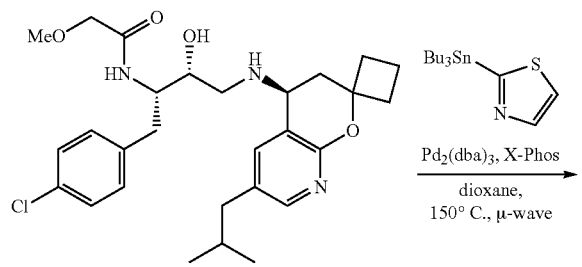

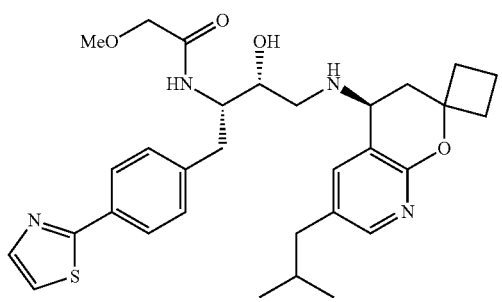

N-((2S,3R)-3-Hydroxy-4-((S)-6-isobutyl-2,2-spirocyclobutyl-3,4-dihydro-2H-pyrano[2,3-b]pyridin-4-ylamino)-1-(4-(thiazol-2-yl)phenyl)butan-2-yl)-2-methoxyacetamide A dry 2-5 mL microwave vial was charged with N-((2S,3R)-1-(4-chlorophenyl)-3-hydroxy-4-((S)-6-isobutyl-2,2-spirocyclobutyl-3,4-dihydro-2H-pyrano[2,3-b]pyridin-4-ylamino)butan-2-yl)-2-methoxyacetamide (300 mg, 581 µmol), X-Phos (553 mg), tris(dibenzylideneacetone)dipalladium(0) (532 mg, 581 µmol), and dioxane (4 mL). The mixture was sonicated for about one minute. 2-(Tributylstannyl)thiazole (640 µl, 2035 µmol) was added, and the vial was immediately heated in a Biotage Initiator microwave reactor at 150° C. for 30 min. The reaction mixture was diluted with DCM and filtered through celite. The filtrate was evaporated, and the residue was purified via chromatography on a 40-g Redi-Sep column, eluting with 0-5% MeOH/DCM. The material thus obtained was further purified by reverse-phase HPLC (10-90% $CH_3CN/H_2O$ with 0.1% TFA) to give the product TFA-salt as a white foam. MS m/z=565.2 [M+H]⁺. Calc'd for $C_{31}H_{41}N_4O_4S$: 565.3.

Example 435

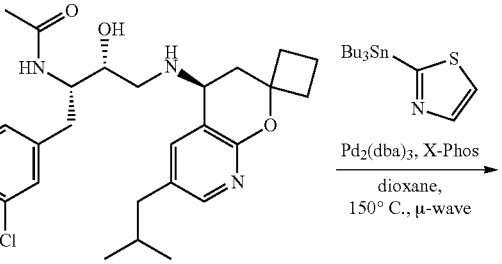

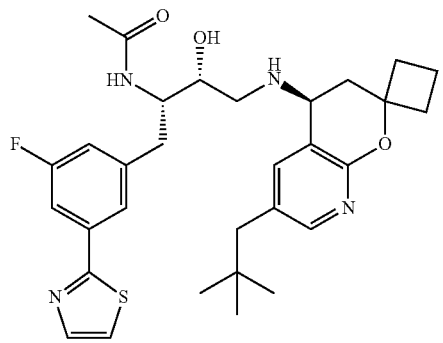

N-((2S,3R)-4-((S)-2,2-Spirocyclobutyl-6-neopentyl-3,4-dihydro-2H-pyrano[2,3-b]pyridin-4-ylamino)-1-(3-fluoro-5-(thiazol-2-yl)phenyl)-3-hydroxybutan-2-yl)acetamide N-((2S,3R)-1-(3-Chloro-5-fluorophenyl)-4-(S)-2,2-spirocyclobutyl-6-neopentyl-3,4-dihydro-2H-chromen-4-ylamino)-3-hydroxybutan-2-yl)acetamide (150 mg, 290 mmol), X-Phos (276 mg), and tris(dibenzylideneacetone)dipalladium(0) (266 mg, 290 mmol) were combined in a microwave tube, which was then sealed, evacuated, and refilled with $N_2(g)$. Dioxane (1.5 mL) and 2-(tributylstannyl)thiazole (274 µl, 870 mmol) were added in sequence, and the mixture was heated in a Biotage Initiator microwave reactor at 150° C. for 30 min. The reaction mixture was filtered through celite, the celite pad was washed with DCM, and the filtrate was evaporated. The residue was purified by chromatography on a 40-g Redi-Sep column eluting with 0%-10% MeOH/DCM. The material thus obtained was further purified by reverse-phase HPLC (10-90% $CH_3CN/H_2O$ with 0.1% TFA) to afford the product TFA-salt as a white foam. MS m/z=566.2 [M+H]+. Calc'd for $C_{31}H_{40}FN_4O_3S$: 567.3

Example 436

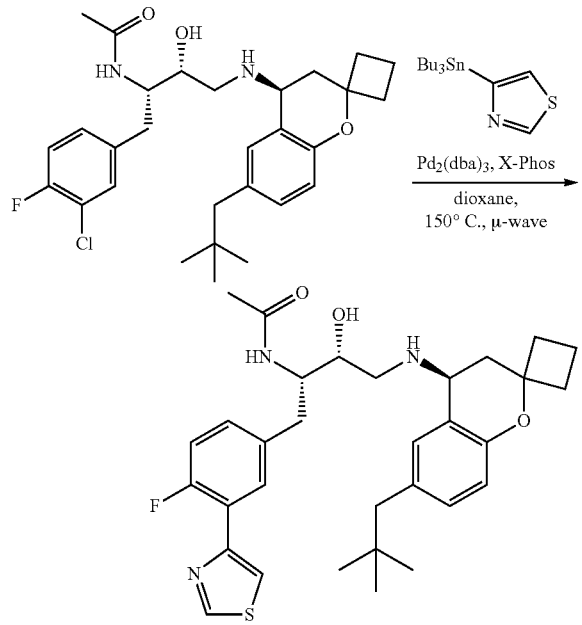

N-((2S,3R)-4-[((S)-2,2-Spirocyclobutyl-6-neopentyl-3,4-dihydro-2H-chromen-4-ylamino)-1-(4-fluoro-3-(thiazol-4-yl)phenyl)-3-hydroxybutan-2-yl]acetamide N-((2S,3R)-1-(3-Chloro-4-fluorophenyl)-4-((S)-2,2-dimethyl-6-neopentyl-3,4-dihydro-2H-chromen-4-ylamino)-3-hydroxybutan-2-yl)acetamide (154.6 mg, 298 μmol), X-Phos (284 mg), and tris(dibenzylideneacetone)dipalladium(0) (273 mg, 298 μmol) were combined in a microwave tube, which was then sealed, evacuated, and refilled with $N_2$(g). Dioxane (1.5 mL) and 4-(tributylstannyl)thiazole (335 mg, 895 μmol) were added in sequence, and the mixture was heated in a Biotage Initiator microwave reactor at 150° C. for 30 min. The reaction mixture was filtered through celite, the celite pad was washed with DCM, and the filtrate was evaporated. The residue was purified by chromatography on a 40-g Redi-Sep column eluting with 0%-10% MeOH/DCM. The material thus obtained was further purified by reverse-phase HPLC (10-90% $CH_3CN/H_2O$ with 0.1% TFA) to afford the product TFA-salt as a white foam. MS m/z=567.2 [M+H]+. Calc'd for $C_{32}H_{41}FN_3O_3S$: 566.3.

Example 437

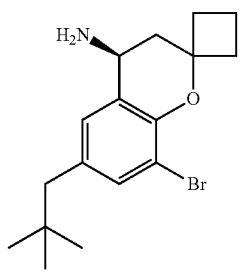 [SMILES: CC(C)(C)Cc1cc(Br)c2c(c1)[C@@H](N)CC1(CCC1)O2]

(S)-8-Bromo-2,2-spirocyclobutyl-6-neopentylchroman-4-amine

Step 1: 6-bromo-2,2-spirocyclobutyl-2,3-dihydrochromen-4-one

To a solution of 1-(5-bromo-2-hydroxyphenyl)ethanone (21.0 g, 98 mmol) in $CH_3CN$ (200 mL) is added pyrrolidine (24 ml, 293 mmol) and HOAc (17 ml, 293 mmol). The reaction was heated to 65° C. and stirred 9 h. The mixture was cooled to rt, concentrated in vacuo, then diluted with EtOAc (300 mL), and $H_2O$ (400 mL). The organic layer was extracted and the aqueous layer extracted with EtOAc (2×200 mL). The combined organic layers were washed with 10% $Na_2CO_3$ (200 mL), saturated NaCl (200 mL), dried ($Na_2SO_4$), and concentrated to give a brown oil. The crude product was purified by ISCO (330 g $SiO_2$, 0-20% $CH_2Cl_2$/Hexanes) to give 6-bromo-2,2-spirocyclobutyl-2,3-dihydrochromen-4-one as a yellow solid of 92% purity.

Step 2: (R)-6-bromo-2,2-spirocyclobutyl-3,4-dihydro-2H-chromen-4-ol (S)-2-Methyl-CBS-oxazaborolidine (3.72 ml, 3.72 mmol) and borane-dimethyl sulfide (11.3 ml, 119 mmol) were dissolved in toluene (500 mL) and cooled to −10° C. A solution of 6-bromo-2,2-spirocyclobutyl-2,3-dihydrochromen-4-one (19.85 g, 74.3 mmol) in toluene (60 mL) was added dropwise via syringe pump over 1 h. The mixture was stirred at −10° C. for an additional 20 min the reaction warmed to 0° C., and 2N HCl (100 mL) was added carefully. The phases were separated and the aqueous layer was extracted with EtOAc (3×150 mL). The combined organic layers were dried (MgSO$_4$) and concentrated to give a clear oil. The crude product was purified by filtration through a silica plug, and used without purification in the next step.

Step 3: (R)-(6-bromo-2,2-spirocyclobutyl-3,4-dihydro-2H-chromen-4-yloxy)(tert-butyl)dimethylsilane To a solution of (R)-6-bromo-2,2-spirocyclobutyl-3,4-dihydro-2H-chromen-4-ol (20.0 g, 74.3 mmol) in $CH_2Cl_2$ (300 mL) at rt is added TEA (15.5 ml, 111 mmol), then tert-butyldimethylsilyl triflate (17.1 ml, 74.3 mmol). The reaction is stirred at rt 45 min. The reaction is quenched with $H_2O$ (200 mL) and 1 N HCl (50 mL). The aqueous layer is extracted with EtOAc (2×200 mL) and the combined organic layers were dried (MgSO$_4$) and concentrated to give a purple oil. The crude product was purified by ISCO (330 g SiO$_2$, 0-10% EtOAc/Hexane) to give (R)-(6-bromo-2,2-spirocyclobutyl-3,4-dihydro-2H-chromen-4-yloxy)(tert-butyl)dimethylsilane as a yellow oil.

Step 4: (R)-tert-butyl(2,2-spirocyclobutyl-6-neopentyl-3,4-dihydro-2H-chromen-4-yloxy)dimethylsilane To a solution of (R)-(6-bromo-2,2-spirocyclobutyl-3,4-dihydro-2H-chromen-4-yloxy)(tert-butyl)dimethylsilane (10.0 g, 26 mmol), and PdCl$_2$(dppf)$_2$ (2 g, 3 mmol) in THF (100 ml) was added neopentylzinc(II) iodide (73 ml, 37 mmol). The reaction mixture was stirred at rt overnight and then heated at 65° C. 2 h. The reaction was cooled to rt and quenched with saturated NH$_4$Cl. The reaction was extracted with EtOAc (3×), washed with brine, dried (MgSO$_4$), and concentrated to give (R)-tert-butyl(2,2-spirocyclobutyl-6-neopentyl-3,4-dihydro-2H-chromen-4-yloxy)dimethylsilane as a dark brown oil which was used in the next step without purification.

Step 5: (R)-(8-bromo-2,2-spirocyclobutyl-6-neopentyl-3,4-dihydro-2H-chromen-4-yloxy)(tert-butyl)dimethylsilane A mixture of crude (R)-tert-butyl(2,2-spirocyclobutyl-6-neopentyl-3,4-dihydro-2H-chromen-4-yloxy)dimethylsilane (10 g, 27 mmol), sodium bromide (1.7 ml, 53 mmol), and Oxone monopersulfate compound (15 ml, 27 mmol) in acetone/H$_2$O (200 ml, 1:1) was stirred at rt 2 h. The reaction was quenched with aqueous sodium sulfite (4 eq., in 200 ml of H$_2$O) extracted with EtOAc (3×), dried (MgSO$_4$), and concentrated to give (R)-(8-bromo-2,2-spirocyclobutyl-6-neopentyl-3,4-dihydro-2H-chromen-4-yloxy)(tert-butyl)dimethylsilane as a dark brown oil which was used in the next step without purification.

Step 6: (R)-8-bromo-2,2-spirocyclobutyl-6-neopentyl-3,4-dihydro-2H-chromen-4-ol To a solution of (R)-(8-bromo-2,2-spirocyclobutyl-6-neopentyl-3,4-dihydro-2H-chromen-4-yloxy)(tert-butyl)dimethylsilane (12 g, 26 mmol) in THF (50 ml) was added n-Bu$_4$NF (50 mL, 1.0 M in THF, 50 mmol), and the mixture was stirred overnight at rt. To the reaction was added H$_2$O, and the reaction solution was extracted with EtOAc (3×), the organic layers were dried over MgSO$_4$, concentrated, and purified by ISCO (10% EtOAc/Hexanes) to give (R)-8-bromo-2,2-spirocyclobutyl-6-neopentyl-3,4-dihydro-2H-chromen-4-ol as a light yellow oil.

Step 7: (S)-4-azido-8-bromo-2,2-spirocyclobutyl-6-neopentyl-3,4-dihydro-2H-chromene To a solution of (R)-8-bromo-2,2-spirocyclobutyl-6-neopentyl-3,4-dihydro-2H-chromen-4-ol (6.65 g, 19.6 mmol) in CH$_2$Cl$_2$ (20 ml) at 0° C. was added diphenylphosphoryl azide (5.49 ml, 25.5 mmol) dropwise. After stirring 15 min., DBU (3.84 ml, 25.5 mmol) was added dropwise and the reaction stirred at rt 24 h. H$_2$O was added and the reaction was extracted with ether (3×). The combined organic layers were dried (MgSO$_4$) and concentrated to give (S)-4-azido-8-bromo-2,2-spirocyclobutyl-6-neopentyl-3,4-dihydro-2H-chromene as a brown oil which was used in the next step without purification.

Step 8: (S)-8-bromo-2,2-spirocyclobutyl-6-neopentyl-3,4-dihydro-2H-chromen-4-amine To a solution of (S)-4-azido-8-bromo-2,2-spirocyclobutyl-6-neopentyl-3,4-dihydro-2H-chromene (7.14 g, 20 mmol), and 5 N aqueous NaOH (6 ml, 29 mmol) in THF (50 ml) at 0° C. was added trimethylphosphine (3 ml, 1.0M in THF, 29 mmol). The reaction mixture was stirred 2 h at 0° C. The reaction was diluted with EtOAc, washed with H$_2$O, brine, and dried (MgSO$_4$). The filtrates were concentrated and purified by ISCO (2% MeOH/CH$_2$Cl$_2$) to give the title compound as a yellow oil.

Example 438

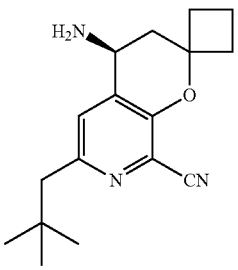 [SMILES: CC(C)(C)Cc1cc2c(c(C#N)n1)OC1(CCC1)C[C@@H]2N]

4-Amino-2,2-spirocyclobutyl-6-neopentyl-3,4-dihydro-2H-pyrano[2,3-c]pyridine-8-carbonitrile

Step 1: tert-Butyl allyl (8-cyano-2,2-spirocyclobutyl-6-neopentyl-3,4-dihydro-2H-pyrano[2,3-c]pyridin-4-yl)carbamate To a solution of (5)-tert-butyl allyl(8-chloro-2,2-spirocyclobutyl-6-neopentyl-3,4-dihydro-2H-pyrano[2,3-c]pyridin-4-yl)carbamate (862 mg, 1982 mmol) in DMF (10 mL) under Ar is added zinc(II) cyanide (465 mg, 3963 μmol) and Pd(PPh$_3$)$_4$ (458 mg, 396 mmol). The mixture was sealed and stirred at 95° C. 19 h. The reaction was filtered through a plug of celite [CH$_2$Cl$_2$ wash (2×20 mL)], the filtrates diluted with water (10 mL) and extracted with CH$_2$Cl$_2$ (3×20 mL). The combined organic layers were dried (Na$_2$SO$_4$), and concentrated to give a clear oil. The crude product contained DMF which was removed by dissolving in EtOAc (10 mL) and extraction with H$_2$O (2×10 mL). The organic layer was dried (Na$_2$SO$_4$) and concentrated. The crude product was purified by ISCO (0-25% EtOAc/Hexane) to give racemized tert-butyl allyl (8-cyano-2,2-spirocyclobutyl-6-neopentyl-3,4-dihydro-2H-pyrano[2,3-c]pyridin-4-yl)carbamate as a clear, colorless oil.

Step 2: 4-amino-2,2-spirocyclobutyl-6-neopentyl-3,4-dihydro-2H-pyrano[2,3-c]pyridine-8-carbonitrile To a 150 mL RBF with tert-butyl allyl(8-cyano-2,2-spirocyclobutyl-6-neopentyl-3,4-dihydro-2H-pyrano[2,3-c]pyridin-4-yl)carbamate (270 mg, 634 mmol) and CH$_2$Cl$_2$ (5 mL) is added TFA (587 μl, 7613 mmol) and the reaction was allowed to stir at rt 4 h. The reaction was diluted with CH$_2$Cl$_2$ (50 mL) washed with sat'd NaHCO$_3$ (2×100 mL) and the organic layer degassed with Argon for 10 minutes. The degassed solution was treated with 1,3-dimethylpyrimidine-2,4,6(1H,3H,5H)-trione (307 mg, 1967 mmol) and Pd(PPh$_3$)$_4$ (41.8 mg, 36.2 mmol) and stirred a rt for 18 h. The reaction mixture was washed with NaOH (1N, 2×25 mL), then HCl (2N, 2×30 mL). The acidic aqueous layer was then basified to pH 14 with NaOH (5N, 30 mL) and extracted with DCM (3×50 mL). The combined organic layers were dried (Na₂SO₄) and concentrated in vacuo to give the title compound as a clear, colorless oil.

Example 439

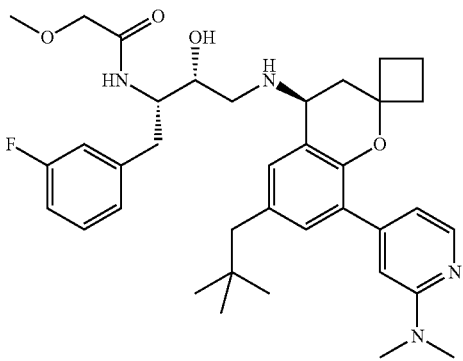 [SMILES: COCC(=O)N[C@@H](Cc1cccc(F)c1)[C@H](O)CN[C@H]1CC2(CCC2)Oc2c(-c3ccnc(N(C)C)c3)cc(CC(C)(C)C)cc21]

N-((1S,2R)-3-(((4S)-8-(2-(dimethylamino)-4-pyridinyl)-6-(2,2-dimethylpropyl)-3,4-dihydrospiro
[chromene-2,1'-cyclobutan]-4-yl) amino)-1-(3-fluorobenzyl)-2-hydroxypropyl)-2-methoxyacetamide
di-TFA salts A mixture of N-((1S,2R)-3-(((4S)-8-(2-chloro-4-pyridinyl)-6-(2,2-dimethylpropyl)-3,4-dihydrospiro[chromene-2,1'-cyclobutan]-4-yl)amino)-1-(3-fluorobenzyl)-2-hydroxypropyl)-2-methoxyacetamide (0.071 g, 0.09 mmol), tris(dibenzylideneacetone)dipalladium (0) (0.008 g, 0.009 mmol), 2-dicyclohexylphosphino-2'-(N,N-dimethylamino)biphenyl (0.03 g, 0.09 mmol), dimethylamine (2.0M solution in THF, 0.2 ml, 0.3 mmol), and lithium bis(trimethylsilyl)amide (1.0M solution in THF, 0.6 ml, 0.6 mmol) was heated at 140° C. in 30 min. The mixture was concentrated, taken up in H₂O, extracted with DCM (3×), dried over MgSO₄, concentrated and purified by chromatography (Shimadzu system) to give the expected product with 95% purity as di-TFA salt. MS (M+1): 633.3.

Example 440

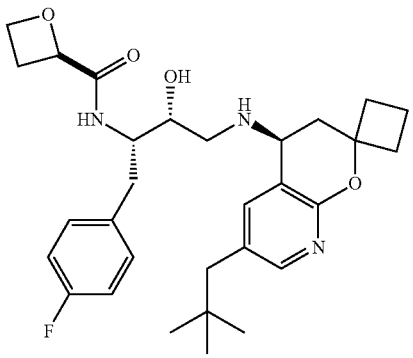

(2R)-N-((1S,2R)-3-(((4'S)-6'-(2,2-Dimethylpropyl)-
3',4'-dihydrospiro[cyclobutane-1,2'-pyrano[2,3-b]
pyridin]-4'-yl) amino)-1-((4-fluorophenyl)methyl)-2-
hydroxypropyl)-2-oxetanecarboxamide Step 1: (±)-Oxetane-2-carboxylic acid (±)-Oxetane-2-carboxylic acid was prepared from commercially available (±)-oxetan-2-ylmethanol by Jones oxidation, following the procedure described in WO 2005-JP3755 20050304.

Step 2: (2R)-N-((1S,2R)-3-((4'S)-6'-(2,2-Dimethylpropyl)-3',4'-dihydrospiro[cyclobutane-1,2'-pyrano
[2,3-b]pyridin]-4'-yl)amino)-1-((4-fluorophenyl)
methyl)-2-hydroxypropyl)-2-oxetanecarboxamide The title compound was prepared by coupling (±)-oxetane-2-carboxylic acid with (2R,3S)-3-amino-1-((S)-2,2-spirocyclobutyl-6-neopentylchroman-4-ylamino)-4-(4-fluorophenyl)butan-2-ol using conditions described in Example 42. MS m/z 526 (M+1).

Example 441

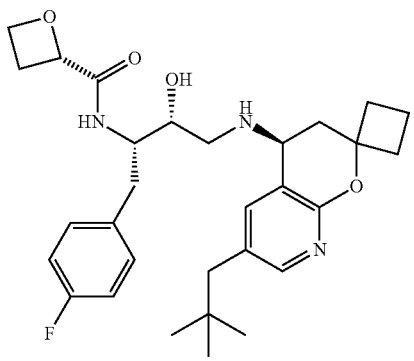

(2S)-N-((1S,2R)-3-(((4'S)-6'-(2,2-Dimethylpropyl)-
3',4'-dihydrospiro[cyclobutane-1,2'-pyrano[2,3-b]
pyridin]-4'-yl)amino)-1-((4-fluorophenylmethyl)-2-
hydroxypropyl)-2-oxetanecarboxamide The title compound was prepared by a method analogous to that described in Example 440, using the other product isolated from Example 440, step 1. MS m/z 526 (M+1).

The following examples in Table 2 were prepared by methods and Steps analogous to those described in Examples 41-51, 421-436 and 439-441 hereinabove. Provided also is the mass spectral data and additional data, including BACE enzyme and cell-based assay data (IC₅₀'s in uM), human and rat liver microsomal data and CYP enzyme inhibition data, related to each example where available.

TABLE 2

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 442 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-hydroxypropanamide | 514.3 | 0.013 | 0.016 | 117.333 | 150.333 | 0.75 | 6.75 |
| 443 | (2S)-N-((1S,2R)-1-(1,3-benzodioxol-5-ylmethyl)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxypropyl)-2-methoxypropanamide | 597.2 | 0.065 | 0.175 | 190 | 232 | | |
| 444 | (2R)-N-((1S,2R)-1-(1,3-benzodioxol-5-ylmethyl)-3-(((4'S)-8'-(dimethylamino)-6'-(2,2-dimethylpropyl)-3',4'-dihydrospiro[cyclobutane-1,2'-pyrano[2,3-c]pyridin]-4'-yl)amino)-2-hydroxypropyl)-2-methoxypropanamide | 597.2 | 0.298 | 0.777 | 399 | 662 | 7.5 | 9.4 |
| 445 | N-((1S,2R)-1-(1,3-benzodioxol-5-ylmethyl)-2-hydroxy-3-(((4'S)-6'-(3,3,3-trifluoropropyl)-3',4'-dihydrospiro[cyclobutane-1,2'-pyrano[2,3-b]pyridin]-4'-yl)amino)propyl)-2-methoxyacetamide | 566.3 | 0.754 | 0.621 | 24 | 121 | 0.2 | 4.1 |
| 446 | N-((1S)-2-(1,3-benzodioxol-5-yl)-1-((5R)-3-((4'S)-6'-((1R)-1-fluoro-2,2-dimethylpropyl)-3',4'-dihydrospiro[cyclobutane-1,2'-pyrano[2,3-b]pyridin]-4'-yl)-2-oxo-1,3-oxazolidin-5-yl)ethyl)-2-methoxyacetamide | 584.3 | 6.319 | 10.000 | 150 | 106 | 0.2 | 1.2 |
| 447 | N-((1S,2R)-1-(1,3-benzodioxol-5-ylmethyl)-3-(((4'S)-6'-((1R)-1-fluoro-2,2-dimethylpropyl)-3',4'-dihydrospiro[cyclobutane-1,2'-pyrano[2,3-b]pyridin]-4'-yl)amino)-2-methoxypropyl)-2-methoxyacetamide | 572.4 | 2.639 | 3.990 | | | 14 | 14 |
| 448 | N-((1S,2R)-3-(((4'S)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-1-(4-fluorobenzyl)-2-hydroxypropyl)-2-methoxyacetamide | 580.4 | 0.106 | 0.153 | | 79 | 0.1 | 1.8 |
| 449 | N-((1S,2R)-3-(((4'R)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-1-(4-fluorobenzyl)-2-hydroxypropyl)-2-methoxyacetamide | 580.4 | 2.904 | 2.966 | | 163 | 0.1 | 0.8 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 450 | (1S)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-3-oxocyclopentanecarboxamide | 578.1 | 0.150 | 0.183 | 76 | 170 | 0.4 | 8.6 |
| 451 | N-((1S,2R)-3-(((4'S)-6'-(2,2-dimethylpropyl)-8'-(1,3-thiazol-2-yl)-3',4'-dihydrospiro[cyclobutane-1,2'-pyrano[2,3-c]pyridin]-4'-yl)amino)-1-(4-fluorobenzyl)-2-hydroxypropyl)-2-methoxyacetamide | 597.3 | 0.019 | 0.271 | 248 | 682 | 0.6 | 9.4 |
| 452 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-fluoropropanamide | 542.3 | 0.016 | 0.039 | 45 | 174 | 0.3 | 2.1 |
| 453 | (2S)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)tetrahydro-2-furancarboxamide | 566.4 | 0.022 | 0.037 | 25 | 125 | 0.2 | 3.6 |
| 454 | (2R)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)tetrahydro-2-furancarboxamide | 566.4 | 0.020 | 0.027 | 36 | 166 | 0.3 | 1.8 |
| 455 | (2R)-N-((1S,2R)-1-(1,3-benzodioxol-5-ylmethyl)-3-(((4S)-2-(2,2-dimethylpropyl)-4,7-dihydro-5H-spiro[1-benzothiophene-6,1'-cyclobutan]-4-yl)amino)-2-hydroxypropyl)-2-methoxypropanamide | 557.4 | 0.049 | 0.231 | 211 | 201 | 2.6 | 5.5 |
| 456 | (2S)-N-((1S,2R)-1-(1,3-benzodioxol-5-ylmethyl)-3-(((4S)-2-(2,2-dimethylpropyl)-4,7-dihydro-5H-spiro[1-benzothiophene-6,1'-cyclobutan]-4-yl)amino)-2-hydroxypropyl)-2-methoxypropanamide | 557.3 | 0.359 | 0.723 | 74 | 97 | 0.9 | 3.1 |
| 457 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2,2-dimethyl-3-oxobutanamide | 580.2 | 0.792 | 0.905 | 44 | 90 | 0.1 | 2.4 |
| 458 | N-((1S,2R)-1-(3,5-difluorobenzyl)-2-hydroxy- | 583.4 | 0.017 | 0.012 | 25.5 | 188.5 | 0.1 | 0.9 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | 3-(((4S)-8-(1H-imidazol-1-yl)-6-(2-methylpropyl)-3,4-dihydrospiro[chromene-2,1'-cyclobutan]-4-yl)amino)propyl)-2-methoxyacetamide | | | | | | | |
| 459 | (2R)-N-((1S,2R)-1-(3,5-difluorobenzyl)-2-hydroxy-3-(((4S)-6-(2-methylpropyl)-8-(1,3-thiazol-2-yl)-3,4-dihydrospiro[chromene-2,1'-cyclobutan]-4-yl)amino)propyl)-2-methoxypropanamide | 614.3 | 0.004 | 0.046 | 399 | 399 | 0.4 | 10.2 |
| 460 | N-((1S,2R)-1-(3,5-difluorobenzyl)-2-hydroxy-3-(((4S)-6-(2-methylpropyl)-8-(1,3-thiazol-2-yl)-3,4-dihydrospiro[chromene-2,1'-cyclobutan]-4-yl)amino)propyl)-2-methoxyacetamide | 600.3 | 0.001 | 0.028 | 775 | 775 | 0.8 | 3.9 |
| 461 | (2R)-N-((1S,2R)-1-(3,5-difluorobenzyl)-2-hydroxy-3-(((4S)-8-(1H-imidazol-1-yl)-6-(2-methylpropyl)-3,4-dihydrospiro[chromene-2,1'-cyclobutan]-4-yl)amino)propyl)-2-methoxypropanamide | 597.4 | 0.026 | 0.028 | 28 | 126 | 0 | 2.2 |
| 462 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((3R)-tetrahydro-3-furanylmethyl)propyl)-2-(methyloxy)acetamide | 490.3 | 0.432 | 0.649 | 107 | 68 | 8.5 | 16.9 |
| 463 | N-((1S,2R)-1-(3,5-difluorobenzyl)-3-(((4S)-6-(2,2-dimethylpropyl)-8-(1,3-thiazol-2-yl)-3,4-dihydrospiro[chromene-2,1'-cyclobutan]-4-yl)amino)-2-hydroxypropyl)-2-methoxyacetamide | 614.3 | 0.003 | 0.048 | 682 | 662 | 1.1 | 7.2 |
| 464 | N-((1S,2R)-3-(((4S)-8-bromo-6-(2,2-dimethylpropyl)-3,4-dihydrospiro[chromene-2,1'-cyclobutan]-4-yl)amino)-1-((3,5-difluorophenyl)methyl)-2-hydroxypropyl)-2-(methyloxy)acetamide | 610.2 | 0.004 | 0.091 | 463 | 364 | 1.5 | 11.5 |
| 465 | N-((1S,2R)-1-(3,5-difluorobenzyl)-3-(((4'S)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-2-hydroxypropyl)acetamide | 568.4 | 0.019 | 0.032 | 18.5 | 51.5 | 0.1 | 1 |
| 466 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)-3-oxobutanamide | 526.7 | 0.004 | 0.008 | 296 | 165 | 1.2 | 8.9 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 467 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)-2,2-dimethyl-3-oxobutanamide | 553.7 | 0.063 | 0.209 | 399 | 292 | 0.4 | 7.3 |
| 468 | N-((1S,2R)-3-(((4'S)-6'-(2,2-dimethylpropyl)-7'-methyl-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)acetamide | 528.4 | 0.097 | 0.108 | 736 | 662 | 0.5 | 9.6 |
| 469 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((3S)-tetrahydro-3-furanylmethyl)propyl)acetamide | 460.2 | 0.137 | 0.162 | 60 | 35 | 16.4 | 27 |
| 470 | N-((1S,2R)-1-((3-cyanophenyl)methyl)-3-((((4'S)-6'-(2,2-dimethylpropyl)-3,3-difluoro-3',4'-dihydrospiro[cyclobutane-1,2'-pyrano[2,3-b]pyridin]-4'-yl)amino)-2-hydroxypropyl)-2-(methyloxy)acetamide | | 0.004 | 0.014 | 579 | 560 | 1.1 | 5.8 |
| 471 | (2R)-N-((1S,2R)-1-((3-cyanophenyl)methyl)-3-((((4'S)-6'-(2,2-dimethylpropyl)-3,3-difluoro-3',4'-dihydrospiro[cyclobutane-1,2'-pyrano[2,3-b]pyridin]-4'-yl)amino)-2-hydroxypropyl)-2-(methyloxy)propanamide | | 0.004 | 0.012 | 569 | 536 | 1.1 | 10.3 |
| 472 | (2R)-N-((1S,2R)-1-((3-cyanophenyl)methyl)-3-((((4'S)-6'-(2,2-dimethylpropyl)-3,3-difluoro-3',4'-dihydrospiro[cyclobutane-1,2'-pyrano[2,3-b]pyridin]-4'-yl)amino)-2-hydroxypropyl)tetrahydro-2-furancarboxamide | | 0.005 | 0.015 | 736 | 775 | 0.8 | 7.1 |
| 473 | N-((1S,2R)-1-((3-cyanophenyl)methyl)-3-((((4'S)-6'-(2,2-dimethylpropyl)-3,3-difluoro-3',4'-dihydrospiro[cyclobutane-1,2'-pyrano[2,3-b]pyridin]-4'-yl)amino)-2-hydroxypropyl)-3-fluoro-2-pyridinecarboxamide | | 0.009 | 0.063 | 590 | 775 | 0.6 | 2.4 |
| 474 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-(methyloxy)-4-pyridinyl)methyl)propyl)-2-(methyloxy)acetamide | 527.3 | 0.013 | 0.022 | 172 | 174 | 2 | 6.5 |
| 475 | N-((1S,2R)-1-(3,5-difluorobenzyl)-3-(((4S)-6- | 596.4 | 0.018 | 0.008 | 26 | 128.5 | 0.05 | 1.75 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | (2,2-dimethylpropyl)-8-(1H-imidazol-1-yl)-3,4-dihydrospiro[chromene-2,1'-cyclobutan]-4-yl)amino)-2-hydroxypropyl)-2-methoxyacetamide | | | | | | | |
| 476 | (2R)-N-((1S,2R)-1-(3,5-difluorobenzyl)-2-hydroxy-3-(((4S)-8-(1H-imidazol-5-yl)-6-(2-methylpropyl)-3,4-dihydrospiro[chromene-2,1'-cyclobutan]-4-yl)amino)propyl)-2-methoxypropanamide | 597.4 | 0.028 | 0.005 | 329 | 408 | 0.6 | 12.3 |
| 477 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2,2-difluoropropanamide | 534.2 | 0.012 | 0.104 | 118 | 337 | 0.3 | 3.2 |
| 478 | N-((1S,2R)-1-(4-fluorobenzyl)-2-hydroxy-3-(((4S)-8-(1H-imidazol-1-yl)-6-(2-methylpropyl)-3,4-dihydrospiro[chromene-2,1'-cyclobutan]-4-yl)amino)propyl)-2-methoxyacetamide | 565.4 | 0.056 | 0.068 | 24 | 157 | 0.1 | 2.2 |
| 479 | N-((1S,2R)-1-((3,5-difluorophenyl)methyl)-3-(((4S)-6-(2,2-dimethylpropyl)-8-(methylamino)-3,4-dihydrospiro[chromene-2,1'-cyclobutan]-4-yl)amino)-2-hydroxypropyl)-2-(methyloxy)acetamide | 560.3 | 0.011 | 0.017 | 167 | 329 | 1.8 | 6.4 |
| 480 | N-((1S,2R)-1-(3,5-difluorobenzyl)-2-hydroxy-3-(((4S)-8-(1H-imidazol-5-yl)-6-(2-methylpropyl)-3,4-dihydrospiro[chromene-2,1'-cyclobutan]-4-yl)amino)propyl)-2-methoxyacetamide | 583.2 | 0.023 | 0.006 | 272 | 405 | 0.5 | 10.1 |
| 481 | N-((1S,2R)-1-(3,5-difluorobenzyl)-3-(((4'S)-6'-(2,2-dimethylpropyl)-8'-(1,3-thiazol-5-yl)-3',4'-dihydrospiro[cyclobutane-1,2'-pyrano[2,3-c]pyridin]-4'-yl)amino)-2-hydroxypropyl)acetamide | 585.2 | 0.004 | 0.123 | 155 | 177 | 0.2 | 7.9 |
| 482 | (2R)-N-((1S,2R)-1-(4-fluorobenzyl)-2-hydroxy-3-(((4S)-8-(1H-imidazol-1-yl)-6-(2-methylpropyl)-3,4-dihydrospiro[chromene-2,1'-cyclobutan]-4-yl)amino)propyl)-2-methoxypropanamide | 579.4 | 0.150 | 0.422 | 27 | 194 | 0.1 | 3.6 |
| 483 | (2S)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-fluoropropanamide | 542.4 | 0.018 | 0.049 | 83 | 308 | 0.1 | 3.8 |

TABLE 2-continued

| Ex. No | IUPAC NAME | Observed MS | BACE1 FRET assay (uM) | HEK cell assay (uM) | HLM (uL/min/ mg) | RLM (uL/min/ mg) | 3A4 IC50 (uM) | 2D6 IC50 (uM) |
|---|---|---|---|---|---|---|---|---|
| 484 | (2R)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-fluoropropanamide | 542.4 | 0.029 | 0.056 | 42 | 114 | 0.2 | 2.3 |
| 485 | N-((1S,2R)-1-(1,3-benzodioxol-5-ylmethyl)-3-(((4'S)-6'-(2,2-dimethylpropyl)-7'-fluoro-3',4'-dihydrospiro[cyclobutane-1,2'-pyrano[2,3-b]pyridin]-4'-yl)amino)-2-hydroxypropyl)-2-methoxyacetamide | 558.4 | 0.120 | 0.378 | 43 | 106 | 0.1 | 1.7 |
| 486 | N-((1S,2R)-1-(3,5-difluorobenzyl)-3-(((4S)-6-(2,2-dimethylpropyl)-8-(1,3-thiazol-5-yl)-3,4-dihydrospiro[chromene-2,1'-cyclobutan]-4-yl)amino)-2-hydroxypropyl)-2-methoxyacetamide | 613.4 | 0.004 | 0.033 | 408 | 380 | 0.2 | 12.8 |
| 487 | N-((1S,2R)-1-((3,5-difluorophenyl)methyl)-3-(((4S)-6-(2,2-dimethylpropyl)-8-(2-fluorophenyl)-3,4-dihydrospiro[chromene-2,1'-cyclobutan]-4-yl)amino)-2-hydroxypropyl)-2-(methyloxy)acetamide | 625.3 | 0.015 | 0.118 | 394 | 387 | 1.6 | 21.4 |
| 488 | N-((1S,2R)-1-(3,5-difluorobenzyl)-3-(((4S)-6-(2,2-dimethylpropyl)-8-(4-pyridinyl)-3,4-dihydrospiro[chromene-2,1'-cyclobutan]-4-yl)amino)-2-hydroxypropyl)-2-methoxyacetamide | 607.4 | 0.009 | 0.010 | 31 | 82 | 0.1 | 1.6 |
| 489 | N-((1S,2R)-1-(3,5-difluorobenzyl)-3-(((4S)-6-(2,2-dimethylpropyl)-8-(3-pyridinyl)-3,4-dihydrospiro[chromene-2,1'-cyclobutan]-4-yl)amino)-2-hydroxypropyl)-2-methoxyacetamide | 607.4 | 0.007 | 0.020 | 399 | 775 | 0.4 | 3.9 |
| 490 | N-((1S,2R)-1-(3,5-difluorobenzyl)-2-hydroxy-3-(((4S)-6-(2-methylpropyl)-8-(1,3-thiazol-5-yl)-3,4-dihydrospiro[chromene-2,1'-cyclobutan]-4-yl)amino)propyl)-2-methoxyacetamide | 600.3 | 0.003 | 0.029 | 344 | 249 | 0.2 | 7.5 |
| 491 | (2R)-N-((1S,2R)-1-(3,5-difluorobenzyl)-2-hydroxy-3-(((4S)-6-(2-methylpropyl)-8-(1,3-thiazol-5-yl)-3,4-dihydrospiro[chromene-2,1'-cyclobutan]-4-yl)amino)propyl)-2-methoxypropanamide | 614.3 | 0.004 | 0.036 | 345 | 285 | 0.2 | 6.2 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 421 | N-((1S,2R)-3-(((4'S)-6'-(2,2-dimethylpropyl)-8'-(4-morpholinyl)-3',4'-dihydrospiro[cyclobutane-1,2'-pyrano[2,3-c]pyridin]-4'-yl)amino)-1-((4-fluorophenyl)methyl)-2-hydroxypropyl)acetamide | 569.2 | 0.134 | 0.054 | 211 | 151 | 1.3 | 3.6 |
| 492 | N-((1S,2R)-3-(((4'R)-8'-cyano-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)-2-(methyloxy)acetamide | 539.4 | 5.043 | 0.462 | 94 | 190 | 0.4 | 8.2 |
| 493 | N-((1S,2R)-3-(((4'S)-8'-cyano-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)-2-(methyloxy)acetamide | 539.4 | 0.044 | 0.471 | 95 | 221 | 0.6 | 11.6 |
| 494 | N-((1S,2R)-1-(3,5-difluorobenzyl)-3-(((4'S)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-2-hydroxypropyl)-2-methoxyacetamide | 598.4 | 0.020 | 0.072 | 30 | 63 | 0.2 | 1.2 |
| 495 | (2R)-N-((1S,2R)-1-(3,5-difluorobenzyl)-3-(((4'S)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-2-hydroxypropyl)-2-methoxypropanamide | 612.4 | 0.020 | 0.080 | 41 | 62 | 0.1 | 2 |
| 496 | N-((1S,2R)-3-(((4'S)-6'-(2-cyano-2-methylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)acetamide | 524.8 | 0.024 | 0.102 | 89 | 139 | 4.7 | 27 |
| 497 | N-((1S,2R)-3-(((4'S)-8'-(cyclobutylamino)-6'-(2,2-dimethylpropyl)-3',4'-dihydrospiro[cyclobutane-1,2'-pyrano[2,3-c]pyridin]-4'-yl)amino)-1-((4-fluorophenyl)methyl)-2-hydroxypropyl)acetamide | 553.4 | 0.077 | 0.100 | 157 | 172 | 3.3 | 2.6 |
| 498 | N-((1S,2R)-1-(1,3-benzodioxol-5-ylmethyl)-3-(((4S)-6-((2R)-2-fluoropropyl)-3,4-dihydrospiro[chromene-2,1'-cyclobutan]-4-yl)amino)-2-hydroxypropyl)-2-methoxyacetamide | 529.1 | 0.268 | 0.377 | 119 | 206 | 0.5 | 0.7 |
| 499 | (2S)-N-((1S,2R)-1-(1,3-benzodioxol-5-ylmethyl)-3-(((4S)-6-((2R)-2-fluoropropyl)-3,4-dihydrospiro[chromene- | 543.1 | 1.364 | 0.473 | 156 | 213 | 0.3 | 0.7 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | 2,1'-cyclobutan]-4-yl)amino)-2-hydroxypropyl)-2-methoxypropanamide | | | | | | | |
| 500 | N-((1S,2R)-3-(((4'R)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-1-(3-fluorobenzyl)-2-hydroxypropyl)acetamide | 550.4 | 1.741 | 1.948 | 50 | 286 | 0.1 | 1.7 |
| 501 | (2R)-N-((1S,2R)-3-(((4'R)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-1-(3-fluorobenzyl)-2-hydroxypropyl)-2-methoxypropanamide | 594.4 | 5.304 | >10.000000 | 86 | 175 | 0.1 | 2.8 |
| 502 | N-((1S,2R)-3-(((4'R)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-1-(3-fluorobenzyl)-2-hydroxypropyl)-2-methoxyacetamide | 580.4 | 1.995 | 1.852 | 54 | 158 | 0.1 | 0.8 |
| 503 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-oxetanecarboxamide | 552.4 | 0.021 | 0.017 | 23 | 130 | 0.2 | 3.3 |
| 504 | N-((1S,2R)-3-(((4'S)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-1-(3-fluorobenzyl)-2-hydroxypropyl)-2-methoxyacetamide | 580.4 | 0.014 | 0.028 | 16 | 87 | 0.1 | 2.3 |
| 505 | N-((1S,2R)-3-(((4S)-6-(2,2-dimethylpropyl)-8-(1H-imidazol-1-yl)-3,4-dihydrospiro[chromene-2,1'-cyclobutan]-4-yl)amino)-1-(3-fluorobenzyl)-2-hydroxypropyl)-2-methoxyacetamide | 578.4 | 0.019 | 0.006 | 51.5 | 153 | 0.1 | 1.9 |
| 506 | N-((1S,2R)-3-(((4'S)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-1-(3-fluorobenzyl)-2-hydroxypropyl)acetamide | 550.4 | 0.021 | 0.020 | 14 | 61 | 0.1 | 2.2 |
| 507 | (2R)-N-((1S,2R)-3-(((4'S)-6'-(2,2-dimethylpropyl)-8'-(1H-imidazol-1-yl)-3',4'-dihydrospiro[cyclobutane-1,2'-pyrano[2,3-c]pyridin]-4'-yl)amino)-1-(3-fluorobenzyl)-2-hydroxypropyl)-2-methoxypropanamide | 594.4 | 0.022 | 0.057 | 14 | 95 | 0.1 | 1.9 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 508 | N-((1S,2R)-1-(3,5-difluorobenzyl)-3-(((4'S)-6'-(2,2-dimethylpropyl)-8'-(1H-imidazol-5-yl)-3',4'-dihydrospiro[cyclobutane-1,2'-pyrano[2,3-c]pyridin]-4'-yl)amino)-2-hydroxypropyl)-2-methoxyacetamide | 598.4 | 0.024 | 0.005 | 17 | 43 | 0.1 | 1.2 |
| 509 | N-((1S,2R)-1-(3,5-difluorobenzyl)-3-(((4'R)-6'-(2,2-dimethylpropyl)-8'-(1H-imidazol-5-yl)-3',4'-dihydrospiro[cyclobutane-1,2'-pyrano[2,3-c]pyridin]-4'-yl)amino)-2-hydroxypropyl)-2-methoxyacetamide | 598.4 | 0.487 | 0.077 | 74 | 70 | 0.1 | 2.3 |
| 510 | N-((1S,2R)-1-(3,5-difluorobenzyl)-3-(((4'S)-6'-(2,2-dimethylpropyl)-8'-(1,3-thiazol-4-yl)-3',4'-dihydrospiro[cyclobutane-1,2'-pyrano[2,3-c]pyridin]-4'-yl)amino)-2-hydroxypropyl)acetamide | 585.4 | 0.008 | 0.017 | 380 | 358 | 1.1 | 10.3 |
| 511 | (2R)-N-((1S,2R)-3-(((4'S)-6'-(2-cyano-2-methylpropyl)-3',4'-dihydrospiro[cyclobutane-1,2'-pyrano[2,3-b]pyridin]-4'-yl)amino)-1-((3,5-difluorophenyl)methyl)-2-hydroxypropyl)-2-(methyloxy)propanamide | 557.2 | 0.007 | 0.011 | 382 | 203 | 2.4 | 14.5 |
| 512 | N-((1S,2R)-1-((3-fluorophenyl)methyl)-3-(((4S)-6-((2S)-2-fluoropropyl)-3,4-dihydrospiro[chromene-2,1'-cyclobutan]-4-yl)amino)-2-hydroxypropyl)-2-(methyloxy)acetamide | 503.2 | 0.028 | 0.061 | 614 | 829 | 5.7 | 0.5 |
| 513 | N-((1S,2R)-1-(4-fluorobenzyl)-2-hydroxy-3-(((4S)-8-(1H-imidazol-5-yl)-6-(2-methylpropyl)-3,4-dihydrospiro[chromene-2,1'-cyclobutan]-4-yl)amino)propyl)-2-methoxyacetamide | 565.4 | 0.088 | 0.013 | 143 | 82 | 0.2 | 2.5 |
| 514 | N-((1S,2R)-3-(((4S)-8-bromo-6-(2-methylpropyl)-3,4-dihydrospiro[chromene-2,1'-cyclobutan]-4-yl)amino)-1-((3-fluorophenyl)methyl)-2-hydroxypropyl)-2-(methyloxy)acetamide | 577.3, 579.3 | 0.003 | 0.128 | 682 | 560 | 1.5 | 6 |
| 515 | (2R)-N-((1S,2R)-3-(((4S)-8-bromo-6-(2-methylpropyl)-3,4-dihydrospiro[chromene-2,1'-cyclobutan]-4-yl)amino)-1-((3-fluorophenyl)methyl)-2-hydroxypropyl)-2-(methyloxy)propanamide | 591.3, 593.3 | 0.003 | 0.125 | 775 | 399 | 1.3 | 9.4 |
| 516 | (2R)-N-((1S,2R)-1-(1,3-benzodioxol-5-ylmethyl)-3-(((4'S)-6'-(2,2-dimethylpropyl)-3',4'-dihydrospiro[cyclobutane- | 552 | 0.018 | 0.020 | 31 | 94 | 0.1 | 3.3 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | 1,2'-pyrano[2,3-b]pyridin]-4'-yl)amino)-2-hydroxypropyl)-2-oxetanecarboxamide | | | | | | | |
| 517 | N-((1S,2R)-1-(1,3-benzodioxol-5-ylmethyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)acetamide | 522.2 | 0.178 | 0.202 | 32 | 51 | 0.5 | 7.8 |
| 518 | N-((1S,2R)-1-(1,3-benzodioxol-5-ylmethyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)-2-methoxyacetamide | 552.3 | 0.131 | 0.340 | 26 | 82 | 0.3 | 2.7 |
| 519 | (2R)-N-((1S,2R)-1-(1,3-benzodioxol-5-ylmethyl)-2-hydroxy-3-(((4'S)-6'-(2,2,2-trifluoroethyl)-3',4'-dihydrospiro[cyclobutane-1,2'-pyrano[2,3-b]pyridin]-4'-yl)amino)propyl)-2-methoxypropanamide | 566.3 | 0.255 | 0.810 | 33 | 71 | 0.3 | 7.4 |
| 440 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-oxetanecarboxamide | 526 | 0.016 | 0.035 | 209 | 242 | 0.7 | 8.2 |
| 520 | N-((1S,2R)-1-(3-fluorobenzyl)-2-hydroxy-3-(((4S)-8-(1H-imidazol-1-yl)-6-(2-methylpropyl)-3,4-dihydrospiro[chromene-2,1'-cyclobutan]-4-yl)amino)propyl)-2-methoxyacetamide | 565.4 | 0.018 | 0.009 | 32 | 144 | 0.1 | 0.9 |
| 521 | (2R)-N-((1S,2R)-1-(3-fluorobenzyl)-2-hydroxy-3-(((4S)-8-(1H-imidazol-1-yl)-6-(2-methylpropyl)-3,4-dihydrospiro[chromene-2,1'-cyclobutan]-4-yl)amino)propyl)-2-methoxypropanamide | 579.4 | 0.019 | 0.015 | 27 | 142 | 0.1 | 1.9 |
| 522 | (2R)-N-((1S,2R)-3-(((4S)-6-(2,2-dimethylpropyl)-8-(1H-imidazol-1-yl)-3,4-dihydrospiro[chromene-2,1'-cyclobutan]-4-yl)amino)-1-(3-fluorobenzyl)-2-hydroxypropyl)-2-methoxypropanamide | 592.4 | 0.044 | 0.013 | 43 | 141 | 0.1 | 3.1 |
| 523 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2,2-dimethoxyacetamide | 570.4 | 0.019 | 0.033 | 37 | 94 | 0.1 | 5.4 |
| 524 | (2R)-N-((1S,2R)-1-(3-fluorobenzyl)-2-hydroxy-3-(((4S)-6-(2-methylpropyl)-8-(1,3-thiazol-4-yl)-3,4- | 596.3 | 0.008 | 0.065 | 492 | 472 | 0.5 | 7.5 |

TABLE 2-continued

| Ex. No | IUPAC NAME | Observed MS | BACE1 FRET assay (uM) | HEK cell assay (uM) | HLM (uL/min/ mg) | RLM (uL/min/ mg) | 3A4 IC50 (uM) | 2D6 IC50 (uM) |
|---|---|---|---|---|---|---|---|---|
| | dihydrospiro[chromene-2,1'-cyclobutan]-4-yl)amino)propyl)-2-methoxypropanamide | | | | | | | |
| 525 | (2S)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-oxetanecarboxamide | 552.3 | 0.021 | 0.019 | 32 | 101 | 0.2 | 3.1 |
| 526 | N-((1S,2R)-1-(3-fluorobenzyl)-2-hydroxy-3-(((4S)-6-(2-methylpropyl)-8-(1,3-thiazol-4-yl)-3,4-dihydrospiro[chromene-2,1'-cyclobutan]-4-yl)amino)propyl)-2-methoxyacetamide | 582.3 | 0.006 | 0.053 | 351 | 503 | 0.6 | 7.3 |
| 527 | (2R)-N-((1S,2R)-3-(((4'S)-6'-(2,2-dimethylpropyl)-8'-(4-pyridinyl)-3',4'-dihydrospiro[cyclobutane-1,2'-pyrano[2,3-c]pyridin]-4'-yl)amino)-1-(4-fluorobenzyl)-2-hydroxypropyl)-2-methoxypropanamide | 605.2 | 0.222 | 1.953 | 33 | 108 | 0.1 | 0.6 |
| 528 | N-((1S,2R)-1-(3,5-difluorobenzyl)-3-(((4'S)-6'-(2,2-dimethylpropyl)-8'-(4-pyridinyl)-3',4'-dihydrospiro[cyclobutane-1,2'-pyrano[2,3-c]pyridin]-4'-yl)amino)-2-hydroxypropyl)-2-methoxyacetamide | 609.2 | 0.010 | 0.023 | 19 | 72 | 0.1 | 1.3 |
| 529 | N-((1S,2R)-3-(((4'S)-6'-(2,2-dimethylpropyl)-8'-(1H-imidazol-4-yl)-3',4'-dihydrospiro[cyclobutane-1,2'-pyrano[2,3-c]pyridin]-4'-yl)amino)-1-(4-fluorobenzyl)-2-hydroxypropyl)-2-methoxyacetamide | 580.4 | 0.023 | 0.012 | 37 | 40 | 0.1 | 0.7 |
| 530 | N-((1S,2R)-1-(3-fluorobenzyl)-3-(((4S)-6-(2-fluoro-2-methylpropyl)-8-(4-pyridinyl)-3,4-dihydrospiro[chromene-2,1'-cyclobutan]-4-yl)amino)-2-hydroxypropyl)-2-methoxyacetamide | 594.4 | 0.015 | 0.010 | | | | |
| 531 | N-((1S,2R)-3-(((4'S)-6'-(2,2-dimethylpropyl)-8'-(4-pyridinyl)-3',4'-dihydrospiro[cyclobutane-1,2'-pyrano[2,3-c]pyridin]-4'-yl)amino)-1-(3-fluorobenzyl)-2-hydroxypropyl)-2-methoxyacetamide | 591.4 | 0.013 | 0.029 | 40 | 159 | 0.2 | 1.3 |
| 532 | N-((1S,2R)-3-(((4'S)-6'-(2,2-dimethylpropyl)-8'-(4-pyridinyl)-3',4'-dihydrospiro[cyclobutane-1,2'-pyrano[2,3-c]pyridin]-4'-yl)amino)-1-(3-fluorobenzyl)-2-hydroxypropyl)acetamide | 561.4 | 0.012 | 0.022 | 40 | 91 | 0.2 | 2.6 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 533 | (2R)-N-((1S,2R)-3-(((4'S)-6'-(2,2-dimethylpropyl)-8'-(4-pyridinyl)-3',4'-dihydrospiro[cyclobutane-1,2'-pyrano[2,3-c]pyridin]-4'-yl)amino)-1-(3-fluorobenzyl)-2-hydroxypropyl)-2-methoxypropanamide | 605.4 | 0.013 | 0.044 | 29 | 163 | 0 | 1.4 |
| 534 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(4-pyridinylmethyl)propyl)-2-(methyloxy)propanamide | 511.2 | 0.023 | 0.014 | 178 | 113 | 0.5 | 3.6 |
| 535 | N-((1S,2R)-3-(((4S)-6-(2,2-dimethylpropyl)-8-(4-pyridinyl)-3,4-dihydrospiro[chromene-2,1'-cyclobutan]-4-yl)amino)-1-(3-fluorobenzyl)-2-hydroxypropyl)-2-methoxyacetamide | 589.4 | 0.009 | 0.006 | 49 | 79 | 0.1 | 2.5 |
| 536 | N-((1S,2R)-3-(((4S)-6-(2-chloro-2-methylpropyl)-8-(4-pyridinyl)-3,4-dihydrospiro[chromene-2,1'-cyclobutan]-4-yl)amino)-1-(3-fluorobenzyl)-2-hydroxypropyl)-2-methoxyacetamide | 610.3 | 0.019 | 0.011 | | | 27 | 27 |
| 537 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((2-(methyloxy)-4-pyridinyl)methyl)propyl)-2-(methyloxy)propanamide | 541.3 | 0.020 | 0.028 | 194 | 125 | 1 | 3 |
| 538 | N-((1S,2R)-1-(4-fluorobenzyl)-3-(((4S)-6-(2-fluoro-2-methylpropyl)-8-(4-pyridinyl)-3,4-dihydrospiro[chromene-2,1'-cyclobutan]-4-yl)amino)-2-hydroxypropyl)-2-methoxyacetamide | 594.2 | 0.047 | 0.043 | | | | |
| 539 | (2R)-N-((1S,2R)-1-(1,3-benzodioxol-5-ylmethyl)-3-(((3'S,4'R)-6'-(2,2-dimethylpropyl)-3'-fluoro-3',4'-dihydrospiro[cyclobutane-1,2'-pyrano[2,3-b]pyridin]-4'-yl)amino)-2-hydroxypropyl)-2-methoxypropanamide | 572 | 4.767 | 0.147 | 61 | 161 | 0.1 | 6.5 |
| 540 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)formamide | 470 | 0.014 | 0.074 | 264 | 347 | 1.2 | 2.3 |
| 541 | N-((1S,2R)-3-(((4'S)-6'-(2,2-dimethylpropyl)-8'-(4-pyridinyl)-3',4'-dihydrospiro[cyclobutane- | 573.4 | 0.020 | 0.055 | 31 | 192 | 0.1 | 2.1 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | 1,2'-pyrano[2,3-c]pyridin]-4'-yl)amino)-2-hydroxy-1-(phenylmethyl)propyl)-2-(methyloxy)acetamide | | | | | | | |
| 542 | N-((1S,2R)-1-benzyl-3-(((4'S)-6'-(2,2-dimethylpropyl)-8'-(4-pyridinyl)-3',4'-dihydrospiro[cyclobutane-1,2'-pyrano[2,3-c]pyridin]-4'-yl)amino)-2-hydroxypropyl)acetamide | 543.4 | 0.024 | 0.103 | 36 | 193 | 0.2 | 27 |
| 543 | (2R)-N-((1S,2R)-1-benzyl-3-(((4'S)-6'-(2,2-dimethylpropyl)-8'-(4-pyridinyl)-3',4'-dihydrospiro[cyclobutane-1,2'-pyrano[2,3-c]pyridin]-4'-yl)amino)-2-hydroxypropyl)-2-methoxypropanamide | 587.4 | 0.037 | 0.255 | 41 | 242 | 0.1 | 2.6 |
| 544 | N-((1S,2R)-3-(((4S)-8-bromo-6-(2-methylpropyl)-3,4-dihydrospiro[chromene-2,1'-cyclobutan]-4-yl)amino)-2-hydroxy-1-(phenylmethyl)propyl)-2-(methyloxy)acetamide | 559.2, 561.2 | 0.005 | 0.937 | 399 | 662 | 1.8 | 7 |
| 545 | (2R)-N-((1S,2R)-3-(((4S)-8-bromo-6-(2-methylpropyl)-3,4-dihydrospiro[chromene-2,1'-cyclobutan]-4-yl)amino)-2-hydroxy-1-(phenylmethyl)propyl)-2-(methyloxy)propanamide | 573.3, 575.3 | 0.007 | 1.485 | 775 | 775 | 1.1 | 8.2 |
| 546 | N-((1S,2R)-1-benzyl-2-hydroxy-3-(((4S)-8-(1H-imidazol-1-yl)-6-(2-methylpropyl)-3,4-dihydrospiro[chromene-2,1'-cyclobutan]-4-yl)amino)propyl)-2-methoxyacetamide | 547.4 | 0.025 | 0.033 | 75 | 267 | 0.1 | 3.8 |
| 547 | (2R)-N-((1S,2R)-1-benzyl-2-hydroxy-3-(((4S)-8-(1H-imidazol-1-yl)-6-(2-methylpropyl)-3,4-dihydrospiro[chromene-2,1'-cyclobutan]-4-yl)amino)propyl)-2-methoxypropanamide | 561.4 | 0.042 | 0.073 | 53 | 260 | 0.1 | 4.4 |
| 548 | (2S)-N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)tetrahydro-2-furancarboxamide | 552.3 | 0.074 | 0.623 | 57 | 184 | 0.3 | 3.7 |
| 549 | N-((1S,2R)-3-(((4'S)-6'-(2,2-dimethylpropyl)-8'-(4-pyridinyl)-3',4'-dihydrospiro[cyclobutane-1,2'-pyrano[2,3-c]pyridin]-4'-yl)amino)-1-(4-fluorobenzyl)-2-hydroxypropyl)-2-methoxyacetamide | 591.4 | 0.071 | 0.296 | 38 | 122 | 0.1 | 2 |
| 550 | N-((1S,2R)-3-(((4S)-6-chloro-8-(4-pyridinyl)-3,4-dihydrospiro[chromene-2,1'-cyclobutan]-4- | 554 | 0.042 | 0.474 | 338 | 315 | 0.2 | 0.5 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | yl)amino)-1-(3-fluorobenzyl)-2-hydroxypropyl)-2-methoxyacetamide | | | | | | | |
| 551 | (2R)-N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)tetrahydro-2-furancarboxamide | 552.3 | 0.044 | 0.367 | 33 | 112 | 0.1 | 5.7 |
| 552 | (2S)-N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-fluoropropanamide | 528.3 | 0.049 | 0.369 | 73 | 253 | 0.2 | 2.3 |
| 553 | N-((1S,2R)-3-(((4S)-6-chloro-8-(1H-imidazol-1-yl)-3,4-dihydrospiro[chromene-2,1'-cyclobutan]-4-yl)amino)-1-(3-fluorobenzyl)-2-hydroxypropyl)-2-methoxyacetamide | 543.2 | 0.146 | | 47 | 86 | | |
| 441 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-oxetanecarboxamide | 526 | 0.012 | 0.012 | 416 | 124 | 1.1 | 27 |
| 554 | (2R)-N-((1S,2R)-1-(1,3-benzodioxol-5-ylmethyl)-3-(((3'R,4'R)-6'-(2,2-dimethylpropyl)-3'-fluoro-3',4'-dihydrospiro[cyclobutane-1,2'-pyrano[2,3-b]pyridin]-4'-yl)amino)-2-hydroxypropyl)-2-methoxypropanamide | 572 | 0.057 | 1.025 | 63 | 173 | 0.2 | 6.5 |
| 555 | (2R)-N-((1S,2R)-1-(1,3-benzodioxol-5-ylmethyl)-3-(((4S)-6-((2S)-2-fluoropropyl)-3,4-dihydrospiro[chromene-2,1'-cyclobutan]-4-yl)amino)-2-hydroxypropyl)-2-methoxypropanamide | 543.1 | 3.425 | >10.000000 | 269 | 543 | 0.4 | 0.9 |
| 556 | (2R)-N-((1S,2R)-1-(1,3-benzodioxol-5-ylmethyl)-3-(((4S)-6-((2R)-2-fluoropropyl)-3,4-dihydrospiro[chromene-2,1'-cyclobutan]-4-yl)amino)-2-hydroxypropyl)-2-methoxypropanamide | 543.2 | 0.718 | 0.446 | 211 | 353 | 0.3 | 1 |
| 557 | N-((1S,2R)-1-(1,3-benzodioxol-5-ylmethyl)-3-(((4S)-6-((2S)-2-fluoropropyl)-3,4-dihydrospiro[chromene-2,1'-cyclobutan]-4-yl)amino)-2- | 529.2 | 3.787 | >10.000000 | 193 | 344 | 0.3 | 0.5 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | hydroxypropyl)-2-methoxyacetamide | | | | | | | |
| 558 | N-((1S,2R)-1-(1,3-benzodioxol-5-ylmethyl)-3-(((4S)-6-((2R)-2-fluoropropyl)-3,4-dihydrospiro[chromene-2,1'-cyclobutan]-4-yl)amino)-2-hydroxypropyl)-2-methoxyacetamide | 529.1 | 0.250 | 0.336 | 167 | 362 | | |
| 559 | N-((1S,2R)-1-((3-fluorophenyl)methyl)-3-(((4S)-6-((2R)-2-fluoropropyl)-3,4-dihydrospiro[chromene-2,1'-cyclobutan]-4-yl)amino)-2-hydroxypropyl)-2-(methyloxy)acetamide | 503.2 | 0.027 | 0.038 | 706 | 829 | 7.1 | 1.1 |
| 560 | N-((1S,2R)-3-(((4S)-6-chloro-8-(4-pyridinyl)-3,4-dihydrospiro[chromene-2,1'-cyclobutan]-4-yl)amino)-1-(3,5-difluorobenzyl)-2-hydroxypropyl)-2-methoxyacetamide | 572.3 | 0.049 | 0.058 | 209 | 829 | 0.2 | 0.4 |
| 561 | (2R)-N-((1S,2R)-3-(((4S)-6-chloro-8-(4-pyridinyl)-3,4-dihydrospiro[chromene-2,1'-cyclobutan]-4-yl)amino)-1-(3,5-difluorobenzyl)-2-hydroxypropyl)-2-methoxypropanamide | 586.3 | 0.092 | 0.262 | 113 | 426 | 0.1 | 0.4 |
| 562 | N-((1S,2R)-3-(((4S)-6-(2,2-dimethylpropyl)-8-(4-pyridinyl)-3,4-dihydrospiro[chromene-2,1'-cyclobutan]-4-yl)amino)-1-(4-fluorobenzyl)-2-hydroxypropyl)-2-methoxyacetamide | 589.4 | 0.027 | 0.021 | 24 | 60 | 0.1 | 3.6 |
| 563 | N-((1S,2R)-1-(3-fluorobenzyl)-2-hydroxy-3-(((4S)-8-(1H-imidazol-1-yl)-6-((1R)-1-(1H-imidazol-1-yl)-2,2-dimethylpropyl)-3,4-dihydrospiro[chromene-2,1'-cyclobutan]-4-yl)amino)propyl)-2-methoxyacetamide | 645.4 | 12.041 | >10.000000 | 40 | 40 | 0.1 | 0.4 |
| 564 | (2R)-N-((1S,2R)-1-(3-fluorobenzyl)-3-(((4S)-6-(2-fluoro-2-methylpropyl)-8-(4-pyridinyl)-3,4-dihydrospiro[chromene-2,1'-cyclobutan]-4-yl)amino)-2-hydroxypropyl)-2-methoxypropanamide | 608.4 | 0.032 | 0.029 | | | | |
| 565 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-((1-methylethyl)oxy)acetamide | 542 | 0.049 | 0.267 | 921 | 829 | 0.6 | 23.8 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 566 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)butanamide | 542 | 0.026 | 0.165 | 392 | 590 | 0.3 | 13 |
| 567 | (2R)-N-((1S,2R)-1-(3-fluorobenzyl)-2-hydroxy-3-(((4S)-6-(2-hydroxy-2-methylpropyl)-8-(4-pyridinyl)-3,4-dihydrospiro[chromene-2,1'-cyclobutan]-4-yl)amino)propyl)-2-methoxypropanamide | 606.3 | 0.039 | 0.009 | 67 | 120 | 0.1 | 2.2 |
| 568 | N-((1S,2R)-1-(3,5-difluorobenzyl)-3-(((4'S)-6'-(2,2-dimethylpropyl)-8'-(3-pyridinylamino)-3',4'-dihydrospiro[cyclobutane-1,2'-pyrano[2,3-c]pyridin]-4'-yl)amino)-2-hydroxypropyl)-2-methoxyacetamide | 624.3 | 0.025 | 0.019 | 214 | 304 | 0.2 | 9.3 |
| 569 | N-((1S,2R)-3-(((4'S)-6'-(1,1-difluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)acetamide | 550.2 | 0.165 | 0.992 | 238 | 423 | 0.7 | 27 |
| 570 | N-((1S,2R)-3-(((4'S)-6'-(1,1-difluoro-2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)acetamide | 520.2 | 0.136 | 0.405 | 101 | 162 | 0.8 | 7.1 |
| 571 | N-((1S,2R)-1-(3,5-difluorobenzyl)-3-(((4'S)-6'-(2,2-dimethylpropyl)-8'-(4-pyridinylamino)-3',4'-dihydrospiro[cyclobutane-1,2'-pyrano[2,3-c]pyridin]-4'-yl)amino)-2-hydroxypropyl)-2-methoxyacetamide | 624.3 | 0.053 | 0.003 | 142 | 193 | 0.1 | 2.3 |
| 572 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-(methyloxy)butanamide | 542 | 0.102 | 0.094 | 290 | 569 | 0.2 | 8.1 |
| 573 | N-((1S,2R)-1-(1,3-benzodioxol-5-ylmethyl)-3-(((4'S)-6'-(1,1-difluoro-2,2-dimethylpropyl)-3',4'-dihydrospiro[cyclobutane-1,2'-pyrano[2,3-b]pyridin]-4'-yl)amino)-2-hydroxypropyl)-2-methoxyacetamide | 576.1 | 0.280 | 0.627 | 40 | 187 | 0.1 | 3.2 |
| 574 | N-((1S,2R)-1-(1,3-benzodioxol-5-ylmethyl)-3-(((4'S)-6'-(1,1-difluoro-2,2-dimethylpropyl)-3',4'- | 546.1 | 0.220 | 0.606 | 46 | 146 | 0.2 | 3.5 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
|  | dihydrospiro[cyclobutane-1,2'-pyrano[2,3-b]pyridin]-4'-yl)amino)-2-hydroxypropyl)acetamide |  |  |  |  |  |  |  |
| 575 | N-((1S,2R)-1-(1,3-benzodioxol-5-ylmethyl)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxypropyl)-2-methoxyacetamide | 538.2 | 0.010 | 0.016 | 33 | 194 | 0.1 | 1.5 |
| 576 | N-((1S,2R)-1-(1,3-benzodioxol-5-ylmethyl)-3-(((4'S)-6'-((1S)-2,2-dimethylcyclopropyl)-3',4'-dihydrospiro[cyclobutane-1,2'-pyrano[2,3-b]pyridin]-4'-yl)amino)-2-hydroxypropyl)-2-methoxyacetamide | 538.2 | 0.328 | 0.249 | 31 | 209 | 0.1 | 2.7 |
| 577 | (2R)-N-((1S,2R)-1-(4-fluorobenzyl)-3-(((4S)-6-(2-fluoro-2-methylpropyl)-8-(4-pyridinyl)-3,4-dihydrospiro[chromene-2,1'-cyclobutan]-4-yl)amino)-2-hydroxypropyl)-2-methoxypropanamide | 608.2 | 0.115 | 0.057 |  |  |  |  |
| 578 | (2R)-N-((1S,2R)-1-(1,3-benzodioxol-5-ylmethyl)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxypropyl)-2-methoxypropanamide | 552.2 | 0.018 | 0.019 | 36 | 185 | 0.1 | 2 |
| 579 | N-((1S,2R)-1-(3,5-difluorobenzyl)-3-(((4S)-6-(2-fluoro-2-methylpropyl)-8-(4-pyridinyl)-3,4-dihydrospiro[chromene-2,1'-cyclobutan]-4-yl)amino)-2-hydroxypropyl)-2-methoxyacetamide | 612.2 | 0.014 | 0.005 |  |  |  |  |
| 580 | (2R)-N-((1S,2R)-1-(1,3-benzodioxol-5-ylmethyl)-3-(((4'S)-6'-((1S)-2,2-dimethylcyclopropyl)-3',4'-dihydrospiro[cyclobutane-1,2'-pyrano[2,3-b]pyridin]-4'-yl)amino)-2-hydroxypropyl)-2-methoxypropanamide | 552.2 | 0.357 | 0.776 | 42 | 186 | 0.1 | 4.4 |
| 581 | N-((1S,2R)-3-(((4S)-6-chloro-8-(1H-imidazol-1-yl)-3,4-dihydrospiro[chromene-2,1'-cyclobutan]-4-yl)amino)-1-(3,5-difluorobenzyl)-2-hydroxypropyl)-2-methoxyacetamide | 561.3 | 0.081 | 0.075 | 91 | 124 |  |  |
| 582 | N-((1S,2R)-3-(((4S)-6-chloro-8-(4-pyridinyl)-3,4-dihydrospiro[chromene-2,1'-cyclobutan]-4-yl)amino)-1-(3,5-difluorobenzyl)-2-hydroxypropyl)acetamide | 542.2 | 0.024 | 0.057 | 97 | 829 | 0.1 | 0.4 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 583 | (2R)-N-((1S,2R)-1-(3,5-difluorobenzyl)-3-(((4'S)-6'-(2,2-dimethylpropyl)-8'-(4-pyridinyl)-3',4'-dihydrospiro[cyclobutane-1,2'-pyrano[2,3-c]pyridin]-4'-yl)amino)-2-hydroxypropyl)-2-methoxypropanamide | 623.3 | 0.015 | 0.030 | 14 | 80 | 0 | 1.2 |
| 584 | N-((1S,2R)-1-(3,5-difluorobenzyl)-3-(((4'S)-6'-(2,2-dimethylpropyl)-8'-(4-pyridinyl)-3',4'-dihydrospiro[cyclobutane-1,2'-pyrano[2,3-c]pyridin]-4'-yl)amino)-2-hydroxypropyl)acetamide | 579.3 | 0.011 | 0.013 | 18 | 50 | 0.1 | 14.5 |
| 585 | (2R)-N-((1S,2R)-3-(((4S)-6-(2,2-dimethylpropyl)-8-(4-pyridinyl)-3,4-dihydrospiro[chromene-2,1'-cyclobutan]-4-yl)amino)-1-(3-fluorobenzyl)-2-hydroxypropyl)-2-methoxypropanamide | 603.3 | 0.016 | 0.012 | 65.5 | 120 | 0.05 | 0.75 |
| 586 | N-((1S,2R)-1-(3,5-difluorobenzyl)-2-hydroxy-3-(((4S)-6-(2-methylpropyl)-8-(4-pyridinyl)-3,4-dihydrospiro[chromene-2,1'-cyclobutan]-4-yl)amino)propyl)-2-methoxyacetamide | 594.3 | 0.009 | 0.006 | 31 | 65 | 0.1 | 1.3 |
| 587 | (2R)-N-((1S,2R)-1-(3,5-difluorobenzyl)-2-hydroxy-3-(((4S)-6-(2-methylpropyl)-8-(4-pyridinyl)-3,4-dihydrospiro[chromene-2,1'-cyclobutan]-4-yl)amino)propyl)-2-methoxypropanamide | 608.3 | 0.012 | 0.006 | 29 | 73 | 0 | 2.1 |
| 588 | N-((1S,2R)-1-(3-fluorobenzyl)-3-(((4S)-6-(2-fluoro-2-methylpropyl)-8-(1H-imidazol-1-yl)-3,4-dihydrospiro[chromene-2,1'-cyclobutan]-4-yl)amino)-2-hydroxypropyl)-2-methoxyacetamide | 583.3 | 0.027 | 0.006 | 25 | 74 | 0.1 | 0.6 |
| 589 | N-((1S,2R)-1-(3-fluorobenzyl)-2-hydroxy-3-(((4S)-8-(1H-imidazol-1-yl)-6-(2-methyl-1-propen-1-yl)-3,4-dihydrospiro[chromene-2,1'-cyclobutan]-4-yl)amino)propyl)-2-methoxyacetamide | 563.3 | 0.257 | 0.105 | 27 | 217 | 0.2 | 0.2 |
| 423 | N-((1S,2R)-1-(3-fluorobenzyl)-2-hydroxy-3-(((4S)-8-(1H-imidazol-1-yl)-6-(2-methoxy-2-methylpropyl)-3,4-dihydrospiro[chromene-2,1'-cyclobutan]-4-yl)amino)propyl)-2-methoxyacetamide | 595.3 | 0.579 | 0.063 | 35 | 132 | 0.1 | 0.3 |
| 590 | (2R)-N-((1S,2R)-1-(3,5-difluorobenzyl)-3-(((4S)-6-(2-fluoro-2-methylpropyl)-8-(4-pyridinyl)-3,4- | 626.2 | 0.024 | 0.007 | 60 | 105 | 0 | 0.6 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | dihydrospiro[chromene-2,1'-cyclobutan]-4-yl)amino)-2-hydroxypropyl)-2-methoxypropanamide | | | | | | | |
| 591 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2,2-bis(methyloxy)acetamide | | 0.010 | 0.018 | 356 | 375 | 0.6 | 10.3 |
| 592 | N-((1S,2R)-3-(((4S)-6-(2,2-dimethylpropyl)-8-(4-pyridinyl)-3,4-dihydrospiro[chromene-2,1'-cyclobutan]-4-yl)amino)-1-(3-fluorobenzyl)-2-hydroxypropyl)acetamide | 559.3 | 0.010 | 0.004 | 14 | 73 | 0 | 1.7 |
| 593 | N-((1S,2R)-1-(3-fluorobenzyl)-2-hydroxy-3-(((4S)-6-((1S)-1-hydroxy-2,2-dimethylpropyl)-8-(1H-imidazol-1-yl)-3,4-dihydrospiro[chromene-2,1'-cyclobutan]-4-yl)amino)propyl)-2-methoxyacetamide | 595.3 | 1.591 | 0.312 | 14 | 29 | 0.1 | 1 |
| 594 | N-((1S,2R)-3-(((4S)-6-chloro-8-(1H-imidazol-1-yl)-3,4-dihydrospiro[chromene-2,1'-cyclobutan]-4-yl)amino)-1-(3-fluorobenzyl)-2-hydroxypropyl)acetamide | 513.2 | 0.158 | 0.077 | 44 | 61 | 0 | 0.3 |
| 595 | N-((1S,2R)-3-(((4S)-6-chloro-8-(4-pyridinyl)-3,4-dihydrospiro[chromene-2,1'-cyclobutan]-4-yl)amino)-1-(3-fluorobenzyl)-2-hydroxypropyl)acetamide | 524.2 | 0.077 | 0.051 | 147 | 736 | 0.1 | 0.5 |
| 596 | N-((1S,2R)-1-(3,5-difluorobenzyl)-3-(((4'S)-6'-(2,2-dimethylpropyl)-8'-(1-methyl-1H-imidazol-2-yl)-3',4'-dihydrospiro[cyclobutane-1,2'-pyrano[2,3-c]pyridin]-4'-yl)amino)-2-hydroxypropyl)-2-methoxyacetamide | 612.3 | 0.041 | 0.009 | 26 | 39 | 0.1 | 2.9 |
| 597 | N-((1S,2R)-1-(3,5-difluorobenzyl)-3-(((4'S)-6'-(2,2-dimethylpropyl)-8'-(1-methyl-1H-imidazol-5-yl)-3',4'-dihydrospiro[cyclobutane-1,2'-pyrano[2,3-c]pyridin]-4'-yl)amino)-2-hydroxypropyl)-2-methoxyacetamide | 612.3 | 0.034 | 0.011 | 22 | 35 | 0 | 2.8 |
| 598 | N-((1S,2R)-1-((3,5-difluorophenyl)methyl)-3-((((4'S)-6'-(2,2-dimethylpropyl)-8'-(phenylamino)-3',4'-dihydrospiro[cyclobutane-1,2'-pyrano[2,3-c]pyridin]-4'-yl)amino)-2-hydroxypropyl)acetamide | 593.2 | 0.023 | 0.260 | 103 | 102 | 6.9 | 27 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 599 | N-((1S,2R)-1-((3,5-difluorophenyl)methyl)-3-(((4'S)-6'-(2,2-dimethylpropyl)-8'-(phenylamino)-3',4'-dihydrospiro[cyclobutane-1,2'-pyrano[2,3-c]pyridin]-4'-yl)amino)-2-hydroxypropyl)-2-(methyloxy)acetamide | 623.2 | 0.018 | 0.395 | 120 | 125 | 6.4 | 27 |
| 600 | (2R)-N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-fluoropropanamide | 528.3 | 0.030 | 0.035 | | | | |
| 601 | (2S)-N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-fluoropropanamide | 528.3 | 0.044 | 0.062 | | | | |
| 602 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(4-pyridinyl)benzyl)-2-hydroxypropyl)acetamide | 561.2 | 0.023 | 0.018 | 124 | 78 | 0.16 | 0.4 |
| 603 | N-((1S,2R)-1-benzyl-2-hydroxy-3-(((4S)-6-(2-methylpropyl)-8-(4-pyridinyl)-3,4-dihydrospiro[chromene-2,1'-cyclobutan]-4-yl)amino)propyl)-2-methoxyacetamide | 558.3 | 0.010 | 0.010 | 76 | 172 | 0 | 2.7 |
| 604 | (2R)-N-((1S,2R)-1-benzyl-2-hydroxy-3-(((4S)-6-(2-methylpropyl)-8-(4-pyridinyl)-3,4-dihydrospiro[chromene-2,1'-cyclobutan]-4-yl)amino)propyl)-2-methoxypropanamide | 572.3 | 0.018 | 0.013 | 89 | 215 | 0 | 2.7 |
| 605 | N-((1S,2R)-1-(4-fluorobenzyl)-2-hydroxy-3-(((4S)-6-(2-methylpropyl)-8-(4-pyridinyl)-3,4-dihydrospiro[chromene-2,1'-cyclobutan]-4-yl)amino)propyl)-2-methoxyacetamide | 576.3 | 0.014 | 0.016 | 73 | 71 | 0 | 2.3 |
| 606 | (2R)-N-((1S,2R)-1-(4-fluorobenzyl)-2-hydroxy-3-(((4S)-6-(2-methylpropyl)-8-(4-pyridinyl)-3,4-dihydrospiro[chromene-2,1'-cyclobutan]-4-yl)amino)propyl)-2-methoxypropanamide | 590.3 | 0.041 | 0.026 | 51 | 85 | 0 | 2 |
| 607 | N-((1S,2R)-1-(3-fluorobenzyl)-2-hydroxy-3-(((4S)-6-(2-methylpropyl)-8-(4-pyridinyl)-3,4-dihydrospiro[chromene-2,1'-cyclobutan]-4-yl)amino)propyl)-2-methoxyacetamide | 576.3 | 0.010 | 0.007 | 65 | 72 | 0 | 1.7 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 608 | (2S)-N-((1S,2R)-3-(((4'S)-6'-(2,2-difluoropropyl)-3',4'-dihydrospiro[cyclobutane-1,2'-pyrano[2,3-b]pyridin]-4'-yl)amino)-1-((3-fluorophenyl)methyl)-2-hydroxypropyl)-2-fluoropropanamide | 524.1 | 0.008 | 0.016 | 232 | 183 | 4.5 | 12.2 |
| 609 | (2R)-N-((1S,2R)-1-(3-fluorobenzyl)-2-hydroxy-3-(((4S)-6-(2-methylpropyl)-8-(4-pyridinyl)-3,4-dihydrospiro[chromene-2,1'-cyclobutan]-4-yl)amino)propyl)-2-methoxypropanamide | 590.3 | 0.008 | 0.005 | 64 | 137 | 0.1 | 2 |
| 610 | N-((1S,2R)-3-(((4'S)-6'-(2,2-dimethylpropyl)-8'-(phenylamino)-3',4'-dihydrospiro[cyclobutane-1,2'-pyrano[2,3-c]pyridin]-4'-yl)amino)-1-((4-fluorophenyl)methyl)-2-hydroxypropyl)acetamide | 575.4 | 0.199 | 10.000 | 102 | 213 | 27 | 27 |
| 611 | N-((1S,2R)-3-(((4S)-6-((2S)-2-fluoropropyl)-3,4-dihydrospiro[chromene-2,1'-cyclobutan]-4-yl)amino)-2-hydroxy-1-(phenylmethyl)propyl)-2-(methyloxy)acetamide | 485.4 | 0.103 | 0.116 | 644 | 775 | 18.4 | 1.2 |
| 612 | N-((1S,2R)-3-(((4'S)-6'-(2,2-dimethylpropyl)-8'-(phenylamino)-3',4'-dihydrospiro[cyclobutane-1,2'-pyrano[2,3-c]pyridin]-4'-yl)amino)-1-((4-fluorophenyl)methyl)-2-hydroxypropyl)-2-(methyloxy)acetamide | 605.3 | 0.210 | 10.000 | 176 | 245 | 27 | 27 |
| 613 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(4-pyridinyl)benzyl)-2-hydroxypropyl)-2-methoxyacetamide | 591.1 | 0.020 | 0.011 | 228 | 142 | 0.16 | 0.3 |
| 614 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(4-pyridinyl)benzyl)-2-hydroxypropyl)acetamide | 561.2 | 0.012 | 0.008 | 244 | 107 | 0.16 | 0.4 |
| 615 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1H-imidazol-1-yl)benzyl)propyl)acetamide | 532.2 | 0.060 | 0.007 | 59 | 32 | 0.16 | 0.16 |
| 616 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(4-pyridinyl)benzyl)propyl)acetamide | 543.2 | 0.017 | 0.010 | 228 | 96 | 0.16 | 0.3 |
| 617 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1- | 549.2 | 0.004 | 0.006 | 71 | 70 | 0.16 | 0.9 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | (3-(1,3-thiazol-2-yl)benzyl)propyl)acetamide | | | | | | | |
| 618 | N-((1S,2R)-3-(((4S)-6-(2,2-dimethylpropyl)-3,4-dihydrospiro[chromene-2,1'-cyclobutan]-4-yl)amino)-2-hydroxy-1-(3-(4-pyridinyl)benzyl)propyl)acetamide | 542.2 | 0.031 | 0.038 | 413 | 344 | 0.16 | 0.3 |
| 619 | N-((1S,2R)-1-(3-cyanobenzyl)-2-hydroxy-3-(((4S)-6-(2-methylpropyl)-8-(4-pyridinyl)-3,4-dihydrospiro[chromene-2,1'-cyclobutan]-4-yl)amino)propyl)-2-methoxyacetamide | 583.2 | 0.012 | 0.006 | 35 | 85 | 0 | 1.5 |
| 620 | (2R)-N-((1S,2R)-1-(3-cyanobenzyl)-2-hydroxy-3-(((4S)-6-(2-methylpropyl)-8-(4-pyridinyl)-3,4-dihydrospiro[chromene-2,1'-cyclobutan]-4-yl)amino)propyl)-2-methoxypropanamide | only NMR | 0.010 | 0.005 | 48 | 105 | 0 | 1.9 |
| 621 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-2-yl)benzyl)-2-hydroxypropyl)acetamide | 567.2 | 0.001 | 0.010 | 45 | 64 | 0.16 | 0.9 |
| 433 | N-((1S,2R)-3-(((4S)-6-(2,2-dimethylpropyl)-3,4-dihydrospiro[chromene-2,1'-cyclobutan]-4-yl)amino)-1-(3-fluoro-5-(4-pyridinyl)benzyl)-2-hydroxypropyl)acetamide | 560.2 | 0.021 | 0.038 | 492 | 590 | 1.1 | 0.2 |
| 622 | (2R)-N-((1S,2R)-1-(3,5-difluorobenzyl)-2-hydroxy-3-(((4S)-8-(1-methyl-1H-imidazol-5-yl)-6-(2-methylpropyl)-3,4-dihydrospiro[chromene-2,1'-cyclobutan]-4-yl)amino)propyl)-2-methoxypropanamide | 611.3 | 0.026 | 0.007 | 32 | 161 | 0 | 6.6 |
| 623 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(3-pyridinyl)benzyl)propyl)acetamide | 543.2 | 0.008 | 0.006 | 829 | 601 | 0.16 | 1.3 |
| 624 | N-((1S,2R)-1-((7-bromo-1,3-benzodioxol-5-yl)methyl)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxypropyl)acetamide | 592 | 0.200 | 0.081 | 48 | 150 | 0.16 | 1.2 |
| 625 | N-((1S,2R)-3-(((4S)-6-(2,2-dimethylpropyl)-3,4-dihydrospiro[chromene-2,1'-cyclobutan]-4-yl)amino)-1-(4-fluoro-3-(4-pyridinyl)benzyl)-2-hydroxypropyl)acetamide | 560.2 | 0.042 | 0.057 | 389 | 330 | 0.16 | 0.2 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 626 | (2R)-N-((1S,2R)-1-(1,3-benzodioxol-5-ylmethyl)-3-(((5'S)-3'-(2,2-dimethylpropyl)-8'-oxo-5',8'-dihydro-6'H-spiro[cyclobutane-1,7'-quinolin]-5'-yl)amino)-2-hydroxypropyl)-2-methoxypropanamide | 566.7 | 0.133 | 0.108 | 153 | 260 | 0.5 | 14.4 |
| 627 | N-((1S,2R)-3-(((4'S)-6'-(1,1-difluoro-2,2-dimethylpropyl)-3',4'-dihydrospiro[cyclobutane-1,2'-pyrano[2,3-b]pyridin]-4'-yl)amino)-1-((3,5-difluorophenyl)methyl)-2-hydroxypropyl)acetamide | 538.2 | 0.007 | 0.047 | 829 | 166 | 2.1 | 26.1 |
| 628 | N-((1S,2R)-2-hydroxy-3-(((4S)-6-(2-methylpropyl)-8-(4-pyridinyl)-3,4-dihydrospiro[chromene-2,1'-cyclobutan]-4-yl)amino)-1-(4-pyridinylmethyl)propyl)-2-methoxyacetamide | 559.3 | 0.045 | 0.007 | 94 | 239 | 0.1 | 1.9 |
| 629 | N-((1S,2R)-3-(((4'S)-8'-(1,3-benzodioxol-5-yl)-6'-(2,2-dimethylpropyl)-3',4'-dihydrospiro[cyclobutane-1,2'-pyrano[2,3-c]pyridin]-4'-yl)amino)-1-(3,5-difluorobenzyl)-2-hydroxypropyl)-2-methoxyacetamide | 652.3 | 0.009 | 0.121 | 171 | 209 | 1.2 | 27 |
| 630 | N-((1S,2R)-1-(3,5-difluorobenzyl)-2-hydroxy-3-(((4S)-8-(1-methyl-1H-imidazol-2-yl)-6-(2-methylpropyl)-3,4-dihydrospiro[chromene-2,1'-cyclobutan]-4-yl)amino)propyl)-2-methoxyacetamide | 597.3 | 0.021 | 0.003 | 37 | 220 | 0 | 4 |
| 631 | N-((1S,2R)-1-(3,5-difluorobenzyl)-2-hydroxy-3-(((4S)-8-(1-methyl-1H-imidazol-5-yl)-6-(2-methylpropyl)-3,4-dihydrospiro[chromene-2,1'-cyclobutan]-4-yl)amino)propyl)-2-methoxyacetamide | 597.3 | 0.019 | 0.004 | 36 | 209 | 0.1 | 3.9 |
| 632 | (2R)-N-((1S,2R)-3-(((4S)-6-(2,2-dimethylpropyl)-8-(4-pyridinyl)-3,4-dihydrospiro[chromene-2,1'-cyclobutan]-4-yl)amino)-2-hydroxy-1-(1,3-thiazol-5-ylmethyl)propyl)-2-methoxypropanamide | 593.2 | 0.065 | 0.015 | 57 | 166 | 0 | 3.1 |
| 633 | N-((1S,2R)-3-(((4S)-6-(2,2-dimethylpropyl)-8-(4-pyridinyl)-3,4-dihydrospiro[chromene-2,1'-cyclobutan]-4-yl)amino)-2-hydroxy-1-(1,3-thiazol-5-ylmethyl)propyl)-2-methoxyacetamide | 579.2 | 0.021 | 0.011 | 53 | 153 | 0.1 | 3 |
| 634 | (2R)-N-((1S,2R)-1-benzyl-2-hydroxy-3-(((4S)-8-(1-methyl-1H-imidazol-5-yl)-6-(2-methylpropyl)-3,4-dihydrospiro[chromene- | 574.3 | 0.126 | 0.014 | 50 | 340 | 0.1 | 4.5 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | 2,1'-cyclobutan]-4-yl)amino)propyl)-2-methoxypropanamide | | | | | | | |
| 635 | N-((1S,2R)-1-benzyl-2-hydroxy-3-(((4S)-8-(1-methyl-1H-imidazol-5-yl)-6-(2-methylpropyl)-3,4-dihydrospiro[chromene-2,1'-cyclobutan]-4-yl)amino)propyl)-2-methoxyacetamide | 560.3 | 0.074 | 0.010 | 44 | 420 | 0 | 4.1 |
| 636 | N-((1S,2R)-1-(3-cyanobenzyl)-3-(((4S)-6-(2,2-dimethylpropyl)-8-(4-pyridinyl)-3,4-dihydrospiro[chromene-2,1'-cyclobutan]-4-yl)amino)-2-hydroxypropyl)-2-methoxyacetamide | 596.3 | 0.008 | 0.005 | 32 | 90 | 0.1 | 3 |
| 637 | N-((1S,2R)-1-(3-cyanobenzyl)-3-(((4S)-6-(2,2-dimethylpropyl)-8-(4-pyridinyl)-3,4-dihydrospiro[chromene-2,1'-cyclobutan]-4-yl)amino)-2-hydroxypropyl)acetamide | 566.3 | 0.010 | 0.004 | 34 | 105 | 0.1 | 2.8 |
| 638 | (2R)-N-((1S,2R)-1-(3-cyanobenzyl)-3-(((4S)-6-(2,2-dimethylpropyl)-8-(4-pyridinyl)-3,4-dihydrospiro[chromene-2,1'-cyclobutan]-4-yl)amino)-2-hydroxypropyl)-2-methoxypropanamide | 610.3 | 0.017 | 0.006 | 32 | 92 | 0 | 3 |
| 639 | N-((1S,2R)-3-(((4S)-8-(2-chloro-4-pyridinyl)-6-(2,2-dimethylpropyl)-3,4-dihydrospiro[chromene-2,1'-cyclobutan]-4-yl)amino)-1-(3-fluorobenzyl)-2-hydroxypropyl)-2-methoxyacetamide | 624.3 | 0.005 | 0.025 | 706 | 399 | 1.2 | 1.8 |
| 435 | N-((1S,2R)-3-(((4S)-6-(2,2-dimethylpropyl)-3,4-dihydrospiro[chromene-2,1'-cyclobutan]-4-yl)amino)-1-(3-fluoro-5-(1,3-thiazol-2-yl)benzyl)-2-hydroxypropyl)acetamide | 566.2 | 0.006 | 0.039 | 125 | 197 | 1.4 | 0.3 |
| 640 | N-((1S,2R)-3-(((4S)-6-(2,2-dimethylpropyl)-3,4-dihydrospiro[chromene-2,1'-cyclobutan]-4-yl)amino)-1-(4-fluoro-3-(1,3-thiazol-2-yl)benzyl)-2-hydroxypropyl)acetamide | 566.2 | 0.006 | 0.053 | 59 | 113 | 0.7 | 0.3 |
| 641 | N-((1S,2R)-3-(((4S)-6-(2,2-dimethylpropyl)-3,4-dihydrospiro[chromene-2,1'-cyclobutan]-4-yl)amino)-2-hydroxy-1-(3-(1,3-thiazol-2-yl)benzyl)propyl)acetamide | 548.2 | 0.006 | 0.029 | 102 | 165 | 0.7 | 0.3 |
| 642 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(4-pyridinyl)benzyl)propyl)-2-methoxyacetamide | 573.2 | 0.034 | 0.010 | 182 | 103 | 0.16 | 0.16 |

TABLE 2-continued

| Ex. No | IUPAC NAME | Observed MS | BACE1 FRET assay (uM) | HEK cell assay (uM) | HLM (uL/min/ mg) | RLM (uL/min/ mg) | 3A4 IC50 (uM) | 2D6 IC50 (uM) |
|---|---|---|---|---|---|---|---|---|
| 643 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)acetamide | 567.2 | 0.002 | 0.012 | 68 | 56 | 0.1 | 0.7 |
| 644 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide | 597.2 | 0.002 | 0.007 | 53 | 68 | 0.1 | 0.9 |
| 432 | N-((1S,2R)-3-(((4S)-6-(2,2-dimethylpropyl)-3,4-dihydrospiro[chromene-2,1'-cyclobutan]-4-yl)amino)-1-(4-fluoro-3-(2-furanyl)benzyl)-2-hydroxypropyl)acetamide | 549.2 | 0.006 | 0.332 | 280 | 323 | 1.5 | 3.1 |
| 645 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-((7-(4-pyridinyl)-1,3-benzodioxol-5-yl)methyl)propyl)acetamide | 587.1 | 0.441 | 0.406 | 451 | 62 | 0.1 | 0.3 |
| 646 | N-((1S,2R)-3-(((4S)-6-(2,2-dimethylpropyl)-3,4-dihydrospiro[chromene-2,1'-cyclobutan]-4-yl)amino)-1-(3-fluoro-5-(2-furanyl)benzyl)-2-hydroxypropyl)acetamide | 549.2 | 0.004 | 0.104 | 326 | 344 | 2 | 1.6 |
| 647 | 2-(difluoromethoxy)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)acetamide | 550.2 | 0.008 | 0.039 | 303 | 269 | 0.4 | 2.7 |
| 648 | N-((1S,2R)-3-(((4S)-6-(2,2-dimethylpropyl)-3,4-dihydrospiro[chromene-2,1'-cyclobutan]-4-yl)amino)-1-(4-fluoro-3-(3-pyridinyl)benzyl)-2-hydroxypropyl)acetamide | 560.2 | 0.008 | 0.045 | 551 | 560 | 0.1 | 0.4 |
| 649 | N-((1S,2R)-3-(((4S)-6-(2,2-dimethylpropyl)-3,4-dihydrospiro[chromene-2,1'-cyclobutan]-4-yl)amino)-1-(3-fluoro-5-(3-pyridinyl)benzyl)-2-hydroxypropyl)acetamide | 560.2 | 0.007 | 0.030 | 706 | 482 | 0.3 | 0.5 |
| 650 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-2-yl)benzyl)-2-hydroxypropyl)-2-methoxyacetamide | 597.2 | 0.008 | 0.015 | 14 | 62 | 0.16 | 0.6 |
| 651 | (2R)-N-((1S,2R)-1-(3,4-dihydroxybenzyl)-3-(((4'S)-6'-(2,2-dimethylpropyl)-3',4'-dihydrospiro[cyclobutane-1,2'-pyrano[2,3-b]pyridin]-4'-yl)amino)-2- | 542.2 | 0.008 | 0.012 | 171 | 147 | 1.6 | 10.8 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | hydroxypropyl)-2-methoxypropanamide | | | | | | | |
| 652 | (2R)-N-((1S,2R)-1-(3,5-difluorobenzyl)-3-(((4'S)-6'-(2,2-dimethylpropyl)-8'-(1-methyl-1H-imidazol-5-yl)-3',4'-dihydrospiro[cyclobutane-1,2'-pyrano[2,3-c]pyridin]-4'-yl)amino)-2-hydroxypropyl)-2-methoxypropanamide | 626.3 | 0.028 | 0.020 | 26 | 50 | 0.16 | 2 |
| 653 | (2R)-N-((1S,2R)-2-hydroxy-1-(4-pyridinylmethyl)-3-(((4'S)-6'-(trifluoromethyl)-3',4'-dihydrospiro[cyclobutane-1,2'-pyrano[2,3-b]pyridin]-4'-yl)amino)propyl)-2-methoxypropanamide | 509.2 | 6.735 | 10.000 | 178 | 114 | 0.6 | 5.8 |
| 654 | N-((1S,2R)-3-(((4S)-6-(2,2-dimethylpropyl)-8-(2-methoxy-4-pyridinyl)-3,4-dihydrospiro[chromene-2,1'-cyclobutan]-4-yl)amino)-1-(3-fluorobenzyl)-2-hydroxypropyl)-2-methoxyacetamide | 619.3 | 0.006 | 0.034 | 399 | 477 | 1 | 9.9 |
| 655 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-2-ethoxyacetamide | 528.2 | 0.013 | 0.043 | | | | |
| 656 | N-((1S,2R)-1-(1,3-benzodioxol-5-ylmethyl)-3-(((4'S)-8'-chloro-6'-(2-methylpropyl)-3',4'-dihydrospiro[cyclobutane-1,2'-pyrano[2,3-c]pyridin]-4'-yl)amino)-2-hydroxypropyl)-2-methoxyacetamide | 560.2 | 0.051 | 0.774 | 131 | 180 | 0.1 | 5.3 |
| 657 | (2R)-N-((1S,2R)-1-(1,3-benzodioxol-5-ylmethyl)-3-(((4'S)-8'-chloro-6'-(2-methylpropyl)-3',4'-dihydrospiro[cyclobutane-1,2'-pyrano[2,3-c]pyridin]-4'-yl)amino)-2-hydroxypropyl)-2-methoxypropanamide | 574.2 | 0.030 | 0.524 | 96 | 178 | 0.16 | 5.3 |
| 658 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-5-yl)benzyl)propyl)acetamide | 549.2 | 0.006 | 0.010 | 130 | 120 | 0.1 | 0.3 |
| 659 | N-((1S,2R)-3-(((4S)-6-(2,2-dimethylpropyl)-3,4-dihydrospiro[chromene-2,1'-cyclobutan]-4-yl)amino)-2-hydroxy-1-(3-(1H-imidazol-1-yl)benzyl)propyl)acetamide | 531.2 | 0.076 | 0.024 | 706 | 413 | 0 | 0.2 |
| 660 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluorobenzyl)-2- | 528.2 | 0.003 | 0.018 | 829 | 775 | 0.2 | 1.9 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
|  | hydroxypropyl)-2-ethoxyacetamide |  |  |  |  |  |  |  |
| 661 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-4-fluorobenzyl)-2-hydroxypropyl)-2-methoxyacetamide | 538.2 | 0.003 | 0.011 | 57 | 97 | 0.2 | 1.2 |
| 662 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-5-yl)benzyl)-2-hydroxypropyl)acetamide | 597.2 | 0.004 | 0.025 | 78 | 74 | 0 | 0.2 |
| 663 | N-((1S,2R)-3-(((4S)-6-(2,2-dimethylpropyl)-2,2-dimethyl-3,4-dihydro-2H-pyrano[2,3-b]pyridin-4-yl)amino)-1-(4-fluorobenzyl)-2-hydroxypropyl)-2-methoxyacetamide | 502.3 | 0.013 | 0.021 | 163 | 133 | 1.7 | 10.5 |
| 664 | N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-c]pyridin]-4'-yl)amino)propyl)-2-methoxyacetamide | 526.2 | 0.118 | 0.192 | 193 | 276 | 0.03 | 2.3 |
| 665 | (2R)-N-((1S,2R)-1-(1,3-benzodioxol-5-ylmethyl)-2-hydroxy-3-(((3'S,5'S)-3'-(1-methylethyl)-2',3',5',6'-tetrahydrospiro[cyclobutane-1,7'-furo[2,3-b]pyrano[3,2-e]pyridin]-5'-yl)amino)propyl)-2-methoxypropanamide | 568.1 | 0.927 | 0.249 | 61 | 126 | 0.2 | 4 |
| 666 | (2R)-N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-c]pyridin]-4'-yl)amino)propyl)-2-methoxypropanamide | 540.2 | 0.124 | 0.175 | 140 | 228 | 0.03 | 2.4 |
| 667 | N-((1S,2R)-3-(((4'S)-8'-chloro-6'-(2-methylpropyl)-3',4'-dihydrospiro[cyclobutane-1,2'-pyrano[2,3-c]pyridin]-4'-yl)amino)-1-(3,5-difluorobenzyl)-2-hydroxypropyl)-2-methoxyacetamide | 552.2 | 0.005 | 0.054 | 399 | 682 | 0.6 | 6.3 |
| 668 | N-((1S,2R)-3-(((4S)-6-(2,2-dimethylpropyl)-8-(3-fluoro-4-pyridinyl)-3,4-dihydrospiro[chromene-2,1'-cyclobutan]-4-yl)amino)-1-(3-fluorobenzyl)-2-hydroxypropyl)-2-methoxyacetamide | 607.3 | 0.004 | 0.018 | 118 | 197 | 0.1 | 2.9 |
| 669 | N-((1S,2R)-1-(1,3-benzodioxol-5-ylmethyl)-2-hydroxy-3-(((4'S)-6'-(2-methylpropyl)-8'-(4-pyridinyl)-3',4'-dihydrospiro[cyclobutane-1,2'-pyrano[2,3-c]pyridin]- | 603.2 | 0.034 | 0.087 | 45 | 77 | 0.03 | 0.3 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | 4'-yl)amino)propyl)-2-methoxyacetamide | | | | | | | |
| 670 | (2R)-N-((1S,2R)-1-(1,3-benzodioxol-5-ylmethyl)-2-hydroxy-3-(((4'S)-6'-(2-methylpropyl)-8'-(4-pyridinyl)-3',4'-dihydrospiro[cyclobutane-1,2'-pyrano[2,3-c]pyridin]-4'-yl)amino)propyl)-2-methoxypropanamide | 617.3 | 0.060 | 0.294 | 40 | 100 | 0.03 | 0.8 |
| 671 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-5-yl)benzyl)-2-hydroxypropyl)acetamide | 567.2 | 0.005 | 0.012 | 99 | 48 | 0.1 | 0.4 |
| 672 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-4-yl)benzyl)-2-hydroxypropyl)acetamide | 567.2 | 0.004 | 0.005 | 358 | 134 | 0.4 | 2.7 |
| 673 | N-((1S,2R)-1-(3,5-difluorobenzyl)-2-hydroxy-3-(((4S)-6-(2-methylpropyl)-8-(4-pyridinyl)-3,4-dihydrospiro[chromene-2,1'-cyclobutan]-4-yl)amino)propyl)acetamide | 564.3 | 0.009 | 0.005 | 46 | 118 | 0.03 | 0.8 |
| 674 | (2R)-N-((1S,2R)-1-(1,3-benzodioxol-5-ylmethyl)-3-(((4S)-6-(2,2-dimethylpropyl)-2,2-dimethyl-3,4-dihydro-2H-pyrano[2,3-b]pyridin-4-yl)amino)-2-hydroxypropyl)-2-methoxypropanamide | 542.3 | 0.033 | 0.037 | 26 | 128 | 0.1 | 10.5 |
| 675 | (2R)-N-((1S,2R)-1-(3,4-difluorobenzyl)-3-(((4S)-6-(2,2-dimethylpropyl)-2,2-dimethyl-3,4-dihydro-2H-pyrano[2,3-b]pyridin-4-yl)amino)-2-hydroxypropyl)-2-methoxypropanamide | 534.2 | 0.009 | 0.013 | 543 | 411 | 2 | 21.8 |
| 676 | N-((1S,2R)-1-(3,4-difluorobenzyl)-3-(((4S)-6-(2,2-dimethylpropyl)-2,2-dimethyl-3,4-dihydro-2H-pyrano[2,3-b]pyridin-4-yl)amino)-2-hydroxypropyl)-2-methoxyacetamide | 520.2 | 0.010 | 0.011 | 463 | 411 | 2 | 2.9 |
| 436 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-4-yl)benzyl)-2-hydroxypropyl)acetamide | 567.2 | 0.005 | 0.024 | 135 | 78 | 0.2 | 2.2 |
| 677 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(4-(1,3-thiazol-2-yl)benzyl)propyl)acetamide | 549.2 | 0.015 | 0.028 | 57 | 52 | 0.1 | 1 |
| 678 | N-((1S,2R)-1-(3,5-difluorobenzyl)-3-(((4'S)-6'-((1S)-2,2- | 607.2 | 0.018 | 0.010 | 23 | 79 | 0.1 | 1.3 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | dimethylcyclopropyl)-8'-(4-pyridinyl)-3',4'-dihydrospiro[cyclobutane-1,2'-pyrano[2,3-c]pyridin]-4'-yl)amino)-2-hydroxypropyl)-2-methoxyacetamide | | | | | | | |
| 439 | N-((1S,2R)-3-(((4S)-8-(2-(dimethylamino)-4-pyridinyl)-6-(2,2-dimethylpropyl)-3,4-dihydrospiro[chromene-2,1'-cyclobutan]-4-yl)amino)-1-(3-fluorobenzyl)-2-hydroxypropyl)-2-methoxyacetamide | 632.3 | 0.020 | 0.005 | 601 | 515 | 1.3 | 4.1 |
| 679 | N-((1S,2R)-1-(1,3-benzodioxol-5-ylmethyl)-3-(((4S)-6-(2,2-dimethylpropyl)-2,2-dimethyl-3,4-dihydro-2H-pyrano[2,3-b]pyridin-4-yl)amino)-2-hydroxypropyl)acetamide | 498.3 | 0.019 | 0.012 | 24 | 138 | 0.2 | 5.7 |
| 680 | (2R)-N-((1S,2R)-1-(1,3-benzodioxol-5-ylmethyl)-2-hydroxy-3-(((4'S)-8'-(methylamino)-6'-(2-methylpropyl)-3',4'-dihydrospiro[cyclobutane-1,2'-pyrano[2,3-c]pyridin]-4'-yl)amino)propyl)-2-methoxypropanamide | 569.3 | 0.140 | 0.025 | 220 | 317 | 0.5 | 14 |
| 681 | N-((1S,2R)-1-(1,3-benzodioxol-5-ylmethyl)-2-hydroxy-3-(((4'S)-8'-(methylamino)-6'-(2-methylpropyl)-3',4'-dihydrospiro[cyclobutane-1,2'-pyrano[2,3-c]pyridin]-4'-yl)amino)propyl)-2-methoxyacetamide | 555.3 | 0.064 | 0.014 | 197 | 392 | 0.8 | 9.2 |
| 682 | N-((1S,2R)-1-(3,5-difluorobenzyl)-2-hydroxy-3-(((4'S)-6'-(2-methylpropyl)-8'-(4-pyridinyl)-3',4'-dihydrospiro[cyclobutane-1,2'-pyrano[2,3-c]pyridin]-4'-yl)amino)propyl)-2-methoxyacetamide | 595.3 | 0.009 | 0.011 | 34 | 113 | 0 | 1.1 |
| 426 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1H-imidazol-1-yl)benzyl)-2-hydroxypropyl)acetamide | 550.5 | 0.031 | 0.011 | 22 | 14 | 0.03 | 0.1 |
| 683 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-4-yl)benzyl)-2-hydroxypropyl)-2-methoxyacetamide | 597.2 | 0.009 | 0.031 | 102 | 61 | 0.2 | 2.3 |
| 684 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-5-yl)benzyl)-2- | 597.2 | 0.005 | 0.012 | 56 | 114 | 0.1 | 0.2 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | hydroxypropyl)-2-methoxyacetamide | | | | | | | |
| 685 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(3-methylbenzyl)-2-morpholinecarboxamide | 659 | 0.013 | 0.012 | 662 | 283 | 0.2 | 3.1 |
| 686 | (2R)-N-((1S,2R)-3-(((4'S)-8'-chloro-6'-(2-methylpropyl)-3',4'-dihydrospiro[cyclobutane-1,2'-pyrano[2,3-c]pyridin]-4'-yl)amino)-1-(3,5-difluorobenzyl)-2-hydroxypropyl)-2-methoxypropanamide | 566.2 | 0.003 | 0.052 | 921 | 399 | 0.2 | 6.1 |
| 687 | (2R)-N-((1S,2R)-1-(3,5-difluorobenzyl)-2-hydroxy-3-(((4'S)-6'-(2-methylpropyl)-8'-(4-pyridinyl)-3',4'-dihydrospiro[cyclobutane-1,2'-pyrano[2,3-c]pyridin]-4'-yl)amino)propyl)-2-methoxypropanamide | 609.3 | 0.008 | 0.016 | 27 | 91 | 0.03 | 0.2 |
| 688 | (2R)-N-((1S,2R)-1-(3,5-difluorobenzyl)-2-hydroxy-3-(((4'S)-6'-(2-methylpropyl)-3',4'-dihydrospiro[cyclobutane-1,2'-pyrano[2,3-c]pyridin]-4'-yl)amino)propyl)-2-methoxypropanamide | 532.2 | 0.009 | 0.036 | 921 | 399 | 0.2 | 3 |
| 689 | N-((1S,2R)-1-(3,5-difluorobenzyl)-3-(((4S)-6-ethynyl-8-(1H-imidazol-1-yl)-3,4-dihydrospiro[chromene-2,1'-cyclobutan]-4-yl)amino)-2-hydroxypropyl)-2-methoxyacetamide | 550.2 | 0.038 | 0.027 | 18.5 | 44.5 | 0.03 | 0.2 |
| 690 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-2-yl)benzyl)-2-hydroxypropyl)-2-methoxypropanamide | 611.2 | 0.011 | 0.040 | 40 | 53 | 0.1 | 0.5 |
| 691 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(3-methylbenzyl)-2-morpholinecarboxamide | 659 | 0.078 | 0.104 | 543 | 426 | 0.2 | 3 |
| 692 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(2- | 659 | 0.013 | 0.024 | 706 | 590 | 0.2 | 5.1 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | methylbenzyl)-2-morpholinecarboxamide | | | | | | | |
| 693 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(4-(1,3-thiazol-4-yl)benzyl)propyl)acetamide | 549.2 | 0.043 | 0.060 | 110 | 63 | 0.2 | 2.9 |
| 694 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(4-(1,3-thiazol-5-yl)benzyl)propyl)acetamide | 549.2 | 0.074 | 0.071 | 82 | 66 | 0.2 | 0.3 |
| 695 | N-((1S,2R)-1-(3-fluoro-5-(1,3-thiazol-2-yl)benzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide | 583.2 | 0.004 | 0.011 | 77 | 64 | 0.1 | 0.5 |
| 696 | N-((1S,2R)-3-(((4S)-6-(2,2-dimethylpropyl)-3,4-dihydrospiro[pyrano[2,3-c]pyridine-2,3'-pyrrolidin]-4-yl)amino)-1-(4-fluorobenzyl)-2-hydroxypropyl)-2-methoxyacetamide | 529.2 | 40.000 | 0.778 | 32 | 44 | 2.9 | 27 |
| 697 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(2-methylbenzyl)-2-morpholinecarboxamide | 659 | 0.087 | 0.143 | 775 | 399 | 0.2 | 2.7 |
| 698 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1H-imidazol-1-yl)benzyl)propyl)-2-methoxyacetamide | 562.2 | 0.026 | 0.009 | 58 | 33 | 0.03 | 0.1 |
| 699 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxyacetamide | 579.2 | 0.004 | 0.007 | 54 | 66 | 0.1 | 0.3 |
| 700 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-4-yl)benzyl)propyl)-2-methoxyacetamide | 579.2 | 0.007 | 0.010 | 221 | 115 | 0.1 | 2.7 |
| 701 | N-((1R,2S)-3-(((4S)-6-(2,2-dimethylpropyl)-3,4-dihydrospiro[chromene-2,1'-cyclobutan]-4-yl)amino)-2-hydroxy-1-(3-(1,3-thiazol-2-yl)benzyl)propyl)-2-methoxyacetamide | 578 | 0.008 | 0.033 | 137 | 160 | 0.2 | 0.7 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 702 | N-((1S,2R)-3-(((4S)-6-(2,2-dimethylpropyl)-3,4-dihydrospiro[pyrano[2,3-c]pyridine-2,3'-pyrrolidin]-4-yl)amino)-1-(4-fluorobenzyl)-2-hydroxypropyl)acetamide | 499.2 | 36.359 | 0.454 | 14 | 26 | 1.8 | 13.5 |
| 703 | N-((1S,2R)-1-(3,5-difluorobenzyl)-3-(((4'S)-6'-((1S)-2,2-dimethylcyclopropyl)-8'-(4-pyridinyl)-3',4'-dihydrospiro[cyclobutane-1,2'-pyrano[2,3-c]pyridin]-4'-yl)amino)-2-hydroxypropyl)-2-methoxyacetamide | 607.2 | 1.226 | 0.302 | 32 | 118 | 0.2 | 2.1 |
| 704 | (2R)-N-((1S,2R)-1-(3,5-difluorobenzyl)-2-hydroxy-3-(((4'S)-8'-(1-methyl-1H-imidazol-2-yl)-6'-(2-methylpropyl)-3',4'-dihydrospiro[cyclobutane-1,2'-pyrano[2,3-c]pyridin]-4'-yl)amino)propyl)-2-methoxypropanamide | 612.3 | 0.030 | 0.024 | 20 | 44 | 0.03 | 27 |
| 705 | N-((1S,2R)-3-(((4S)-6-cyclopropyl-8-(1H-imidazol-1-yl)-3,4-dihydrospiro[chromene-2,1'-cyclobutan]-4-yl)amino)-1-(3,5-difluorobenzyl)-2-hydroxypropyl)acetamide | 537.2 | 0.032 | 0.013 | 51 | 36 | 0 | 0.6 |
| 706 | N-((1S,2R)-3-(((4S)-6-cyclopropyl-8-(1H-imidazol-1-yl)-3,4-dihydrospiro[chromene-2,1'-cyclobutan]-4-yl)amino)-1-(3,5-difluorobenzyl)-2-hydroxypropyl)-2-methoxyacetamide | 567.3 | 0.062 | 0.020 | 41 | 33 | 0.1 | 0.3 |
| 707 | (2R)-N-((1S,2R)-3-(((4S)-6-cyclopropyl-8-(1H-imidazol-1-yl)-3,4-dihydrospiro[chromene-2,1'-cyclobutan]-4-yl)amino)-1-(3,5-difluorobenzyl)-2-hydroxypropyl)-2-methoxypropanamide | 581.3 | 0.114 | 0.028 | 14 | 39 | 0.03 | 0.6 |
| 428 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1H-imidazol-2-yl)benzyl)-2-hydroxypropyl)acetamide | 550.2 | 0.061 | 0.013 | 225 | 124 | 0.3 | 1.3 |
| 429 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1H-imidazol-2-yl)benzyl)propyl)acetamide | 532.2 | 3.590 | 0.600 | 88 | 37 | 1.3 | 0.5 |
| 708 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(4- | 659 | 0.154 | 0.257 | 310 | 278 | 0.2 | 6.8 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | methylbenzyl)-2-morpholinecarboxamide | | | | | | | |
| 709 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(4-methylbenzyl)-2-morpholinecarboxamide | 659 | 0.028 | 0.038 | 614 | 375 | 0.3 | 3.7 |
| 710 | (2R)-N-((1S,2R)-1-(3,5-difluorobenzyl)-2-hydroxy-3-(((4'S)-8'-(1-methyl-1H-imidazol-5-yl)-6'-(2-methylpropyl)-3',4'-dihydrospiro[cyclobutane-1,2'-pyrano[2,3-c]pyridin]-4'-yl)amino)propyl)-2-methoxypropanamide | 612.3 | 0.026 | 0.018 | 16 | 39 | 0.1 | 2.8 |
| 426 | N-((1S,2R)-1-(3,5-difluorobenzyl)-3-(((4'S)-6'-((1R)-2,2-dimethylcyclopropyl)-8'-(4-pyridinyl)-3',4'-dihydrospiro[cyclobutane-1,2'-pyrano[2,3-c]pyridin]-4'-yl)amino)-2-hydroxypropyl)-2-methoxyacetamide | 607.2 | 0.005 | 0.005 | 21 | 66 | 0.1 | 1.3 |
| 711 | (2S)-4-benzyl-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-2-morpholinecarboxamide | 645 | 0.040 | 0.124 | 706 | 399 | 0.3 | 8.2 |
| 712 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-5-yl)benzyl)propyl)-2-methoxyacetamide | 579.2 | 0.005 | 0.009 | 74 | 75 | 0.03 | 0.2 |
| 713 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-5-fluorobenzyl)-2-hydroxypropyl)acetamide | 508.2 | 0.003 | 0.015 | 75 | 58 | 0.1 | 1.2 |
| 714 | N-((1S,2R)-1-(3,5-difluorobenzyl)-2-hydroxy-3-(((4'S)-8'-(1-methyl-1H-imidazol-2-yl)-6'-(2-methylpropyl)-3',4'-dihydrospiro[cyclobutane-1,2'-pyrano[2,3-c]pyridin]-4'-yl)amino)propyl)-2-methoxyacetamide | 598.3 | 0.016 | 0.017 | 20 | 43 | 0.03 | 2.2 |
| 715 | N-((1S,2R)-1-(3,5-difluorobenzyl)-2-hydroxy-3-(((4'S)-8'-(1-methyl-1H-imidazol-5-yl)-6'-(2-methylpropyl)-3',4'-dihydrospiro[cyclobutane-1,2'-pyrano[2,3-c]pyridin]-4'-yl)amino)propyl)-2-methoxyacetamide | 598.3 | 0.020 | 0.016 | 19 | 34 | 0.03 | 1.8 |
| 716 | N-((1S,2R)-3-(((4'S)-6'-(2,2-dimethylpropyl)-8'- | 626.2 | 0.032 | 0.025 | 123 | 190 | 0.4 | 1.5 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | (methylamino)-3',4'-dihydrospiro[cyclobutane-1,2'-pyrano[2,3-c]pyridin]-4'-yl)amino)-1-(4-fluoro-3-(1,3-thiazol-2-yl)benzyl)-2-hydroxypropyl)-2-methoxyacetamide | | | | | | | |
| 717 | (2R)-4-benzyl-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-2-morpholinecarboxamide | 645 | 0.013 | 0.011 | 775 | 298 | 0.2 | 3.6 |
| 718 | N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-(3-fluoro-5-(1,3-thiazol-2-yl)benzyl)-2-hydroxypropyl)-2-methoxyacetamide | 601.2 | 0.051 | 0.062 | 113 | 140 | 0.3 | 0.5 |
| 719 | (2R)-N-((1S,2R)-1-(3-chloro-5-fluorobenzyl)-3-(((4'S)-6'-(2-fluoro-2-methylpropyl)-3',4'-dihydrospiro[cyclobutane-1,2'-pyrano[2,3-c]pyridin]-4'-yl)amino)-2-hydroxypropyl)-2-methoxypropanamide | 566.2 | 0.024 | 0.130 | 515 | 775 | 0.4 | 2.4 |
| 720 | N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-ethoxyacetamide | 540.2 | 0.057 | 0.134 | | | | |
| 721 | (2R)-N-((1S,2R)-3-(((4'S)-6'-(2-fluoro-2-methylpropyl)-3',4'-dihydrospiro[cyclobutane-1,2'-pyrano[2,3-c]pyridin]-4'-yl)amino)-1-(3-fluoro-5-(1,3-thiazol-2-yl)benzyl)-2-hydroxypropyl)-2-methoxypropanamide | 615.2 | 0.049 | 0.118 | 111 | 152 | 0.3 | 0.5 |
| 722 | N-((1S,2R)-3-(((1s,3R,4'S)-6'-(2,2-dimethylpropyl)-3-methyl-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide | 611.3 | 0.005 | 0.020 | 50 | 111 | 0.03 | 0.6 |
| 723 | N-((1S,2R)-3-(((1s,3S,4'S)-6'-(2,2-dimethylpropyl)-3-hydroxy-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide | 613.3 | 0.006 | 0.005 | 86 | 199 | 0.6 | 11.2 |
| 724 | N-((1S,2R)-3-(((4'S)-6'-(2-fluoro-2-methylpropyl)-3',4'-dihydrospiro[cyclobutane- | 601.3 | 0.006 | 0.009 | 45 | 38 | 0.2 | 0.9 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
| --- | --- | --- | --- | --- | --- | --- | --- | --- |
| | 1,2'-pyrano[2,3-b]pyridin]-4'-yl)amino)-1-(3-fluoro-5-(1,3-thiazol-2-yl)benzyl)-2-hydroxypropyl)-2-methoxyacetamide | | | | | | | |
| 725 | N-((1S,2R)-1-(3,5-difluorobenzyl)-3-(((7S)-9-(2,2-dimethylpropyl)-5,5-dimethyl-2,3,6,7-tetrahydro-5H-[1,4]oxazino[2,3,4-ij]quinolin-7-yl)amino)-2-hydroxypropyl)acetamide | 529.2 | 0.059 | 0.178 | | | | |
| 726 | N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)propanamide | 510 | 0.044 | 0.048 | 34 | 173 | 0.03 | 1.4 |
| 727 | N-((1S,2R)-1-(4-fluoro-3-(1,3-thiazol-2-yl)benzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide | 583.2 | 0.011 | 0.023 | 45 | 74 | 0.03 | 0.5 |
| 728 | N-((1S,2R)-3-(((4'S)-6'-ethyl-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide | 555.2 | 0.030 | 0.108 | | | | |
| 729 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(5-methyl-1,3-thiazol-2-yl)benzyl)-2-hydroxypropyl)-2-methoxyacetamide | 611.2 | 0.048 | 0.291 | 371 | 399 | 0.4 | 3.9 |
| 730 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-4-(1,3-thiazol-2-yl)benzyl)-2-hydroxypropyl)-2-methoxyacetamide | 597.2 | 0.039 | 0.027 | 57 | 74 | 0.03 | 0.7 |
| 731 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(4-(1,3-thiazol-2-yl)benzyl)propyl)-2-methoxyacetamide | 579.2 | 0.029 | 0.026 | 68 | 63 | 0.03 | 0.9 |
| 732 | N-((1S,2R)-1-(3-fluoro-5-(5-methyl-1,3-thiazol-2-yl)benzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide | 597.2 | 0.018 | 0.083 | 551 | 399 | 0.2 | 2.5 |
| 733 | N-((1S,2R)-1-(3-fluoro-5-(4-methyl-1,3-thiazol-2-yl)benzyl)-2-hydroxy-3-((((4'S)-6'-(2-methylpropyl)- | 597.2 | 0.008 | 0.021 | 249 | 399 | 0.03 | 4.5 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
|  | 3',4'-dihydrospiro[cyclobutane-1,2'-pyrano[2,3-b]pyridin]-4'-yl)amino)propyl)-2-methoxyacetamide | | | | | | | |
| 734 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-((4-methyl-1,3-thiazol-2-yl)methyl)-2-morpholinecarboxamide | 666 | 0.012 | 0.014 | 543 | 335 | 0.1 | 2.4 |
| 735 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(4-(1,3-thiazol-2-yl)benzyl)propyl)-2-methoxypropanamide | 593.2 | 0.049 | 0.060 | 78 | 80 | 0.03 | 1 |
| 736 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxypropanamide | 593.2 | 0.008 | 0.009 | 35 | 51 | 0.03 | 0.5 |
| 737 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)-2-methoxyacetamide | 520.2 | 0.005 | 0.008 | 43 | 45 | 0.03 | 2 |
| 738 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxypropanamide | 611.2 | 0.008 | 0.010 | 50 | 59 | 0.03 | 0.6 |
| 739 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-methyl-2-morpholinecarboxamide | 569 | 0.064 | 0.008 | 266 | 239 | 0.8 | 6.7 |
| 740 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1-methyl-1H-imidazol-2-yl)benzyl)-2-hydroxypropyl)-2-methoxyacetamide | 594.2 | 0.051 | 0.006 | | | | |
| 741 | (2R)-N-((1S,2R)-1-(1,3-benzodioxol-5-ylmethyl)-3-(((4'S)-6'-(2-fluoro-2-methylpropyl)-3',4'-dihydrospiro[cyclobutane-1,2'-pyrano[2,3-b]pyridin]- | 558.2 | 0.352 | 0.329 | 25 | 76 | 0.03 | 5 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | 4'-yl)amino)-2-hydroxypropyl)-2-methoxypropanamide | | | | | | | |
| 742 | (2R)-N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxypropanamide | 615.2 | 0.084 | 0.045 | 39.5 | 42 | 0.7 | 0.95 |
| 743 | N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-(4-fluoro-3-(1,3-thiazol-2-yl)benzyl)-2-hydroxypropyl)-2-methoxyacetamide | 601.2 | 0.016 | 0.037 | 22 | 31 | 0.03 | 0.6 |
| 744 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-methyl-2-morpholinecarboxamide | 569 | 0.372 | 0.075 | 333 | 266 | 0.9 | 11.2 |
| 745 | N-((1S,2R)-3-(((6S)-4-bromo-8,8-dimethyl-7,8-dihydro-6H-[1,3]dioxolo[4,5-h]chromen-6-yl)amino)-1-(4-fluorobenzyl)-2-hydroxypropyl)-2-methoxyacetamide | 553.1 | 5.727 | 0.229 | 179 | 177 | 0.5 | 3.1 |
| 746 | N-((1S,2R)-3-(((6S)-4-bromo-8,8-dimethyl-7,8-dihydro-6H-[1,3]dioxolo[4,5-h]chromen-6-yl)amino)-1-(3,5-difluorobenzyl)-2-hydroxypropyl)-2-methoxyacetamide | 571.1 | 0.275 | 0.185 | 150 | 144 | 0.2 | 3.8 |
| 747 | N-((1S,2R)-3-(((6S)-8,8-dimethyl-4-(2-methylpropyl)-7,8-dihydro-6H-[1,3]dioxolo[4,5-h]chromen-6-yl)amino)-1-(4-fluorobenzyl)-2-hydroxypropyl)-2-methoxyacetamide | 553.2 | 0.209 | 0.243 | 125 | 217 | 0.2 | 9.1 |
| 748 | N-((1S,2R)-1-(3,5-difluorobenzyl)-3-(((6S)-8,8-dimethyl-4-(2-methylpropyl)-7,8-dihydro-6H-[1,3]dioxolo[4,5-h]chromen-6-yl)amino)-2-hydroxypropyl)-2-methoxyacetamide | 571.2 | 0.013 | 0.126 | 190 | 179 | 0.1 | 8.2 |
| 749 | N-((1S,2R)-3-(((4'S)-6'-cyclopropyl-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide | 567.2 | 0.046 | 0.074 | 59 | 51 | 0.3 | 1.6 |
| 750 | N-((1S,2R)-3-(((1s,3S,4'S)-6'-(2,2-dimethylpropyl)-3-methoxy-3',4'-dihydrospiro[cyclobutane- | 627.2 | 0.012 | 0.014 | 190 | 426 | 0.5 | 3.1 |

TABLE 2-continued

| Ex. No | IUPAC NAME | Observed MS | BACE1 FRET assay (uM) | HEK cell assay (uM) | HLM (uL/min/ mg) | RLM (uL/min/ mg) | 3A4 IC50 (uM) | 2D6 IC50 (uM) |
|---|---|---|---|---|---|---|---|---|
| | 1,2'-pyrano[2,3-b]pyridin]-4'-yl)amino)-1-(3-fluoro-5-(1,3-thiazol-2-yl)benzyl)-2-hydroxypropyl)-2-methoxyacetamide | | | | | | | |
| 751 | (2R)-N-((1S,2R)-3-(((1s,3S,4'S)-6'-(2,2-dimethylpropyl)-3-methoxy-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxypropanamide | 641.2 | 0.016 | 0.027 | 192 | 497 | 0.3 | 1.7 |
| 752 | (2R)-N-((1S,2R)-3-(((4'S)-8'-chloro-6'-(2-methylpropyl)-3',4'-dihydrospiro[cyclobutane-1,2'-pyrano[2,3-c]pyridin]-4'-yl)amino)-1-(3-fluoro-5-(1,3-thiazol-2-yl)benzyl)-2-hydroxypropyl)-2-methoxypropanamide | 631.2 | 0.009 | 0.067 | 166 | 137 | 0.1 | 1.3 |
| 573 | N-((1S,2R)-3-(((4'S)-8'-chloro-6'-(2-methylpropyl)-3',4'-dihydrospiro[cyclobutane-1,2'-pyrano[2,3-c]pyridin]-4'-yl)amino)-1-(3-fluoro-5-(1,3-thiazol-2-yl)benzyl)-2-hydroxypropyl)-2-methoxyacetamide | 617.2 | 0.006 | 0.067 | 158 | 123 | 0.2 | 1.4 |
| 754 | N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2,2-dimethoxyacetamide | 556.2 | 0.037 | 0.054 | 29 | 86 | 0.1 | 3.5 |
| 755 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-((2-methyl-1,3-thiazol-4-yl)methyl)-2-morpholinecarboxamide | 666 | 0.012 | 0.007 | 522 | 191 | 0.3 | 3.3 |
| 756 | N-((1S,2R)-1-(3-ethynylbenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide | 506.2 | 0.005 | 0.009 | 53 | 49 | 0 | 1.4 |
| 757 | N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-thiazol-2-yl)benzyl)propyl)-2-methoxyacetamide | 565.2 | 0.007 | 0.018 | 60 | 60 | 0.25 | 0.45 |
| 758 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(4-methyl-1,3-thiazol-2- | 593.2 | 0.006 | 0.014 | 347 | 311 | 0.1 | 4.4 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | yl)benzyl)propyl)-2-methoxyacetamide | | | | | | | |
| 759 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(5-methyl-1,3-thiazol-2-yl)benzyl)propyl)-2-methoxyacetamide | 593.2 | 0.021 | 0.071 | 436 | 399 | 0.3 | 1.5 |
| 760 | (2R)-N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-1-(4-fluoro-3-(1,3-thiazol-2-yl)benzyl)-2-hydroxypropyl)-2-methoxypropanamide | 615.2 | 0.031 | 0.100 | 26 | 31 | 0.3 | 0.8 |
| 761 | (2R)-N-((1S,2R)-1-(3-fluoro-5-(1,3-thiazol-2-yl)benzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxypropanamide | 597.2 | 1.616 | 0.375 | 85 | 74 | 0.1 | 0.7 |
| 762 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-((2-methyl-1,3-thiazol-4-yl)methyl)-2-morpholinecarboxamide | 666 | 0.037 | 0.037 | 297 | 522 | 0.3 | 2.6 |
| 763 | N-((1S,2R)-1-(3-fluorobenzyl)-2-hydroxy-3-(((3'S,5'S)-3'-(1-methylethyl)-2',3',5',6'-tetrahydrospiro[cyclobutane-1,7'-furo[2,3-b]pyrano[3,2-e]pyridin]-5'-yl)amino)propyl)-2-methoxyacetamide | 528.2 | 2.502 | 1.302 | 399 | 399 | 2 | 2 |
| 764 | N-((1S,2R)-3-((6'-(2,2-difluoropropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide | 605.1 | 0.011 | 0.018 | 41 | 33 | 0.3 | 0.7 |
| 765 | (2R)-N-((1S,2R)-3-((6'-(2,2-difluoropropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxypropanamide | 619.2 | 0.021 | 0.054 | 35 | 39 | 0.2 | 0.7 |
| 766 | N-((1S,2R)-3-(((4'S)-6'-ethynyl-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide | 550.2 | 0.055 | 0.272 | 70 | 64 | 0.2 | 1.4 |
| 767 | N-((1S,2R)-1-(1,3-benzodioxol-5-ylmethyl)-2-hydroxy-3-(((4S)-6-(2- | 601.3 | 0.198 | 0.251 | 157 | 150 | 0.1 | 3.6 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
|  | methylpropyl)-8-(2-pyridinyl)-3,4-dihydrospiro[chromene-2,1'-cyclobutan]-4-yl)amino)propyl)-2-methoxyacetamide |  |  |  |  |  |  |  |
| 768 | (2R)-N-((1S,2R)-1-(4-fluoro-3-(1,3-thiazol-2-yl)benzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxypropanamide | 597.2 | 0.022 | 0.105 | 39 | 70 | 0.1 | 0.4 |
| 769 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(1,3-thiazol-2-ylmethyl)-2-morpholinecarboxamide | 652 | 0.010 | 0.013 | 706 | 333 | 0.4 | 5.2 |
| 770 | (2R)-N-((1S,2R)-1-(3-fluoro-5-(1,3-thiazol-2-yl)benzyl)-2-hydroxy-3-(((4S)-6-(2-methylpropyl)-3,4-dihydrospiro[chromene-2,1'-cyclobutan]-4-yl)amino)propyl)-2-methoxypropanamide | 596.2 | 0.010 | 0.052 | 145 | 201 | 0.3 | 0.5 |
| 771 | N-((1S,2R)-1-(3-fluoro-5-(1,3-thiazol-2-yl)benzyl)-2-hydroxy-3-(((4S)-6-(2-methylpropyl)-3,4-dihydrospiro[chromene-2,1'-cyclobutan]-4-yl)amino)propyl)-2-methoxyacetamide | 582.2 | 0.005 | 0.040 | 150 | 201 | 0.7 | 0.5 |
| 772 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-ethoxyacetamide | 554.2 | 0.021 | 0.042 | 28 | 112 | 0.2 | 1.1 |
| 773 | N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide | 595.2 | 0.003 | 0.006 | 62 | 67 | 0.3 | 0.3 |
| 774 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(1,3-thiazol-4-ylmethyl)-2-morpholinecarboxamide | 652 | 0.017 | 0.006 | 111 | 57 | 0.2 | 5.3 |
| 775 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1- | 576.3 | 0.064 | 0.006 | 16 | 14 |  | 0.1 |

TABLE 2-continued

| Ex. No | IUPAC NAME | Observed MS | BACE1 FRET assay (uM) | HEK cell assay (uM) | HLM (uL/min/ mg) | RLM (uL/min/ mg) | 3A4 IC50 (uM) | 2D6 IC50 (uM) |
|---|---|---|---|---|---|---|---|---|
|  | (3-(1-methyl-1H-imidazol-2-yl)benzyl)propyl)-2-methoxyacetamide | | | | | | | |
| 776 | (2R)-N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-thiazol-2-yl)benzyl)propyl)-2-methoxypropanamide | 579.2 | 0.014 | 0.027 | 58 | 61 | 0.2 | 0.7 |
| 777 | (2R)-N-((1S,2R)-1-(3-ethynylbenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxypropanamide | 520.2 | 0.006 | 0.013 | 29 | 38 | 0.1 | 2.1 |
| 778 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(1,1-dioxidotetrahydro-3-thiophenyl)acetamide | 628.2 | 0.048 | 0.050 | 62 | 141 | 0.1 | 8.5 |
| 779 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)tetrahydro-3-thiophenecarboxamide 1,1-dioxide | 614.4 | 0.057 | 0.075 | 36 | 66 | 0.1 | 3.9 |
| 780 | N-((1S,2R)-1-(3-ethynyl-4-fluorobenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide | 524.2 | 0.010 | 0.032 | 61 | 74 | 0.1 | 1.4 |
| 781 | (2R)-N-((1S,2R)-3-(((4'S)-6'-(2,2-dimethylpropyl)-8'-(2-pyridinyl)-3',4'-dihydrospiro[cyclobutane-1,2'-pyrano[2,3-c]pyridin]-4'-yl)amino)-2-hydroxy-1-(1,3-thiazol-5-ylmethyl)propyl)-2-methoxypropanamide | 594.2 | 0.071 | 0.206 | 104 | 82 | 0.4 | 27 |
| 782 | N-((1S,2R)-3-(((4'S)-6'-(2,2-dimethylpropyl)-3',4'-dihydrospiro[cyclobutane-1,2'-pyrano[2,3-c]pyridin]-4'-yl)amino)-1-(3-fluoro-5-(1,3-thiazol-2-yl)benzyl)-2-hydroxypropyl)-2-methoxyacetamide | 597.2 | 0.015 | 0.036 | 94 | 130 | 0.3 | 0.4 |
| 783 | N-((1S,2R)-3-(((4S)-6-cyclopropyl-8-(4-pyridinyl)-3,4-dihydrospiro[chromene-2,1'-cyclobutan]-4-yl)amino)-1-(3,5-difluorobenzyl)-2-hydroxypropyl)-2-methoxyacetamide | 578.2 | 0.031 | 0.029 | 73 | 107 | 0.3 | 0.3 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 784 | (2R)-N-((1S,2R)-3-(((4'S)-6'-ethynyl-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxypropanamide | 564.1 | 0.158 | 0.864 | 51 | 64 | 0.03 | 1 |
| 785 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-oxazol-2-yl)benzyl)propyl)-2-methoxyacetamide | 562.2 | 0.018 | 0.019 | 43 | 37 | 0.1 | 0.4 |
| 434 | N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(4-(1,3-thiazol-2-yl)benzyl)propyl)-2-methoxyacetamide | 565.2 | 0.075 | 0.273 | 80 | 60 | 0.2 | 1.3 |
| 786 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(1,3-thiazol-4-ylmethyl)-2-morpholinecarboxamide | 652 | 0.047 | 0.029 | 169 | 129 | 0.3 | 7.9 |
| 787 | N-((1S,2R)-1-(3-fluoro-4-(1,3-thiazol-2-yl)benzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide | 583.2 | 0.110 | 0.451 | 58 | 79 | 0.2 | 0.8 |
| 788 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(1,3-thiazol-5-ylmethyl)-2-morpholinecarboxamide | 652 | 0.016 | 0.013 | 267 | 157 | 0 | 0.6 |
| 789 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxypropanamide | 593.2 | 0.007 | 0.020 | 42 | 15 | 0.1 | 0.6 |
| 790 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide | 605.2 | 0.008 | 0.007 | 64 | 44 | 0.1 | 0.6 |
| 791 | N-((1S,2R)-3-(((4'S)-6'-(2,2-dimethylpropyl)-3',4'-dihydrospiro[cyclobutane-1,2'-pyrano[2,3-b]pyridin]- | 593.2 | 0.009 | 0.012 | 43 | 33 | 0.1 | 0.6 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | 4'-yl)amino)-2-hydroxy-1-(3-(1,3-thiazol-2-yl)benzyl)propyl)-3-methoxypropanamide | | | | | | | |
| 792 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide | 605.2 | 0.008 | 0.010 | 46 | 35 | 0.1 | 0.6 |
| 793 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)ethanethioamide | 565.2 | 0.030 | 0.067 | 99 | 60 | 0.1 | 0.4 |
| 794 | (2R)-N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxy-1-(1,3-thiazol-5-ylmethyl)propyl)-2-methoxypropanamide | 515.2 | 0.005 | 0.009 | 205 | 132 | 0.5 | 9.8 |
| 795 | (2R)-N-((1R,2S)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-thiazol-2-yl)benzyl)propyl)tetrahydro-2-furancarboxamide | 591.2 | 0.286 | 0.206 | 127 | 64 | 0.2 | 0.6 |
| 796 | (2S)-N-((1R,2S)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-thiazol-2-yl)benzyl)propyl)tetrahydro-2-furancarboxamide | 591.2 | 40.000 | 0.663 | 126 | 58 | 0.2 | 0.6 |
| 797 | N-((1S,2R)-3-(((4'S)-6'-(2,2-difluoropropyl)-3',4'-dihydrospiro[cyclobutane-1,2'-pyrano[2,3-b]pyridin]-4'-yl)amino)-1-(3-fluorobenzyl)-2-hydroxypropyl)-2,2-dimethoxyacetamide | | 0.008 | 0.017 | 256 | 199 | 1.4 | 4.1 |
| 798 | N-((1S,2R)-1-(3-cyanobenzyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2,2-dimethoxyacetamide | | 0.006 | 0.005 | 468 | 423 | 0.5 | 4.7 |
| 799 | N-((1S,2R)-1-(3-chloro-5-fluorobenzyl)-3-(((4'S)-6'-(2,2-difluoropropyl)-3',4'-dihydrospiro[cyclobutane-1,2'-pyrano[2,3-b]pyridin]-4'-yl)amino)-2-hydroxypropyl)-2-methoxyacetamide | | 0.008 | 0.019 | 663 | 236.5 | 0.5 | 4.95 |
| 800 | N-((1S,2R)-1-(3-bromobenzyl)-2-hydroxy-3-(((4'S)-6'-(2-methylpropyl)-3',4'- | 562.1 | 0.004 | 0.013 | 921 | 459 | 0.2 | 1.4 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | dihydrospiro[cyclobutane-1,2'-pyrano[2,3-b]pyridin]-4'-yl)amino)propyl)-2-methoxyacetamide | | | | | | | |
| 801 | (2R)-N-((1S,2R)-1-(3-bromobenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxypropanamide | 574.1 | 0.016 | 0.118 | 399 | 644 | 0.3 | 3.8 |
| 802 | N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1-propyn-1-yl)benzyl)propyl)-2-methoxyacetamide | 520.2 | 0.005 | 0.032 | 60.5 | 191 | 0.1 | 2.15 |
| 803 | (2R)-N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1-propyn-1-yl)benzyl)propyl)-2-methoxypropanamide | 534.2 | 0.022 | 0.132 | | | | |
| 804 | N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-oxazol-2-yl)benzyl)propyl)-2-methoxyacetamide | 548.2 | 0.009 | 0.030 | 61 | 43 | 0.2 | 2.5 |
| 805 | (2R)-N-((1S,2R)-1-(3-chloro-5-fluorobenzyl)-2-hydroxy-3-(((4S)-6-(2-methylpropyl)-3,4-dihydrospiro[chromene-2,1'-cyclobutan]-4-yl)amino)propyl)-2-methoxypropanamide | 547.2 | 0.003 | 0.070 | | | | |
| 806 | N-((1S,2R)-1-(3-fluoro-5-(1,3-thiazol-2-yl)benzyl)-2-hydroxy-3-(((4S)-6-(1-propyn-1-yl)-3,4-dihydrospiro[chromene-2,1'-cyclobutan]-4-yl)amino)propyl)-2-methoxyacetamide | 563.1 | 0.669 | 4.145 | 61 | 92 | 0.2 | 0.6 |
| 807 | N-((1S,2R)-3-(((4'S)-6'-(2,2-dimethylpropyl)-3',4'-dihydrospiro[cyclobutane-1,2'-pyrano[2,3-c]pyridin]-4'-yl)amino)-2-hydroxy-1-(3-(1,3-thiazol-2-yl)benzyl)propyl)-2-methoxyacetamide | 579.2 | 0.019 | 0.054 | | | | |
| 808 | (2R)-N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-ethoxypropanamide | 554 | 0.138 | 0.414 | 49 | 179 | 0.1 | 2.3 |
| 809 | (2S)-N-((1S,2R)-1-(1,3-benzodioxol-5-ylmethyl)-2-hydroxy-3-(((4'S)-6'-(2-methylpropyl)-3',4'- | 554 | 0.269 | 0.513 | 33 | 117 | 0.2 | 6.7 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | dihydrospiro[cyclobutane-1,2'-pyrano[2,3-b]pyridin]-4'-yl)amino)propyl)-2-ethoxypropanamide | | | | | | | |
| 810 | N-((1R,2S)-3-(((4'S)-6'-cyclopentyl-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxyacetamide | 577.2 | 4.485 | 1.340 | 274 | 271 | 0.1 | 0.5 |
| 811 | N-((1S,2R)-2-hydroxy-3-(((4'S)-6'-(1-propyn-1-yl)-3',4'-dihydrospiro[cyclobutane-1,2'-pyrano[2,3-b]pyridin]-4'-yl)amino)-1-(3-(1,3-thiazol-2-yl)benzyl)propyl)-2-methoxyacetamide | 546.2 | 0.309 | 0.736 | 36 | 54 | 0.3 | 1 |
| 812 | N-((1S,2R)-1-(3-bromobenzyl)-2-hydroxy-3-(((4'S)-6'-(1-propyn-1-yl)-3',4'-dihydrospiro[cyclobutane-1,2'-pyrano[2,3-b]pyridin]-4'-yl)amino)propyl)-2-methoxyacetamide | 543.2 | 0.258 | 0.954 | 260 | 345 | 0.4 | 3 |
| 813 | N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxyacetamide | 583.2 | 0.006 | 0.014 | 32 | 27 | 0.5 | 1.1 |
| 814 | N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxy-1-(3-(1,3-thiazol-2-yl)benzyl)propyl)-2-methoxyacetamide | 595.2 | 2.229 | 0.808 | 40 | 112 | 0.5 | 8.1 |
| 815 | (2R)-N-((1R,2S)-1-(3-fluoro-5-(1,3-thiazol-2-yl)benzyl)-2-hydroxy-3-(((4'S)-6'-propyl-3',4'-dihydrospiro[cyclobutane-1,2'-pyrano[2,3-b]pyridin]-4'-yl)amino)propyl)-2-methoxypropanamide | 583.2 | | | 204 | 276 | 0.2 | 0.6 |
| 816 | N-((1S,2R)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-thiazol-2-yl)benzyl)propyl)-2,2-dimethoxyacetamide | 595.2 | 0.008 | 0.024 | 46 | 44 | 0.3 | 0.7 |
| 817 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2,2-dimethoxyacetamide | 609.2 | 0.009 | 0.013 | 33 | 41 | 0.2 | 1.4 |
| 818 | N-((1S,2R)-3-(((4'S)-6'-(2,2-difluoropropyl)-3',4'-dihydrospiro[cyclobutane- | 635.2 | 0.013 | 0.059 | 41 | 46 | 0.6 | 2.3 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
|  | 1,2'-pyrano[2,3-b]pyridin]-4'-yl)amino)-1-(3-fluoro-5-(1,3-thiazol-2-yl)benzyl)-2-hydroxypropyl)-2,2-dimethoxyacetamide |  |  |  |  |  |  |  |
| 819 | N-((1S,2R)-1-benzyl-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-4,4-dimethylpentanamide |  | 0.013 | 0.074 | 736 | 543 | 0.2 | 2 |
| 820 | (2R)-N-((1S,2R)-1-(3-chloro-5-fluorobenzyl)-3-(((4'S)-6'-(2,2-difluoropropyl)-3',4'-dihydrospiro[cyclobutane-1,2'-pyrano[2,3-b]pyridin]-4'-yl)amino)-2-hydroxypropyl)-2-methoxypropanamide |  | 0.022 | 0.021 | 682 | 324 | 0.3 | 3.8 |
| 821 | (2R)-N-((1R,2S)-3-(((4'S)-6'-bromo-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxypropanamide | 621 | 40.000 | 0.558 | 162 | 243 | 0.3 | 0.5 |
| 822 | N-((1S,2R)-3-(((3R,4'S)-6'-(2,2-dimethylpropyl)-3',4,4',5-tetrahydrospiro[furan-3,2'-pyrano[2,3-b]pyridin]-4'-yl)amino)-2-hydroxy-1-(3-(1,3-thiazol-2-yl)benzyl)propyl)-2-methoxyacetamide | 595.2 | 4.417 | 2.762 | 54 | 101 | 0.2 | 4.9 |
| 823 | N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxy-1-(3-(1,3-thiazol-2-yl)benzyl)propyl)-2-methoxyacetamide | 595.2 | 29.938 | 3.161 | 57 | 171 | 0.3 | 3.1 |
| 824 | N-((1S,2R)-3-(((3R,4'S)-6'-(2,2-dimethylpropyl)-3',4,4',5-tetrahydrospiro[furan-3,2'-pyrano[2,3-b]pyridin]-4'-yl)amino)-1-(3-ethynylbenzyl)-2-hydroxypropyl)-2-methoxyacetamide | 536.2 | 2.341 | 0.806 | 21 | 28 | 0.1 | 27 |
| 825 | N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-1-(3-ethynylbenzyl)-2-hydroxypropyl)-2-methoxyacetamide | 536.4 | 0.005 | 0.009 | 17 | 85 | 0.1 | 7.3 |
| 826 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-oxazol-2-yl)benzyl)propyl)-2,2-dimethoxyacetamide | 593.3 | 0.012 | 0.013 | 66 | 55 | 0.2 | 0.9 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 827 | N-((1S,2R)-3-(((3S,4'R)-6'-(2,2-dimethylpropyl)-3',4,4',5-tetrahydrospiro[furan-3,2'-pyrano[2,3-b]pyridin]-4'-yl)amino)-2-hydroxy-1-(3-(1,3-thiazol-2-yl)benzyl)propyl)-2-methoxyacetamide | 595.2 | 0.006 | 0.007 | 97 | 197 | 0.5 | 2.1 |
| 828 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)propanamide | 524.2 | 0.012 | 0.014 | | | | |
| 829 | N-((1S,2R)-3-(((4'S)-6'-(2,2-difluoropropyl)-3',4'-dihydrospiro[cyclobutane-1,2'-pyrano[2,3-b]pyridin]-4'-yl)amino)-1-(3-ethynylbenzyl)-2-hydroxypropyl)-2-methoxyacetamide | | 0.007 | 0.016 | 40 | 23 | 0.2 | 2.3 |
| 830 | N-((1S,2R)-3-(((4'S)-6'-(2,2-difluoropropyl)-3',4'-dihydrospiro[cyclobutane-1,2'-pyrano[2,3-b]pyridin]-4'-yl)amino)-1-(3-ethynylbenzyl)-2-hydroxypropyl)-2,2-dimethoxyacetamide | | 0.007 | 0.023 | 28 | 35 | 0.1 | 1.3 |
| 831 | (2R)-N-((1S,2R)-3-(((4'S)-6'-(2-fluoro-2-methylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxypropanamide | 597.2 | 0.024 | 0.047 | 21 | 45 | 0.2 | 0.8 |
| 832 | N-((1S,2R)-1-(3-ethenylbenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide | 508.2 | 0.007 | 0.038 | | | | |
| 833 | N-((1R,2S)-1-(3-fluoro-5-(1,3-thiazol-2-yl)benzyl)-2-hydroxy-3-(((4'S)-6'-propyl-3',4'-dihydrospiro[cyclobutane-1,2'-pyrano[2,3-b]pyridin]-4'-yl)amino)propyl)-2-methoxyacetamide | 569 | 40.000 | 2.278 | 219 | 189 | 0.3 | 0.9 |
| 834 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-5-fluorobenzyl)-2-hydroxypropyl)-2-methoxypropanamide | 552.2 | 0.005 | 0.011 | 37 | 98 | 0 | 2.5 |
| 835 | (2R)-N-((1S,2R)-1-(3-ethynyl-5-fluorobenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxypropanamide | 538.2 | 0.006 | 0.026 | 48 | 109 | 0 | 2.1 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
| --- | --- | --- | --- | --- | --- | --- | --- | --- |
| 836 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-oxazol-2-yl)benzyl)propyl)-2-methoxypropanamide | 577.3 | 0.013 | 0.015 | 56 | 56 | 0.2 | 0.7 |
| 837 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-4-fluorobenzyl)-2-hydroxypropyl)-2-ethoxyacetamide | 552 | 0.007 | 0.023 | 29 | 72 | 0.1 | 1.6 |
| 838 | N-((1S,2R)-1-(3-ethynylbenzyl)-2-hydroxy-3-(((4'S)-6'-(3,3,3-trifluoro-2,2-dimethylpropyl)-3',4'-dihydrospiro[cyclobutane-1,2'-pyrano[2,3-b]pyridin]-4'-yl)amino)propyl)-2-methoxyacetamide | 574.2 | 0.010 | 0.028 | 34 | 54 | 0.1 | 2 |
| 839 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3,5-di-1,3-thiazol-2-ylbenzyl)-2-hydroxypropyl)-2-methoxyacetamide | 662.2 | 0.258 | 0.477 | 62 | 57 | 0.1 | 0.4 |
| 840 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-ethoxyacetamide | 593.2 | 0.004 | 0.010 | | | | |
| 841 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(2-pyridinyl)benzyl)propyl)-2-methoxyacetamide | 573.1 | 0.009 | 0.018 | 706 | 292 | 0.4 | 3.3 |
| 842 | N-((1S,2R)-3-(((4'S)-6'-ethyl-3',4'-dihydrospiro[cyclobutane-1,2'-pyrano[2,3-b]pyridin]-4'-yl)amino)-1-(3-ethynylbenzyl)-2-hydroxypropyl)-2-methoxyacetamide | 478.2 | 0.026 | 0.065 | 55 | 57 | 0.2 | 4.9 |
| 843 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-4-pentynamide | 548.2 | 0.044 | 0.065 | | | | |
| 844 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)-2,2-dimethoxyacetamide | | 0.005 | 0.006 | 32 | 44 | 0.1 | 1.5 |

TABLE 2-continued

| Ex. No | IUPAC NAME | Observed MS | BACE1 FRET assay (uM) | HEK cell assay (uM) | HLM (uL/min/ mg) | RLM (uL/min/ mg) | 3A4 IC50 (uM) | 2D6 IC50 (uM) |
|---|---|---|---|---|---|---|---|---|
| 845 | N-((1S,2R)-3-(((3R,4'S)-6'-(2,2-dimethylpropyl)-3',4,4',5-tetrahydrospiro[furan-3,2'-pyrano[2,3-b]pyridin]-4'-yl)amino)-2-hydroxy-1-(3-(1,3-thiazol-2-yl)benzyl)propyl)-2-methoxyacetamide | 595.2 | 0.006 | 0.006 | 64 | 152 | 0.5 | 2.9 |
| 846 | N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxy-1-(3-(1,3-thiazol-2-yl)benzyl)propyl)-2-methoxyacetamide | 595.2 | 0.007 | 0.006 | 82 | 128 | 0.7 | 2.3 |
| 847 | N-((1S,2R)-3-(((4'S)-6'-(2,2-dimethylpropyl)-8'-(methylamino)-3',4'-dihydrospiro[cyclobutane-1,2'-pyrano[2,3-c]pyridin]-4'-yl)amino)-1-(3-fluoro-5-(1,3-thiazol-2-yl)benzyl)-2-hydroxypropyl)-2-methoxyacetamide | 626.2 | 0.044 | 0.010 | 102 | 201 | 0.4 | 0.8 |
| 848 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-4-fluorobenzyl)-2-hydroxypropyl)propanamide | 522 | 0.005 | 0.019 | 36 | 60 | 0 | 0.9 |
| 849 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)-2-methoxypropanamide | 534.4 | 0.005 | 0.008 | 18 | 43 | 0.05 | 3.2 |
| 850 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-5-fluorobenzyl)-2-hydroxypropyl)-2-methoxyacetamide | 538.3 | 0.002 | 0.008 | 42 | 95 | 0.05 | 1.7 |
| 851 | N-((1S,2R)-1-(3-bromo-5-(1,3-thiazol-2-yl)benzyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-methoxyacetamide | 659.1 | 0.013 | 0.057 | 71 | 59 | 0.2 | 0.7 |
| 852 | (2R)-N-((1S,2R)-3-(((4'S)-6'-bromo-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxypropanamide | 621.1 | 0.246 | 0.094 | 106 | 156 | 0.3 | 0.3 |
| 853 | (2R)-N-((1S,2R)-1-(3-fluoro-5-(1,3-thiazol-2-yl)benzyl)-2-hydroxy-3-((((4'S)-6'-propyl-3',4'-dihydrospiro[cyclobutane-1,2'-pyrano[2,3-b]pyridin]- | 583.3 | 0.043 | 0.075 | 93 | 101 | 0.4 | 0.7 |

TABLE 2-continued

| Ex. No | IUPAC NAME | Observed MS | BACE1 FRET assay (uM) | HEK cell assay (uM) | HLM (uL/min/ mg) | RLM (uL/min/ mg) | 3A4 IC50 (uM) | 2D6 IC50 (uM) |
|---|---|---|---|---|---|---|---|---|
| | 4'-yl)amino)propyl)-2-methoxypropanamide | | | | | | | |
| 854 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1H-pyrazol-1-yl)benzyl)propyl)-2-methoxyacetamide | 562.4 | 0.007 | 0.007 | 515 | 210 | 0.6 | 2.5 |
| 855 | N-((1S,2R)-1-(4-ethynylbenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide | 506.4 | 0.062 | 0.174 | | | | |
| 856 | N-((1S,2R)-1-(3-ethynyl-5-fluorobenzyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)-2-methoxyacetamide | 524.3 | 0.002 | 0.009 | 63 | 78 | 0.15 | 1 |
| 857 | N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxyacetamide | 577 | 0.004 | 0.008 | 51 | 46 | 0.1 | 0.35 |
| 858 | N-((1S,2R)-1-(3,5-diethynylbenzyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-methoxyacetamide | 544 | 0.005 | 0.147 | 90 | 88 | | 1.1 |
| 859 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluorobenzyl)-2-hydroxypropyl)-4-pentynamide | 522.2 | 0.004 | 0.027 | | | | |
| 860 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)propanamide | 581.2 | 0.004 | 0.015 | 62 | 69 | 0.2 | 0.3 |
| 861 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-4-fluorobenzyl)-2-hydroxypropyl)-2,2-dimethoxyacetamide | 568 | 0.008 | 0.018 | 28 | 64 | | 2.1 |
| 862 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-ethoxyacetamide | 611.2 | 0.004 | 0.009 | 43 | 64 | 0.3 | 0.65 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 863 | 3-((2S,3R)-4-(((4'S)-6'-(2-fluoro-2-methylpropyl)-3',4'-dihydrospiro[cyclobutane-1,2'-pyrano[2,3-b]pyridin]-4'-yl)amino)-3-hydroxy-2-((methoxyacetyl)amino)butyl)benzamide | | 0.013 | 0.033 | | | | |
| 864 | 3-((2S,3R)-2-((dimethoxyacetyl)amino)-4-(((4'S)-6'-(2-fluoro-2-methylpropyl)-3',4'-dihydrospiro[cyclobutane-1,2'-pyrano[2,3-b]pyridin]-4'-yl)amino)-3-hydroxybutyl)benzamide | | 0.040 | 0.117 | | | | |
| 865 | N-((1S,2R)-1-(3-fluoro-5-(1,3-thiazol-2-yl)benzyl)-2-hydroxy-3-(((4'S)-6'-propyl-3',4'-dihydrospiro[cyclobutane-1,2'-pyrano[2,3-b]pyridin]-4'-yl)amino)propyl)-2-methoxyacetamide | 569.2 | 0.086 | 0.879 | 125 | 74 | 0.3 | 0.7 |
| 866 | N-((1S,2R)-3-(((4'S)-6'-(2,2-dimethylpropyl)-4'-methyl-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide | 611.2 | 0.177 | 0.880 | 84 | 90 | 0.2 | 0.9 |
| 867 | N-((1S,2R)-3-(((4'R)-6'-(2,2-dimethylpropyl)-4'-methyl-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxyacetamide | 611.2 | 1.213 | 1.145 | 66 | 119 | | 0.7 |
| 868 | N-((1S,2R)-3-(((3R,4'S)-6'-(2,2-dimethylpropyl)-3',4,4',5-tetrahydrospiro[furan-3,2'-pyrano[2,3-b]pyridin]-4'-yl)amino)-1-(3-ethynylbenzyl)-2-hydroxypropyl)-2-methoxyacetamide | 536.2 | 0.007 | 0.014 | 14 | 86 | 0.4 | 20.6 |
| 869 | N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-1-(3-ethynylbenzyl)-2-hydroxypropyl)-2-methoxyacetamide | 536.2 | 0.006 | 0.010 | 21 | 55 | 0.1 | 9.5 |
| 870 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)-2-ethoxyacetamide | 534.2 | 0.004 | 0.011 | | | 0 | 1.6 |
| 871 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2,2-dimethoxyacetamide | | 0.007 | 0.010 | 59 | 73 | 0.2 | 0.7 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 872 | N-((1S,2R)-1-(3-acetylbenzyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-methoxyacetamide | 538.2 | 0.007 | 0.009 | 382 | 278 | | 5.7 |
| 873 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)propanamide | 504.2 | 0.003 | 0.007 | 35 | 29 | 0 | 0.8 |
| 874 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)cyclopropanecarboxamide | 593.2 | 0.008 | 0.024 | 62 | 74 | 0.2 | |
| 875 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)cyclobutanecarboxamide | 607.2 | 0.006 | 0.020 | 65 | 81 | 0.2 | 0.3 |
| 876 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-1-methylcyclopropanecarboxamide | 607.2 | 0.036 | 0.132 | 64 | 91 | 0.2 | 0.3 |
| 877 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)tetrahydro-2-furancarboxamide | 623.2 | 0.005 | 0.012 | 46 | 64 | 0.2 | 0.7 |
| 878 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-fluoroacetamide | 585.2 | 0.004 | 0.022 | 72 | 65 | 0.2 | |
| 879 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)tetrahydro-2-furancarboxamide | 623.2 | 0.006 | 0.007 | 96 | 77 | 0.2 | −0.6 |
| 880 | (2R)-N-((1S,2R)-3-(((4'S)-6'-(cyclopropylethynyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methoxypropanamide | 605.2 | 20.965 | 0.063 | 71 | 107 | 0.3 | 0.3 |
| 881 | N-((1S,2R)-1-(1,3-benzodioxol-5-ylmethyl)-3-(((4'S)-6'-(2,2- | | 0.144 | 0.813 | 31 | 110 | 0.2 | 4 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | dimethylpropyl)-3',4'-dihydrospiro[cyclobutane-1,2'-pyrano[2,3-b]pyridin]-4'-yl)amino)-2-hydroxypropyl)-2-methylpropanamide | | | | | | | |
| 882 | N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2,2-dimethylpropanamide | | 6.249 | 2.575 | 40 | 103 | 0 | 0.5 |
| 883 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-2-methylpropanamide | | 0.021 | 0.021 | 54 | 52 | 0.1 | |
| 884 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-ethynylbenzyl)-2-hydroxypropyl)-2-methoxypropanamide | 534.4 | 0.251 | 0.097 | 19 | 55 | 0.1 | 3.8 |
| 885 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-ethynylbenzyl)-2-hydroxypropyl)-2-methoxyacetamide | 520.6 | 0.065 | 0.099 | 28 | 67 | 0.1 | 2.8 |
| 886 | N-((1S,2R)-3-(((4'S)-6'-cyclopentyl-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxyacetamide | 577.6 | 0.143 | 0.136 | 55 | 64 | 0.2 | 0.3 |
| 887 | (2R)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-ethoxypropanamide | 568.3 | 0.102 | 0.052 | 37 | 136 | 0 | |
| 888 | (2S)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-ethoxypropanamide | 568.2 | 0.213 | 1.555 | 29 | 140 | 0 | 3.4 |
| 889 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-5-(1,3-thiazol-2-yl)benzyl)-2-hydroxypropyl)-2-methoxyacetamide | 602.4 | 0.653 | 0.989 | | | | |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 890 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)propanamide | 563.2 | 0.011 | 0.414 | 39 | 45 | 0.1 | 0.5 |
| 891 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1-propyn-1-yl)benzyl)propyl)-2-methoxyacetamide | 534.2 | 0.015 | 0.022 | 81 | 303 | 0 | 8.1 |
| 892 | N-((1S,2R)-1-(3,5-dibromobenzyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-methoxyacetamide | 654 | 0.070 | 0.009 | 399 | 274 | 0.1 | 3.9 |
| 893 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-ethoxypropanamide | 607.2 | 0.013 | 0.012 | 36 | 71 | 0 | 1.1 |
| 894 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-ethoxypropanamide | 607.2 | 0.016 | 0.018 | 38 | 88 | 0.1 | 0.9 |
| 895 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1-propyn-1-yl)benzyl)propyl)-2-methoxypropanamide | 548.2 | 0.016 | 0.017 | | | | |
| 896 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)tetrahydro-2-furancarboxamide | 546.4 | 0.006 | 0.009 | 45 | 73 | 0 | 3.8 |
| 897 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)tetrahydro-2-furancarboxamide | 546.4 | 0.005 | 0.007 | 19 | 55 | 0 | 3.6 |
| 898 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(2-fluoro-5- | 611.2 | 0.010 | 0.014 | 67 | 121 | 0.1 | 1 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | (1,3-thiazol-2-yl)benzyl)-2-hydroxypropyl)-2-methoxypropanamide | | | | | | | |
| 899 | (2R)-N-((1S,2R)-1-(5-chloro-2-fluorobenzyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-methoxypropanamide | 562.1 | 0.005 | 0.009 | 443 | 543 | 0.1 | 2.6 |
| 900 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(2-fluoro-5-(1,3-thiazol-2-yl)benzyl)-2-hydroxypropyl)-2-methoxyacetamide | 597.2 | 0.010 | 0.018 | 63 | 55 | 27 | 27 |
| 901 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-oxazol-2-yl)benzyl)propyl)-2-ethoxyacetamide | 577.3 | 0.010 | 0.032 | 74 | 62 | 27 | 24.8 |
| 902 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(5-ethynyl-2-fluorobenzyl)-2-hydroxypropyl)-2-methoxypropanamide | 552.2 | 0.006 | 0.026 | 36 | 70 | 0.1 | 0.9 |
| 903 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(5-ethynyl-2-fluorobenzyl)-2-hydroxypropyl)-2-methoxyacetamide | 538.2 | 0.004 | 0.011 | 38 | 71 | 0.1 | 1.7 |
| 904 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluoro-3-(1,3-thiazol-2-yl)benzyl)-2-hydroxypropyl)-2-ethoxyacetamide | 611.2 | 0.004 | 0.062 | 38 | 47 | 0.1 | 0.5 |
| 905 | (2R)-N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-methoxypropanamide | 591 | | | 60 | 71 | 0.2 | 0.9 |
| 906 | (2R)-N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide | 603 | | | 94 | 63 | 0.1 | 0.4 |
| 907 | (2S)-N-((1S,2R)-3-(((4'S)-6'-((1R)-2,2-dimethylcyclopropyl)-3',4'-dihydrospiro[cyclobutane- | 603 | | | 77 | 78 | 0.1 | 0.5 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| | 1,2'-pyrano[2,3-b]pyridin]-4'-yl)amino)-2-hydroxy-1-(3-(1,3-thiazol-2-yl)benzyl)propyl)tetrahydro-2-furancarboxamide | | | | | | | |
| 908 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(2-fluoro-3-(1,3-thiazol-2-yl)benzyl)-2-hydroxypropyl)-2-methoxyacetamide | 597.2 | 0.071 | 0.100 | 69 | 91 | 0.1 | 0.6 |
| 909 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(2-fluoro-3-(1,3-thiazol-2-yl)benzyl)-2-hydroxypropyl)-2-methoxypropanamide | 611.2 | 0.157 | 0.052 | 76 | 127 | 0.1 | 0.9 |
| 910 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(2-fluoro-3-(1,3-thiazol-2-yl)benzyl)-2-hydroxypropyl)tetrahydro-2-furancarboxamide | 623.2 | 0.079 | 0.079 | 147 | 153 | 0.1 | 2.4 |
| 911 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-2-fluorobenzyl)-2-hydroxypropyl)-2-methoxyacetamide | 538.3 | 0.011 | 0.144 | 62 | 71 | 0.1 | 5.9 |
| 912 | (2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-2-fluorobenzyl)-2-hydroxypropyl)-2-methoxypropanamide | 552.3 | 0.013 | 1.187 | 35 | 60 | 0 | 6.3 |
| 913 | (2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynyl-2-fluorobenzyl)-2-hydroxypropyl)tetrahydro-2-furancarboxamide | 564.2 | 0.021 | 0.063 | 41 | 76 | 0 | 7.1 |
| 914 | N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)-2-ethoxyacetamide | 591.2 | 0.002 | 0.008 | 57 | 61 | 0.2 | 0.2 |
| 915 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-((2S)-tetrahydro-2-furanyl)benzyl)propyl)-2-methoxyacetamide | 566.4 | 1.959 | 0.562 | 921 | 590 | 0.6 | 6.8 |

TABLE 2-continued

| Ex. No | IUPAC NAME | Observed MS | BACE1 FRET assay (uM) | HEK cell assay (uM) | HLM (uL/min/mg) | RLM (uL/min/mg) | 3A4 IC50 (uM) | 2D6 IC50 (uM) |
|---|---|---|---|---|---|---|---|---|
| 916 | N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-((2R)-tetrahydro-2-furanyl)benzyl)propyl)-2-methoxyacetamide | 566.3 | 9.500 | 2.254 | 399 | 644 | 0.4 | 8.1 |
| 917 | N-((1S,2R)-1-(3-bromo-5-methoxybenzyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-methoxyacetamide | 604.0, 606.0 | 0.014 | | | | | |
| 918 | N-((1S)-1-(3-fluoro-5-(1,3-thiazol-2-yl)benzyl)-3-(((4'S)-6'-(2-methylpropyl)-3',4'-dihydrospiro[cyclobutane-1,2'-pyrano[2,3-b]pyridin]-4'-yl)amino)-2-oxopropyl)-2-methoxyacetamide | 581.1 | 0.0164 | >10.0 | 116 | 128 | 0.1 | 0.5 |

The present invention also provides methods for making compounds of Formulas I-IV. In another embodiment of the invention, there is provided a method of making a compound of Formula I, the method comprising the step of reacting a compound 20

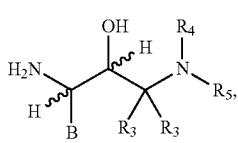

wherein B, $R^3$, $R^4$ and $R^5$ are as defined herein, with a compound having the structure

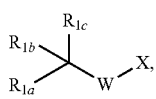

wherein $R^{1a}$, $R^{1b}$, $R^{1c}$ and W are as defined herein and X is a leaving group, to make a compound of Formulas I or II.

In another embodiment of the invention, there is provided a method of making a compound of Formula II, the method comprising the step of reacting a compound 20-A

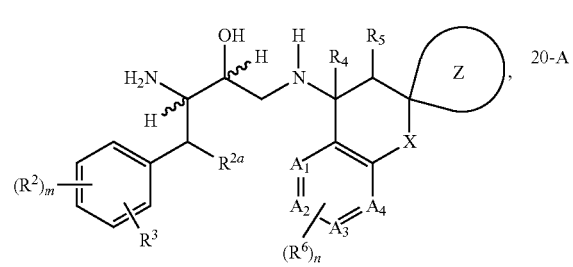

wherein $R^2$, $R^{2a}$, $R^3$, $R^4$, $R^5$, $R^6$, $A^1$, $A^2$, $A^3$, $A^4$, X, Z, m and n are as defined hereinabove with respect to Formula II, with a compound having the structure

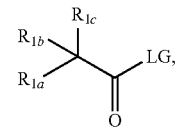

wherein $R^{1a}$, $R^{1b}$ and $R^{1c}$ are as defined hereinabove and LG is a leaving group as defined herein, to prepare the compound of Formula II. In another embodiment, the LG may be selected from a halogen and an HOBt ester.

In another embodiment of the invention, there is provided a method of making a compound of Formula II, the method comprising the step of reacting a compound 20-B

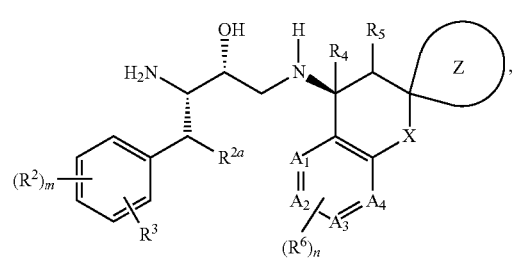

wherein $R^2$, $R^{2a}$, $R^3$, $R^4$, $R^5$, $R^6$, $A^1$, $A^2$, $A^3$, $A^4$, X, Z, m and n are as defined hereinabove with respect to Formula II, with a compound having the structure

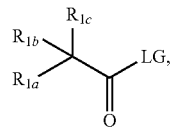

wherein $R^{1a}$, $R^{1b}$ and $R^{1c}$ are as defined hereinabove and LG is a leaving group as defined herein, to prepare the compound of Formula II. In another embodiment, the LG may be selected from a halogen and an HOBt ester.

In another embodiment of the invention, there is provided a method of making a compound of Formula III, the method comprising the step of reacting a compound 20-C

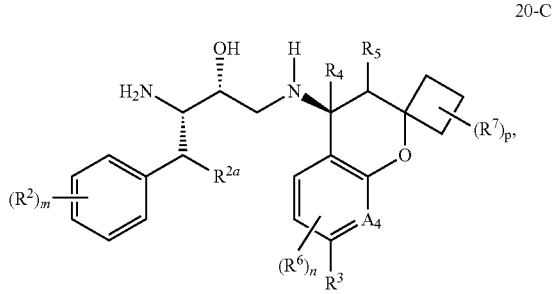

20-C wherein $R^2$, $R^{2a}$, $R^3$, $R^4$, $R^5$, $R^6$, $A^1$, $A^2$, $A^3$, $A^4$, X, Z, m, n and p are as defined hereinabove with respect to Formula III, with a compound having the structure

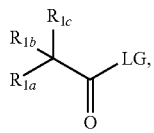

wherein $R^{1a}$, $R^{1b}$ and $R^{1c}$ are as defined hereinabove and LG is a leaving group as defined herein, to prepare the compound of Formula III. In another embodiment, the LG may be selected from a halogen and an HOBt ester.

In another embodiment of the invention, there is provided a method of making a compound of Formula III, the method comprising the step of reacting a compound 20-D

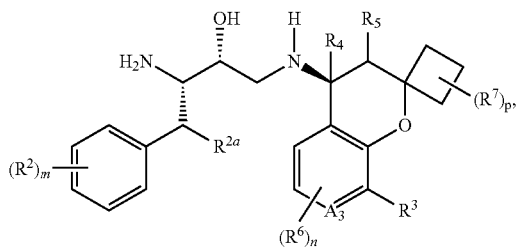

20-D wherein $R^2$, $R^{2a}$, $R^3$, $R^4$, $R^5$, $R^6$, $A^1$, $A^2$, $A^3$, $A^4$, X, Z, m, n and p are as defined hereinabove with respect to Formula III, with a compound having the structure

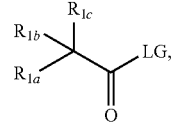

wherein $R^{1a}$, $R^{1b}$ and $R^{1c}$ are as defined hereinabove and LG is a leaving group as defined herein, to prepare the compound of Formula III. In another embodiment, the LG may be selected from a halogen and an HOBt ester.

In another embodiment of the invention, there is provided a method of making a compound of Formula IV, the method comprising the step of reacting a compound 30

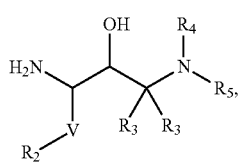

30 wherein V, $R^2$, $R^3$, $R^4$ and $R^5$ are as defined herein, with a compound having the structure A-W-X, wherein A and W are as defined herein with respect to Formula IV and X is a leaving group, to make a compound of Formula IV.

Example 919

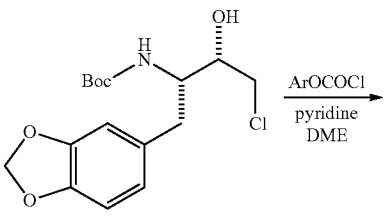

1

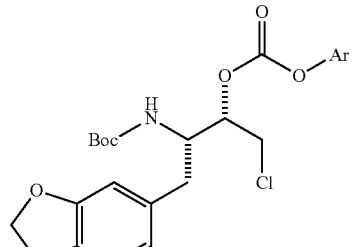

2
Ar = 4-NO₂Ph

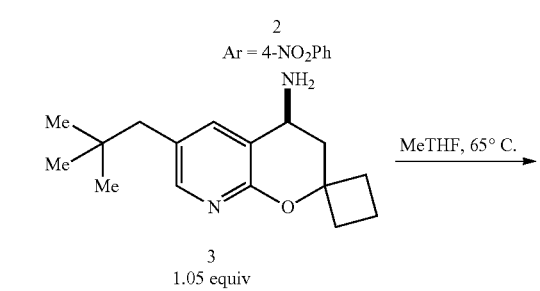

3
1.05 equiv

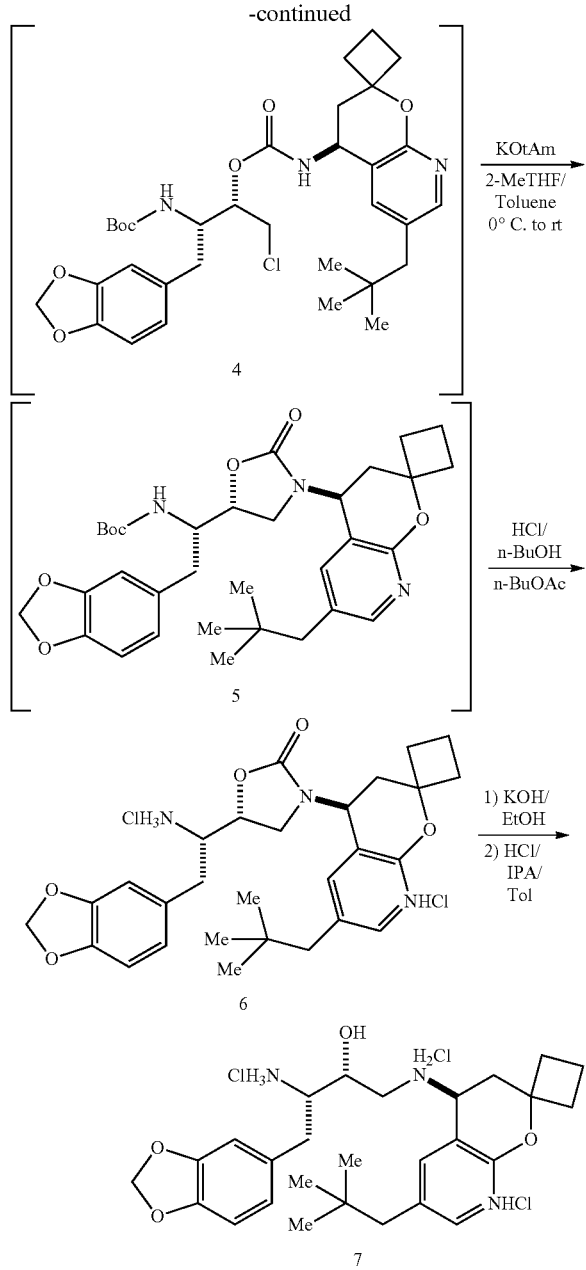

Step 1

A 5 L jacketed reactor was purged with nitrogen for 30 minutes and then charged with 167 g (95 wt % assay) of tert-butyl (2S,3S)-1-(benzo[d][1,3]dioxol-5-yl)-4-chloro-3-hydroxybutan-2-ylcarbamate 1 (1.0 equiv, 485.7 mmol), DME (1000 mL) and pyridine (70 mL, 1.8 equiv, 865.4 mmol). The contents of the reactor were cooled to 0° C. under a blanket of nitrogen and 100 mL of DME was added to help thin out the reaction mixture. A separate 1 L RBF was charged with PNPCF (150 g, 1.5 equiv, 748 mmol.) and 400 mL of DME. The contents of the 1 L RBF were transferred to the 5 L jacketed reactor via cannula over approximately 15 minutes (addition is exothermic; Tmax=8° C. during addition). Once the transfer was complete, the reaction mixture was stirred for 30 minutes at 0° C. and warmed to 25° C. over 10 minutes.

The reaction was judged complete formation of 2 by HPLC (81279-3-2; <0.5%) after about 50 minutes. Water (1500 mL) was added to the reaction mixture at such a rate as to maintain the internal temperature below 50° C. (Tmax=35° C.). The contents of the reactor were warmed to 50° C. and monitored for bisnitrophenylcarbonate hydrolysis by HPLC. At 2 hours the hydrolysis reaction was judged complete (no detectable bisnitrophenyl carbonate) and the reaction mixture was cooled to 20° C. and stirred for 12 hours. A one mL sample of the reaction mixture was pulled, filtered through a 0.45 micron filter and both solids and supernatant were analyzed by HPLC (no detectable 2; solids: no detectable bisnitrophenylcarbonate). The contents of the 5 L reactor were filtered. The mother liquors were recycled through the reactor and passed through the wetcake to facilitate product transfer from the reactor. The wet cake was washed with 2×500 mL of 1:1 DME:water and 2×500 mL water. HPLC analysis of the mother liquors showed no detectable presence of compound 2. The product was dried on the filter by passing nitrogen through wetcake for 2 hours and then dried in vacuo 36 h at 60° C. with a nitrogen bleed. Isolated the product in about 99 wt % adjusted yield. HRMS calcd for $C_{46}H_{50}Cl_2N_4NaO_{18}$ [2M+Na]$^+$ 1039.2395 found 1039.2408.

Step 2: (S)-5-((S)-1-amino-2-(benzo[d][1,3]dioxol-5-yl)ethyl)-3-((S)-2,2-spirocyclobutyl-6-neopentyl-3,4-dihydro-2H-pyrano[2,3-b]pyridin-4-yl)oxazolidin-2-one bis hydrochloride (41.(HCl)$_2$) (6)

A 3-necked 1 L RBF was charged with 2 (118 mmol, 1.0 equiv), 3 (32.5 g, 124 mmol, 1.05 equiv) and 2-Methyl THF (180 mL). The flask was vacuum degassed and back-filled with argon (4×). The contents of the flask were warmed to an internal temperature of 65-70° C. and maintained at this temperature until judged complete by HPLC analysis. After 12 hours, the reaction mixture was cooled to 0° C. internal temperature and a solution of KOt-Am (150 mL, 1.7 M in toluene; 250 mmol; 2.1 equiv) was charged dropwise via addition funnel at such a rate not to exceed 10° C. internal temperature (total addition time=40 minutes; Tmax=10° C.). The reaction mixture was stirred at 0° for 1 hour and a sample was pulled for HPLC analysis, until no remaining 4; and rxn was complete. The reaction was quenched with 20 mL of 10% (wt/wt) aqueous potassium hydrogen carbonate and stirred for 10 minutes at 10° C. A solution of 10% (wt/wt) aqueous potassium carbonate ($K_2CO_3$; 360 mL) was charged and the reaction mixture was warmed to 30° C. and stirred until a clean phase separation was achieved (~10 minutes). The phases were separated and aqueous layer was set aside (labeled as 1$^{st}$ aqueous). The organics were washed with 10% (wt/wt) aqueous $K_2CO_3$ again and the aqueous layer was set aside (labeled as 2$^{nd}$ aqueous). The organics were washed with 240 mL of 25% (wt/wt) aqueous citric acid. The phases were separated and the aqueous layer was set aside (labeled as 3$^{rd}$ aqueous). Washed organics with 240 mL of 10% (wt/wt) aqueous $K_2CO_3$. The phases were separated and the aqueous layer was set aside (labled as 4$^{th}$ aqueous). The organics were concentrated in vacuo and chased with 3×300 mL of n-BuOH. A $^1$H NMR of the solution revealed that there was no detectable toluene or 2-MeTHF in the n-BuOH chases.

The n-BuOH solution of 5 was transferred to a clean 1 L RBF and the total volume of the reaction was adjusted to 180 mL of n-BuOH and HCl (3N in n-BuOH, 117 mL, 3 equiv) was charged and the reaction was warmed to an internal temperature of 75° C. Reaction was judged complete by HPLC after 30 minutes. The reaction was warmed slightly to 80° C. and stirred at 80° C. for 60 minutes. n-BuOAc (400 mL) was charged slowly over 1 hour to the crystallization and upon completion of the addition, the mixture was held at 80° C. for 5 hours and cooled over 10 hours to ambient temperature and stirred for 30 hours. Analysis of the supernatant revealed a mother liquor concentration of 1 mg/mL of 6.(HCl)$_2$ and the reaction mixture was filtered. The mother liquors were recycled to the 1 L RBF and passed back through the wetcake to facilitate the complete transfer of the solids to the filter. The wetcake was rinsed with 2×180 mL of 2:1 mixture of n-BuOAc:n-BuOH and the wetcake was dried on the filter by passing nitrogen through the filter for 2 hours. The solids were loaded into a vacuum oven and dried for 24 hours at 80° C. under vacuum with a nitrogen sweep to afford 6.(HCl)$_2$ (100% isolated yield; 100% LCAP 224 nm; 101 wt % assay; Analytical data for 6.(HCl)$_2$: HRMS calcd for $C_{56}H_{71}N_6O_{10}$ [2M+H] 987.5232 found 987.5218; HRMS calc for $C_{28}H_{36}N_3O_5$ [M+H]$^+$ 494.2655 found 494.4595.

Step 3: (2S,3S)-3-amino-4-(benzo[d][1,3]dioxol-5-yl)-1-(S)-2,2-spirocyclobutyl-6-neopentyl-3,4-dihydro-2H-pyrano[2,3-b]pyridin-4-ylamino)butan-2-ol (30.(HCl)$_3$)

A 1 L 3-necked RBF was charged with 57 g of 6.(HCl)$_2$ and 170 mL of ethanol. The flask was vacuum purged and backfilled with argon (3×). A 5N aqueous potassium hydroxide solution (190 mL) was added to the reaction mixture. The reaction was warmed to an internal temperature of 80° C. and monitored by HPLC. At 18 hours, the reaction mixture was cooled to 25° C. and then a solution of 6N aqueous HCl (120 mL; 6 equiv) was charged to the reaction mixture followed by toluene (340 mL). A sample of the aqueous was pulled for pH (~7) and the pH was adjusted with 50 mL of 5N KOH to >14. The extraction was warmed to an internal temperature of 40° C. and was stirred for 1 hour. The phases were separated and the aqueous layer was back-extracted with 110 mL of toluene. The organics were combined and concentrated to ~1 volume and chased 2×250 mL of IPA. The IPA solution of the reaction mixture was passed through a medium porosity frit to a tared 1 L 3-necked RBF and the volume was adjusted to 3 total volumes of IPA. A sample of this solution was pulled for $^1$H NMR analysis which showed no residual toluene present in solution.

A solution of HCl in IPA (5M, 60 mL, 3 equiv) was charged to the solution of the free diaminoalcohol in IPA over 10. The crystallization mixture was warmed to an internal temperature of 55° C. and 2 volumes of toluene (110 mL) was charged and held for 30 minutes whereupon the desired 7.(HCl)$_3$ salt began to precipitate. The crystallization was held for a further 15 minutes at 55° C. whereupon an additional charge of toluene (385 mL; 6 volumes) was added at such a rate to maintain internal temperature at 55° C. (~10 minute addition time). The crystallization was maintained at 55-60° C. for 2 hours and then cooled to ambient temperature. The contents of the flask were filtered and the mother liquors were recycled to the RBF and then through the filter to facilitate complete solid transfer. The wetcake was washed with 160 mL of 2:1 toluene:IPA and dried on the filter by passing nitrogen through the wetcake for 12 hours. The solids were then loaded into a vacuum oven and dried under vacuum for 24 hours at 85° C. with a nitrogen purge. Isolated 7.(HCl)$_3$ as a colorless solid (93% isolated yield; 102 wt % assay, 99.8% LCAP 224 nm; 93 wt % adjusted yield; 17.7 wt % chloride by IC). Analytical data for 7.(HCl)$_3$: HRMS calc for $C_{27}H_{38}N_3O_4$ [M+H]$^+$ 468.2862 found 468.4176.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H+ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of this invention may also be represented in multiple tautomeric forms. The compounds may also occur in cis- or trans- or E- or Z-double bond isomeric forms. The invention expressly includes all tautomeric forms of the compounds described herein.

All crystal forms of the compounds described herein are expressly included in the present invention.

Biological Evaluation

The compounds of the invention may be modified by appending appropriate functionalities to enhance selective biological properties. Surprisingly, the compounds of the present invention exhibit improved pharmacokinetics and pharmacodynamics, which relate, directly and indirectly, to the ability of the compound to be effective for its intended use. For example, the compounds have been surprisingly found to possess improved clearance and efflux properties, which readily lend themselves to projecting in-vivo PK and PD properties, which in turn assist in projection of therapeutic target coverage for the compounds and projected efficacious dosages via in-vivo absorption, distribution, metabolism and excretion properties. Increased biological penetration into a given biological compartment (e.g., blood, lymphatic system, central nervous system), increase oral availability, increase solubility to allow administration by injection and alter clearance, metabolism and/or rate of excretion are important factors for discovering which compound may be a useful drug and which may not.

Although the pharmacological properties of the compounds of the invention (Formulas I-IV) vary with structural change, in general, activity possessed by compounds of Formulas I-IV may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay (Enzyme Assay Data in Table 1)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. The assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Of the compounds tested, the in-vitro BACE FRET enzyme data for each of Examples 52-363 is provided in Table 1. The vast majority of these examples exhibited activities with $IC_{50}$ values of 5 µM or less in in-vitro BACE FRET assay, and a majority of those same Examples exhibited activities with $IC_{50}$ values of 100 nM or less in the in-vitro BACE FRET assay In Vitro BACE Cell-based Assay:

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 µM or 10 µM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat antirabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 µg/ml in Superblock/TBS (Pierce) that was supplemented with 0.05% Tween 20 (Sigma). Optimal concentration for the detection antibody 6E10-biotinylated was 0.5 µg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Of the compounds tested, the cell based assay data for each of Examples 52-363 is provided in Table 1. The vast majority of those Examples exhibited activities with $IC_{50}$ values of 5 µM or less in the cell-based assay, a majority of those same Examples exhibited activities with $IC_{50}$ values of 1 µM or less in the cell-based assay, and a majority of those same Examples exhibited activities with $IC_{50}$ values of 100 nM or less in the cell-based assay.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry,* 76, 173-181)

Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics,* 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of Abeta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, Abeta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2
 IV: 5% EtOH, 45% Propylene glycol in 5% Dextrose The compounds of the invention can be shown to reduce the formation and/or deposition of Abeta peptide in the brain or in the cerebrospinal fluid of a mouse or rat. For example, many of the Examples tested exhibited activities with percent (%) reduction values of Abeta peptide of up to 78% in the brain or in the cerebrospinal fluid of a rat, when orally administered to the rat at a 30 mg/kg dose and measured after 4 hours. More specifically, Example numbers 484, 488, 523, 578, 600, 643, 644, 650, 661, 677, 690, 695, 699, 736-738, 756-757, 761, 772-773, 776-777, 782, 790, 816-817, 826, 828-830, 834, 835, 840, 844, 847, 849-850, 855-856, 861, 870, 873, 875, 878-879, 893-894, 896-898 and 900-903, exhibited a percent reduction of abeta peptide in the range of from 5% to 80% in the brain of the rat. Example numbers 644, 695, 699, 736-738, 743, 756-757, 761, 772-773, 776-777, 790, 817, 829, 834, 844, 849-850, 855-856, 861, 870, 873, 896-898 and 900-903, exhibited a percent reduction of abeta peptide in the range of greater than or equal to 30% in the brain of the rat. Example numbers 478, 483, 484, 488, 504, 506, 516, 521, 523, 528, 529, 531-533, 535, 541, 542, 575, 578, 583-587, 596-597, 600, 619-621, 628, 630-633, 636, 638, 640-641, 643-644, 650, 652, 661, 671, 673, 677, 682-684, 687, 690, 695, 698, 699, 704-706, 710, 712, 714-716, 722, 724, 747, 730, 731, 736-738, 743, 756-757, 761, 764, 772-773, 775, 776-777, 782, 790, 816-817, 826, 828-830, 831, 834, 836, 837, 840, 844-850, 855-856, 859-861, 868-871, 873-875, 877-879, 883, 885, 893-894, 900 and 902, exhibited a percent reduction of abeta peptide in the range of from 10% to 80% in the cerebrospinal fluid of the rat, when orally administered at 30 mg/kg dose and measured after 4 hours. Example numbers 578, 644, 650, 661, 690, 695, 699, 722, 724, 736-738, 757, 761, 772-773, 776-777, 790, 817, 834, 840, 844, 847, 849-850, 855-856, 861, 870 and 873, exhibited a percent reduction of abeta peptide in the range of greater than or equal to 50% in the cerebrospinal fluid of the rat.

CYP Inhibition Assay:

The CYP enzymes in the body are known to function in the metabolic pathway of a given compound. More specifically, CYP enzymes are responsible for metabolic breakdown of compounds. Thus, modulating the activity of one or more of the various CYP enzymes may influence potential metabolism of an administered compound. Particularly, if the compounds of the present invention were to inhibit the CYP enzyme, they may, thereby, reduce the rate of potential in-vivo metabolism of the compound, thus possibly prolonging the bioavailability of that compound. The compounds of the invention were run in the following CYP assays to determine their potential to inhibit specific CYP enzymes.

CYP3A

Pooled human liver microsomes (0.1 mg/mL) are incubated at about 37° C. in a phosphate buffer (pH 7.4) with the selective 3A substrate midazolam at a concentration of about 2.5 µM in the presence and absence of a test compound (at about 3 µM conc.). The reaction is started with the addition of NADPH (1 mM final concentration). Incubations are stopped after 10 minutes with the addition of organic solvent and 1-hydroxymidazolam metabolite formation is measured by an HPLC MS detection method. The ability of the test compound to inhibit the activity of CYP3A is determined (either % inhibition or an $IC_{50}$ can be measured in uM) by the ratio of the amount of metabolite in the presence of the test compound to the amount of metabolite in the absence of test compound. Data for various compounds of the invention in this assay is provided in Table 3.

CYP2D6

Pooled human liver microsomes (0.25 mg/mL) are incubated at about 37° C. in a phosphate buffer (pH 7.4) with the selective 2D6 substrate bufuralol at a concentration of about 5 µM in the presence and absence of a test compound (at about 3 µM conc.). The reaction is started with the addition of NADPH (1 mM final concentration). Incubations are stopped after 10 minutes with the addition of organic solvent and 1-hydroxybufuralol metabolite formation is measured by an HPLC MS detection method. The ability of the test compound to inhibit the activity of CYP2D6 is determined (either % inhibition or an $IC_{50}$ can be measured in uM) by the ratio of the amount of metabolite in the presence of test compound to the amount of metabolite in the absence of test compound. Data for various compounds of the invention in this assay is provided in Table 3.

Microsomal Stability Assay

The purpose of this assay is to determine to what extent a compound may survive metabolic forces and to help ascertain the degree, time and extent of metabolism of a given compound. Such data is useful for projecting a given compound's ability to remain the plasma and potentially reach a desired target.

Assay:

Pooled human or rat liver microsomes (0.25 mg/mL) are incubated at about 37° C. in a phosphate buffer (pH 7.4) with a test compound (at a concentration of about 1 µM). The reaction is started with the addition of NADPH (1 mM final concentration). Incubations are stopped after 0 or 30 minutes with the addition of organic solvent. Quenched samples are analyzed for unchanged test compound by reverse phase HPLC with tandem mass spectrometric detection. % Turnover is determined by the ratio of the amount (peak area) of unchanged test compound remaining in incubated samples to the amount of unchanged test compound in non-incubated samples (0 minutes). Intrinsic clearance is estimated assuming first order elimination of compound from the incubation over the 30 minute incubation. Data for various compounds of the invention in this assay (human and rat) is provided in Table 3.

Indications

Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide and/or plaque on the brain. In one embodiment of the invention, there is provided a method of treating a disorder related to a beta-secretase enzyme in a subject, the method comprising administering to the subject an effective dosage amount of a compound of Formulas I-IV. In another embodiment, there is provided a method of reducing production of amyloid beta, and of reducing plaque formation. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I, II, II-A, II-B, II-C, II-D, III-A, III-B, III-C and III-D. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about I to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Accordingly, in yet another embodiment of the present invention, there is provided a method of manufacturing a medicament, the method comprising combining an amount of a compound according to Formulas I-IV with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-IV with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I and II may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula II:

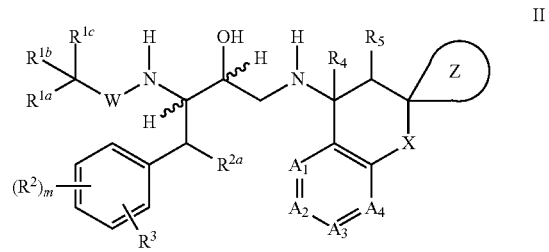

or a pharmaceutically acceptable salt thereof, wherein
each of $A^1$, $A^2$, $A^3$ and $A^4$, independently, is N, CH or $CR^6$, provided that no more than two of $A^1$, $A^2$, $A^3$ and $A^4$ is N;
$R^{1a}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl portion of —O-$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;
$R^{1b}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$, wherein the $C_{1-6}$-alkyl portion of —O-$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;
alternatively, $R^{1a}$ and $R^{1b}$ taken together with the carbon atom to which they are attached form a partially or fully saturated 3-, 4-, 5- or 6-membered ring of carbon atoms optionally including 1-2 heteroatoms selected from O, N, or S, the ring optionally substituted independently with 1-3 substituents of $R^7$;
$R^{1c}$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$;
W is —C(=O)—, —C(=S)—, —OC(=O)—, —NHC(=O)—, —S(=O)$_b$— or —NHS(=O)$_b$—, wherein b is 1 or 2;
each $R^2$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O-$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;
alternatively, two adjacent $R^2$ groups taken together with the carbon atoms to which they are attached form a dioxolyl ring optionally substituted by 1 or 2 halo;
$R^{2a}$ is H or F;
$R^3$ is CN, $C_{2-3}$alkynyl, a partially or fully unsaturated 5- or 6-membered monocyclic ring formed of carbon atoms wherein said ring optionally including 1-3 heteroatoms selected from O, N, or S and optionally substituted with 1-5 substituents of $R^7$, or $R^3$ is F or absent when two adjacent $R^2$ groups taken together with the carbon atoms to which they are attached form a dioxolyl ring;
$R^4$ is H, halo or $C_{1-6}$-alkyl;
$R^5$ is H, halo, haloalkyl, oxo, $C_{1-6}$-alkyl, —O—$C_{1-6}$-alkyl, —S—$C_{1-6}$-alkyl, —NH—$C_{1-6}$alkyl, —N-di-$C_{1-6}$-alkyl, CN, OH or $NH_2$, wherein the $C_{1-6}$-alkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted independently with 1-5 substituents of $R^7$;

X is $CH_2$, $CHR^6$, $CR^6R^6$, $C(=O)$, O, NH, $NR^6$, or $S(O)_o$ wherein o is 0, 1 or 2;

Z is a 3-6 membered spirocyclic ring formed of carbon atoms optionally including 1-3 heteroatoms selected from O, N and S and optionally substituted independently with 1-5 substituents of $R^7$;

each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, $OR^7$, $NHR^7$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O-$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

or $R^6$ is a fully saturated or partially or fully unsaturated 5- or 6-membered monocyclic or bicyclic ring formed of carbon atoms, said ring optionally including 1-4 heteroatoms selected from O, N, or S and optionally substituted with one or more substituents of $R^7$ each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkenyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl; and m is 0, 1, 2 or 3, provided that (1) the compound is not a compound wherein Z is a four membered spirocyclic ring and $R^{1a}$ and $R^{1b}$ are not taken together to form a ring of carbon atoms; and (2) the compound is not (3S)-N-((1S,2R)-1-[(3-cyanophenyl)methyl]-3-(((4S)-6-ethyl-3,4-dihydrospiro[chromene-2,1'-cyclobutan]-4-yl)amino)-2-hydroxypropyl)-1-cyclobutyl-5-oxo-3-pyrrolidinecarboxamide;

N-((1S,2R)-1-((3-cyanophenyl)methyl)-3-(((4S)-6-ethyl-3,4-dihydrospiro[chromene-2, 1'-cyclobutan]-4-yl)amino)-2-hydroxypropyl)tetrahydro-2-furancarboxamide;

N-((1S,2R)-1-((3-cyanophenyl)methyl)-3-(((4S)-6-ethyl-3,4-dihydrospiro[chromene-2, 1'-cyclobutan]-4-yl)amino)-2-hydroxypropyl)propanamide;

N-((1S,2R)-1-((3-cyanophenyl)methyl)-3-(((2S,4S)-6-ethyl-3,4,4',5'-tetrahydrospiro[chromene-2,3'-furan]-4-yl)amino)-2-hydroxypropyl)-2-(methyloxy)acetamide;

2-(((1S,2R)-1-((3-cyanophenyl)methyl)-2-hydroxy-3-(((4S)-6-(4-morpholinyl)-3,4-dihydrospiro[chromene-2,1'-cyclobutan]-4-yl)amino)propyl)amino)-2-oxoethyl dimethylcarbamate;

N~1~-((1S,2R)-3-(((4S)-6-bromo-3,4-dihydrospiro[chromene-2,1'-cyclobutan]-4-yl)amino)-1-((3-cyanophenyl)methyl)-2-hydroxypropyl)-N~2~,N~2~-dimethylglycinamide;

Methyl (4S)-4-(((2R,3S)-4-(3-cyanophenyl)-3-[((N,N-dimethylglycyl)amino)-2-hydroxybutyl)amino)-3,4-dihydrospiro[chromene-2,1'-cyclobutane]-6-carboxylate;

Methyl (4S)-4-(((2R,3S)-3-(acetylamino)-4-(3-cyanophenyl)-2-hydroxybutyl)amino)-3,4-dihydrospiro[chromene-2,1'-cyclobutane]-6-carboxylate; and Methyl (4S)-4-(((2R,3S)-4-(3-cyanophenyl)-2-hydroxy-3-(((methyloxy)acetyl)amino)butyl)amino)-3,4-dihydrospiro[chromene-2,1'-cyclobutane]-6-carboxylate.

2. The compound of claim 1, or a pharmaceutically acceptable salt thereof, wherein $R^{1a}$ and $R^{1b}$ taken together with the carbon atom to which they are attached form a partially or fully saturated 4-, 5- or 6-membered ring of carbon atoms optionally including 1-2 heteroatoms selected from O, N, or S, the ring optionally substituted independently with 1-3 substituents of $R^7$ and $R^{1c}$ is H.

3. The compound of claim 1, or a pharmaceutically acceptable salt thereof, wherein $R^3$ is $C_{2-3}$alkynyl or a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of $R^7$.

4. The compound of claim 1, or a pharmaceutically acceptable salt thereof, wherein $A^1$ is CH;

$A^2$ is $CR^6$;

each of $A^3$ and $A^4$, independently, CH, $CR^6$ or N, provided no more than one of $A^3$ and $A^4$ is N;

$R^{1a}$ and $R^{1b}$ taken together with the carbon atom to which they are attached form a partially or fully saturated 5- or 6-membered ring of carbon atoms optionally including 1-2 heteroatoms selected from O, N, or S, the ring optionally substituted independently with 1-3 substituents of $R^7$;

$R^{1c}$ is H;

W is —$C(=O)$—;

each $R^2$, independently, is halo, haloalkyl, $C_{1-4}$-alkyl, —O—$C_{1-4}$-alkyl, —S—$C_{1-4}$-alkyl, —NH—$C_{1-4}$-alkyl, —N-di-$C_{1-4}$-alkyl, CN, OH, $NH_2$, $C_{2-4}$-alkenyl, $C_{2-4}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

alternatively, two adjacent $R^2$ groups taken together with the carbon atoms to which they are attached form a dioxolyl ring optionally substituted by 1 or 2 halo;

$R^{2a}$ is H;

$R^3$ is a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, said ring optionally substituted with 1-5 substituents of $R^7$, or $R^3$ is absent when two adjacent $R^2$ groups taken together with the carbon atoms to which they are attached form a dioxolyl ring;

$R^4$ is H or $C_{1-4}$-alkyl;

$R^5$ is H, halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH or $NH_2$;

X is $CH_2$, $CHR^6$, C(=O) or O;

Z is a cyclopropyl, cyclobutyl or cyclopentyl ring wherein 0, 1 or 2 carbon atoms of the ring are, independently, replaced with an oxygen atom and the ring optionally substituted independently with 1-5 substituents of $R^7$; and each $R^6$, independently, is halo, haloalkyl, $C_{1-6}$-alkyl, —O—$C_{1-6}$-alkyl, —S—$C_{1-6}$alkyl, —NH—$C_{1-6}$-alkyl, —N-di-$C_{1-6}$-alkyl, CN, $OR^7$, $NHR^7$, $C_{2-6}$-alkenyl, $C_{2-6}$-alkynyl, $C_{3-8}$-cycloalkyl, $C_{4-8}$-cycloalkenyl or a ring selected from phenyl, pyridyl, pyrimidyl, pyridazinyl, pyrazinyl, triazinyl, thiophenyl, furyl, pyrrolyl, pyrazolyl, imidazolyl, triazolyl, tetrazolyl, thiazolyl, oxazolyl, isoxazolyl, isothiazolyl, thiadiazolyl, oxadiazolyl, pyrrolidinyl, oxazolinyl, isoxazolinyl, thiazolinyl, pyrazolinyl, morpholinyl, piperidinyl, piperazinyl and pyranyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl, ring and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$.

5. The compound of claim 4, or a pharmaceutically acceptable salt thereof, wherein ring Z is

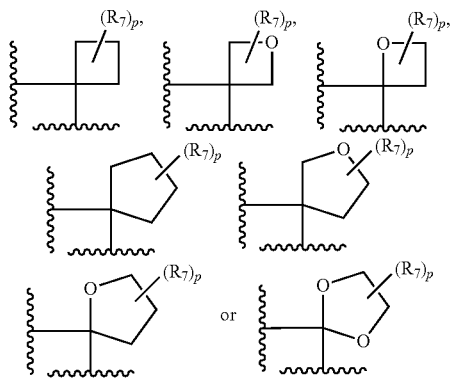

wherein $R^7$ is as defined in claim 1; and
p is 0, 1, 2, 3 or 4.

6. The compound of claim 1, or a pharmaceutically acceptable salt thereof, having a general Formula II-A:

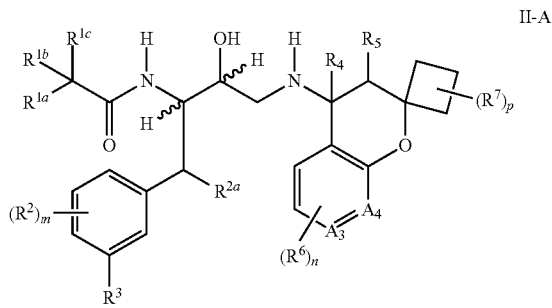

II-A wherein
each of $A^3$ and $A^4$, independently, CH, $CR^6$ or N, provided no more than one of $A^3$ and $A^4$ is N;

$R^{1a}$ and $R^{1b}$ taken together with the carbon atom to which they are attached form a partially or fully saturated 4-, 5- or 6-membered ring of carbon atoms optionally including 1-2 heteroatoms selected from O, N, or S, the ring optionally substituted independently with 1-3 substituents of $R^7$;

$R^{1c}$ is H, F, Cl, methyl, ethyl, methoxyl, ethyoxyl, CN, OH or $NH_2$;

each $R^2$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O-$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

alternatively, two adjacent $R^2$ groups taken together with the carbon atoms to which they are attached form a dioxolyl ring optionally substituted by 1 or 2 halo;

$R^{2a}$ is H or F;

$R^3$ is CN, $C_{2-3}$alkynyl or a ring selected from imidazolyl, thiazolyl, pyridyl, pyrazolyl, furyl, pyrimidyl, pyridazinyl, pyrazinyl, triazinyl, thiophenyl, pyrrolyl, triazolyl, tetrazolyl, oxazolyl, isoxazolyl, isothiazolyl, thiadiazolyl or oxadiazolyl, said ring optionally substituted with 1-3 substituents of $R^7$, or $R^3$ F or absent when two adjacent $R^2$ groups taken together with the carbon atoms to which they are attached form a dioxolyl ring;

$R^4$ is H, halo or $C_{1-4}$-alkyl;

$R^5$ is H, halo, haloalkyl, $C_{1-4}$-alkyl, —O—$C_{1-4}$-alkyl, —S—$C_{1-4}$-alkyl, —NH—$C_{1-4}$-alkyl, CN, OH or $NH_2$, wherein the $C_{1-6}$-alkyl and the $C_{1-4}$-alkyl portion of —O-$C_{1-4}$-alkyl, —S—$C_{1-4}$-alkyl and —N—$C_{1-4}$-alkyl are optionally substituted independently with 1-3 substituents of $R^7$;

each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, $OR^7$, $NHR^7$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O-$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;

each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;

m is 0, 1, 2 or 3;
n is 0, 1 or 2; and
p is 0, 1 or 2.

7. The compound of claim 6, or a pharmaceutically acceptable salt thereof, wherein
$R^{1a}$ and $R^{1b}$ taken together with the carbon atom to which they are attached form a partially or fully saturated 4- or 5-membered ring of carbon atoms optionally including 1 or 2 oxygen atoms and optionally substituted independently with 1-3 substituents of $R^7$;
$R^{1c}$ is H, F, Cl, methyl or ethyl;
each $R^2$, independently, is F, Cl, Br, $CF_3$, $C_2F_5$, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, OH, $NH_2$, $C_{2-6}$-alkenyl, $C_{2-6}$-alkynyl or $C_{3-8}$-cycloalkyl, wherein the $C_{1-6}$-alkyl, $C_{2-6}$-alkenyl, $C_{2-6}$-alkynyl, $C_{3-8}$-cycloalkyl and the $C_{1-6}$-alkyl portion of —O—$C_{1-6}$-alkyl, —S—$C_{1-6}$-alkyl, —NH—$C_{1-6}$-alkyl and —N-di-$C_{1-6}$-alkyl are optionally substituted with 1-3 substituents of $R^7$;
$R^3$ is $C_{2-3}$alkynyl or a ring selected from 1H-imidazol-1-yl, 1H-imidazol-2-yl, 1H-imidazol-4-yl, 1H-imidazol-5-yl, 1,3-thiazol-5-yl, 1,3-thiazol-4-yl, 1,3-thiazol-2-yl, 4-pyridyl, 3-pyridyl, 2-pyridyl, pyrimidyl, pyridazinyl, pyrazinyl, pyrazolyl, 1,3-oxazol-2-yl, 1,3-oxazol-4-yl, 1,3-oxazol-5-yl, isoxazolyl, isothiazolyl, thiadiazolyl and oxadiazolyl, said ring optionally substituted with 1-3 substituents of $R^7$;
$R^4$ is H, F or methyl;
$R^5$ is H, halo, haloalkyl, $C_{1-4}$-alkyl, —O—$C_{1-4}$-alkyl, —S—$C_{1-4}$-alkyl, —NH—$C_{1-4}$-alkyl, CN, OH or $NH_2$, wherein the $C_{1-6}$-alkyl and the $C_{1-4}$-alkyl portion of —O-$C_{1-4}$-alkyl, —S—$C_{1-4}$-alkyl and —N—$C_{1-4}$-alkyl are optionally substituted independently with 1-3 substituents of $R^7$;
each $R^6$, independently, is halo, haloalkyl, $C_{1-6}$-alkyl, —O—$C_{1-6}$-alkyl, —S—$C_{1-6}$-alkyl, —NH—$C_{1-6}$-alkyl, —N-di-$C_{1-6}$-alkyl, CN, $OR^7$, $NHR^7$, $C_{2-6}$-alkenyl, $C_{2-6}$-alkynyl, $C_{3-8}$-cycloalkyl or $C_{4-8}$-cycloalkenyl, wherein the $C_{1-6}$-alkyl, $C_{2-6}$-alkenyl, $C_{2-6}$-alkynyl, $C_{3-8}$-cycloalkyl, $C_{4-8}$-cycloalkenyl and the $C_{1-6}$-alkyl portion of —O-$C_{1-6}$-alkyl, —S—$C_{1-6}$-alkyl, —NH—$C_{1-6}$-alkyl and —N-di-$C_{1-6}$-alkyl are optionally substituted with 1-5 substituents of $R^7$;
each $R^7$, independently, is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{2-10}$-cycloalkenyl, $C_{3-10}$-alkylamino-, $C_{4-10}$-dialkylamino-, $C_{1-10}$-alkoxyl, $C_{1-10}$-thioalkoxyl or a fully saturated or partially or fully unsaturated 3-8 membered monocyclic or a 6-12 membered bicyclic, said ring system formed of carbon atoms optionally including 1-3 heteroatoms if monocyclic or 1-6 heteroatoms if bicyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-5 substituents of halo, haloalkyl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, cyclobutyl, pentyl, cyclopentyl, hexyl, cyclohexyl, $C_{1-10}$-alkylamino-, $C_{1-10}$-dialkylamino-, $C_{1-10}$-thioalkoxyl, benzyl or phenyl;
m is 0, 1 or 2;
n is 0 or 1; and
p is 0, 1 or 2.

8. The compound of claim 1, or a pharmaceutically acceptable salt thereof, selected from
(2R)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)tetrahydro-2-furancarboxamide;
N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-oxetanecarboxamide;
(2R)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-oxetanecarboxamide;
(2S)-N-((1S,2R)-3-((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide;
(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide;
N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-1-(3-ethynylbenzyl)-2-hydroxypropyl)-2-methoxyacetamide;
N-((1S,2R)-3-(((3S,4'R)-6'-(2,2-dimethylpropyl)-3',4,4',5-tetrahydrospiro[furan-3,2'-pyrano[2,3-b]pyridin]-4'-yl)amino)-2-hydroxy-1-(3-(1,3-thiazol-2-yl)benzyl)propyl)-2-methoxyacetamide;
N-((1S,2R)-3-(((3S,4'S)-6'-(2,2-dimethylpropyl)-3',4,4',5-tetrahydrospiro[furan-3,2'-pyrano[2,3-b]pyridin]-4'-yl)amino)-2-hydroxy-1-(3-(1,3-thiazol-2-yl)benzyl)propyl)-2-methoxyacetamide;
N-((1S,2R)-1-((3-cyanophenyl)methyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-1-cyclobutyl-4,4-dimethyl-5-oxo-3-pyrrolidinecarboxamide;
1-cyclobutyl-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((3-fluorophenyl)methyl)-2-hydroxypropyl)-4,4-dimethyl-5-oxo-3-pyrrolidinecarboxamide;
1-cyclobutyl-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorophenyl)methyl)-2-hydroxypropyl)-5-oxo-3-pyrrolidinecarboxamide;
(2S)-N-((1S,2R)-3-(((4'S)-6'-((1,1-difluoroethyl)oxy)-3',4'-dihydrospiro[cyclobutane-1,2'-pyrano[2,3-b]pyridin]-4'-yl)amino)-1-((3-fluorophenyl)methyl)-2-hydroxypropyl)-5-oxotetrahydro-2-furancarboxamide;
(2S)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)tetrahydro-2-furancarboxamide;
(2R)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)tetrahydro-2-furancarboxamide;
(2R)-N-((1S,2R)-1-((3-cyanophenyl)methyl)-3-(((4'S)-6'-(2,2-dimethylpropyl)-3,3-difluoro-3',4'-dihydrospiro[cyclobutane-1,2'-pyrano[2,3-b]pyridin]-4'-yl)amino)-2-hydroxypropyl)tetrahydro-2-furancarboxamide;
(2R)-N-((1S,2R)-3-(((4'S)-6'-(2,2-dimethylpropyl)-3',4'-dihydrospiro[cyclobutane-1,2'-pyrano[2,3-b]pyridin]-

4'-yl)amino)-1-((4-fluorophenyl)methyl)-2-hydroxypropyl)-2-oxetanecarboxamide;
(2S)-N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-oxetanecarboxamide;
(2R)-N-((1S,2R)-1-(1,3-benzodioxol-5-ylmethyl)-2-hydroxy-3-(((4'S)-6'-(2-methylpropyl)-3',4'-dihydrospiro[cyclobutane-1,2'-pyrano[2,3-b]pyridin]-4'-yl)amino)propyl)tetrahydro-2-furancarboxamide;
(2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-((4-fluorophenyl)methyl)-2-hydroxypropyl)-2-oxetanecarboxamide;
(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(3-methylbenzyl)-2-morpholinecarboxamide;
(2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(3-methylbenzyl)-2-morpholinecarboxamide;
(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(2-methylbenzyl)-2-morpholinecarboxamide;
(2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(2-methylbenzyl)-2-morpholinecarboxamide;
(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(4-methylbenzyl)-2-morpholinecarboxamide;
(2S)-4-benzyl-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-2-morpholinecarboxamide;
(2R)-4-benzyl-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-2-morpholinecarboxamide;
(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-methyl-2-morpholinecarboxamide;
(2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-methyl-2-morpholinecarboxamide;
(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-((2-methyl-1,3-thiazol-4-yl)methyl)-2-morpholinecarboxamide;
(2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-((2-methyl-1,3-thiazol-4-yl)methyl)-2-morpholinecarboxamide;
(2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(1,3-thiazol-2-ylmethyl)-2-morpholinecarboxamide;
(2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-((1,3-thiazol-2-ylmethyl)-2-morpholinecarboxamide;
N-((1S,2R)-1-(1,3-benzodioxol-5-ylmethyl)-3-(((4'S)-6'-(2,2-dimethylpropyl)-3',4'-dihydrospiro[cyclobutane-1,2'-pyrano[2,3-b]pyridin]-4'-yl)amino)-2-hydroxypropyl)-2-(1,1-dioxidotetrahydro-3-thiophenyl)acetamide;
N-((1S,2R)-1-(1,3-benzodioxol-5-ylmethyl)-3-(('S)-6'-(2,2-dimethylpropyl)-3',4'-dihydrospiro[cyclobutane-1,2'-pyrano[2,3-b]pyridin]-4'-yl)amino)-2-hydroxypropyl)tetrahydro-3-thiophenecarboxamide 1,1-dioxide;
(2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(4-fluorobenzyl)-2-hydroxypropyl)-4-(1,3-thiazol-4-ylmethyl)-2-morpholinecarboxamide;
(2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide;
(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide;
(2R)-N-((1R,2S)-2-hydroxy-3-(((4'S)-6'-(2-methylpropyl)-3',4'-dihydrospiro[cyclobutane-1,2'-pyrano[2,3-b]pyridin]-4'-yl)amino)-1-(3-(1,3-thiazol-2-yl)benzyl)propyl)tetrahydro-2-furancarboxamide;
N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)cyclopropanecarboxamide;
N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)cyclobutanecarboxamide;
N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)-1-methylcyclopropanecarboxamide;
(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-fluoro-5-(1,3-thiazol-2-yl)benzyl)-2-hydroxypropyl)tetrahydro-2-furancarboxamide;
(2S)-N-((1S,2R)-3-(((4'S)-6'-(2,2-dimethylpropyl)-3',4'-dihydrospiro[cyclobutane-1,2'-pyrano[2,3-b]pyridin]-

4'-yl)amino)-1-(3-fluoro-5-(1,3-thiazol-2-yl)benzyl)-2-hydroxypropyl)tetrahydro-2-furancarboxamide;

(2R)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)tetrahydro-2-furancarboxamide;

(2S)-N-((1S,2R)-3-(((4'S)-6'-(2,2-dimethylpropyl)-3',4'-dihydrospiro[cyclobutane-1,2'-pyrano[2,3-b]pyridin]-4'-yl)amino)-1-(3-ethynylbenzyl)-2-hydroxypropyl)tetrahydro-2-furancarboxamide;

(2R)-N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide; and (2R)-N-((1S,2R)-3-(((4'S)-6'-((1R)-2,2-dimethylcyclopropyl)-3',4'-dihydrospiro[cyclobutane-1,2'-pyrano[2,3-b]pyridin]-4'-yl)amino)-2-hydroxy-1-(3-(1,3-thiazol-2-yl)benzyl)propyl)tetrahydro-2-furancarboxamide.

9. A pharmaceutical composition comprising a compound according to claim 1 and a pharmaceutically acceptable excipient.

10. A pharmaceutical composition comprising a compound according to claim 6 and a pharmaceutically acceptable excipient.

11. A pharmaceutical composition comprising a compound according to claim 8 and a pharmaceutically acceptable excipient.

12. A process for preparing a compound of claim 1, the process comprising the step of reacting a compound 20

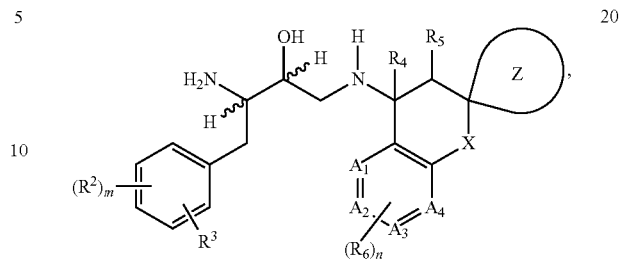

wherein R2, R3, $R^4$, $R^5$, $R^6$, A1, A2, A3, A4, X, Z, m and n are as defined in claim 1, with a compound having the structure

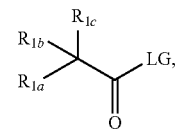

wherein $R^{1a}$, $R^{1b}$ and $R^{1c}$ are as defined in claim 1 and LG is a leaving group selected from a halogen and an HOBt ester, to prepare the compound of claim 1.

* * * * *